US008883827B2

(12) United States Patent
Holsworth et al.

(10) Patent No.: US 8,883,827 B2
(45) Date of Patent: Nov. 11, 2014

(54) AZOLE DERIVATIVES AS WTN PATHWAY INHIBITORS

(75) Inventors: Daniel Holsworth, San Diego, CA (US); Jo Waaler, Oslo (NO); Ondrej Machon, Prague (CZ); Stefan Krauss, Eidsvoll Verk (NO)

(73) Assignee: Oslo University Hospital HF (NO)

( * ) Notice: Subject to any disclaimer, the term of this patent is extended or adjusted under 35 U.S.C. 154(b) by 0 days.

(21) Appl. No.: 13/376,202

(22) PCT Filed: Jun. 7, 2010

(86) PCT No.: PCT/GB2010/001118
§ 371 (c)(1),
(2), (4) Date: Apr. 4, 2012

(87) PCT Pub. No.: WO2010/139966
PCT Pub. Date: Dec. 9, 2010

(65) Prior Publication Data
US 2012/0208828 A1    Aug. 16, 2012

(30) Foreign Application Priority Data

Jun. 5, 2009   (EP) .................................. 09251497

(51) Int. Cl.
*A61K 31/4245*   (2006.01)
*A61K 31/4196*   (2006.01)
*A61P 35/04*   (2006.01)
*C07D 413/14*   (2006.01)
*C07D 401/04*   (2006.01)
*C07D 413/12*   (2006.01)

(52) U.S. Cl.
CPC ............ *C07D 413/12* (2013.01); *C07D 413/14* (2013.01); *C07D 401/04* (2013.01)
USPC ........................... 514/340; 514/364; 514/384

(58) Field of Classification Search
USPC .......................................... 514/364, 340, 384
See application file for complete search history.

(56) References Cited

U.S. PATENT DOCUMENTS

| 6,080,772 A | * | 6/2000 | Tang et al. .................... 514/370 |
| 2005/0272779 A1 | | 12/2005 | Edwards et al. |
| 2008/0287452 A1 | | 11/2008 | Bursavich et al. |
| 2009/0131336 A1 | | 5/2009 | Cho et al. |

FOREIGN PATENT DOCUMENTS

| WO | 2004014881 A2 | 2/2004 |
| WO | 2005004818 A2 | 1/2005 |
| WO | 2005080356 A1 | 9/2005 |
| WO | 2006014185 A1 | 2/2006 |
| WO | 2007040982 A1 | 4/2007 |
| WO | 2007139967 A2 | 12/2007 |
| WO | 2008011557 A2 | 1/2008 |
| WO | 2009005269 A2 | 1/2009 |
| WO | 2009030996 A1 | 3/2009 |
| WO | 2009051556 A1 | 4/2009 |
| WO | 2009054785 A1 | 4/2009 |
| WO | 2009054794 A1 | 4/2009 |
| WO | 2010139966 A1 | 12/2010 |

OTHER PUBLICATIONS

Schafer et al. Drug Discovery Today, 2008, 13 (21/22), 913-916.*
Horig et al. Journal of Translational Medicine 2004, 2(44),p. 1-8.*
Hirayama, et al.; "Identification of Novel Chemical Inhibitors for Ubiquitin C-Terminal Hydrolase-L3 by Virtual Screening"; Bioorganic & Medicinal Chemistry; 15; pp. 6810-6818; (2007).
International Search Report; Interntional Application No. PCT/GB2010/001118; International Filing Date Jun. 7, 2010; Date of Mailing Jul. 30, 2010; 5 pages.
International Preliminary Report on Patentability; International Application No. PCT/GB2011/052441; International Filing Date Dec. 8, 2011; Date of Mailing Jun. 20, 2013; 8 pages.
International Preliminary Report and Written Opinion; International Application No. PCT/GB2011/052441; International Filing Date Dec. 8, 2011; Date of Mailing Mar. 5, 2012.
U.S. Appl. No. 13/992,879, filed Jun. 10, 2013.

* cited by examiner

Primary Examiner — Yong Chu
(74) Attorney, Agent, or Firm — Cantor Colburn LLP

(57) ABSTRACT

The present invention relates to new compounds of formula I, to processes for their preparation, to pharmaceutical formulations containing such compounds and to their use in therapy. Such compounds find particular use in the treatment and/or prevention of conditions or diseases which are affected by over-activation of signaling in the Wnt pathway. For example, these may be used in preventing and/or retarding proliferation of tumor cells, for example carcinomas such as colon carcinomas.

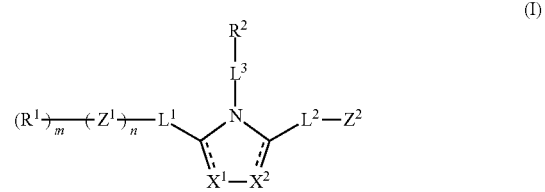

1 Claim, 14 Drawing Sheets

SEQUENCE LISTING

```
<160> NUMBER OF SEQ ID NOS: 10

<210> SEQ ID NO 1
<211> LENGTH: 23
<212> TYPE: DNA
<213> ORGANISM: Artificial Sequence
<220> FEATURE:
<223> OTHER INFORMATION: primer

<400> SEQUENCE: 1
cccaagcccc atagtgccca aag                                           23

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
``` cagggggaggc atcgcagggt c                                    21

<210> SEQ ID NO 3
<211> LENGTH: 18
<212> TYPE: DNA
<213> ORGANISM: Artificial Sequence
<220> FEATURE:
<223> OTHER INFORMATION: primer

<400> SEQUENCE: 3
gcggcgaggg gcaagggc                                          18

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
cgccgaggca tggacacccg                                        20

<210> SEQ ID NO 5
<211> LENGTH: 19
<212> TYPE: DNA
<213> ORGANISM: Artificial Sequence
<220> FEATURE:
<223> OTHER INFORMATION: primer

<400> SEQUENCE: 5
tcactccaag ccggccgcc                                         19

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
tcccgggtgc ttcggcctat g                                      21

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7 gcccccctctg ctgatgcccc ca                                    22

<210> SEQ ID NO 8
<211> LENGTH: 18
<212> TYPE: DNA
<213> ORGANISM: Artificial Sequence
<220> FEATURE:
<223> OTHER INFORMATION: primer

<400> SEQUENCE: 8
tgggtggcag tggcatgg                                          18

<210> SEQ ID NO 9
<211> LENGTH: 21
<212> TYPE: DNA

```
<213> ORGANISM: Artificial Sequence
<220> FEATURE:
<223> OTHER INFORMATION: primer

<400> SEQUENCE: 9
tggttggaga gctcatttgg a                                              21

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
gcactctcgt cggtgactgt t                                              21
```

AZOLE DERIVATIVES AS WTN PATHWAY INHIBITORS

CROSS-REFERENCE TO RELATED APPLICATIONS

This application is a 371 of PCT/GB2010/001118, filed Jun. 6, 2010, which claims the benefit of priority to EP application No. 09251497.5, filed on Jun. 5, 2009, under provisions of 35 U.S.C. 119 and the International Convention for the protection of Industrial Property, which is incorporated herein by reference.

The present invention relates to novel compounds, to pharmaceutical formulations containing such compounds and to their use in therapy, in particular as Wnt pathway inhibitors for reducing the proliferation of tumor cells. The invention further relates to processes for the preparation of such compounds and to intermediates formed during these processes.

The Wnt family of glycoproteins control a variety of developmental processes including cell fate specification, proliferation, polarity and migration. Consequently, the Wnt pathway is instrumental in ensuring proper tissue development in embryos and tissue maintenance in adults. There are at least three signaling pathways involved in the signal transduction process. The canonical (or β-catenin dependent) Wnt pathway was discovered first and has been studied most. In the absence of a Wnt signal, the transcriptional activator β-catenin is actively degraded in the cell by the actions of a protein complex. Within this complex the Axin and adenomatous polyposis coli (APC) proteins form a scaffold that facilitates β-catenin phosphorylation by casein-kinase 19α (CK1α) and glycogen synthase kinase 3β (GSK-3β). Phosphorylated β-catenin is subsequently recognised and ubiquitinylated, resulting in its proteasomal degradation. Levels of free β-catenin consequently remain low, which allows the DNA-binding T-cell factor/lymphoid enhancer factor (Tcf/Lef) proteins to interact with transcriptional co-repressors to block target gene expression in the nucleus. Binding of Wnt to Fzd-LRP (low-density lipoprotein receptor-related protein) receptor complexes at the membrane results in the formation of Dishevelled (Dvl)-Fzd complexes and relocation of Axin from the destruction complex to the cell membrane. This allows β-catenin to accumulate and enter the nucleus where it interacts with members of the Tcf/Lef family and converts the Tcf proteins into potent transcriptional activators by recruiting co-activator proteins ensuring efficient activation of Wnt target genes.

Canonical Wnt signaling is over-activated in a variety of tumors where it plays a central role in cell growth and tumor progression (Barker et al., Nat. Rev. Drug. Discov. 5: 997-1014, 2006; Grigoryan et al., Genes Dev. 22: 2308-2341, 2008; and Shitashige et al., Cancer Sci. 99: 631-637, 2008). About 90% of sporadic colon cancers show aberrant Wnt signaling (Liu et al., Nat. Genet. 26: 146-147, 2000; and Morin et al., Science 275: 1787-1790, 1997), while all pancreatic adenocarcinomas exhibit alterations in Wnt/Notch signaling (Jones et al., Science 321: 1801-1806, 2008).

Wnt activating mutations are present in a variety of cancers including gastric cancer, hepatocellular carcinoma, Wilms tumor of the kidney, medulloblastoma, melanoma, non-small cell lung cancer, ovarian endometriod cancer, anaplastic thyroid cancer and prostate cancer (Barker et al. supra). Mutations in the adenomatous polyposis coli gene (APC), β-catenin, or Axin genes lead to accumulation of nuclear β-catenin and such mutations are frequently associated with colon cancer (Morin et al. supra). Furthermore, alterations in extracellular proteins which silence Wnt signaling including secreted frizzled related proteins (SFRPs) (Suzuki et al., Nat. Genet. 36: 417-422, 2004), Dickkopf (Dkk) (Aguilera et al., Oncogene 25: 4116-4121, 2006) and members of the Wnt inhibitor factor (WIF) family (Mazieres et al., Cancer Res. 64: 4717-4720, 2004) can also lead to abnormal pathway activity (Polakis, Curr. Opin. Genet. Dev. 17: 45-51, 2007).

Blocking canonical Wnt activity in colorectal and other Wnt deregulated cancers has been shown to cause cell cycle arrest in G and this is a crucial step in inhibiting tumor cell growth (van de W M et al., Cell 111: 241-250, 2002; and Sukhdeo et al., Proc. Natl. Acad. Sci. USA 104: 7516-7521, 2007). In recent years, several classes of small-molecules have been shown to act as Wnt inhibitors. These drugs exert their inhibitory effects at various levels of the Wnt signaling pathway. Small molecules, interfering with nuclear TCF/β-catenin binding and with the cyclic AMP response element-binding protein (CBP), have been identified and described (Emami et al., Proc. Natl. Acad. Sci. USA 101: 12682-12687, 2004; and Lepourcelet M et al., Cancer Cell 5: 91-102, 2004). Topo IIα and PARP-1 (Shitashige et al., Cancer Sci. 99: 631-637, 2008) or TBP, BRG1, BCL9, pygopus and Hyrax (Barker et al. supra) have been proposed to be potential targets for inhibiting canonical Wnt signaling. Since elevated levels of β-catenin in the nucleus are a common feature of abnormal canonical Wnt signaling, down-regulation of canonical Wnt activity by reducing the presence of β-catenin represents a potential therapeutic strategy.

We have now found a novel class of compounds which exhibit an activity in blocking canonical Wnt signaling, and in particular which are capable of reducing levels of nuclear β-catenin. To the extent that these are able to affect the stability of activated β-catenin downstream of APC and GSK-3β, these are considered to offer broader potential than other compounds known to act further upstream in the canonical Wnt signaling pathway. Such compounds are suitable for inhibiting the proliferation of tumor cells in general and, in particular, those associated with breast cancer, non-small cell lung cancer, pancreatic and colorectal cancers. They are especially suitable for inhibiting the growth of colon carcinoma cells.

The invention provides compounds of general formula I:

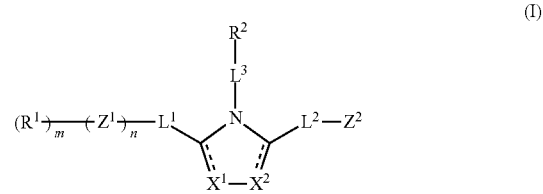

(wherein
a dashed line indicates an optional bond;
$X^1$ and $X^2$ are independently selected from N, $NR_e$, O, S, $CR_f$ and $CR_gR_h$;
where each $R_e$, $R_f$, $R_g$ and $R_h$ group is independently selected from hydrogen and $C_{1-6}$ alkyl optionally substituted by one or more (e.g. 1, 2 or 3) substituents selected from halogen, CN, $NO_2$ and OR" (where R" is hydrogen or $C_{1-4}$ alkyl);
$Z^1$ represents an unsaturated, 5- to 10-membered mono- or bicyclic heterocyclic ring, which ring may optionally be fused with a 5- or 6-membered ring containing one or more atoms independently selected from C, N, O and S;

$Z^2$ represents
(a) $C_{1-6}$ alkyl,
(b) $C_{2-6}$ alkenyl,
(c) $C_{2-6}$ alkynyl,
(d) an aryl or heteroaryl group optionally substituted by one or more (e.g. 1, 2, 3 or 4) groups $R_a$;
  where each $R_a$ may be identical or different and may be selected from halogen (i.e. F, Cl, Br, I), $C_{1-6}$ alkyl (preferably $C_{1-3}$ alkyl), $C_{2-4}$ alkenyl, $C_{2-4}$ alkynyl, $C_{1-4}$ haloalkyl (e.g. $CF_3$), —CN, —$NO_2$, —OR, —SR, —C(O)R, —C(O)OR, —OC(O)R, —OC(O)$NR_2$, —$NR_2$, —NR—C(O)R, —NR—C(O)OR, —S(O)R, —S(O)$_2$R, —S(O)OR or —S(O)$_2$ $NR_2$ group (where each R is independently H, $C_{1-6}$ alkyl, $C_{1-6}$ haloalkyl, $C_{2-6}$ alkenyl or $C_{2-6}$ alkynyl); or
(e) a 5- or 6-membered saturated heterocyclic ring which contains at least one heteroatom selected from nitrogen, oxygen and sulphur, preferably at least one heteroatom selected from nitrogen and oxygen;
$R^1$ represents
(a) hydrogen,
(b) $C_{1-6}$ alkyl,
(c) —$OC_{1-6}$ alkyl,
(d) hydroxy,
(e) —$NR'_2$ (where each R' is independently hydrogen, a $C_{1-6}$ alkyl or $C_{1-6}$ haloalkyl group),
(f) an aryl or heteroaryl group optionally substituted by one or more (e.g. 1, 2, 3 or 4) groups $R_b$;
  where each $R_b$ may be identical or different and may be selected from halogen (i.e. F, Cl, Br, I), $C_{1-6}$ alkyl (preferably $C_{1-3}$ alkyl) optionally interrupted by one or more —O—, —S— or —NR— groups (preferably by one or two —O— atoms), $C_{2-4}$ alkenyl, $C_{2-4}$ alkynyl, $C_{1-4}$ haloalkyl (e.g. $CF_3$), —CN, —$NO_2$, —OR, —SR, —C(O)R, —C(O)OR, —OC(O)R, —OC(O)$NR_2$, —C(O)$NR_2$, —$NR_2$, —NR—C(O)R, —NR—C(O)OR, —S(O)R, —S(O)$_2$R, —S(O)OR or —S(O)$_2$ $NR_2$ group (where each R is independently H, $C_{1-6}$ alkyl, $C_{1-6}$ haloalkyl, $C_{2-6}$ alkenyl or $C_{2-6}$ alkynyl); or
  where two $R_b$ groups present on adjacent ring atoms form, together with the intervening ring atoms, a 5- or 6-membered carbocyclic or heterocyclic ring; or
(g) —CONR""$_2$ (where each R"" is independently H or $C_{1-6}$ alkyl, e.g. $C_{1-3}$ alkyl);
$R^2$ represents
(a) hydrogen,
(b) $C_{1-6}$ alkyl,
(c) —$OC_{1-6}$ alkyl,
(d) $C_{2-6}$ alkenyl,
(e) an aryl or heteroaryl group optionally substituted by one or more (e.g. 1, 2, 3 or 4) groups $R_c$;
  where each $R_c$ may be identical or different and may be selected from halogen (i.e. F, Cl, Br, I), $C_{1-6}$ alkyl (preferably $C_{1-3}$ alkyl), $C_{2-4}$ alkenyl, $C_{2-4}$ alkynyl, $C_{1-4}$ haloalkyl (e.g. $CF_3$), —CN, —$NO_2$, —OR, —SR, —C(O)R, —C(O)OR, —OC(O)R, —OC(O)$NR_2$, —$NR_2$, —NR—C(O)R, —NR—C(O)OR, —S(O)R, —S(O)$_2$R or —S(O)OR group (where each R is independently H, $C_{1-6}$ alkyl, $C_{1-6}$ haloalkyl, $C_{2-6}$ alkenyl or $C_{2-6}$ alkynyl); or
(f) a 5- or 6-membered saturated heterocyclic ring which contains at least one heteroatom selected from nitrogen, oxygen and sulphur, preferably at least one heteroatom selected from nitrogen and oxygen, or
(g) a $C_{3-6}$ cycloalkylene group, preferably a $C_5$- or $C_6$-cycloalkylene group;

$L^1$ represents a $C_{1-6}$ alkylene group optionally substituted by one or more (e.g. 1 or 2) groups $R_d$, wherein one or more (preferably one to three) methylene groups may each additionally be replaced by a group $Y^1$;
  where each $Y^1$ is independently selected from —O—, —S—, —NH—, —NR'''—, —NR'''—C(O)—, —C(O)—NR'''—, —C(O)—, —S(O$_2$)—, —S(O)—, —CR'''=N—, —CH=CH—, —C≡C—, a $C_{3-6}$ cycloalkylene group and a 3- to 7-membered saturated heterocyclic ring (where each R''' is independently hydrogen or $C_{1-6}$ alkyl);
  where each $R_d$ may be identical or different and may be selected from $C_{1-6}$ alkyl (preferably $C_{1-3}$ alkyl), hydroxy, $C_{1-6}$ alkoxy (e.g. $C_{1-3}$ alkoxy) and halogen (i.e. F, Cl, Br and I, preferably F);
$L^2$ and $L^3$ each independently represents a bond or an optionally substituted $C_{1-6}$ alkylene group;
m is 0 or 1; and
n is 0 or 1)
the stereoisomers, pharmaceutically acceptable salts, and prodrugs thereof.

In formula I, where $Z^2$ is a 5- or 6-membered saturated heterocyclic ring, this preferably contains at least one nitrogen atom. Preferred rings are those containing a single nitrogen atom optionally in combination with a single oxygen atom. Examples of such groups include piperidinyl, pyrrolidinyl, morpholinyl, piperazinyl, pyrazolidinyl and imidazolidinyl. Amongst these groups, piperidinyl, pyrrolidinyl and morpholinyl are particularly preferred.

In the definition of $R^1$, where two adjacent groups $R_b$ on the aryl or heteroaryl ring together form a 5- or 6-membered ring, preferably this will be a heterocyclic ring which may, for example, be selected from 1,4-dioxane, 1,3-dioxolane, pyridine, pyrrolidine, pyrroline, pyrrole, furan and piperidine. Such rings may further contain one or more carbonyl or thiocarbonyl functionalities such that these include oxo and thio systems. Examples of such systems include lactams, lactones, cyclic imides, etc. Where the groups $R_b$ link to form a carbocyclic ring, this may be a cyclopentyl or cyclohexyl ring.

Where $R^2$ is a saturated heterocyclic ring, this will generally contain one or more nitrogen or oxygen atoms. Examples of such groups include piperidinyl, pyrrolidinyl, morpholinyl, piperazinyl, pyrazolidinyl, imidazolidinyl and tetrahydrofuryl. Of these, tetrahydrofuryl is particularly preferred.

In any of the embodiments of the invention herein described, it is envisaged that in the definition of the linker $L^1$ any or all methylene groups can be replaced by a group $Y^1$. Suitable linkers, $L^1$, therefore include groups which contain no methylene moiety (i.e. where all such groups have been replaced by a group $Y^1$). However, it is generally preferred that at least one methylene group will be present in the linker, $L^1$.

In formula I, $L^3$ is preferably a direct bond or a —$CH_2$— group.

Preferred compounds in accordance with the invention are those of general formula II:

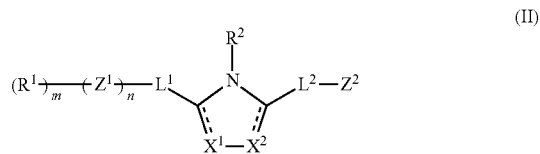

(II)

(wherein a dashed line indicates an optional bond;

$X^1$ and $X^2$ are independently selected from N, $NR_e$, O, S, $CR_f$ and $CR_gR_h$;

where each $R_e$, $R_f$, $R_g$ and $R_h$ group is independently selected from hydrogen and $C_{1-6}$ alkyl optionally substituted by one or more (e.g. 1, 2 or 3) substituents selected from halogen, CN, $NO_2$ and OR" (where R" is hydrogen or $C_{1-4}$ alkyl);

$Z^1$ represents an unsaturated, 5- to 7-membered heterocyclic ring which ring may optionally be fused with a 5- or 6-membered ring containing one or more atoms independently selected from C, N, O and S;

$Z^2$ represents (a) $C_{1-6}$ alkyl, (b) $C_{2-6}$ alkenyl, (c) $C_{2-6}$ alkynyl, or (d) an aryl or heteroaryl group optionally substituted by one or more (e.g. 1, 2, 3 or 4) groups $R_a$;

where each $R_a$ may be identical or different and may be selected from halogen (i.e. F, Cl, Br, I), $C_{1-6}$ alkyl (preferably $C_{1-3}$ alkyl), $C_{2-4}$ alkenyl, $C_{2-4}$ alkynyl, $C_{1-4}$ haloalkyl (e.g. $CF_3$), —CN, —$NO_2$, —OR, —SR, —C(O)R, —C(O)OR, —OC(O)R, —OC(O)$NR_2$, —$NR_2$, —NR—C(O)R, —NR—C(O)OR, —S(O)R, —S(O)$_2$R or —S(O)OR group (where each R is independently H, $C_{1-6}$ alkyl, $C_{1-6}$ haloalkyl, $C_{2-6}$ alkenyl or $C_{2-6}$ alkynyl);

$R^1$ represents (a) hydrogen, (b) $C_{1-6}$ alkyl, (c) —$OC_{1-6}$ alkyl, (d) hydroxy, (e) —$NR'_2$ (where each R' is independently hydrogen, a $C_{1-6}$ alkyl or $C_{1-6}$ haloalkyl group), or (f) an aryl or heteroaryl group optionally substituted by one or more (e.g. 1, 2, 3 or 4) groups $R_b$;

where each $R_b$ may be identical or different and may be selected from halogen (i.e. F, Cl, Br, I), $C_{1-6}$ alkyl (preferably $C_{1-3}$ alkyl), $C_{2-4}$ alkenyl, $C_{2-4}$ alkynyl, $C_{1-4}$ haloalkyl (e.g. $CF_3$), —CN, —$NO_2$, —OR, —SR, —C(O)R, —C(O)OR, —OC(O)R, —OC(O)$NR_2$, —$NR_2$, —NR—C(O)R, —NR—C(O)OR, —S(O)R, —S(O)$_2$R or —S(O)OR group (where each R is independently H, $C_{1-6}$ alkyl, $C_{1-6}$ haloalkyl, $C_{2-6}$ alkenyl or $C_{2-6}$ alkynyl);

$R^2$ represents (a) hydrogen, (b) $C_{1-6}$ alkyl, (c) —$OC_{1-6}$ alkyl, (d) $C_{2-6}$ alkenyl, or (e) an aryl group optionally substituted by one or more (e.g. 1, 2, 3 or 4) groups $R_c$;

where each $R_c$ may be identical or different and may be selected from halogen (i.e. F, Cl, Br, I), $C_{1-6}$ alkyl (preferably $C_{1-3}$ alkyl), $C_{2-4}$ alkenyl, $C_{2-4}$ alkynyl, $C_{1-4}$ haloalkyl (e.g. $CF_3$), —CN, —$NO_2$, —OR, —SR, —C(O)R, —C(O)OR, —OC(O)R, —OC(O)$NR_2$, —$NR_2$, —NR—C(O)R, —NR—C(O)OR, —S(O)R, —S(O)$_2$R or —S(O)OR group (where each R is independently H, $C_{1-6}$ alkyl, $C_{1-6}$ haloalkyl, $C_{2-6}$ alkenyl or $C_{2-6}$ alkynyl);

$L^1$ represents a $C_{1-6}$ alkylene group optionally substituted by one or more (e.g. 1 or 2) groups $R_d$, wherein one or two methylene groups (preferably one methylene group) may each additionally be replaced by a group $Y^1$;

where each $Y^1$ is independently selected from —O—, —S—, —NH—, —NR'''—, —NR'''—C(O)—, —C(O)—NR'''—, —C(O)—, —S(O$_2$)—, —S(O)—, a $C_{3-6}$ cycloalkylene group and a 3- to 7-membered saturated heterocyclic ring (where each R''' is independently hydrogen or $C_{1-6}$ alkyl); where each $R_d$ may be identical or different and may be selected from $C_{1-6}$ alkyl (preferably $C_{1-3}$ alkyl), hydroxy and $C_{1-6}$ alkoxy (e.g. $C_{1-3}$ alkoxy);

$L^2$ represents a bond or an optionally substituted $C_{1-6}$ alkylene group;

m is 0 or 1; and n is 0 or 1)

the stereoisomers, pharmaceutically acceptable salts, and prodrugs thereof.

Particularly preferred compounds in accordance with the invention are those of formula I or II wherein:

$X^1$ and $X^2$ are independently selected from N, $NR_e$, $CR_f$ and $CR_gR_h$;

where each $R_e$, $R_f$, $R_g$ and $R_h$ group is independently selected from hydrogen and $C_{1-6}$ alkyl optionally substituted by one or more (e.g. 1, 2 or 3) substituents selected from halogen, CN, $NO_2$ and OR" (where R" is hydrogen or $C_{1-4}$ alkyl);

$Z^1$ represents a 5-membered heterocyclic ring containing two or three heteroatoms selected from N, O and S;

$Z^2$ represents phenyl or pyridyl optionally substituted by one or more (e.g. 1, 2, 3 or 4) groups $R_a$;

where each $R_a$ may be identical or different and may be selected from halogen (i.e. F, Cl, Br, I), $C_{1-6}$ alkyl (preferably $C_{1-3}$ alkyl), $C_{2-4}$ alkenyl, $C_{2-4}$ alkynyl, $C_{1-4}$ haloalkyl (e.g. $CF_3$), —CN, —$NO_2$, —OR, —SR, —C(O)R, —C(O)OR, —OC(O)R, —OC(O)$NR_2$, —$NR_2$, —NR—C(O)R, —NR—C(O)OR, —S(O)R, —S(O)$_2$R or —S(O)OR group (where each R is independently H, $C_{1-6}$ alkyl, $C_{1-6}$ haloalkyl, $C_{2-6}$ alkenyl or $C_{2-6}$ alkynyl);

$R^1$ represents (a) hydrogen, (b) $C_{1-6}$ alkyl, (c) an aryl or heteroaryl group optionally substituted by one or more (e.g. 1, 2, 3 or 4) groups $R_b$;

where each $R_b$ may be identical or different and may be selected from halogen (i.e. F, Cl, Br, I), $C_{1-6}$ alkyl (preferably $C_{1-3}$ alkyl), $C_{2-4}$ alkenyl, $C_{2-4}$ alkynyl, $C_{1-4}$ haloalkyl (e.g. $CF_3$), —CN, —$NO_2$, —OR, —SR, —C(O)R, —C(O)OR, —OC(O)R, —OC(O)$NR_2$, —$NR_2$, —NR—C(O)R, —NR—C(O)OR, —S(O)R, —S(O)$_2$R or —S(O)OR group (where each R is independently H, $C_{1-6}$ alkyl, $C_{1-6}$ haloalkyl, $C_{2-6}$ alkenyl or $C_{2-6}$ alkynyl);

$R^2$ represents (a) hydrogen, (b) $C_{1-6}$ alkyl, (c) $C_{2-4}$ alkenyl, or (d) an aryl group optionally substituted by one or more (e.g. 1, 2, 3 or 4) groups $R_c$;

where each $R_c$ may be identical or different and may be selected from halogen (i.e. F, Cl, Br, I), $C_{1-6}$ alkyl (preferably $C_{1-3}$ alkyl), $C_{2-4}$ alkenyl, $C_{2-4}$ alkynyl, $C_{1-4}$ haloalkyl (e.g. $CF_3$), —CN, —$NO_2$, —OR, —SR, —C(O)R, —C(O)OR, —OC(O)R, —OC(O)$NR_2$, —$NR_2$, —NR—C(O)R, —NR—C(O)OR, —S(O)R, —S(O)$_2$R or —S(O)OR group (where each R is independently H, $C_{1-6}$ alkyl, $C_{1-6}$ haloalkyl, $C_{2-6}$ alkenyl or $C_{2-6}$ alkynyl);

$L^1$ represents a $C_{1-6}$ alkylene group optionally substituted by one or more (e.g. 1 or 2) groups $R_d$, wherein one or two methylene groups (e.g. one methylene group) may each additionally be replaced by a group $Y^1$;
  where each $Y_1$ is independently selected from —O—, —S—, —NH—, —NR'''—, —NR'''—C(O)—, —C(O)—NR'''— and a $C_{3-6}$ cycloalkylene group (where each R''' is independently hydrogen or $C_{1-6}$ alkyl);
  where each $R_d$ may be identical or different and may be selected from $C_{1-6}$ alkyl (preferably $C_{1-3}$ alkyl), hydroxy and $C_{1-6}$ alkoxy (e.g. $C_{1-3}$ alkoxy);
$L^2$ represents a bond or an optionally substituted $C_{1-4}$ alkylene group;
  m is 0 or 1, preferably 1; and
  n is 0 or 1, preferably 1)
the stereoisomers, pharmaceutically acceptable salts and prodrugs thereof.

More particularly preferred compounds according to the invention are those of formula I or II wherein:
  $X^1$ and $X^2$ are independently selected from N and $CR_f$;
  where $R_f$ is hydrogen or $C_{1-6}$ alkyl;
  $Z^1$ represents a 5-membered heterocyclic ring containing two nitrogen atoms and one oxygen atom;
  $Z^2$ represents phenyl or pyridyl optionally mono-substituted by group $R_a$;
    where $R_a$ may be selected from halogen (i.e. F, Cl, Br, I), hydroxy and $C_{1-6}$ alkoxy (e.g. $C_{1-3}$ alkoxy);
  $R^1$ represents
    (a) hydrogen,
    (b) $C_{1-6}$ alkyl, or
    (c) an aryl group optionally mono-substituted by group $R_b$;
    where $R_b$ is selected from halogen (i.e. F, Cl, Br, I), $C_{1-6}$ alkyl (preferably $C_{1-3}$ alkyl) and $C_{1-6}$ alkoxy (e.g. $C_{1-3}$ alkoxy);
  $R^2$ represents
    (a) hydrogen,
    (b) $C_{1-6}$ alkyl,
    (c) $C_{2-3}$ alkenyl, or
    (d) an aryl group optionally mono- or di-substituted by a group $R_c$;
    where each $R_c$ may be identical or different and may be selected from halogen (i.e. F, Cl, Br, I), $C_{1-6}$ alkyl (preferably $C_{1-3}$ alkyl) and $C_{1-6}$ alkoxy (e.g. $C_{1-3}$ alkoxy);
  $L^1$ represents a $C_{1-4}$ alkylene group optionally substituted by one or more groups $R_d$, wherein one or two methylene groups are each additionally replaced by a group $Y^1$;
    where each $Y^1$ is independently selected from —O—, —S—, —NH—, —NR'''—, —NR'''—C(O)—, —C(O)—NR'''— and a $C_{3-6}$ cycloalkylene group (where each R''' is independently hydrogen or $C_{1-6}$ alkyl);
    where each $R_d$ may be identical or different and may be selected from $C_{1-6}$ alkyl (preferably $C_{1-3}$ alkyl), hydroxy and $C_{1-6}$ alkoxy (e.g. $C_{1-3}$ alkoxy);
  $L^2$ represents a bond, or a $C_{1-2}$ alkylene group;
  m is 0 or 1, preferably 1; and
  n is 0 or 1, preferably 1)
the stereoisomers, pharmaceutically acceptable salts and prodrugs thereof.

In preferred embodiments, $X^1$ and $X^2$ are independently selected from N and $CR_f$ (where $R_f$ is as hereinbefore defined, preferably hydrogen or $C_{1-4}$ alkyl).

Preferably, at least one of $X^1$ and $X^2$ is N. For example, $X^1$ may be N and $X^2$ is $CR_f$ or $X^1$ may be $CR_f$ and $X^2$ may be N (where $R_f$ is as hereinbefore defined, preferably hydrogen or $C_{1-4}$ alkyl).

Most preferably, both $X^1$ and $X^2$ are N. Particularly preferred compounds in accordance with the invention are thus compounds of formulae Ia and IIa:

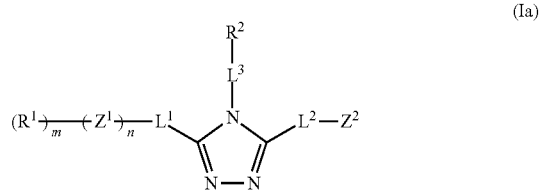

(Ia)

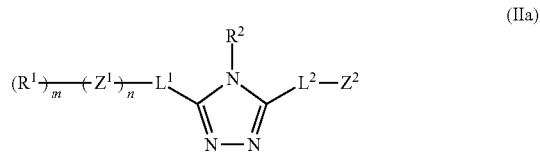

(IIa)

(wherein $Z^1$, $Z^2$, $R^1$, $R^2$, $L^1$, $L^2$, $L^3$, m and n are as hereinbefore defined); the stereoisomers, pharmaceutically acceptable salts and prodrugs thereof.

Examples of group $Z^1$ in formula I, II, Ia and IIa include the following:

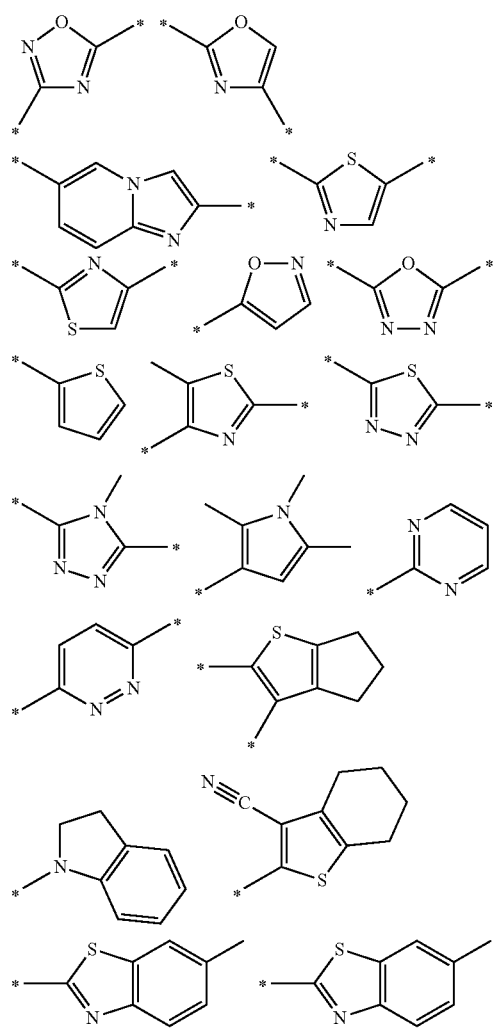

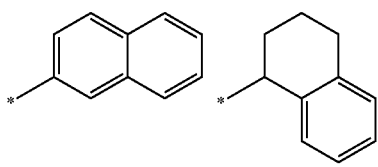

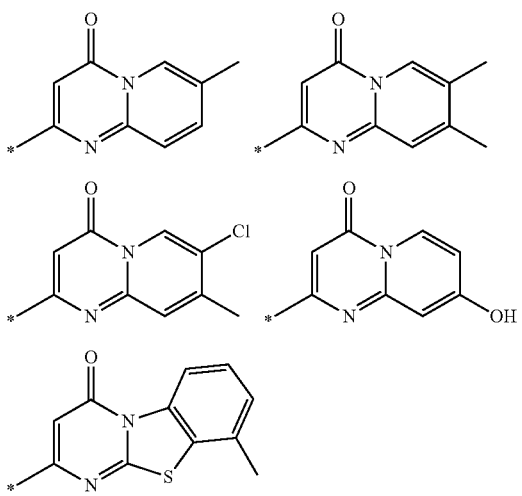

Of these structures, the following are particularly preferred for $Z^1$:

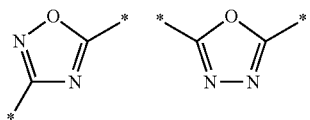

In a yet further preferred aspect the invention thus provides the following compounds of formulae Ib, IIb, Ic and IIc:

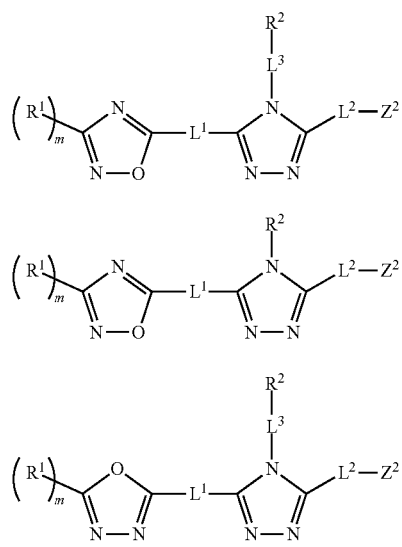

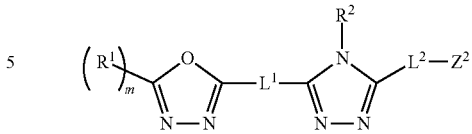

(wherein $Z^2$, $R^1$, $R^2$, $L^1$, $L^2$, $L^3$ and m are as hereinbefore defined); the stereoisomers, pharmaceutically acceptable salts and prodrugs thereof.

In preferred embodiments, $Z^2$ represents an optionally substituted aryl or heteroaryl group, preferably a phenyl or pyridyl group optionally substituted by one or two (preferably one) groups $R_a$ in which each $R_a$ is independently halogen (preferably Cl or F), hydroxy or $C_{1-6}$ alkoxy (preferably $C_{1-3}$ alkoxy, e.g. methoxy); or $Z^2$ represents or a saturated 5- or 6-membered heterocyclic ring. Particularly preferably, $Z^2$ represents an optionally substituted aryl or heteroaryl group, for example an optionally substituted phenyl or pyridyl group. When substituted, the substituents on the phenyl or pyridyl ring may independently be selected from the group consisting of hydroxy, methoxy, ethoxy, chloro and fluoro. One or more of such groups may be present on the ring and in any ring position. However, it is preferred that one or two such groups will be present. Where two substituents are present these will generally be identical.

Examples of group $Z^2$ include the following:

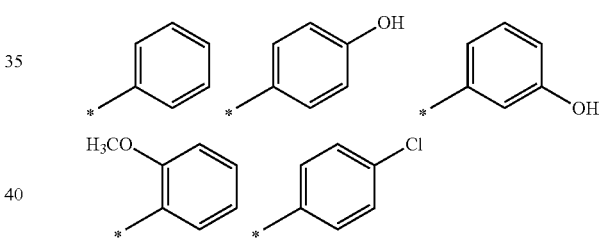

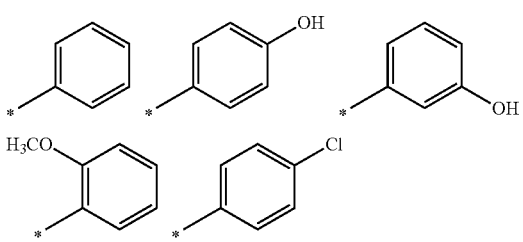

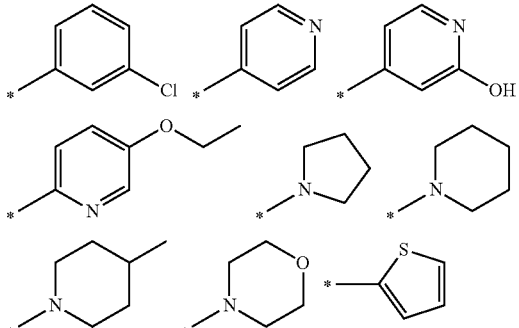

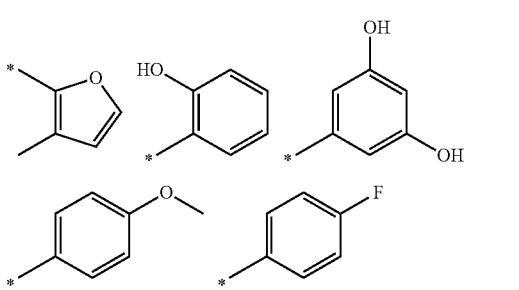

-continued

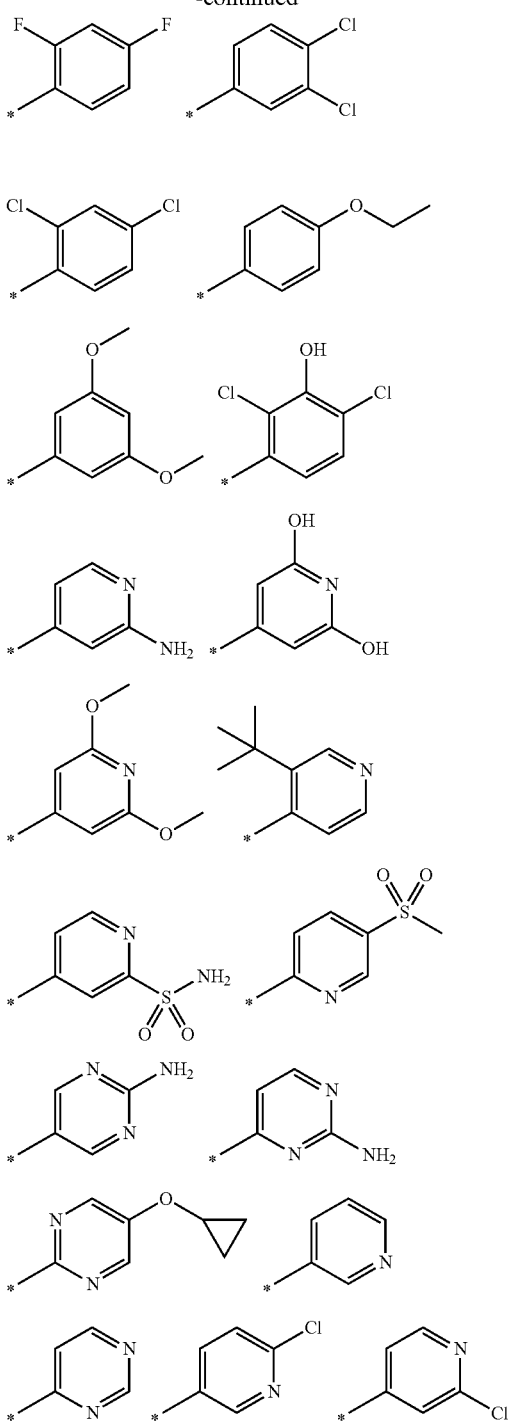

In preferred embodiments, $R^1$ represents hydrogen, $C_{1-6}$ alkyl (e.g. methyl, ethyl, isopropyl), or phenyl or pyridyl optionally substituted by one or two (preferably one) groups $R_b$ in which each $R_b$ is independently halogen (e.g. F, Cl or Br), hydroxy, $C_{1-6}$ alkyl (preferably $C_{1-3}$ alkyl, e.g. methyl) or $C_{1-6}$ alkoxy (preferably $C_{1-3}$ alkoxy, e.g. methoxy). Particularly preferably, $R^1$ represents an optionally substituted phenyl ring. In the case where the phenyl ring is substituted, preferred substituents include unsubstituted alkyl groups (e.g. methyl).

Examples of group $R^1$ include the following:

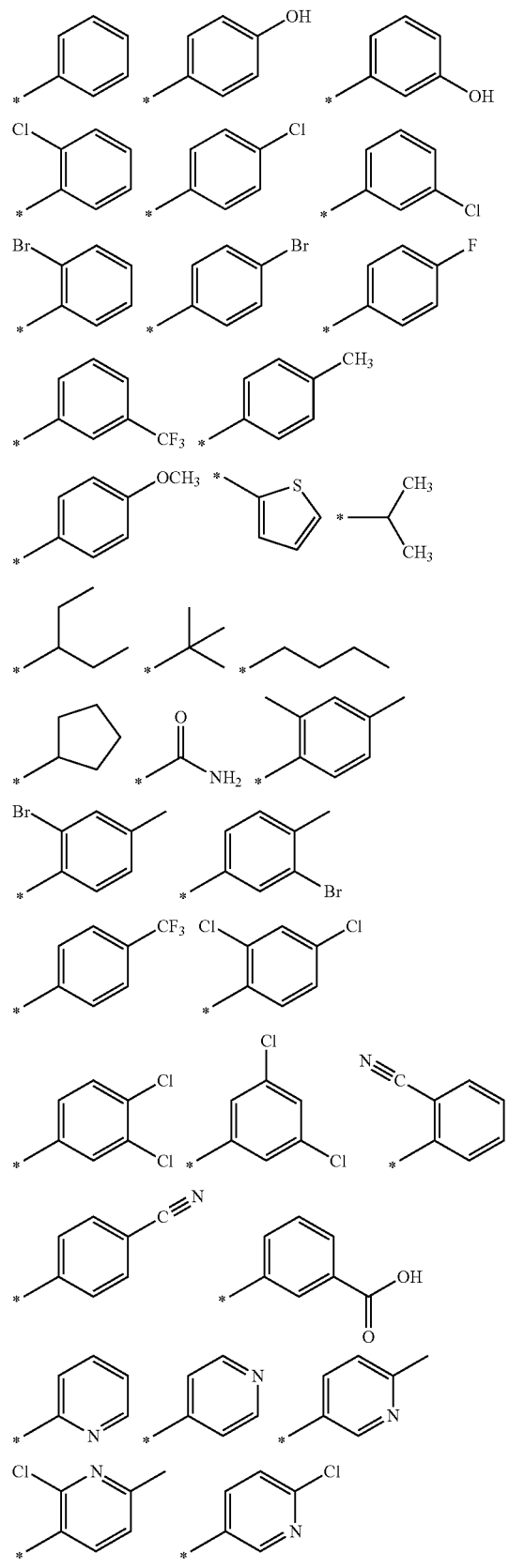

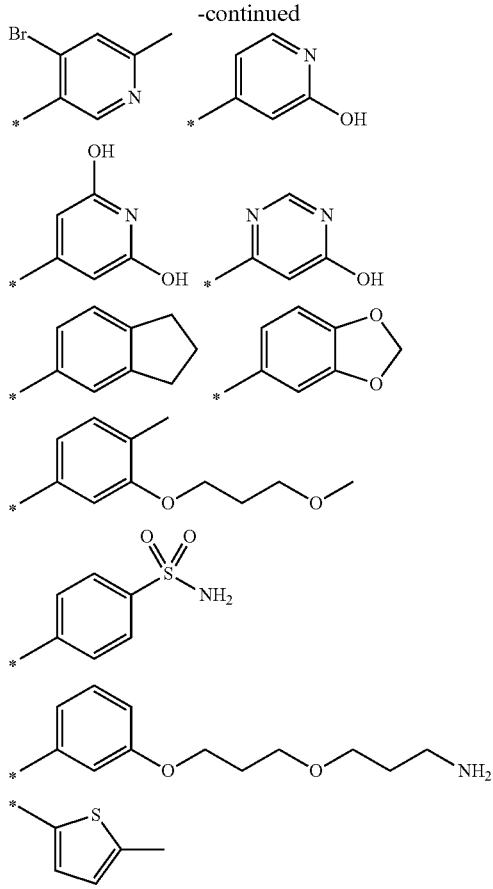

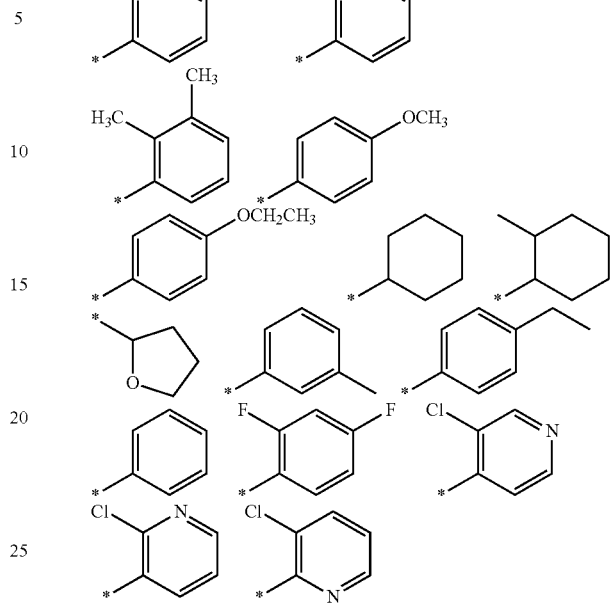

In preferred embodiments, R² represents hydrogen, C₁₋₆ alkyl (e.g. methyl, ethyl) or C₂₋₃ alkenyl (e.g. propen-1-yl); phenyl or pyridyl optionally substituted by one or two groups R in which each $R_c$ is independently halogen (e.g. F or Cl), C₁₋₆ alkoxy (preferably C₁₋₃ alkoxy, e.g. methoxy or ethoxy); cyclohexyl optionally substituted by one or more alkyl groups; or tetrahydrofuryl. Particularly preferably, R² is optionally substituted phenyl. When substituted, the ring substituents on the phenyl group may independently be selected from the group consisting of C₁₋₃ alkyl (e.g. methyl or ethyl), methoxy, ethoxy, chloro and fluoro. One or more of such groups may be present on the ring and in any ring position. However, it is preferred that one or two such groups will be present. Particularly preferably, the phenyl ring will be substituted by a single chloro group either in the ortho or para-position, e.g. in the ortho-position.

Examples of group R² include the following:

In preferred embodiments, L¹ is C₁₋₄ alkylene optionally substituted by one or two groups $R_d$ in which each $R_d$ is independently C₁₋₆ alkyl (e.g. methyl) and one or two methylene groups (e.g. one methylene group) are each replaced by a group Y¹ where Y¹ is —O—, —S—, —NH—, —NH—C(O)—, —C(O)—NH—, C₃, C₄ or C₅-cycloalkylene, or a 6-membered heterocyclic ring containing a single oxygen atom.

Yet more preferred as linker groups L¹ are C₁₋₄ alkylene groups optionally substituted by one or two groups $R_d$ in which each $R_d$ is independently C₁₋₃ alkyl (e.g. methyl) and one or two methylene groups (e.g. one methylene group) are each replaced by a group Y¹ where Y¹ is —O—, —S—, —NH—, —NH—C(O)— or —C(O)—NH—.

Particularly preferably, L¹ is a C₁₋₃ alkylene (e.g. a C₂ alkylene) which is optionally substituted by one or two (preferably one) methyl groups and in which one methylene group is optionally replaced by —S—. Where the linker is substituted by two methyl groups, it is preferred that these are present on different carbon atoms of the linker backbone. Examples of preferred linkers L¹ include —CH(CH₃)—S—, —S—CH(CH₃)—, —CH₂—CH₂—, —CH₂—S— and —S—CH₂—.

Examples of L¹ include the following:

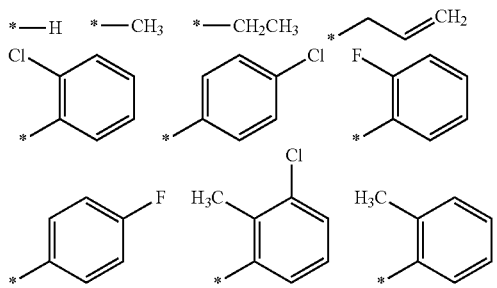

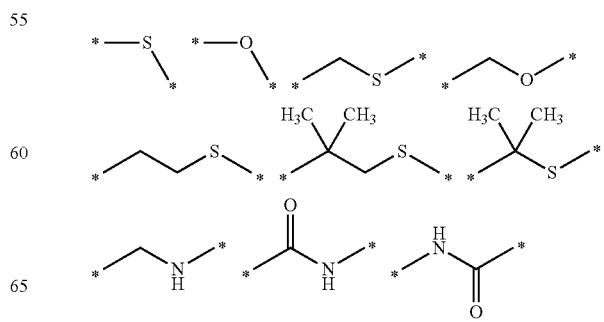

-continued

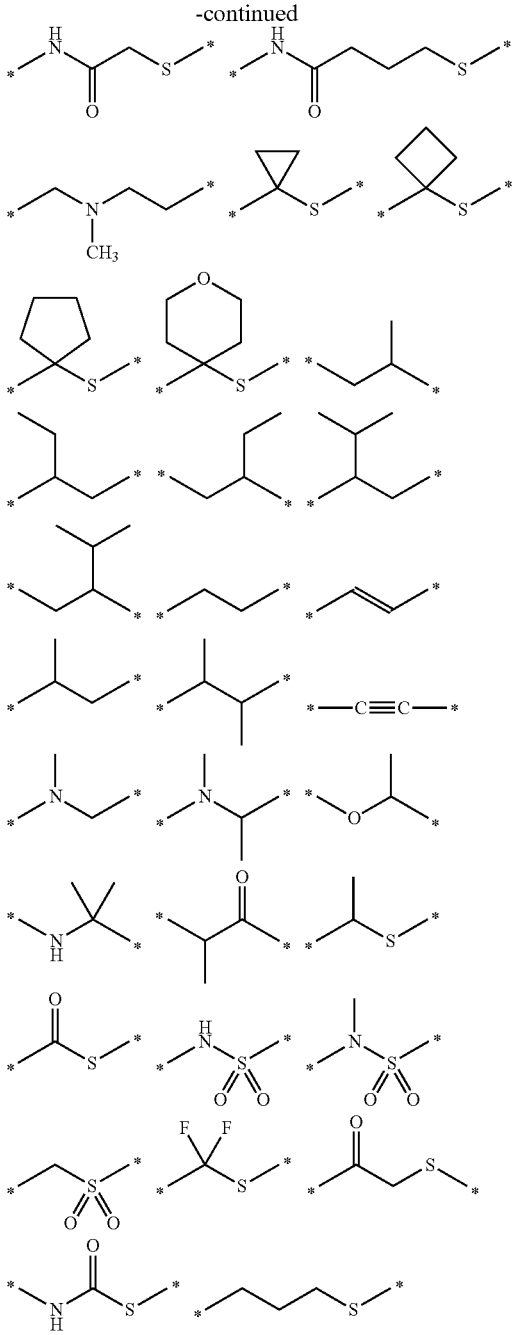

-continued

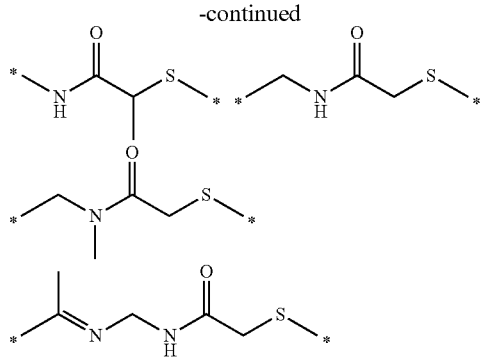

In preferred embodiments $L^2$ is a bond or a $C_{1-2}$ alkylene group, preferably methylene.

In preferred embodiments, $L^3$ is a bond.

Particularly preferred compounds according to the invention are the following compounds of formulae IId and IIe:

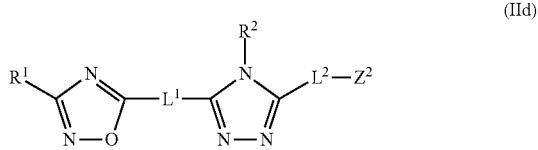

(IId)

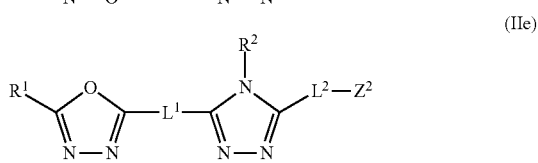

(IIe)

(wherein
$Z^2$ is an optionally substituted pyridyl, phenyl or pyrimidinyl ring, preferably a phenyl ring substituted by two halo atoms (e.g. Cl or F), or a pyridyl ring optionally substituted by a halo atom (e.g. Cl) or by an alkoxy group (e.g. ethoxy);

$R^1$ is a substituted phenyl or pyridyl ring, preferably a phenyl or pyridyl ring substituted by a $C_{1-6}$ alkyl (e.g. methyl) group;

$R^2$ is an optionally substituted phenyl ring, preferably a phenyl ring substituted by one halo atom (e.g. Cl);

$L^1$ is —$CH_2$—S—, —S—$CH_2$—, —$CH(CH_3)$—S— or —S—$CH(CH_3)$—; and $L^2$ is a bond)

the stereoisomers, pharmaceutically acceptable salts and prodrugs thereof.

The following are examples of particularly preferred compounds in accordance with the invention:

| Compound No. | Structure |
|---|---|
| (1) | ![structure] |

-continued

| Compound No. | Structure |
| --- | --- |
| (2) | 5-{2-[4-(4-methoxyphenyl)-5-(pyridin-4-yl)-4H-1,2,4-triazol-3-ylthio]ethyl}-3-(p-tolyl)-1,2,4-oxadiazole |
| (3) | 4-(4-chlorophenyl)-3-{[3-(p-tolyl)-1,2,4-oxadiazol-5-yl]methylthio}-5-(pyridin-4-yl)-4H-1,2,4-triazole |
| (4) | 4-(4-methoxyphenyl)-3-{[3-(p-tolyl)-1,2,4-oxadiazol-5-yl]methoxy}-5-(pyridin-4-yl)-4H-1,2,4-triazole |
| (5) | 3-{[3-(4-chlorophenyl)-1,2,4-oxadiazol-5-yl]methylthio}-4-(4-methoxyphenyl)-5-(pyridin-4-yl)-4H-1,2,4-triazole |
| (6) | 2-[4-(4-methoxyphenyl)-5-(pyridin-4-yl)-4H-1,2,4-triazol-3-yl]-N,N-dimethylethanamine |

-continued

| Compound No. | Structure |
| --- | --- |
| (7) | 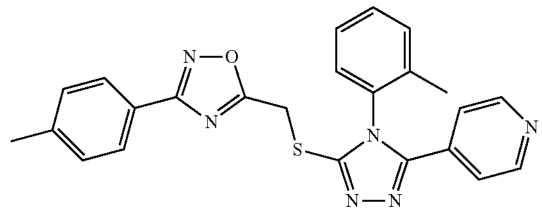 [SMILES: Cc1ccc(-c2noc(CSc3nnc(-c4ccncc4)n3-c3ccccc3C)n2)cc1] |
| (8) | 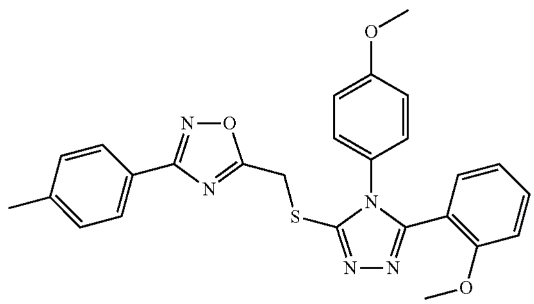 [SMILES: COc1ccc(-n2c(SCc3nc(-c4ccc(C)cc4)no3)nnc2-c2ccccc2OC)cc1] |
| (9) | 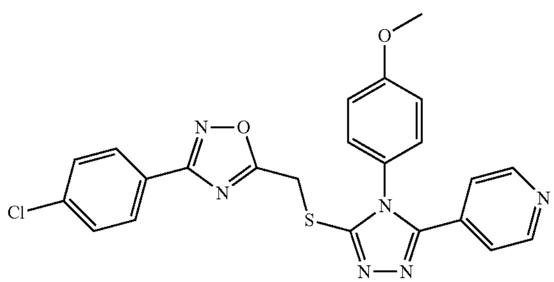 [SMILES: COc1ccc(-n2c(SCc3nc(-c4ccc(Cl)cc4)no3)nnc2-c2ccncc2)cc1] |
| (10) | 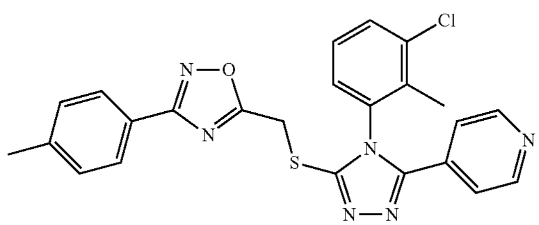 [SMILES: Cc1ccc(-c2noc(CSc3nnc(-c4ccncc4)n3-c3cccc(Cl)c3C)n2)cc1] |
| (11) | 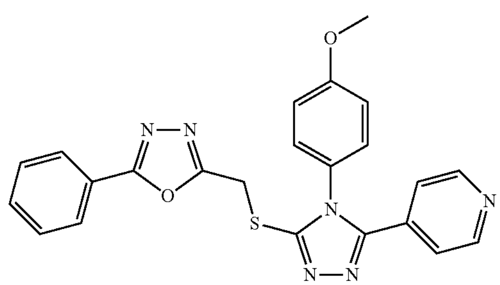 [SMILES: COc1ccc(-n2c(SCc3nnc(-c4ccccc4)o3)nnc2-c2ccncc2)cc1] |
| (12) | 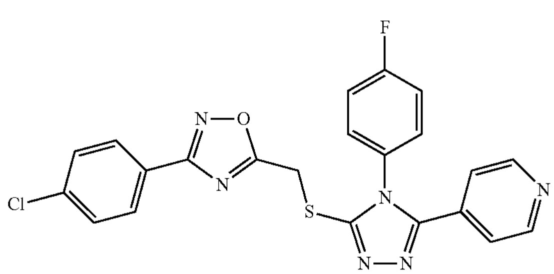 [SMILES: Fc1ccc(-n2c(SCc3nc(-c4ccc(Cl)cc4)no3)nnc2-c2ccncc2)cc1] |

| Compound No. | Structure |
|---|---|
| (13) | 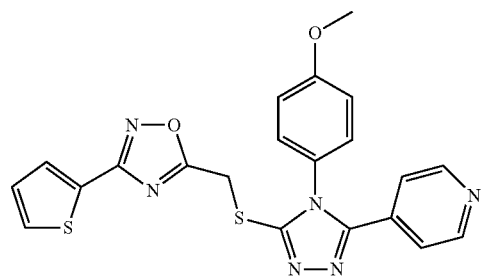 [SMILES: COc1ccc(-n2c(SCc3nc(-c4cccs4)no3)nnc2-c2ccncc2)cc1] |
| (14) | 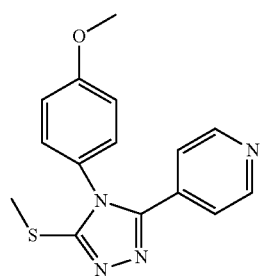 [SMILES: COc1ccc(-n2c(SC)nnc2-c2ccncc2)cc1] |
| (15) | 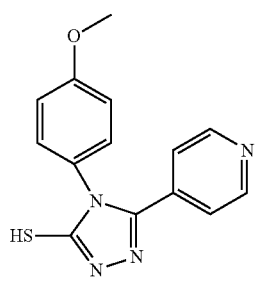 |
| (16) | 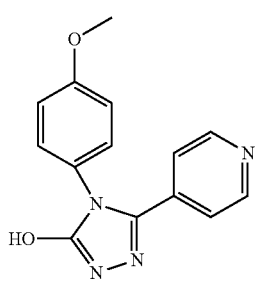 [SMILES: COc1ccc(-n2c(S)nnc2-c2ccncc2)cc1] |
| (17) | 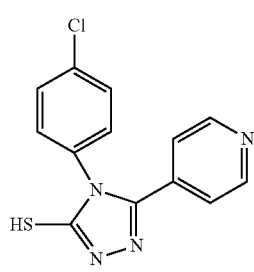 [SMILES: Sc1nnc(-c2ccncc2)n1-c1ccc(Cl)cc1] |

-continued
| Compound No. | Structure |
|---|---|
| (18) | 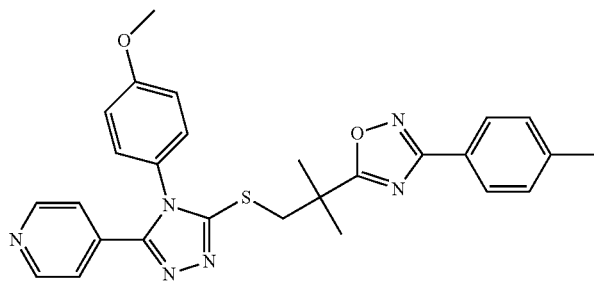 [SMILES: COc1ccc(-n2c(SCC(C)(C)c3nc(-c4ccc(C)cc4)no3)nnc2-c2ccncc2)cc1] |
| (19) | 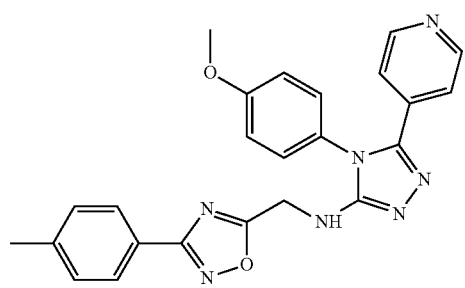 [SMILES: COc1ccc(-n2c(NCc3nc(-c4ccc(C)cc4)no3)nnc2-c2ccncc2)cc1] |
| (20) | 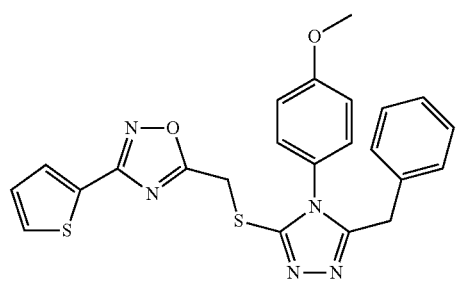 [SMILES: COc1ccc(-n2c(Cc3ccccc3)nnc2SCc2nc(-c3cccs3)no2)cc1] |
| (21) | 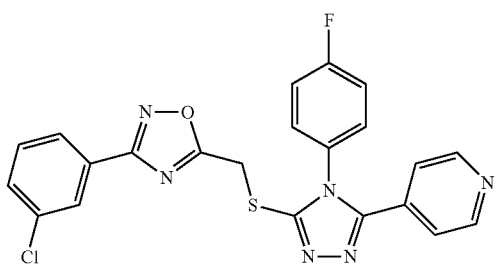 [SMILES: Fc1ccc(-n2c(SCc3nc(-c4cccc(Cl)c4)no3)nnc2-c2ccncc2)cc1] |
| (22) | 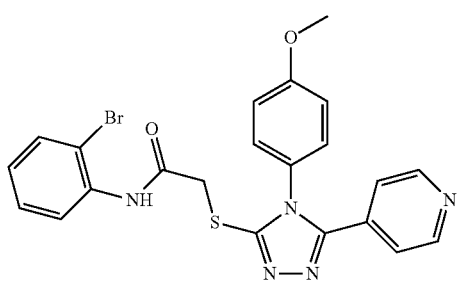 [SMILES: COc1ccc(-n2c(SCC(=O)Nc3ccccc3Br)nnc2-c2ccncc2)cc1] |

-continued
| Compound No. | Structure |
| --- | --- |
| (23) | 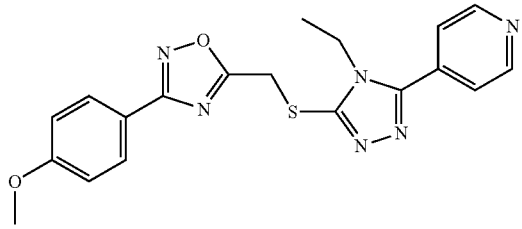 [SMILES: CCn1c(SCc2nc(-c3ccc(OC)cc3)no2)nnc1-c1ccncc1] |
| (24) | 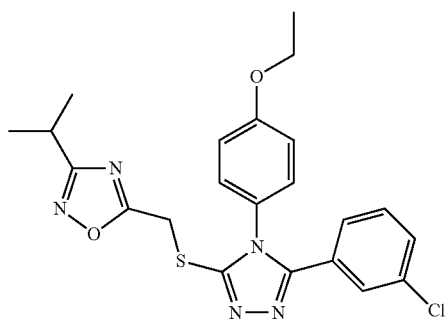 [SMILES: CCOc1ccc(-n2c(SCc3nc(C(C)C)no3)nnc2-c2cccc(Cl)c2)cc1] |
| (25) | 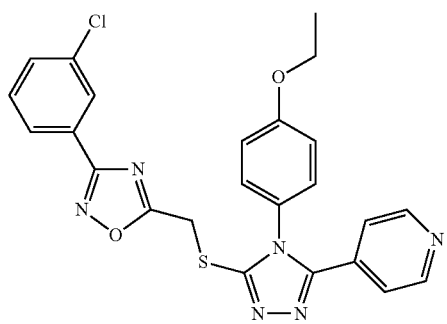 [SMILES: CCOc1ccc(-n2c(SCc3nc(-c4cccc(Cl)c4)no3)nnc2-c2ccncc2)cc1] |
| (26) | 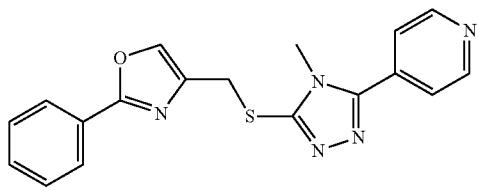 [SMILES: Cn1c(SCc2coc(-c3ccccc3)n2)nnc1-c1ccncc1] |
| (27) | 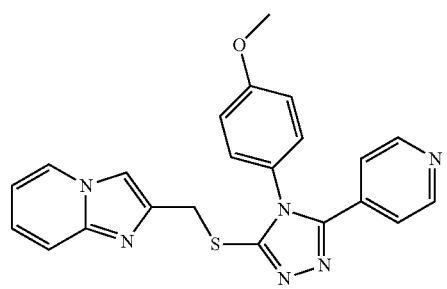 [SMILES: COc1ccc(-n2c(SCc3cn4ccccc4n3)nnc2-c2ccncc2)cc1] |

| Compound No. | Structure |
|---|---|
| (28) | 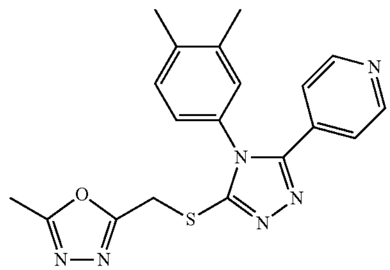 [SMILES: Cc1nnc(CSc2nnc(-c3ccncc3)n2-c2ccc(C)c(C)c2)o1] |
| (29) | 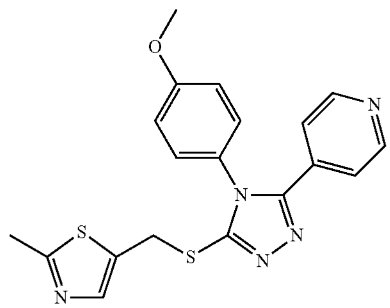 [SMILES: COc1ccc(-n2c(SCc3cnc(C)s3)nnc2-c2ccncc2)cc1] |
| (30) | 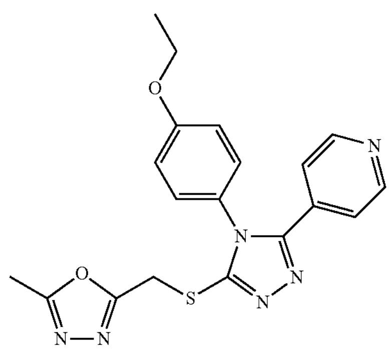 [SMILES: CCOc1ccc(-n2c(SCc3nnc(C)o3)nnc2-c2ccncc2)cc1] |
| (31) | 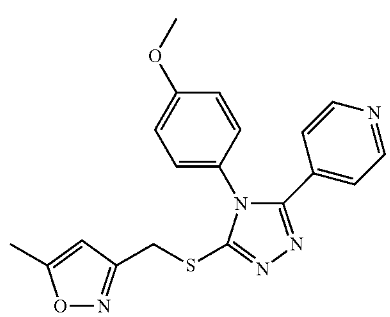 [SMILES: COc1ccc(-n2c(SCc3cc(C)on3)nnc2-c2ccncc2)cc1] |
| (32) | 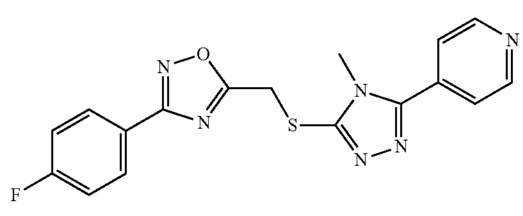 [SMILES: Cn1c(SCc2nc(-c3ccc(F)cc3)no2)nnc1-c1ccncc1] |

-continued
| Compound No. | Structure |
|---|---|
| (33) | 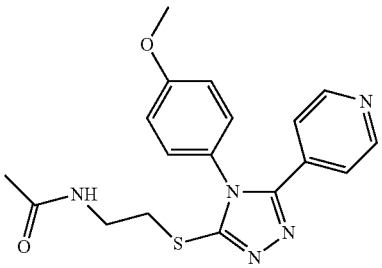 [SMILES: COc1ccc(-n2c(SCCNC(C)=O)nnc2-c2ccncc2)cc1] |
| (34) | 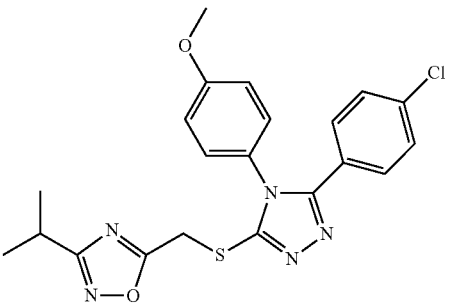 [SMILES: COc1ccc(-n2c(SCc3nc(C(C)C)no3)nnc2-c2ccc(Cl)cc2)cc1] |
| (35) | 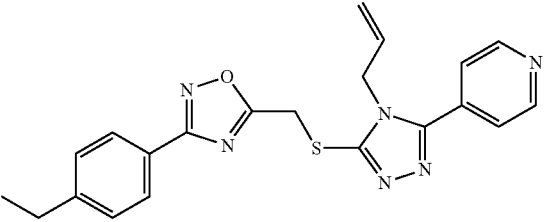 [SMILES: C=CCn1c(SCc2nc(-c3ccc(CC)cc3)no2)nnc1-c1ccncc1] |
| (36) | 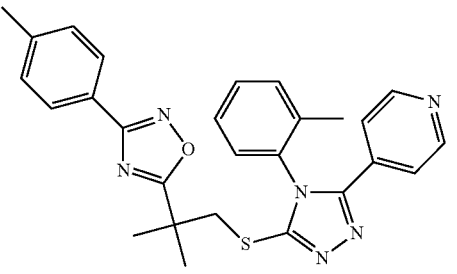 [SMILES: Cc1ccc(-c2noc(C(C)(C)CSc3nnc(-c4ccncc4)n3-c3ccccc3C)n2)cc1] |
| (37) | 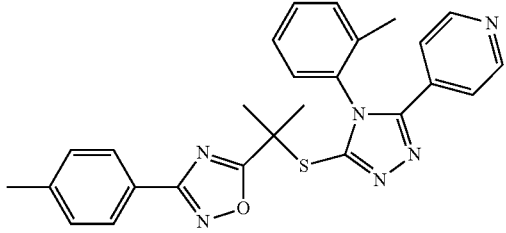 [SMILES: Cc1ccc(-c2noc(C(C)(C)Sc3nnc(-c4ccncc4)n3-c3ccccc3C)n2)cc1] |
| (38) | 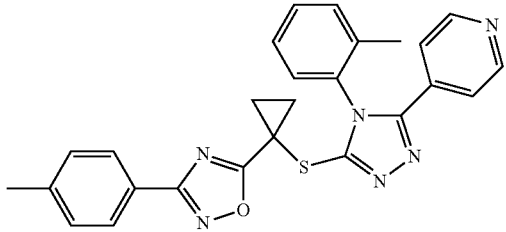 [SMILES: Cc1ccc(-c2noc(C3(Sc4nnc(-c5ccncc5)n4-c4ccccc4C)CC3)n2)cc1] |

-continued
| Compound No. | Structure |
|---|---|
| (39) | 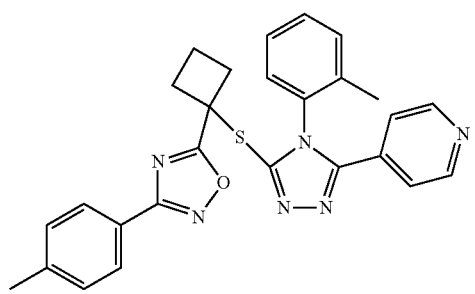 [SMILES: Cc1ccc(-c2noc(C3(Sc4nnc(-c5ccncc5)n4-c4ccccc4C)CCC3)n2)cc1] |
| (40) | 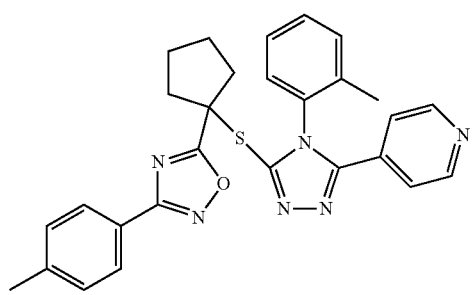 [SMILES: Cc1ccc(-c2noc(C3(Sc4nnc(-c5ccncc5)n4-c4ccccc4C)CCCC3)n2)cc1] |
| (41) | 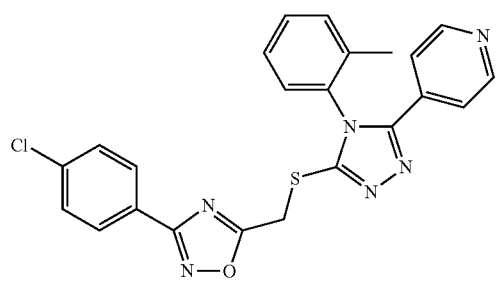 [SMILES: Cc1ccccc1-n1c(SCc2nc(-c3ccc(Cl)cc3)no2)nnc1-c1ccncc1] |
| (42) | 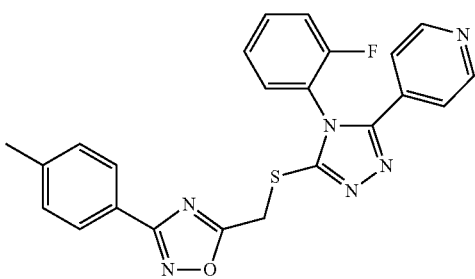 [SMILES: Cc1ccc(-c2noc(CSc3nnc(-c4ccncc4)n3-c3ccccc3F)n2)cc1] |
| (43) | 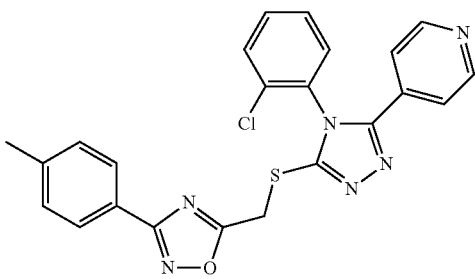 [SMILES: Cc1ccc(-c2noc(CSc3nnc(-c4ccncc4)n3-c3ccccc3Cl)n2)cc1] |

-continued
| Compound No. | Structure |
|---|---|
| (44) | 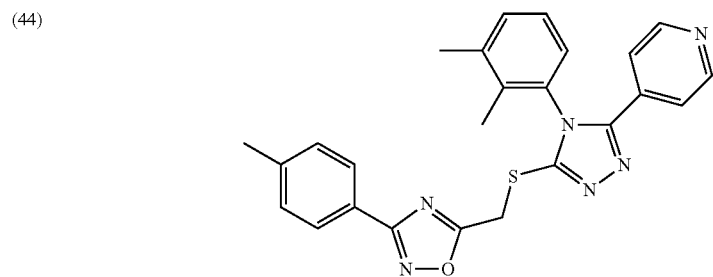 |
| (45) | 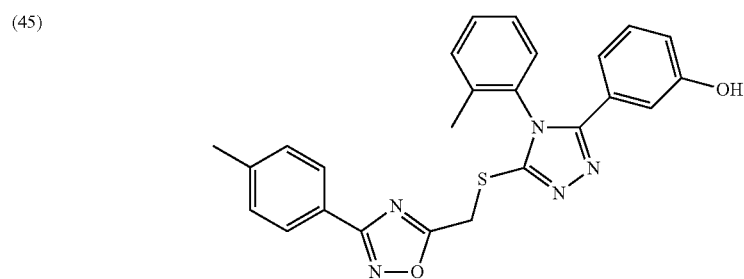 |
| (46) | 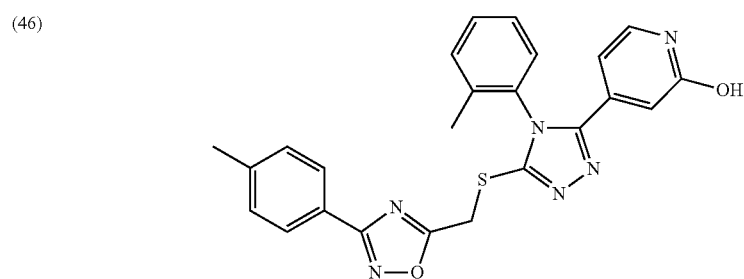 |
| (47) | 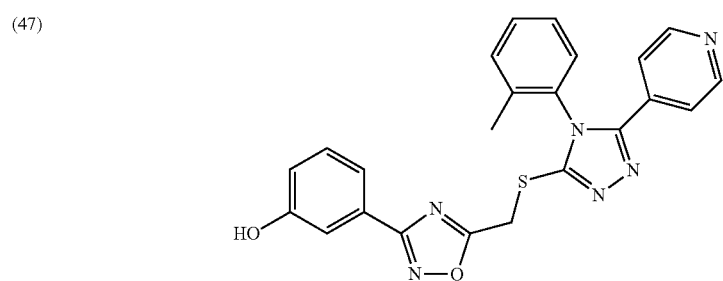 |
| (48) | 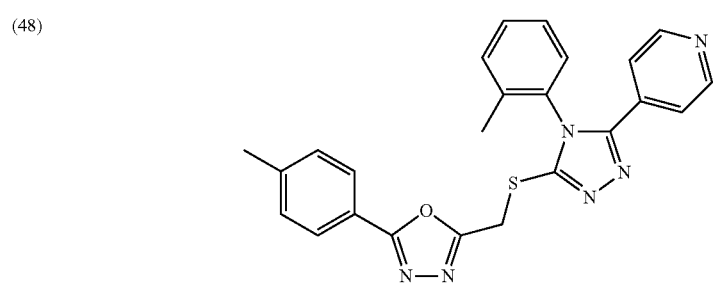 |

-continued
| Compound No. | Structure |
|---|---|
| (49) | 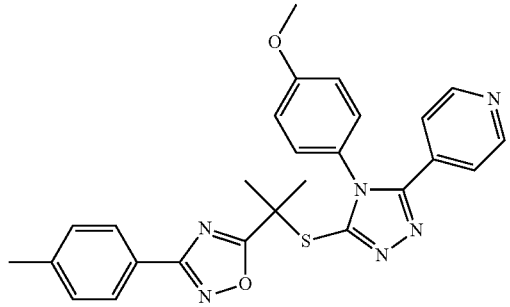 [SMILES: COc1ccc(-n2c(SC(C)(C)c3nc(-c4ccc(C)cc4)no3)nnc2-c2ccncc2)cc1] |
| (50) | 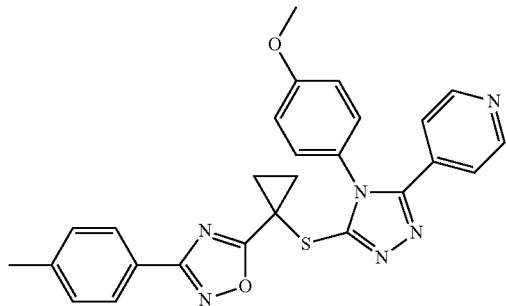 [SMILES: COc1ccc(-n2c(SC3(c4nc(-c5ccc(C)cc5)no4)CC3)nnc2-c2ccncc2)cc1] |
| (51) | 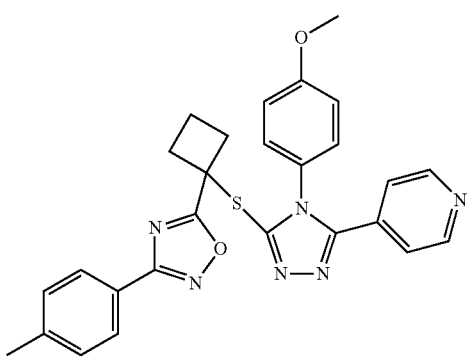 [SMILES: COc1ccc(-n2c(SC3(c4nc(-c5ccc(C)cc5)no4)CCC3)nnc2-c2ccncc2)cc1] |
| (52) | 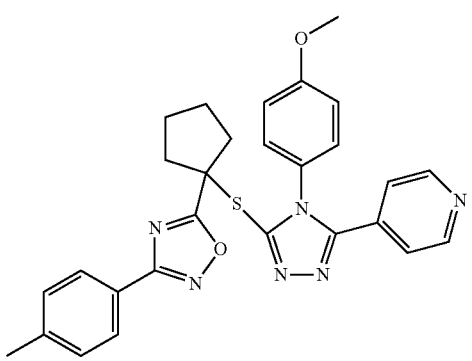 [SMILES: COc1ccc(-n2c(SC3(c4nc(-c5ccc(C)cc5)no4)CCCC3)nnc2-c2ccncc2)cc1] |

-continued

| Compound No. | Structure |
|---|---|
| (53) | 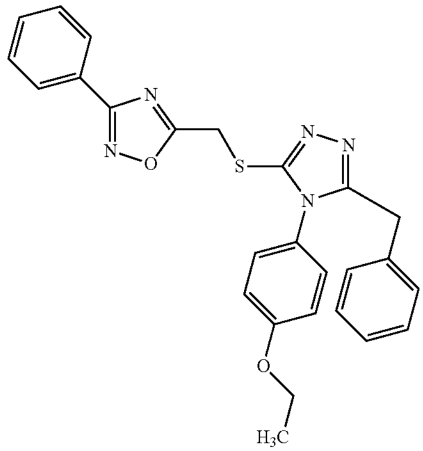 [SMILES: CCOc1ccc(-n2c(Cc3ccccc3)nnc2SCc2nc(-c3ccccc3)no2)cc1] |
| (54) | 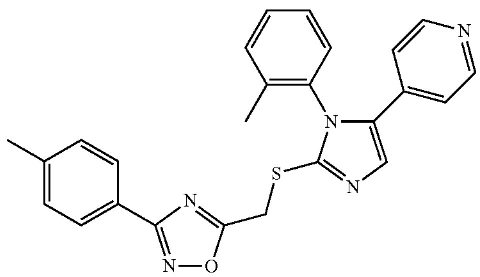 |
| (55) | 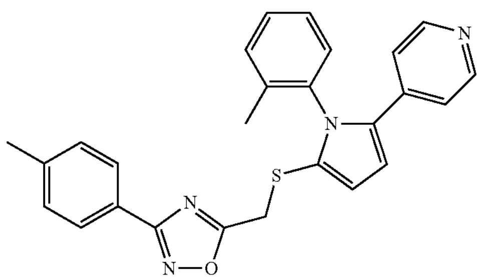 |
| (56) | 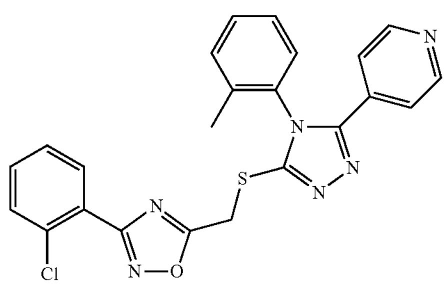 [SMILES: Cc1ccccc1-n1c(SCc2nc(-c3ccccc3Cl)no2)nnc1-c1ccncc1] |
| (57) | 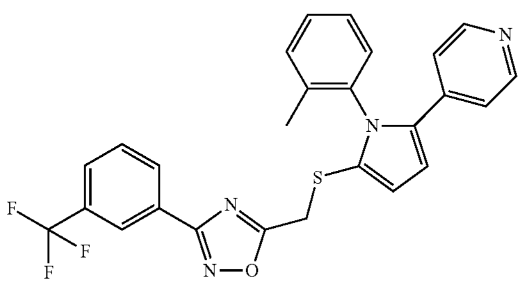 [SMILES: Cc1ccccc1-n1c(SCc2nc(-c3cccc(C(F)(F)F)c3)no2)ccc1-c1ccncc1] |

| Compound No. | Structure |
|---|---|
| (58) | 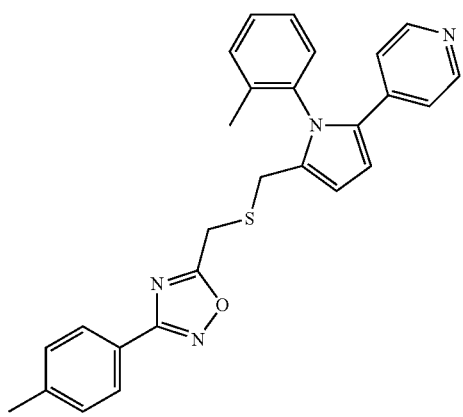 [SMILES: Cc1ccc(-c2noc(CSCc3ccc(-c4ccncc4)n3-c3ccccc3C)n2)cc1] |
| (59) | 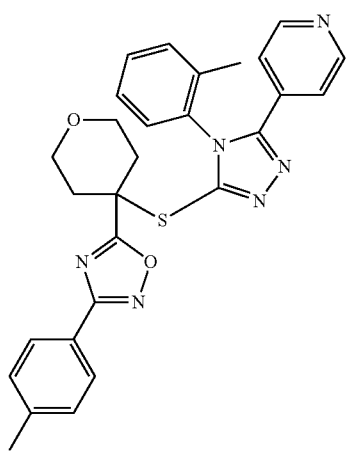 [SMILES: Cc1ccc(-c2noc(C3(Sc4nnc(-c5ccncc5)n4-c4ccccc4C)CCOCC3)n2)cc1] |
| (60) | 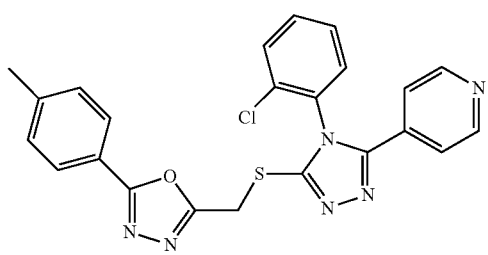 [SMILES: Cc1ccc(-c2nnc(CSc3nnc(-c4ccncc4)n3-c3ccccc3Cl)o2)cc1] |
| (61) | 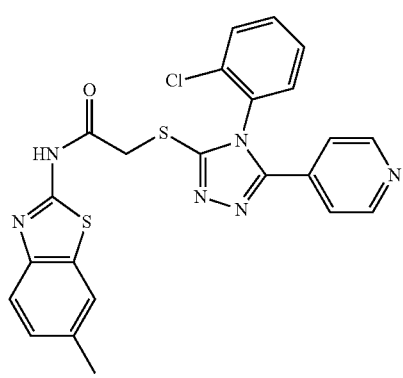 [SMILES: Cc1ccc2nc(NC(=O)CSc3nnc(-c4ccncc4)n3-c3ccccc3Cl)sc2c1] |

| Compound No. | Structure |
|---|---|
| (62) | 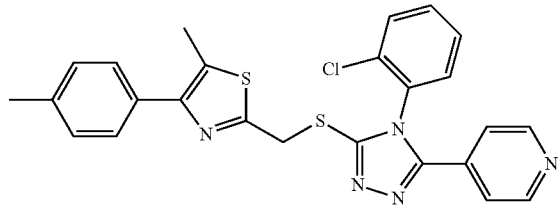 [SMILES: Cc1ccc(-c2nc(CSc3nnc(-c4ccncc4)n3-c3ccccc3Cl)sc2C)cc1] |
| (63) | 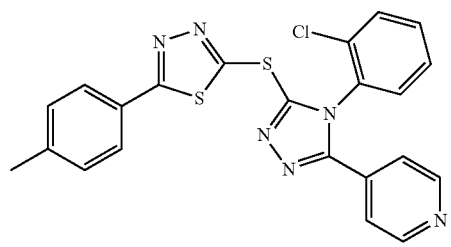 [SMILES: Cc1ccc(-c2nnc(Sc3nnc(-c4ccncc4)n3-c3ccccc3Cl)s2)cc1] |
| (64) | 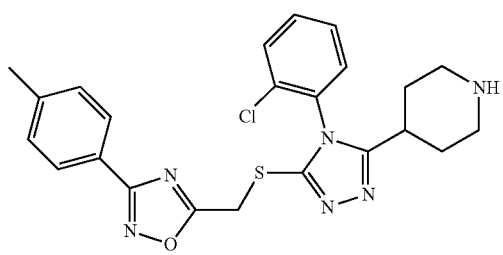 [SMILES: Cc1ccc(-c2noc(CSc3nnc(C4CCNCC4)n3-c3ccccc3Cl)n2)cc1] |
| (65) | 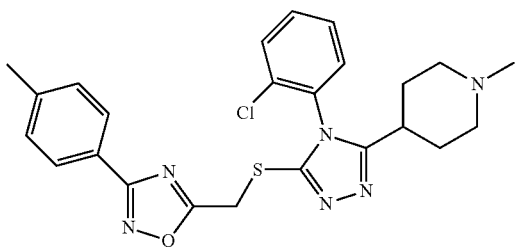 |
| (66) | 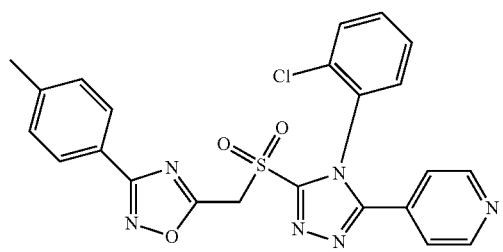 [SMILES: Cc1ccc(-c2noc(CS(=O)(=O)c3nnc(-c4ccncc4)n3-c3ccccc3Cl)n2)cc1] |

| Compound No. | Structure |
|---|---|
| (67) | 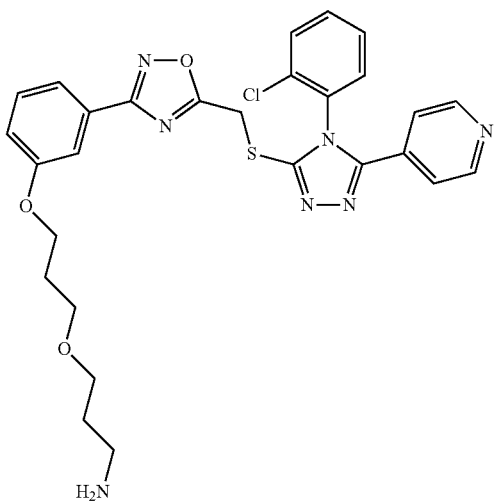 [SMILES: NCCCOCCCOc1cccc(-c2noc(CSc3nnc(-c4ccncc4)n3-c3ccccc3Cl)n2)c1] |
| (68) | 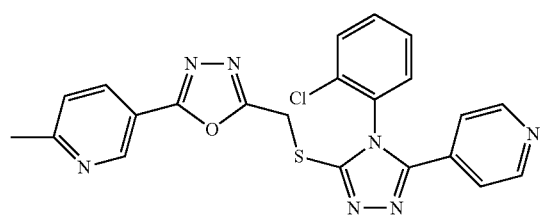 [SMILES: Cc1ccc(-c2nnc(CSc3nnc(-c4ccncc4)n3-c3ccccc3Cl)o2)cn1] |
| (69) | 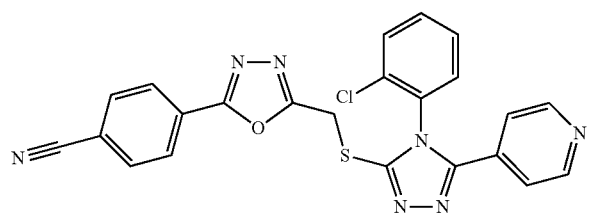 [SMILES: N#Cc1ccc(-c2nnc(CSc3nnc(-c4ccncc4)n3-c3ccccc3Cl)o2)cc1] |
| (70) | 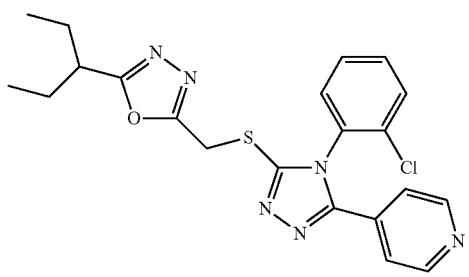 [SMILES: CCC(CC)c1nnc(CSc2nnc(-c3ccncc3)n2-c2ccccc2Cl)o1] |
| (71) | 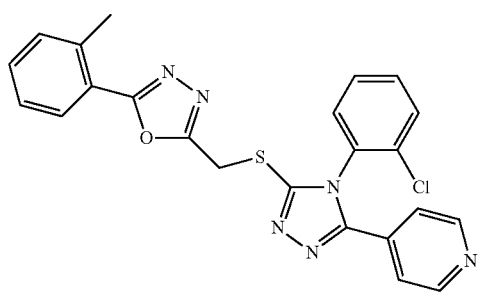 [SMILES: Cc1ccccc1-c1nnc(CSc2nnc(-c3ccncc3)n2-c2ccccc2Cl)o1] |

-continued
| Compound No. | Structure |
|---|---|
| (72) | 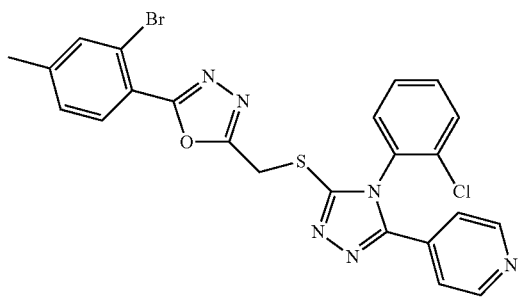 [SMILES: Cc1ccc(-c2nnc(CSc3nnc(-c4ccncc4)n3-c3ccccc3Cl)o2)c(Br)c1] |
| (73) | 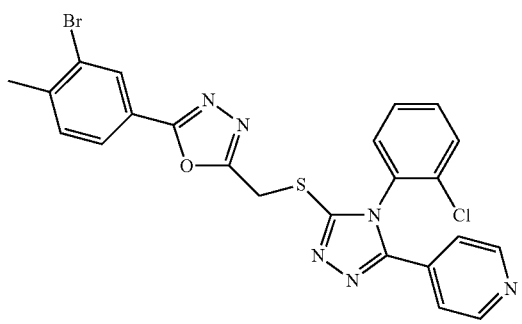 [SMILES: Cc1ccc(-c2nnc(CSc3nnc(-c4ccncc4)n3-c3ccccc3Cl)o2)cc1Br] |
| (74) | 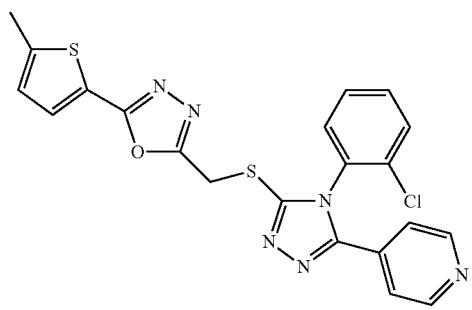 [SMILES: Cc1ccc(-c2nnc(CSc3nnc(-c4ccncc4)n3-c3ccccc3Cl)o2)s1] |
| (75) | 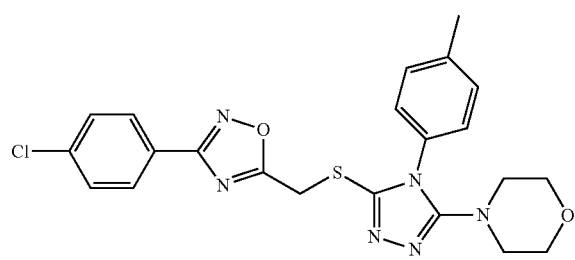 [SMILES: Cc1ccc(-n2c(SCc3nc(-c4ccc(Cl)cc4)no3)nnc2N2CCOCC2)cc1] |
| (76) | 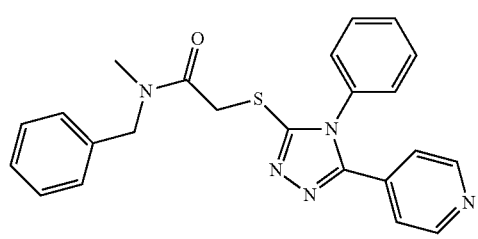 [SMILES: CN(Cc1ccccc1)C(=O)CSc1nnc(-c2ccncc2)n1-c1ccccc1] |

-continued
| Compound No. | Structure |
|---|---|
| (77) | 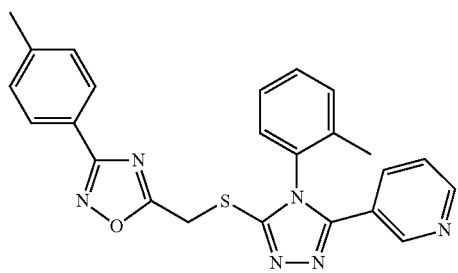 [SMILES: Cc1ccc(-c2noc(CSc3nnc(-c4cccnc4)n3-c3ccccc3C)n2)cc1] |
| (78) | 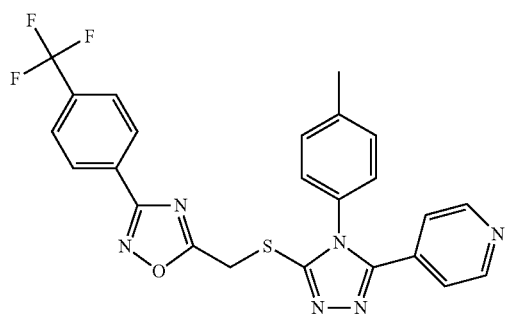 [SMILES: Cc1ccc(-n2c(SCc3nc(-c4ccc(C(F)(F)F)cc4)no3)nnc2-c2ccncc2)cc1] |
| (79) | 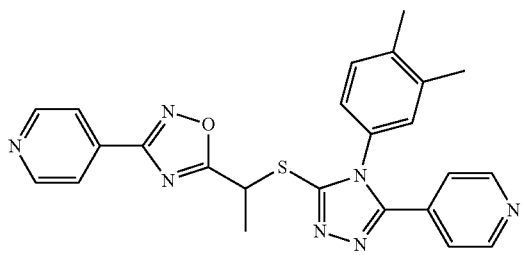 [SMILES: Cc1ccc(-n2c(SC(C)c3nc(-c4ccncc4)no3)nnc2-c2ccncc2)cc1C] |
| (80) | 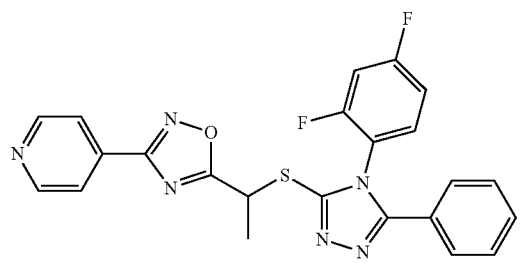 [SMILES: CC(Sc1nnc(-c2ccccc2)n1-c1ccc(F)cc1F)c1nc(-c2ccncc2)no1] |
| (81) | 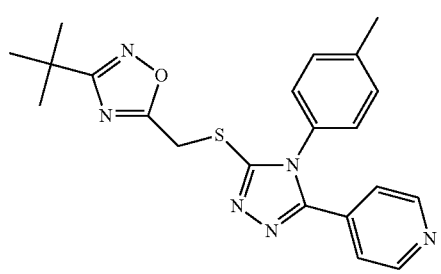 [SMILES: Cc1ccc(-n2c(SCc3nc(C(C)(C)C)no3)nnc2-c2ccncc2)cc1] |

-continued
| Compound No. | Structure |
|---|---|
| (82) | 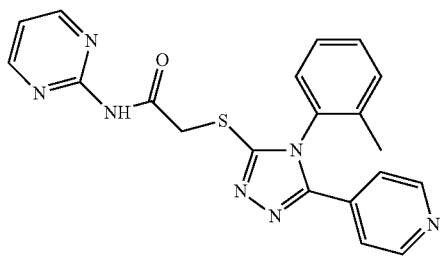 [SMILES: Cc1ccccc1-n1c(SCC(=O)Nc2ncccn2)nnc1-c1ccncc1] |
| (83) | 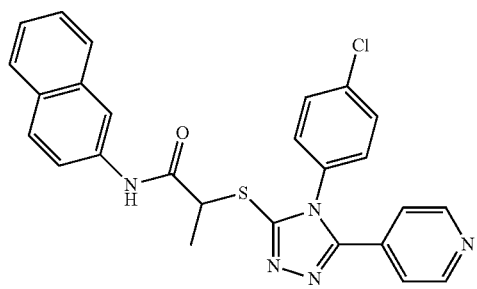 [SMILES: CC(Sc1nnc(-c2ccncc2)n1-c1ccc(Cl)cc1)C(=O)Nc1ccc2ccccc2c1] |
| (84) | 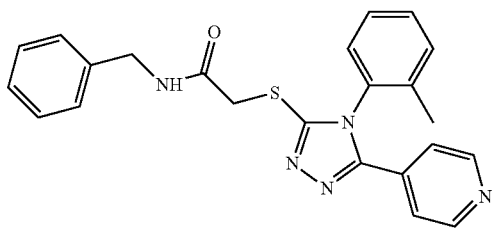 [SMILES: Cc1ccccc1-n1c(SCC(=O)NCc2ccccc2)nnc1-c1ccncc1] |
| (85) | 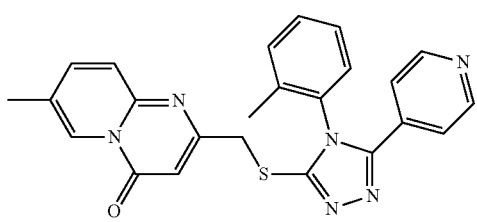 [SMILES: Cc1ccc2nc(CSc3nnc(-c4ccncc4)n3-c3ccccc3C)cc(=O)n2c1] |
| (86) | 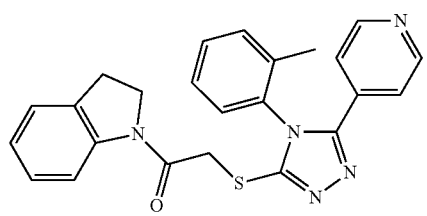 [SMILES: Cc1ccccc1-n1c(SCC(=O)N2CCc3ccccc32)nnc1-c1ccncc1] |
| (87) | 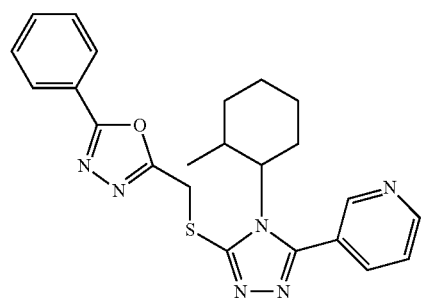 [SMILES: CC1CCCCC1n1c(SCc2nnc(-c3ccccc3)o2)nnc1-c1cccnc1] |

-continued
| Compound No. | Structure |
|---|---|
| (88) | 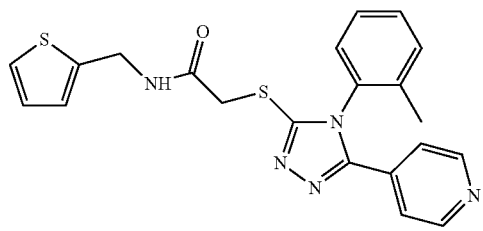 [SMILES: Cc1ccccc1-n1c(SCC(=O)NCc2cccs2)nnc1-c1ccncc1] |
| (89) | 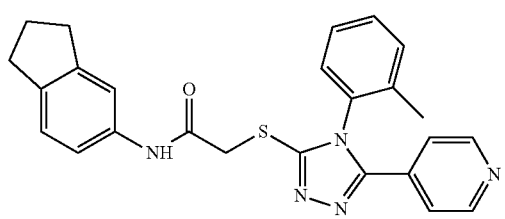 [SMILES: Cc1ccccc1-n1c(SCC(=O)Nc2ccc3c(c2)CCC3)nnc1-c1ccncc1] |
| (90) | 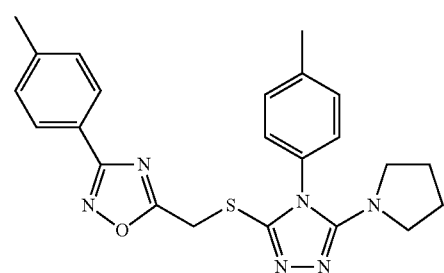 [SMILES: Cc1ccc(-c2noc(CSc3nnc(N4CCCC4)n3-c3ccc(C)cc3)n2)cc1] |
| (91) | 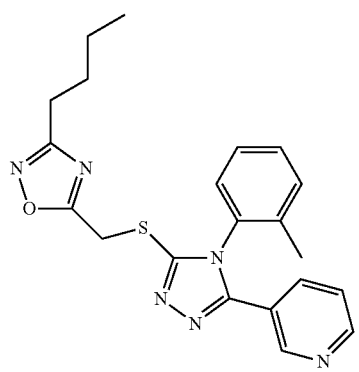 [SMILES: CCCCc1noc(CSc2nnc(-c3cccnc3)n2-c2ccccc2C)n1] |
| (92) | 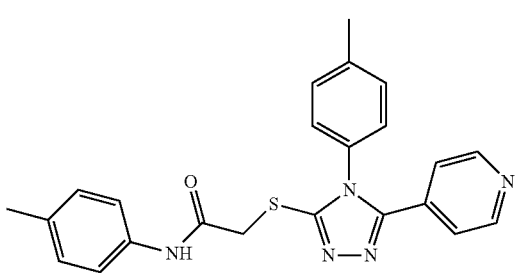 [SMILES: Cc1ccc(NC(=O)CSc2nnc(-c3ccncc3)n2-c2ccc(C)cc2)cc1] |

-continued
| Compound No. | Structure |
|---|---|
| (93) | 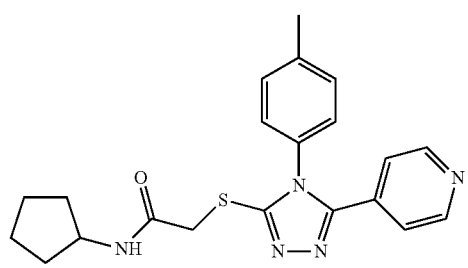 [SMILES: Cc1ccc(-n2c(SCC(=O)NC3CCCC3)nnc2-c2ccncc2)cc1] |
| (94) | 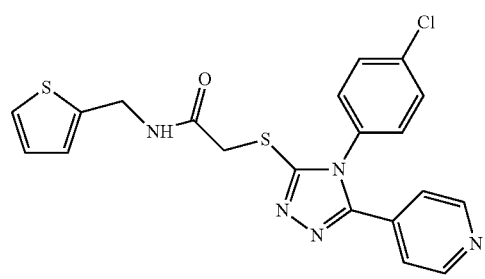 [SMILES: O=C(CSc1nnc(-c2ccncc2)n1-c1ccc(Cl)cc1)NCc1cccs1] |
| (95) | 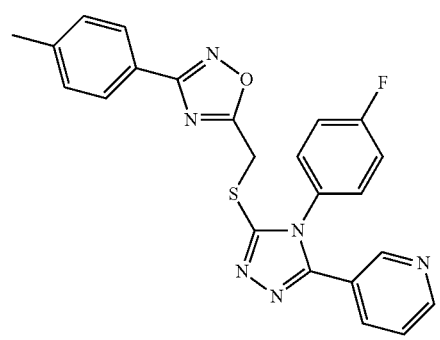 [SMILES: Cc1ccc(-c2noc(CSc3nnc(-c4cccnc4)n3-c3ccc(F)cc3)n2)cc1] |
| (96) | 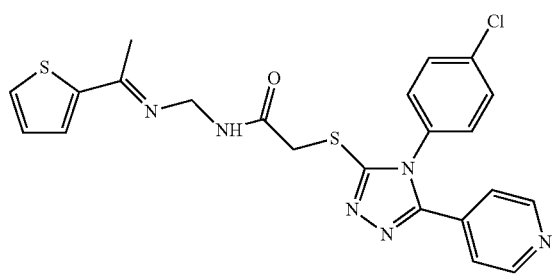 [SMILES: C/C(=N\CNC(=O)CSc1nnc(-c2ccncc2)n1-c1ccc(Cl)cc1)c1cccs1] |
| (97) | 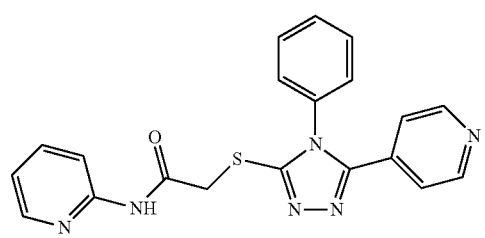 [SMILES: O=C(CSc1nnc(-c2ccncc2)n1-c1ccccc1)Nc1ccccn1] |

| Compound No. | Structure |
|---|---|
| (98) | 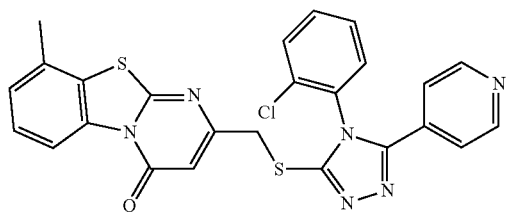 [SMILES: Cc1cccc2c1sc1nc(CSc3nnc(-c4ccncc4)n3-c3ccccc3Cl)cc(=O)n12] |
| (99) | 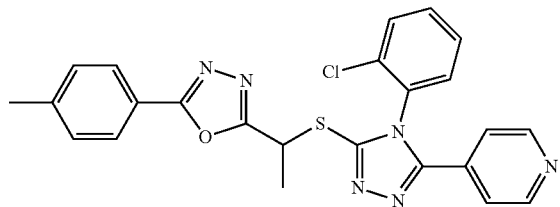 [SMILES: Cc1ccc(-c2nnc(C(C)Sc3nnc(-c4ccncc4)n3-c3ccccc3Cl)o2)cc1] |
| (100) | 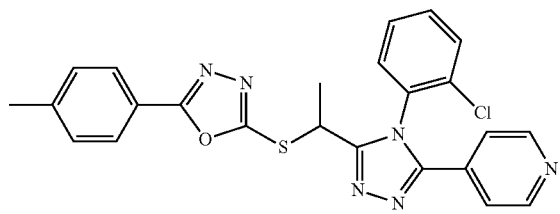 [SMILES: Cc1ccc(-c2nnc(SC(C)c3nnc(-c4ccncc4)n3-c3ccccc3Cl)o2)cc1] |
| (101) | 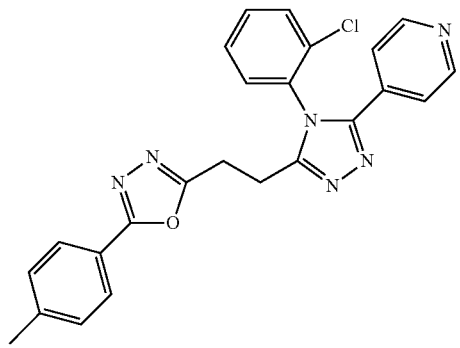 [SMILES: Cc1ccc(-c2nnc(CCc3nnc(-c4ccncc4)n3-c3ccccc3Cl)o2)cc1] |
| (102) | 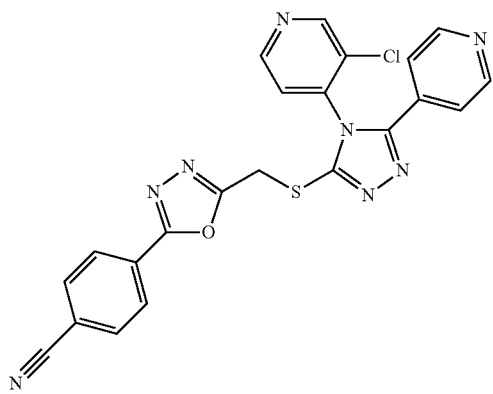 [SMILES: N#Cc1ccc(-c2nnc(CSc3nnc(-c4ccncc4)n3-c3ccncc3Cl)o2)cc1] |

| Compound No. | Structure |
|---|---|
| (103) | 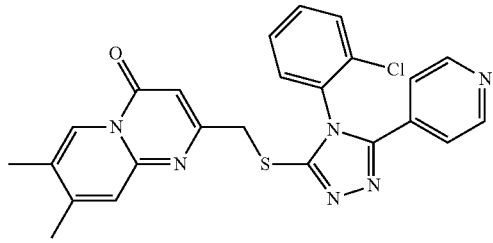 [SMILES: Cc1cc2nc(CSc3nnc(-c4ccncc4)n3-c3ccccc3Cl)cc(=O)n2cc1C] |
| (104) | 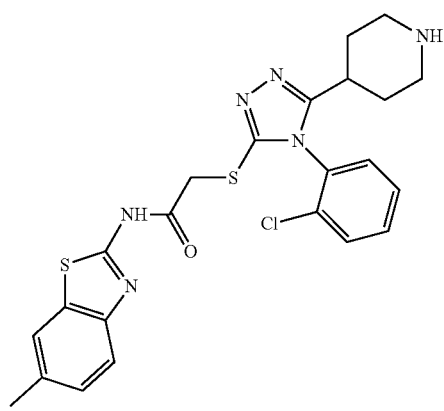 [SMILES: Cc1ccc2nc(NC(=O)CSc3nnc(C4CCNCC4)n3-c3ccccc3Cl)sc2c1] |
| (105) | 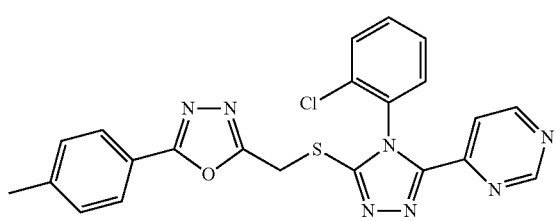 [SMILES: Cc1ccc(-c2nnc(CSc3nnc(-c4ccncn4)n3-c3ccccc3Cl)o2)cc1] |
| (106) | 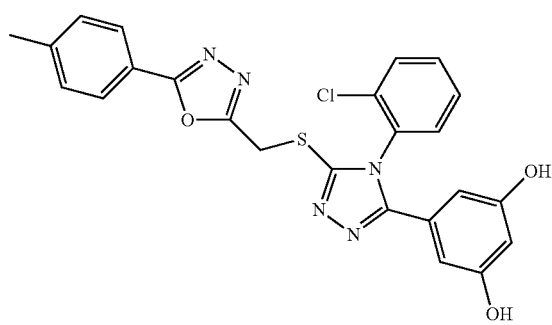 [SMILES: Cc1ccc(-c2nnc(CSc3nnc(-c4cc(O)cc(O)c4)n3-c3ccccc3Cl)o2)cc1] |
| (107) | 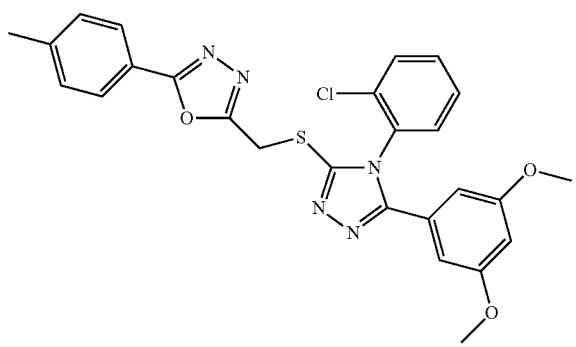 |

| Compound No. | Structure |
|---|---|
| (108) | 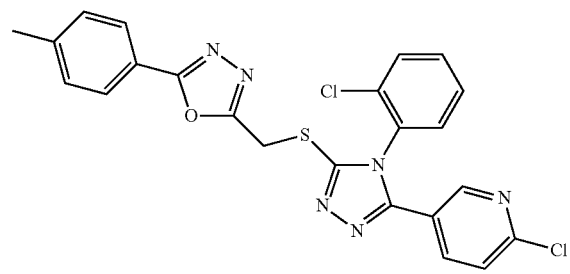 [SMILES: Cc1ccc(-c2nnc(CSc3nnc(-c4ccc(Cl)nc4)n3-c3ccccc3Cl)o2)cc1] |
| (109) | 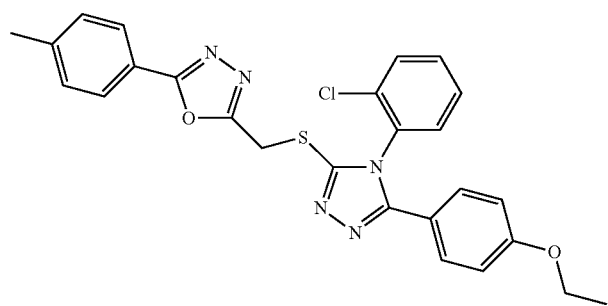 [SMILES: CCOc1ccc(-c2nnc(SCc3nnc(-c4ccc(C)cc4)o3)n2-c2ccccc2Cl)cc1] |
| (110) | 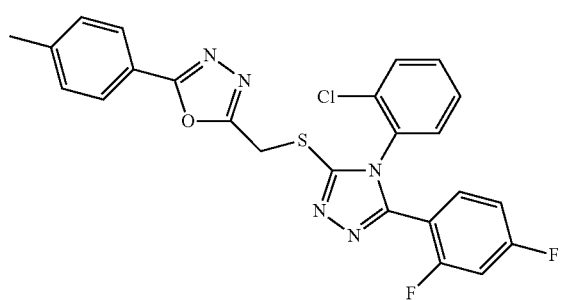 [SMILES: Cc1ccc(-c2nnc(CSc3nnc(-c4ccc(F)cc4F)n3-c3ccccc3Cl)o2)cc1] |
| (111) | 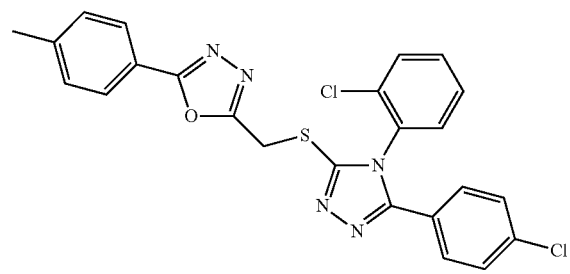 [SMILES: Cc1ccc(-c2nnc(CSc3nnc(-c4ccc(Cl)cc4)n3-c3ccccc3Cl)o2)cc1] |
| (112) | 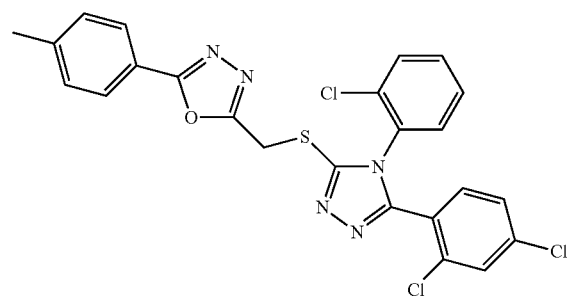 [SMILES: Cc1ccc(-c2nnc(CSc3nnc(-c4ccc(Cl)cc4Cl)n3-c3ccccc3Cl)o2)cc1] |

-continued
| Compound No. | Structure |
|---|---|
| (113) | 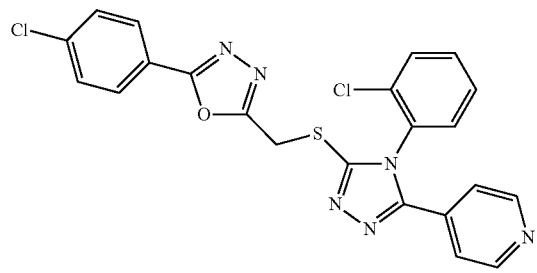 [SMILES: Clc1ccc(-c2nnc(CSc3nnc(-c4ccncc4)n3-c3ccccc3Cl)o2)cc1] |
| (114) | 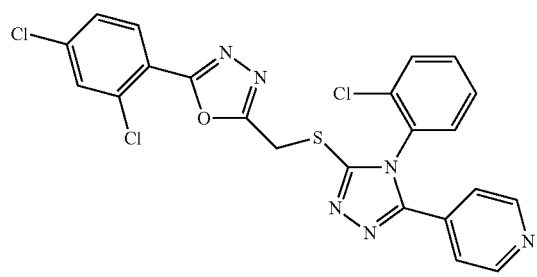 [SMILES: Clc1ccc(-c2nnc(CSc3nnc(-c4ccncc4)n3-c3ccccc3Cl)o2)c(Cl)c1] |
| (115) | 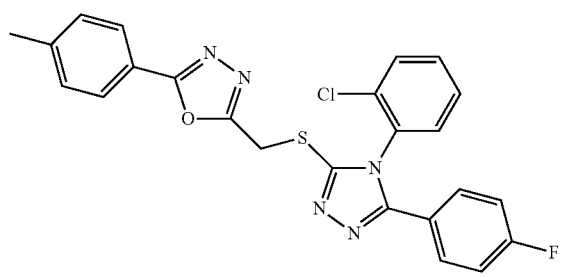 [SMILES: Cc1ccc(-c2nnc(CSc3nnc(-c4ccc(F)cc4)n3-c3ccccc3Cl)o2)cc1] |
| (116) | 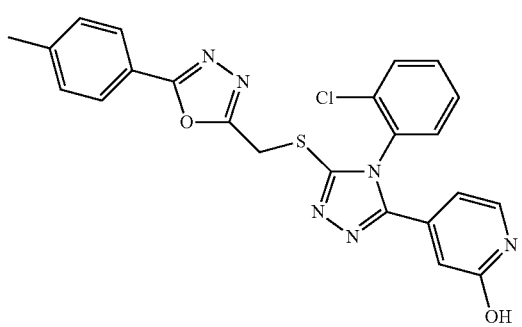 [SMILES: Cc1ccc(-c2nnc(CSc3nnc(-c4ccnc(O)c4)n3-c3ccccc3Cl)o2)cc1] |
| (117) | 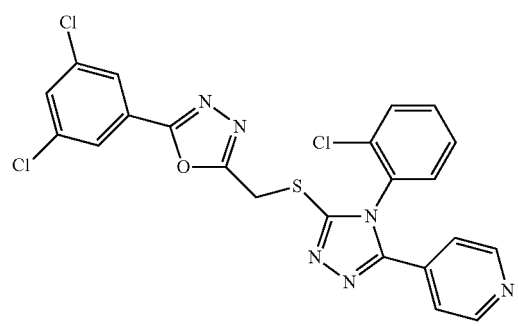 [SMILES: Clc1cc(Cl)cc(-c2nnc(CSc3nnc(-c4ccncc4)n3-c3ccccc3Cl)o2)c1] |

-continued
| Compound No. | Structure |
|---|---|
| (118) | 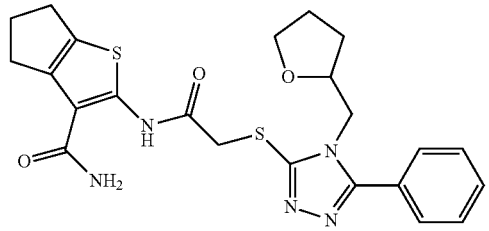 [SMILES: NC(=O)c1c(NC(=O)CSc2nnc(-c3ccccc3)n2CC2CCCO2)sc2c1CCC2] |
| (119) | 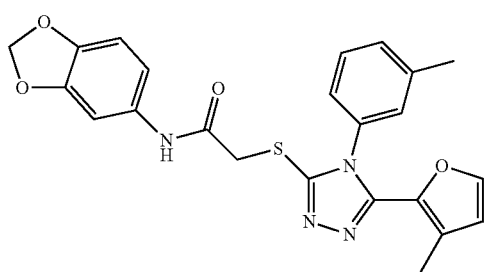 [SMILES: Cc1cccc(-n2c(SCC(=O)Nc3ccc4c(c3)OCO4)nnc2-c2occc2C)c1] |
| (120) | 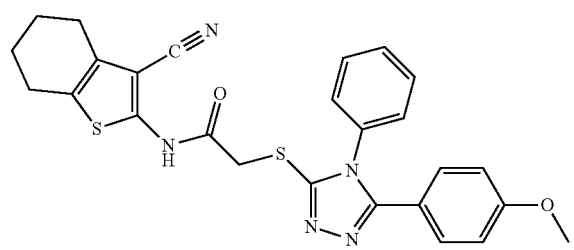 [SMILES: COc1ccc(-c2nnc(SCC(=O)Nc3sc4c(c3C#N)CCCC4)n2-c2ccccc2)cc1] |
| (121) | 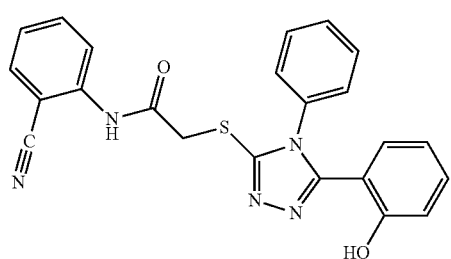 [SMILES: N#Cc1ccccc1NC(=O)CSc1nnc(-c2ccccc2O)n1-c1ccccc1] |
| (122) | 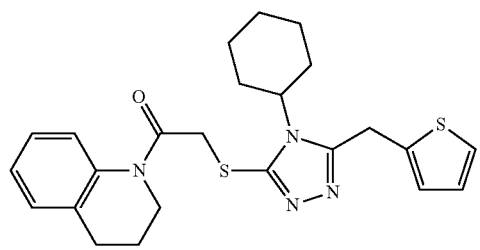 [SMILES: O=C(CSc1nnc(Cc2cccs2)n1C1CCCCC1)N1CCCc2ccccc21] |
| (123) | 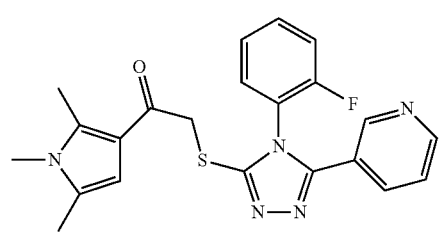 [SMILES: Cc1cc(C(=O)CSc2nnc(-c3cccnc3)n2-c2ccccc2F)c(C)n1C] |

|Compound No.|Structure|
|---|---|
|(124)| 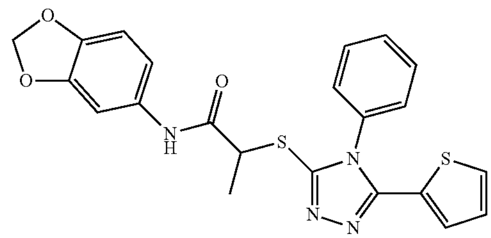 [SMILES: CC(Sc1nnc(-c2cccs2)n1-c1ccccc1)C(=O)Nc1ccc2c(c1)OCO2] |
|(125)| 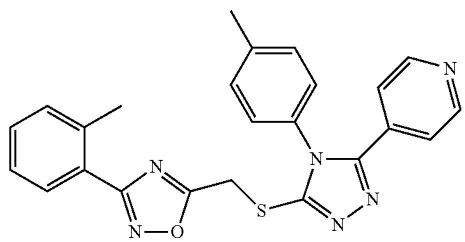 [SMILES: Cc1ccc(-n2c(SCc3nc(-c4ccccc4C)no3)nnc2-c2ccncc2)cc1] |
|(126)| 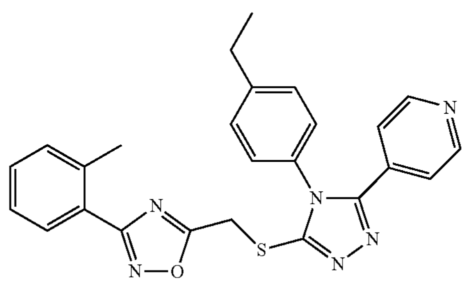 [SMILES: CCc1ccc(-n2c(SCc3nc(-c4ccccc4C)no3)nnc2-c2ccncc2)cc1] |
|(127)| 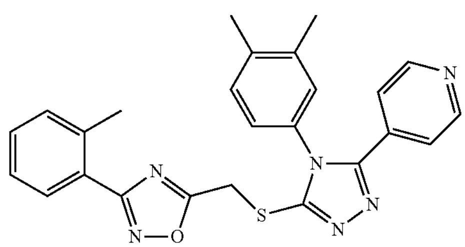 [SMILES: Cc1ccc(-n2c(SCc3nc(-c4ccccc4C)no3)nnc2-c2ccncc2)cc1C] |
|(128)| 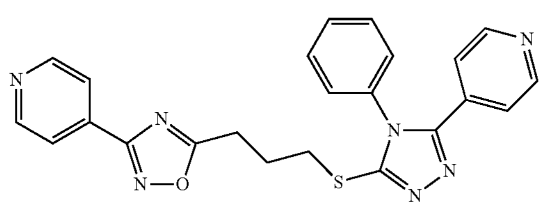 [SMILES: c1ccc(-n2c(SCCCc3nc(-c4ccncc4)no3)nnc2-c2ccncc2)cc1] |
|(129)| 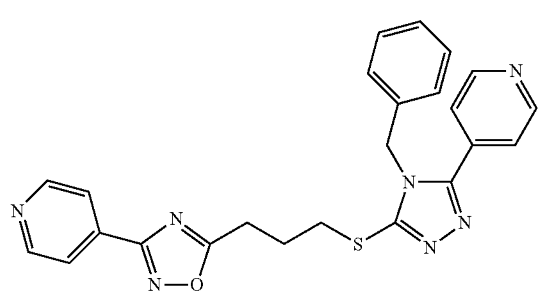 [SMILES: c1ccc(Cn2c(SCCCc3nc(-c4ccncc4)no3)nnc2-c2ccncc2)cc1] |

-continued

| Compound No. | Structure |
|---|---|
| (130) | 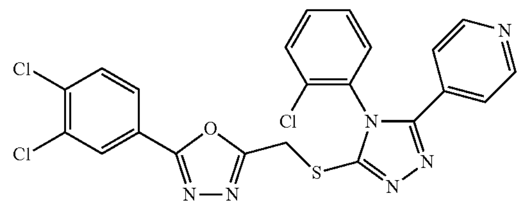 [SMILES: Clc1ccc(-c2nnc(CSc3nnc(-c4ccncc4)n3-c3ccccc3Cl)o2)cc1Cl] |
| (131) | 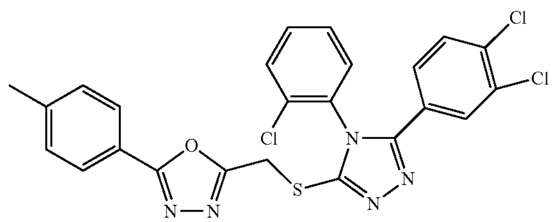 [SMILES: Cc1ccc(-c2nnc(CSc3nnc(-c4ccc(Cl)c(Cl)c4)n3-c3ccccc3Cl)o2)cc1] |
| (132) | 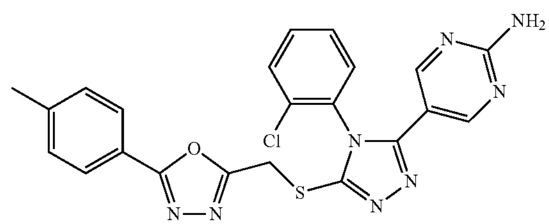 [SMILES: Cc1ccc(-c2nnc(CSc3nnc(-c4cnc(N)nc4)n3-c3ccccc3Cl)o2)cc1] |
| (133) | 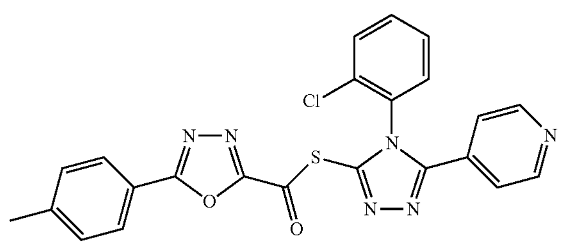 [SMILES: Cc1ccc(-c2nnc(C(=O)Sc3nnc(-c4ccncc4)n3-c3ccccc3Cl)o2)cc1] |
| (134) | 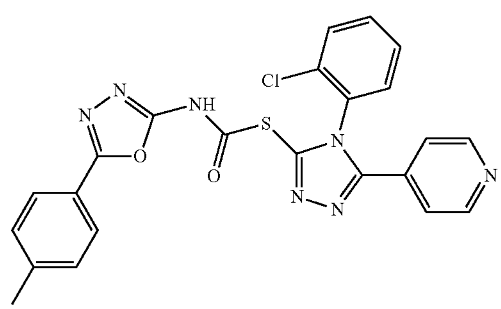 [SMILES: Cc1ccc(-c2nnc(NC(=O)Sc3nnc(-c4ccncc4)n3-c3ccccc3Cl)o2)cc1] |
| (135) | 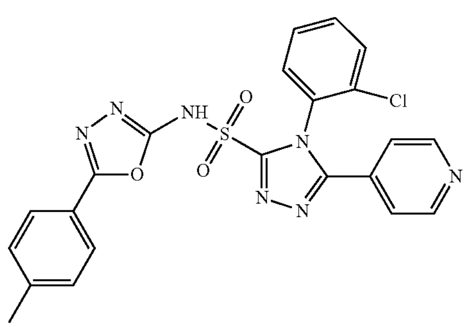 [SMILES: Cc1ccc(-c2nnc(NS(=O)(=O)c3nnc(-c4ccncc4)n3-c3ccccc3Cl)o2)cc1] |

| Compound No. | Structure |
|---|---|
| (136) | 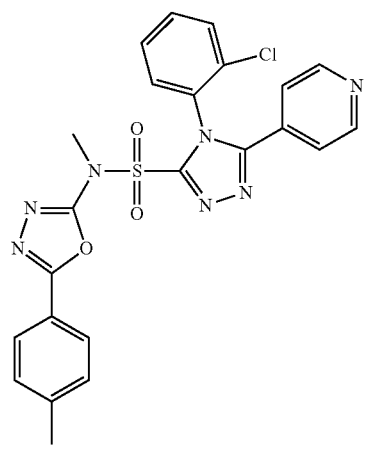 [SMILES: Cc1ccc(-c2nnc(N(C)S(=O)(=O)c3nnc(-c4ccncc4)n3-c3ccccc3Cl)o2)cc1] |
| (137) | 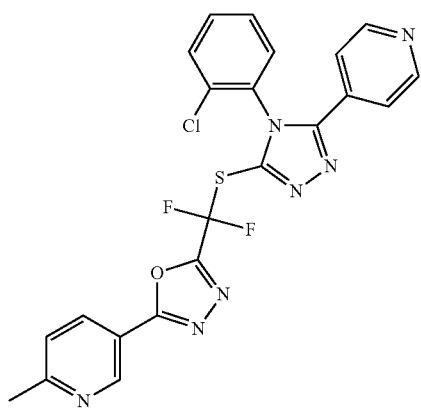 [SMILES: Cc1ccc(-c2nnc(C(F)(F)Sc3nnc(-c4ccncc4)n3-c3ccccc3Cl)o2)cn1] |
| (138) | 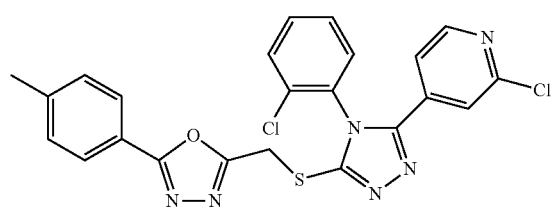 [SMILES: Cc1ccc(-c2nnc(CSc3nnc(-c4ccnc(Cl)c4)n3-c3ccccc3Cl)o2)cc1] |
| (139) | 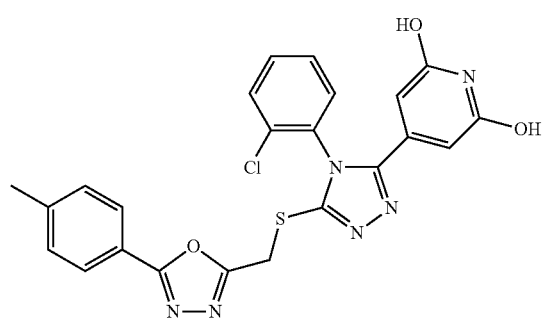 [SMILES: Cc1ccc(-c2nnc(CSc3nnc(-c4cc(O)nc(O)c4)n3-c3ccccc3Cl)o2)cc1] |

| Compound No. | Structure |
|---|---|
| (140) | 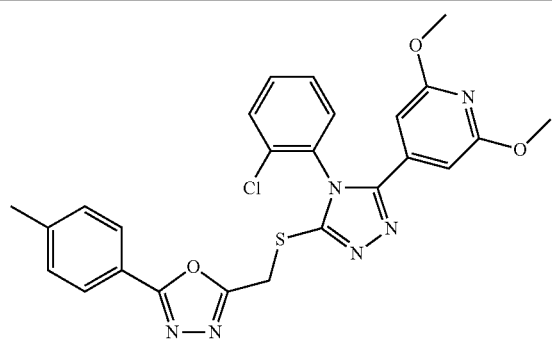 |
| (141) | 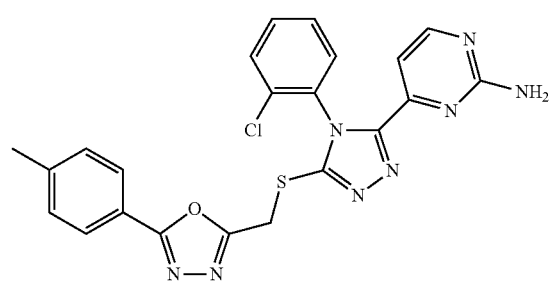 [SMILES: Cc1ccc(-c2nnc(CSc3nnc(-c4ccnc(N)n4)n3-c3ccccc3Cl)o2)cc1] |
| (142) | 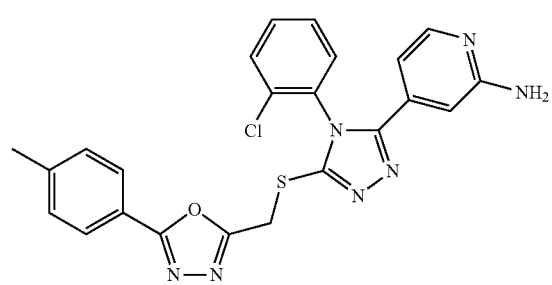 [SMILES: Cc1ccc(-c2nnc(CSc3nnc(-c4ccnc(N)c4)n3-c3ccccc3Cl)o2)cc1] |
| (143) | 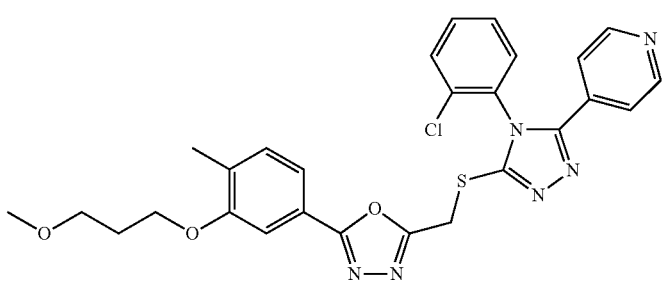 [SMILES: COCCCOc1cc(-c2nnc(CSc3nnc(-c4ccncc4)n3-c3ccccc3Cl)o2)ccc1C] |
| (144) | 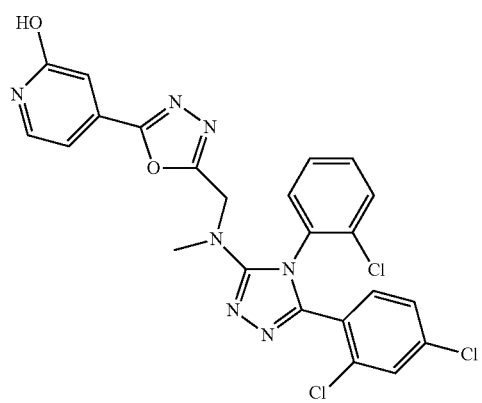 [SMILES: CN(Cc1nnc(-c2ccnc(O)c2)o1)c1nnc(-c2ccc(Cl)cc2Cl)n1-c1ccccc1Cl] |

| Compound No. | Structure |
|---|---|
| (145) | 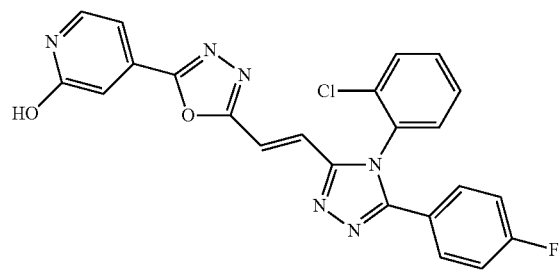 [SMILES: Oc1cc(-c2nnc(/C=C/c3nnc(-c4ccc(F)cc4)n3-c3ccccc3Cl)o2)ccn1] |
| (146) | 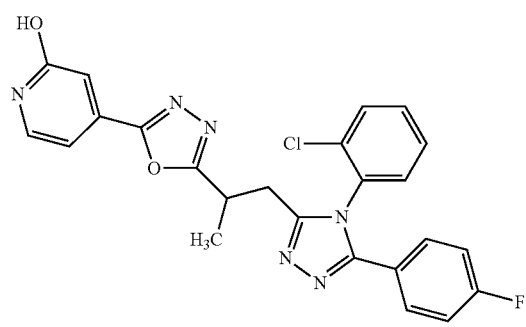 [SMILES: CC(Cc1nnc(-c2ccc(F)cc2)n1-c1ccccc1Cl)c1nnc(-c2ccnc(O)c2)o1] |
| (147) | 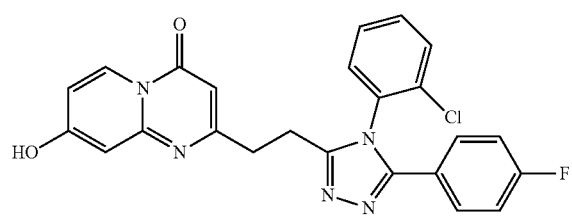 [SMILES: O=c1cc(CCc2nnc(-c3ccc(F)cc3)n2-c2ccccc2Cl)nc2cc(O)ccn12] |
| (148) | 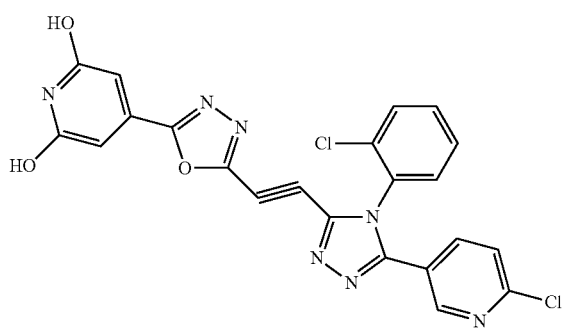 [SMILES: Oc1cc(-c2nnc(C#Cc3nnc(-c4ccc(Cl)nc4)n3-c3ccccc3Cl)o2)cc(O)n1] |
| (149) | 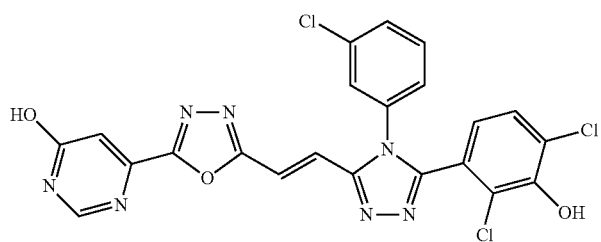 [SMILES: Oc1cc(-c2nnc(/C=C/c3nnc(-c4ccc(Cl)c(O)c4Cl)n3-c3cccc(Cl)c3)o2)ncn1] |

| Compound No. | Structure |
|---|---|
| (150) | 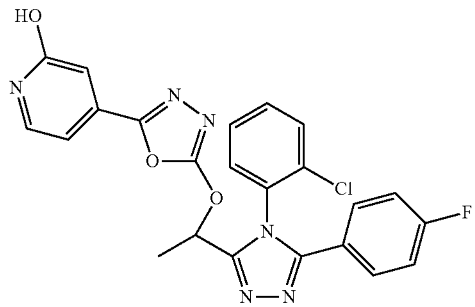 [SMILES: CC(Oc1nnc(-c2ccnc(O)c2)o1)c1nnc(-c2ccc(F)cc2)n1-c1ccccc1Cl] |
| (151) | 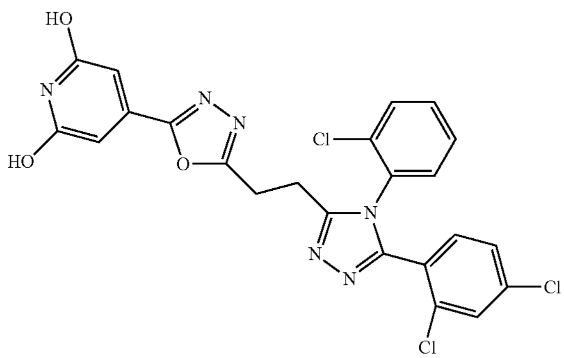 [SMILES: Oc1cc(-c2nnc(CCc3nnc(-c4ccc(Cl)cc4Cl)n3-c3ccccc3Cl)o2)cc(O)n1] |
| (152) | 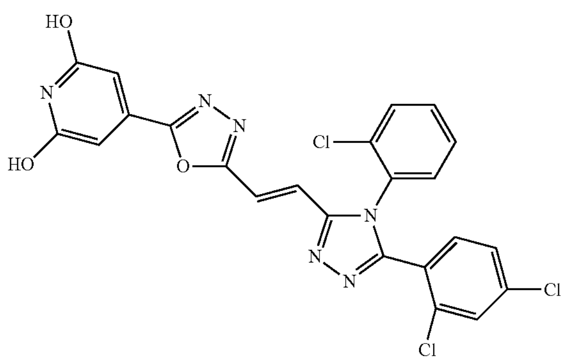 [SMILES: Oc1cc(-c2nnc(/C=C/c3nnc(-c4ccc(Cl)cc4Cl)n3-c3ccccc3Cl)o2)cc(O)n1] |
| (153) | 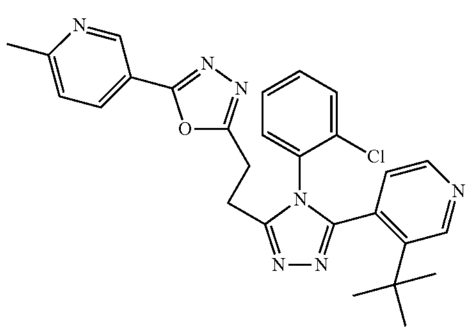 [SMILES: Cc1ccc(-c2nnc(CCc3nnc(-c4ccncc4C(C)(C)C)n3-c3ccccc3Cl)o2)cn1] |
| (154) | 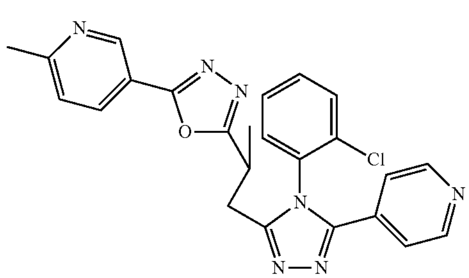 [SMILES: Cc1ccc(-c2nnc(C(C)Cc3nnc(-c4ccncc4)n3-c3ccccc3Cl)o2)cn1] |

| Compound No. | Structure |
|---|---|
| (155) | 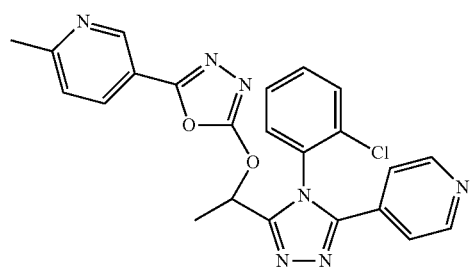 [SMILES: Cc1ccc(-c2nnc(OC(C)c3nnc(-c4ccncc4)n3-c3ccccc3Cl)o2)cn1] |
| (156) | 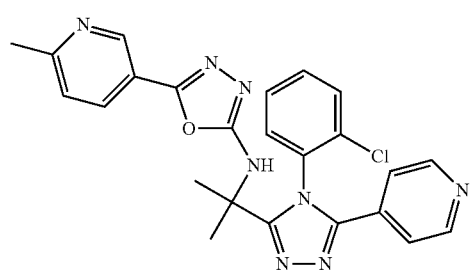 [SMILES: Cc1ccc(-c2nnc(NC(C)(C)c3nnc(-c4ccncc4)n3-c3ccccc3Cl)o2)cn1] |
| (157) | 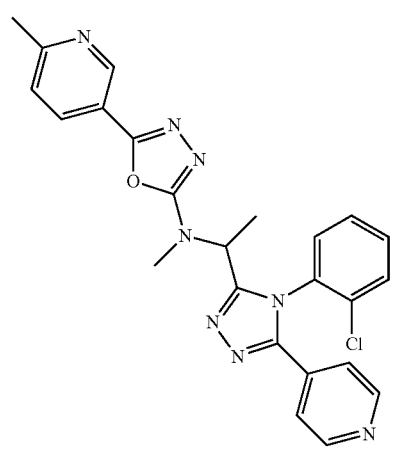 [SMILES: Cc1ccc(-c2nnc(N(C)C(C)c3nnc(-c4ccncc4)n3-c3ccccc3Cl)o2)cn1] |
| (158) | 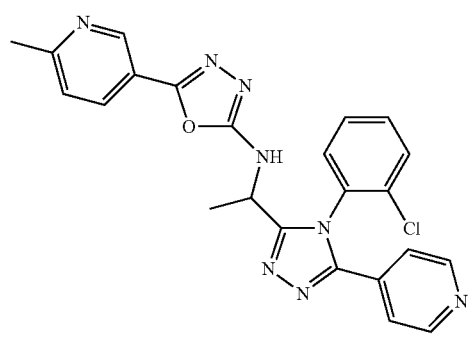 [SMILES: Cc1ccc(-c2nnc(NC(C)c3nnc(-c4ccncc4)n3-c3ccccc3Cl)o2)cn1] |

| Compound No. | Structure |
|---|---|
| (159) | 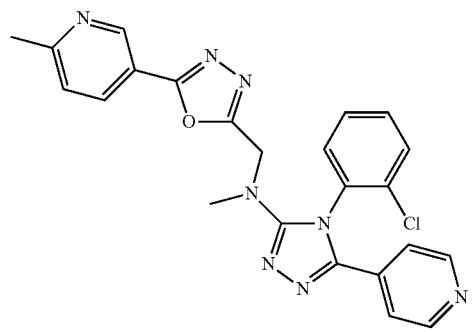 [SMILES: Cc1ccc(-c2nnc(CN(C)c3nnc(-c4ccncc4)n3-c3ccccc3Cl)o2)cn1] |
| (160) | 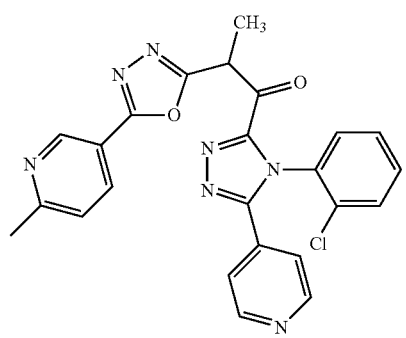 [SMILES: Cc1ccc(-c2nnc(C(C)C(=O)c3nnc(-c4ccncc4)n3-c3ccccc3Cl)o2)cn1] |
| (161) | 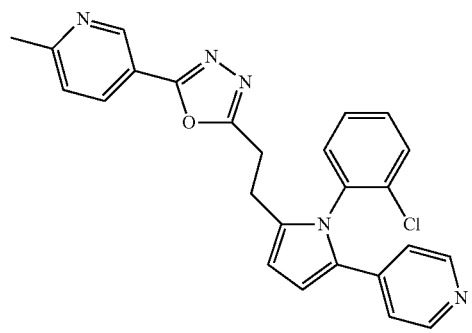 [SMILES: Cc1ccc(-c2nnc(CCc3ccc(-c4ccncc4)n3-c3ccccc3Cl)o2)cn1] |
| (162) | 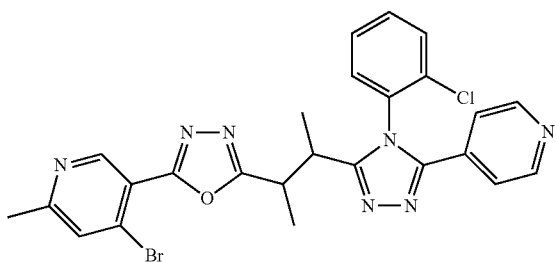 [SMILES: Cc1cc(Br)c(-c2nnc(C(C)C(C)c3nnc(-c4ccncc4)n3-c3ccccc3Cl)o2)cn1] |
| (163) | 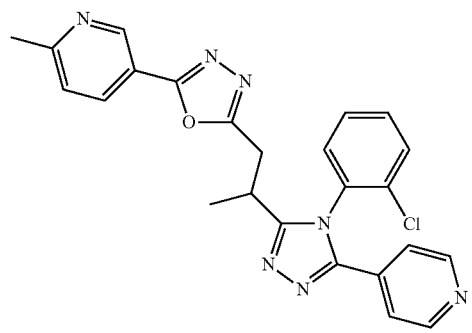 [SMILES: Cc1ccc(-c2nnc(CC(C)c3nnc(-c4ccncc4)n3-c3ccccc3Cl)o2)cn1] |

| Compound No. | Structure |
|---|---|
| (164) | 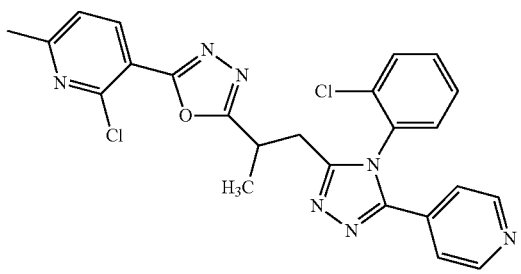 [SMILES: Cc1ccc(-c2nnc(C(C)Cc3nnc(-c4ccncc4)n3-c3ccccc3Cl)o2)c(Cl)n1] |
| (165) | 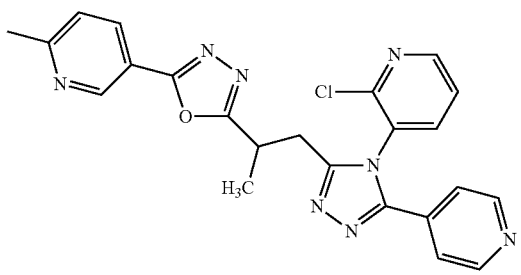 [SMILES: Cc1ccc(-c2nnc(C(C)Cc3nnc(-c4ccncc4)n3-c3cccnc3Cl)o2)cn1] |
| (166) | 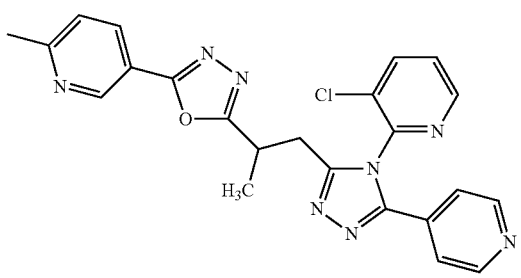 [SMILES: Cc1ccc(-c2nnc(C(C)Cc3nnc(-c4ccncc4)n3-c3ncccc3Cl)o2)cn1] |
| (167) | 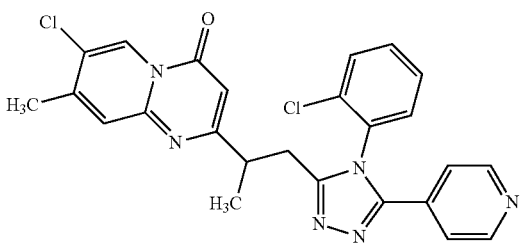 [SMILES: Cc1cc2nc(C(C)Cc3nnc(-c4ccncc4)n3-c3ccccc3Cl)cc(=O)n2cc1Cl] |
| (168) | 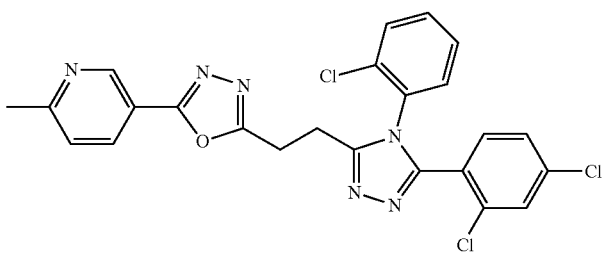 [SMILES: Cc1ccc(-c2nnc(CCc3nnc(-c4ccc(Cl)cc4Cl)n3-c3ccccc3Cl)o2)cn1] |

| Compound No. | Structure |
|---|---|
| (169) | 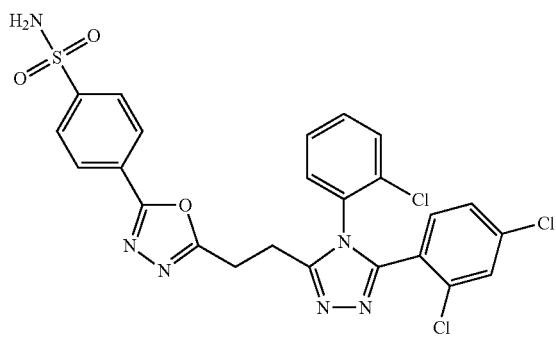 [SMILES: NS(=O)(=O)c1ccc(-c2nnc(CCc3nnc(-c4ccc(Cl)cc4Cl)n3-c3ccccc3Cl)o2)cc1] |
| (170) | 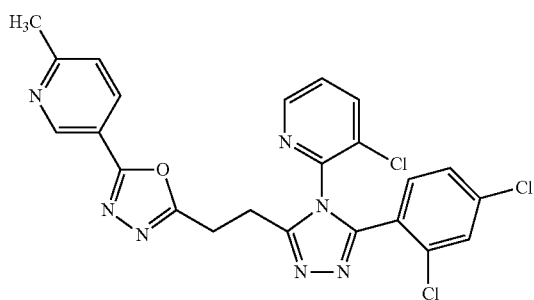 [SMILES: Cc1ccc(-c2nnc(CCc3nnc(-c4ccc(Cl)cc4Cl)n3-c3ncccc3Cl)o2)cn1] |
| (171) | 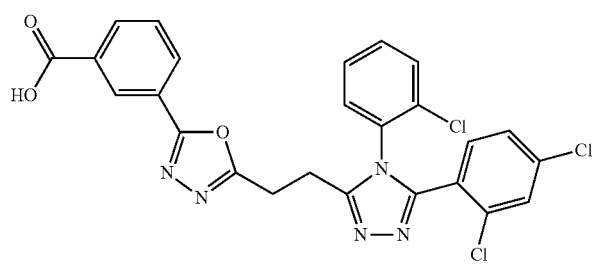 [SMILES: O=C(O)c1cccc(-c2nnc(CCc3nnc(-c4ccc(Cl)cc4Cl)n3-c3ccccc3Cl)o2)c1] |
| (172) | 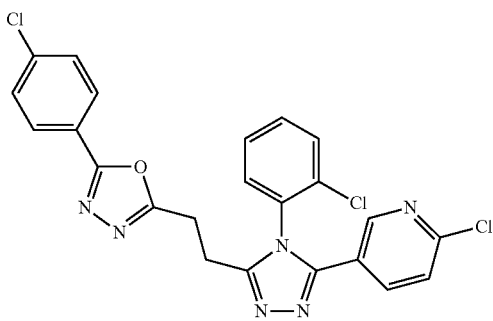 [SMILES: Clc1ccc(-c2nnc(CCc3nnc(-c4ccc(Cl)nc4)n3-c3ccccc3Cl)o2)cc1] |
| (173) | 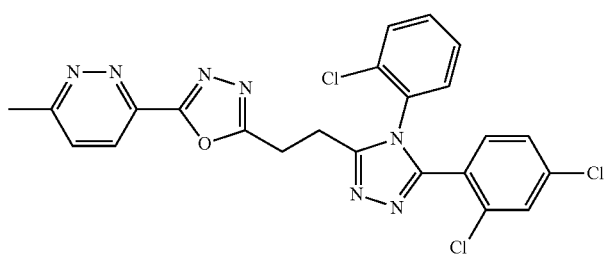 |

| Compound No. | Structure |
|---|---|
| (174) | 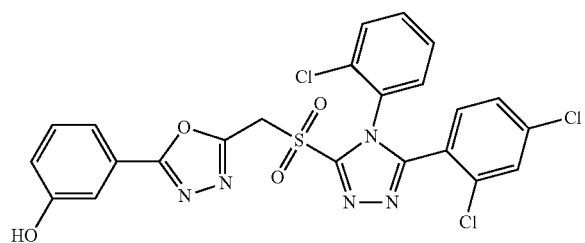 [SMILES: O=S(=O)(Cc1nnc(-c2cccc(O)c2)o1)c1nnc(-c2ccc(Cl)cc2Cl)n1-c1ccccc1Cl] |
| (175) | 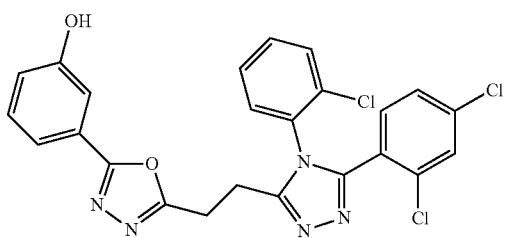 [SMILES: Oc1cccc(-c2nnc(CCc3nnc(-c4ccc(Cl)cc4Cl)n3-c3ccccc3Cl)o2)c1] |
| (176) | 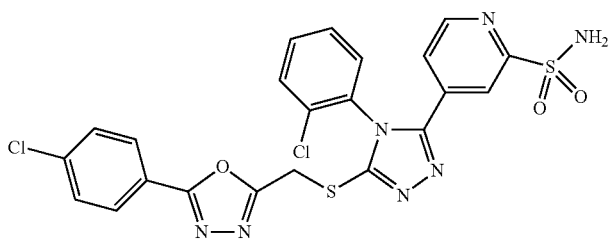 [SMILES: NS(=O)(=O)c1cc(-c2nnc(SCc3nnc(-c4ccc(Cl)cc4)o3)n2-c2ccccc2Cl)ccn1] |
| (177) | 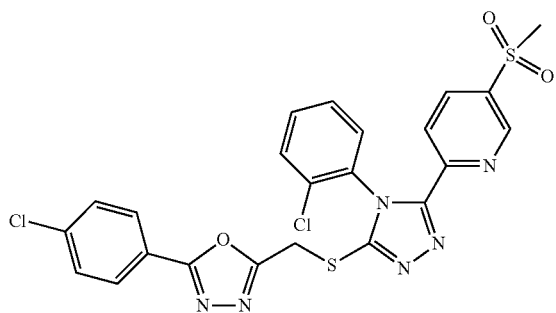 [SMILES: CS(=O)(=O)c1ccc(-c2nnc(SCc3nnc(-c4ccc(Cl)cc4)o3)n2-c2ccccc2Cl)nc1] |
| (178) | 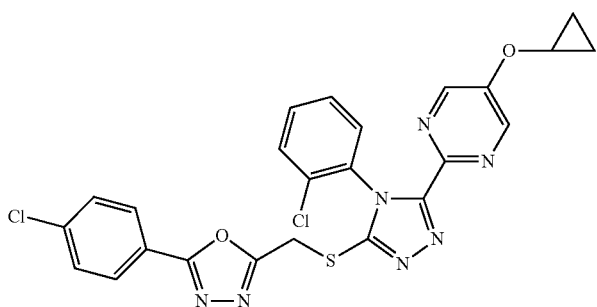 [SMILES: Clc1ccc(-c2nnc(CSc3nnc(-c4ncc(OC5CC5)cn4)n3-c3ccccc3Cl)o2)cc1] |
| (179) | 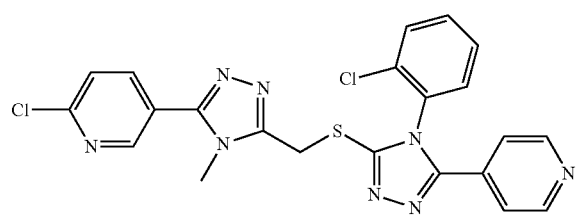 [SMILES: Cn1c(CSc2nnc(-c3ccncc3)n2-c2ccccc2Cl)nnc1-c1ccc(Cl)nc1] |

| Compound No. | Structure |
|---|---|
| (180) | 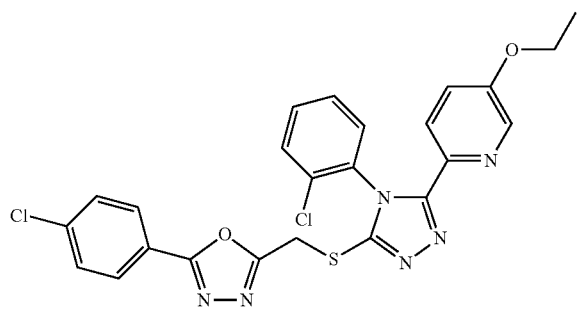 [SMILES: CCOc1ccc(-c2nnc(SCc3nnc(-c4ccc(Cl)cc4)o3)n2-c2ccccc2Cl)nc1] |

Particularly preferred compounds in accordance with the invention are Compound Nos. (1), (2), (3), (4), (5), (6), (7), (11), (18) and (19), especially Compound Nos. (1), (7), (11), (19) and their isomers, pharmaceutically acceptable salts thereof and prodrugs. More particularly preferred compounds in accordance with the invention are Compound Nos. (1) and (7), e.g. Compound No. (1).

Other preferred compounds according to the invention are Compound Nos. (43), (45), (46), (60), (68), (99), (100), (103), (108), (109), (110), (112), (113) and (132), their isomers, pharmaceutically acceptable salts thereof and prodrugs. Amongst these compounds, (43), (60), (108), (109), (110) and (112) are particularly preferred, especially (43) and (60), their isomers, pharmaceutically acceptable salts thereof and prodrugs.

Unless otherwise stated, all substituents are independent of one another.

In the case where a subscript is the integer 0 (i.e. zero), it is intended that the group to which the subscript refers is absent, i.e. there is a direct bond between the groups either side of that particular group or, in the case where the group to which the subscript refers is a terminal group (as in the case of group $R^1$), the group to which this is attached becomes the terminal group in the molecule.

Unless otherwise stated, any reference herein to a "bond" is intended to refer to a saturated bond.

In the case where an asterisk (*) is present in any of the structural formulae of any of the substituents provided herein, this is to be understood as indicating the point of attachment of that substituent to the remainder of the molecule. Where any of these formulae include two asterisks (denoting two points of attachment), either one of these may be linked to a desired point of attachment on the remainder of the molecule. The orientation of such structures specifically presented herein is not intended to imply that these must be linked in the orientation which is given.

Unless otherwise stated, the term "halo" or "halogen atom" may be fluoro, chloro, bromo, or iodo. Preferably, this is fluoro or chloro.

As used herein, the term "alkyl" refers to a saturated hydrocarbon group and is intended to cover both straight-chained and branched alkyl groups. Examples of such groups include methyl, ethyl, n-propyl, iso-propyl, n-butyl, iso-butyl, sec-butyl, tert-butyl, n-pentyl, iso-pentyl, neo-pentyl, n-hexyl, etc. An alkyl group preferably contains from 1-6 carbon atoms, e.g. 1-4 carbon atoms. Unless otherwise stated, any alkyl group mentioned herein may optionally be substituted by one or more groups, which may be identical or different, for example hydroxy, alkoxy, acyloxy, amino or halogen atoms (e.g. F, Cl or Br).

As used herein, the term "alkenyl" refers to an alkyl group having one or more carbon-carbon double bonds and includes both straight-chained and branched alkenyl groups. The term "$C_{2-6}$ alkenyl" refers to an alkenyl group having from 2 to 6 carbon atoms and one or more (e.g. one or two) double bonds. Examples of such groups include vinyl, allyl, propenyl, iso-propenyl, butenyl, iso-butenyl, crotyl, pentenyl and hexenyl. Unless otherwise stated, any alkenyl group mentioned herein may optionally be substituted by one or more groups, which may be identical or different, for example hydroxy, alkoxy, acyloxy, amino or halogen atoms (e.g. F, Cl or Br).

As used herein, the term "alkynyl" refers to an alkyl group having one or more carbon-carbon triple bonds and includes both straight-chained and branched alkynyl groups. Unless otherwise stated, any alkynyl group mentioned herein may optionally be substituted by one or more groups, which may be identical or different, for example hydroxy, alkoxy, acyloxy, amino or halogen atoms (e.g. F, Cl or Br).

As used herein, the term "haloalkyl" refers to an alkyl group having one or more halo substituents. Examples of such groups include —$CH_2F$, —$CHF_2$, —$CF_3$, —$CCl_3$, —$CHCl_2$, —$CH_2 CF_3$, etc.

As used herein, the term "alkylene" refers to a linking alkyl group and is intended to cover any straight-chained or branched alkylene group. Examples of such groups include methylene, ethylene, ethane-1,1-diyl, propylene, propane-2, 2-diyl, 1-methylethylene, butylene, 1-methylpropylene, 1,1-dimethylethylene, 1,2-dimethylethylene, etc.

As used herein, the term "cycloalkyl" is intended to cover any cyclic alkyl group. Such groups can include mono- or polycyclic ring systems (e.g. having 2 fused rings). These may have from 3-20 carbon atoms, preferably 3-14 carbons, more preferably 3-10 carbons, e.g. 3-7 carbons. Examples of such groups include cyclopropyl, cyclobutyl, cyclopentyl, cyclohexyl, cycloheptyl, etc.

As used herein, the term "unsaturated heterocyclic ring" is intended to cover any 5-, 6- or 7-membered, mono-, di or tri-unsaturated heterocyclic ring which contains at least one heteroatom selected from nitrogen, oxygen and sulphur. Where such rings are bicyclic, these may contain up to 10 ring atoms, with each ring including at least one heteroatom selected from nitrogen, oxygen and sulphur. The heterocyclic ring structure (whether mono- or bicyclic) may be linked to the remainder of the molecule through a carbon atom or, if present, through a nitrogen atom. For example, it may be linked through two carbon atoms, through two nitrogen atoms, or through one carbon and one nitrogen atom. Preferably it will be linked to the remainder of the molecule through two carbon atoms. Unless otherwise stated, any heterocyclic ring mentioned herein may optionally be substituted by one or more groups, which may be identical or different, for example hydroxy, $C_{1-6}$ alkyl, $C_{1-6}$ alkoxy, amino, cyano, nitro or halogen atoms (e.g. F, Cl or Br). A heterocyclic ring may further contain one or more carbonyl or thiocarbonyl functionalities such that this includes oxo and thio-systems.

Illustrative examples of "unsaturated heterocyclic rings" are the heterocycles pyrrole, 2H-pyrrole, furan, pyrroline, thiophene, pyrazole, imidazole, oxazole, isoxazole, pyrazoline, imidazoline, thiazole, isothiazole, thiadiazole, pyridine, 2H-pyran, 4H-pyran, pyridazine, pyrimidine, pyrazine, 1,3-dioxine, 1,4-dioxine and triazole. Of these, thiazole, thiadiazole, pyrimidine, pyridazine, pyrazole, thiophene and triazole are particularly preferred.

As used herein, the term "saturated heterocyclic ring" is intended to cover any 3-, 4-, 5-, 6- or 7-membered heterocyclic ring which contains at least one heteroatom selected from nitrogen, oxygen and sulphur. The ring may be linked to the remainder of the molecule through two carbon atoms, through two nitrogen atoms, or through one carbon and one nitrogen atom. Preferably, the ring will be linked to the rest of the molecule by two bonds extending from the same ring carbon atom.

As used herein, the term "aryl" is intended to cover aromatic ring systems. Such ring systems may be monocyclic or polycyclic (e.g. bicyclic) and contain at least one unsaturated aromatic ring. Where these contain polycyclic rings, these may be fused. Preferably such systems contain from 6-20 carbon atoms, e.g. either 6 or 10 carbon atoms. Examples of such groups include phenyl, 1-napthyl and 2-napthyl. A preferred aryl group is phenyl. Unless stated otherwise, any "aryl" group may be substituted by one or more substituents, which may be identical or different, for example $C_{1-4}$ alkyl groups, hydroxy, methoxy, trifluoromethoxy and halo groups.

As used herein, the term "heteroaryl" is intended to cover heterocyclic aromatic groups. Such groups may be monocyclic or bicyclic and contain at least one unsaturated heteroaromatic ring system. Where these are monocyclic, these comprise 5- or 6-membered rings which contain at least one heteroatom selected from nitrogen, oxygen and sulphur and contain sufficient conjugated bonds to form an aromatic system. Where these are bicyclic, these may contain from 9-11 ring atoms. Examples of heteroaryl groups include thiophene, thienyl, pyridyl, thiazolyl, furyl, pyrrolyl, triazolyl, imidazolyl, oxadiazolyl, oxazolyl, pyrazolyl, imidazolonyl, oxazolonyl, thiazolonyl, tetrazolyl, thiadiazolyl, benzimidazolyl, benzooxazolyl, benzofuryl, indolyl, isoindolyl, pyridonyl, pyridazinyl, pyrimidinyl, imidazopyridyl, oxazopyridyl, thiazolopyridyl, imidazopyridazinyl, oxazolopyridazinyl, thiazolopyridazinyl and purinyl. Unless stated otherwise, any "heteroaryl" may be substituted by one or more substituents, which may be identical or different, for example $C_{1-4}$ alkyl groups, hydroxy, methoxy, trifluoromethoxy and halo groups.

The term "prodrug" is intended to encompass any compound which under physiological conditions is converted into any of the compounds herein described, i.e. a compound of formula I, II, Ia, IIa, Ib, IIb, Ic, IIc, IId or IIe. Suitable prodrugs include compounds which are hydrolysed under physiological conditions to the desired molecule.

The compounds according to the invention may be prepared from readily available starting materials using synthetic methods known in the art. Preferably, the compounds are obtained in accordance with the following methods which form part of the invention:

(a) (in order to prepare compounds of formula I or II in which $L^1$ represents a group —$(CH_2)_p$—X—$(CH_2)_q$— in which X is O, S or NH; p is an integer from 1 to 5; q is an integer from 0 to 4; and the sum of p and q is an integer from 1 to 5):

reacting a compound of general formula III:

$(R^1)_m$—$(Z^1)_n$—$(CH_2)_p$-L     (III)

(wherein $R^1$, $Z^1$, m, n and p are as hereinbefore defined; and L denotes a leaving group such as a halogen atom, e.g. Cl or Br)

with a compound of general formula IV:

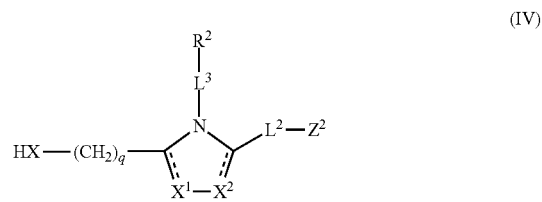

(wherein $X^1$, $X^2$, $Z^2$, $R^2$, $L^2$, $L^3$, X and q are as hereinbefore defined).

The reaction is conveniently carried out in a solvent or mixture of solvents, such as for example a polar solvent such as acetone, DMF, DMSO or dioxane, optionally in the presence of an inorganic or organic base, expediently at temperatures up to 150° C., preferably at temperatures between −20 and 80° C.

(b) (in order to prepare compounds of formula I or II in which $L^1$ represents a group —$(CH_2)_p$—X—$(CH_2)_q$— in which X is O, S or NH; p is an integer from 0 to 4; q is an integer from 1 to 5; and the sum of p and q is an integer from 1 to 5): reacting a compound of general formula V:

$(R^1)_m$—$(Z^1)_n$—$(CH_2)_p$—XH     (V)

(wherein $R^1$, $Z^1$, m, n, p and X are as hereinbefore defined) with a compound of general formula VI:

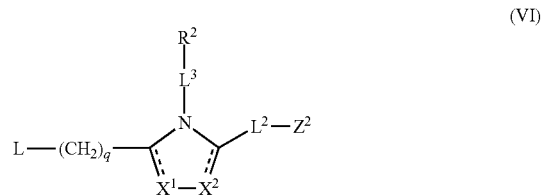

(wherein $X^1$, $X^2$, $Z^2$, $R^2$, $L^2$, $L^3$ and q are as hereinbefore defined; and L denotes a leaving group such as a halogen atom, e.g. Cl or Br).

The reaction is conveniently carried out in a solvent or mixture of solvents, such as for example a polar solvent such as acetone, DMF, DMSO or dioxane, optionally in the presence of an inorganic or organic base, expediently at temperatures up to 150° C., preferably at temperatures between −20 and 80° C.

(c) (in order to prepare compounds of formula I or II in which $X^1$ and $X^2$ are both N and $Z^1$ is absent):
reacting a compound of general formula VII:

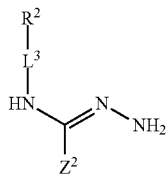
(VII)

(wherein $Z^2$, $R^2$ and $L^3$ are as hereinbefore defined) with a compound of general formula VIII:

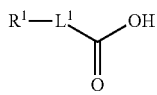
(VIII)

(wherein $R^1$ and $L^1$ are as hereinbefore defined).

The reaction is conveniently carried out in a solvent or mixture of solvents, such as for example a polar solvent such as acetone, DMF, DMSO or dioxane, at a temperature between 0 and 100° C. A particular example of this reaction is where $L^1$ is a group —$CH_2$—$N(CH_3)$—$(CH_2)_2$— and $R^1$ is hydrogen.

(d) (in order to prepare compounds of formula I or II in which $L^1$ represents a group —$(CH_2)_p$—$SO_2$—$(CH_2)_q$— in which p is an integer from 0 to 5; q is an integer from 0 to 5; and the sum of p and q is an integer from 1 to 5):
oxidising a compound of general formula IX:

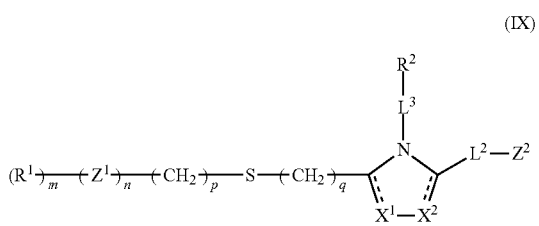
(IX)

(wherein $X^1$, $X^2$, $Z^1$, $Z^2$, $R^1$, $R^2$, $L^2$, $L^3$, m, n, p and q are as hereinbefore defined).

Suitable oxidising agents and conditions capable of oxidising sulfide to sulfone include: magnesium monoperoxyphthalate (MMPP) in dichloromethane on silica gel support in methylene chloride solvent at ambient temperature; $NaIO_4$ in dichloromethane at ambient temperature; $H_2O_2$/MTO (methyltrioxorhenium)/ethanol at ambient temperature; oxone in acetonitrile at 0° C.; and meta-chloroperoxybenzoic acid which may be used in dichloromethane at ambient temperature.

(e) (in order to prepare compounds of formula I or II in which $Z^2$ represents a group:

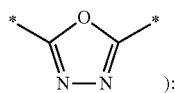
):

dehydrating a compound of the general formula X:

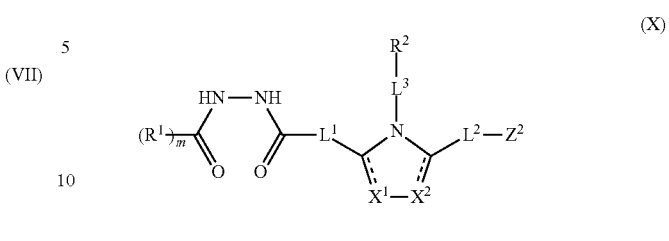
(X)

(wherein $X^1$, $X^2$, $Z^2$, $R^1$, $R^2$, $L^1$, $L^2$, $L^3$ and m are as hereinbefore defined);

Any conventional agent may be used to effect dehydration. A particular example is phosphoryl chloride.

(f) if desired, resolving a compound of general formula I or II thus obtained into the stereoisomers thereof; and/or (g) converting a compound of general formula I or II thus obtained into a salt thereof, particularly a pharmaceutically acceptable salt thereof.

The compounds used as starting materials are either known from the literature or may be commercially available. Alternatively, these may be obtained by methods known from the literature.

The invention includes all optical isomers and stereoisomers of the compounds herein disclosed. In particular, the invention extends to the enantiomers of any of the compounds having a chiral centre either in the group $L^1$, $Z^1$ or $R^1$. Enantiomers of those compounds having a chiral centre in the linker group $L^1$ form a particularly preferred aspect of the invention. Examples of such compounds are the enantiomers of compounds (99) and (100) having the following structures:

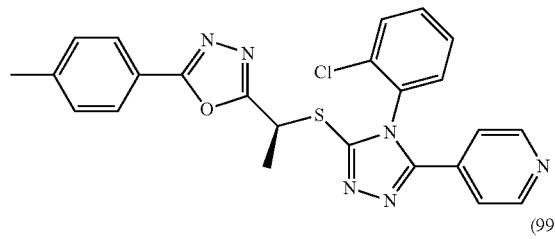
(99a)

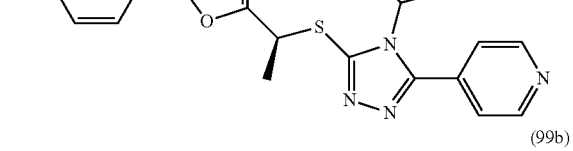
(99b)

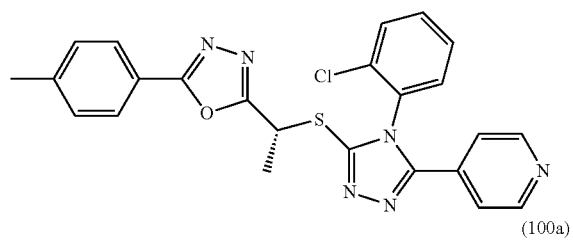
(100a)

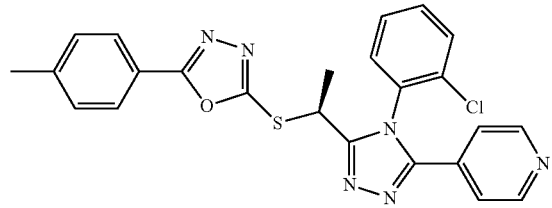

-continued (100b)

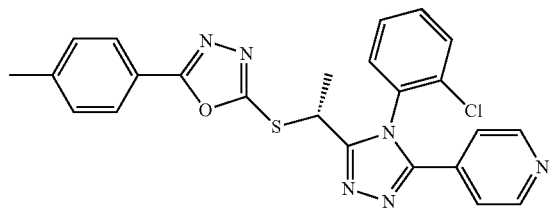

The compounds of general formulae I, II, Ia, IIa, Ib, IIb, Ic, IIc, IId and IIe may be resolved into their enantiomers and/or diastereomers. For example, where these contain only one chiral centre, these may be provided in the form of a racemate or may be provided as pure enantiomers, i.e. in the R- or S-form. Any of the compounds which occur as racemates may be separated into their enantiomers by methods known in the art, such as column separation on chiral phases or by recrystallisation from an optically active solvent. Those compounds with at least two asymmetric carbon atoms may be resolved into their diastereomers on the basis of their physical-chemical differences using methods known per se, e.g. by chromatography and/or fractional crystallisation, and where these compounds are obtained in racemic form, they may subsequently be resolved into the enantiomers.

The compounds according to the invention may be converted into a salt thereof, particularly into a pharmaceutically acceptable salt thereof with an inorganic or organic acid or base. Acids which may be used for this purpose include hydrochloric acid, hydrobromic acid, sulphuric acid, sulphonic acid, methanesulphonic acid, phosphoric acid, fumaric acid, succinic acid, lactic acid, citric acid, tartaric acid, maleic acid, acetic acid, trifluoroacetic acid and ascorbic acid. Bases which may be suitable for this purpose include alkali and alkaline earth metal hydroxides, e.g. sodium hydroxide, potassium hydroxide or cesium hydroxide, ammonia and organic amines such as diethylamine, triethylamine, ethanolamine, diethanolamine, cyclohexylamine and dicyclohexylamine. Procedures for salt formation are conventional in the art.

In a further aspect there is provided pharmaceutical formulations comprising a compound of formula I, II, Ia, IIa, Ib, IIb, Ic, IIc, IId or IIe as herein defined, or a pharmaceutically acceptable salt thereof, together with one or more pharmaceutically acceptable carriers or excipients.

The compounds according to the invention and their pharmaceutically acceptable salts have valuable pharmacological properties, particularly an inhibitory effect on β-catenin. In view of their ability to inhibit signaling in the Wnt pathway, and in particular to reduce the levels of nuclear β-catenin, the compounds according to the invention and their pharmaceutically acceptable salts are suitable for the treatment and/or prevention of any condition or disease which may be affected by over-activation of signaling in the Wnt pathway, in particular those conditions or diseases which involve activation of β-catenin.

The term "Wnt signaling pathway" is used to refer to the chain of events normally mediated by Wnt, LRP (LDL-receptor related protein), Frizzled and β-catenin, among others, and resulting in changes in gene expression and other phenotypic changes typical of Wnt activity.

The Wnt pathway plays a central role in the pathology of a variety of cancers. The compounds of the invention are thus particularly suitable for preventing and/or retarding proliferation of tumor cells, in particular carcinomas such as adenocarcinomas. More specifically, the compounds are effective in treatment and/or prevention of the following cancers: colon cancers (such as colorectal cancer), pancreatic cancer (e.g. pancreas adenocarcinoma), gastric cancer, liver cancers (e.g. hepatocellular and hepatoblastoma carcinomas), Wilms tumor of the kidney, medulloblastoma, skin cancers (e.g. melanoma), non-small cell lung cancer, cervical cancer, ovarian cancers (e.g. ovarian endometrial cancer), bladder cancer, thyroid cancers (e.g. anaplastic thyroid cancer), head and neck cancer, breast cancer and prostate cancer. Particularly preferably, the compounds herein described may be used in the treatment and/or prevention of breast cancer, non-small cell lung cancer, ovarian, thyroid, colorectal and pancreatic cancers. Treatment or prevention of breast, non-small cell lung, pancreatic and colorectal cancers represents a particularly preferred aspect of the invention.

As used herein, the term "proliferation" refers to cells undergoing mitosis. The term "retarding proliferation" indicates that the compounds inhibit proliferation of a cancer cell. In preferred embodiments, "retarding proliferation" indicates that DNA replication is at least 10% less than that observed in untreated cells, more preferably at least 25% less, yet more preferably at least 50% less, e.g. 75%, 90% or 95% less than that observed in untreated cancer cells.

The term "carcinoma" refers to any malignant growth which arises from epithelial cells. Exemplary carcinomas include basal cell carcinoma, squamous cell carcinoma and adenocarcinoma. Adenocarcinomas are malignant tumors originating in the glandular epithelium and include colorectal, pancreatic, breast and prostate cancers.

Viewed from a further aspect the invention thus provides a compound of formula I, II, Ia, IIa, Ib, IIb, Ic, IIc, IId or IIe, or a pharmaceutically acceptable salt thereof, for use in therapy.

Unless otherwise specified, the term "therapy" as used herein is intended to include both treatment and prevention.

In a still further aspect the invention provides a compound of formula I, II, Ia, IIa, Ib, IIb, Ic, IIc, IId or IIe, or a pharmaceutically acceptable salt thereof, for use in the treatment or prevention of colon cancers (such as colorectal cancer), pancreatic cancer, gastric cancer, liver cancers (e.g. hepatocellular and hepatoblastoma carcinomas), Wilms tumor of the kidney, medulloblastoma, skin cancers (e.g. melanoma), non-small cell lung cancer, cervical cancer, ovarian endometrial cancer, bladder cancer, anaplastic thyroid cancer, head and neck cancer, breast cancer or prostate cancer.

In another aspect the invention provides the use of a compound of formula I, II, Ia, IIa, Ib, IIb, Ic, IIc, IId or IIe, or a pharmaceutically acceptable salt thereof, in the manufacture of a medicament for use in a method of treatment or prevention of colon cancers (such as colorectal cancer), pancreatic cancer, gastric cancer, liver cancers (e.g. hepatocellular and hepatoblastoma carcinomas), Wilms tumor of the kidney, medulloblastoma, skin cancers (e.g. melanoma), non-small cell lung cancer, cervical cancer, ovarian endometrial cancer, bladder cancer, anaplastic thyroid cancer, head and neck cancer, breast cancer or prostate cancer.

Also provided is a method of treatment of a human or non-human animal body to combat or prevent colon cancers (such as colorectal cancer), pancreatic cancer, gastric cancer, liver cancers (e.g. hepatocellular and hepatoblastoma carcinomas), Wilms tumor of the kidney, medulloblastoma, skin cancers (e.g. melanoma), non-small cell lung cancer, cervical cancer, ovarian endometrial cancer, bladder cancer, anaplastic thyroid cancer, head and neck cancer, breast cancer, or prostate cancer, said method comprising the step of administering to said body an effective amount of a compound of formula I, II, Ia, IIa, Ib, IIb, Ic, IIc, IId or IIe as herein defined or a pharmaceutically acceptable salt thereof.

The dosage required to achieve the desired activity will depend on the compound which is to be administered, the patient, the nature and severity of the condition, the method and frequency of administration and may be varied or adjusted according to choice. Typically, the dosage may be expected to be in the range from 1 to 100 mg, preferably 1 to 30 mg (when administered intravenously) and from 1 to 1000 mg, preferably from 1 to 200 mg (when administered orally).

The compounds of the invention may be formulated with one or more conventional carriers and/or excipients according to techniques well known in the art. Typically, the compositions will be adapted for oral or parenteral administration, for example by intradermal, subcutaneous, intraperitoneal or intravenous injection. Suitable pharmaceutical forms thus include plain or coated tablets, capsules, suspensions and solutions containing the active component optionally together with one or more conventional inert carriers and/or diluents, such as corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propylene glycol, stearylalcohol, carboxymethylcellulose or fatty substances such as hard fat or suitable mixtures of any of the above.

The pharmacological properties of the compounds of the invention can be analysed using standard assays for functional activity. Detailed protocols for testing of the compounds of the invention are provided in the Examples.

The invention will now be described in more detail in the following non-limiting Examples and with reference to the accompanying figures in which:

FIG. 1 shows the results of a compound specificity assay in a reporter system using Luciferase (Luc) measurement in HEK293 cells transfected with the SuperTOPFlash plasmid and treated with compound No. 1 at 0.1-10 µM. Positive control (+) 30% Wnt3a-CM and negative control (−) no stimulation. The dashed line indicates the $IC_{50}$ threshold. Values in Luc assays are the mean of a minimum of three independent experiments.

FIG. 2 shows the effects of 1 or 10 (or 25) µM of compound No. 1 in: A) Shh Light2 cells (Gli 1-Luc)—positive control (+) Shh-CM, negative control (−) no stimulation, Shh inhibitor (cyclopamine) as further control; B) HEK293 cells transfected with NF-κB reporter plasmid (NF-κB-Luc)—positive control (+) 10 ng/ml TNFα and negative control (−) no stimulation (values in Luc assays are the mean of a minimum of three independent experiments); and C) SW480 cells—dose-dependent inhibition of ST-d1EGFP reporter depicted as the ratio of ST-d1EGFP values versus CMV-d1EGFP expression in parallel control SW480 cell line.

Figure 7:
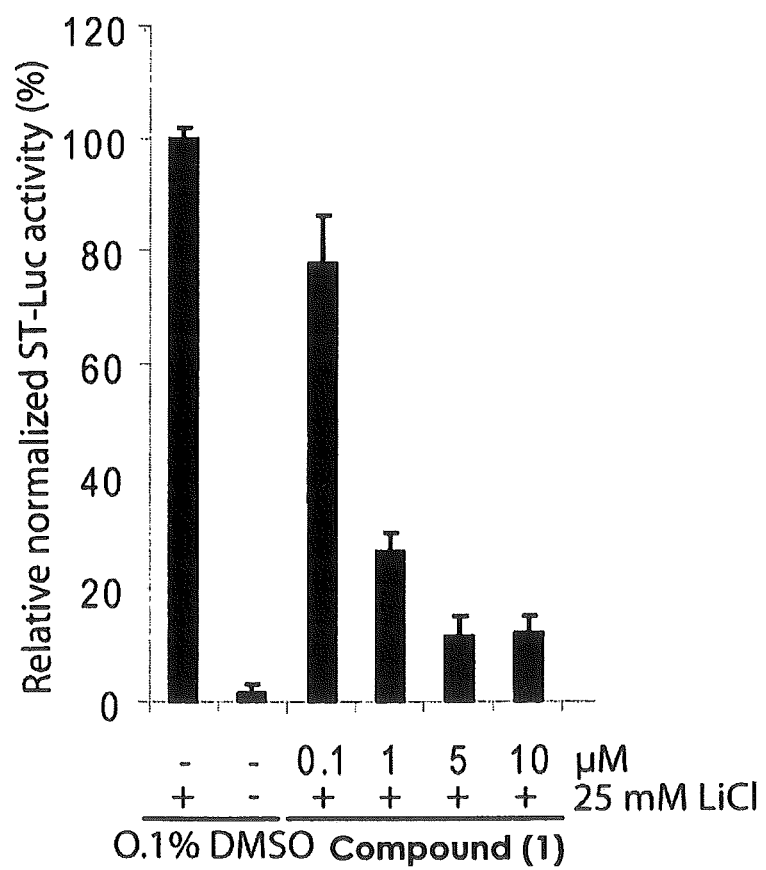

FIG. 7 shows that the intracellular stimulation of the canonical Wnt pathway by LiCl at the level of GSK-3β is counteracted by compound No. 1 in the 0.1-10 µM range. Positive control (+) 25 mM LiCl and negative control (−) without LiCl. Results shown are averages of three independent experiments.

FIG. 8 shows changes in β-catenin levels after treatment of cells with compound No. 1: A) Western blot of lysates from SW480 cells with antibodies against β-catenin. The total amount of normal β-catenin (β-catenin) decreases 72 hours after adding compounds and in particular the active β-catenin (non-phosphorylated active β-catenin, ABC) is barely detectable at 1 µM of compound No. 1. A degradable form (phosphorylated at the N-terminal, pβ-catenin) is increased temporarily 24 hours after adding compound No. 1 (representative data from several assays are shown); and B) immunohistochemistry with antibodies against β-catenin in SW480 cells (β-catenin) and merged (β-catenin DAPI) pictures. The amount of the nuclear (and probably also cytoplasmic) β-catenin is greatly diminished after exposure to compound No. 1 for 72 hours. β-catenin in cellular membranes is present.

Figure 9:
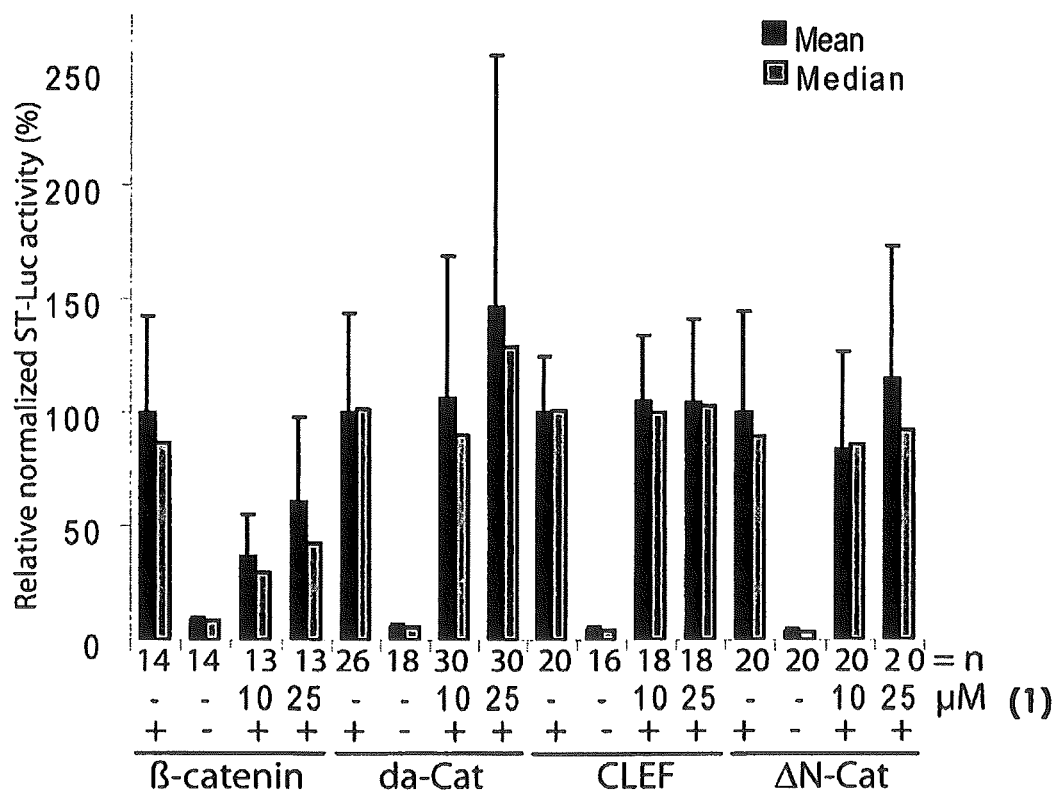

FIG. 9 shows HEK293 cells transiently co-transfected with ST-Luc reporter and full-length β-catenin, β-catenin with point mutations at phospholylation sites (da-Cat), N-terminal deletion of β-catenin (ΔN-Cat) or β-catenin transactivation domain fused to LEF-1 (CLEF). 10-20 fold induction was achieved by diluting plasmid constructs in the range of nanograms per 48-well. "n" represents the number of single wells from multiple independent experiments. Relatively high standard deviations are due to weak reproducibility of transfection efficiency with very small doses of plasmids (nanograms per well).

Figure 10:
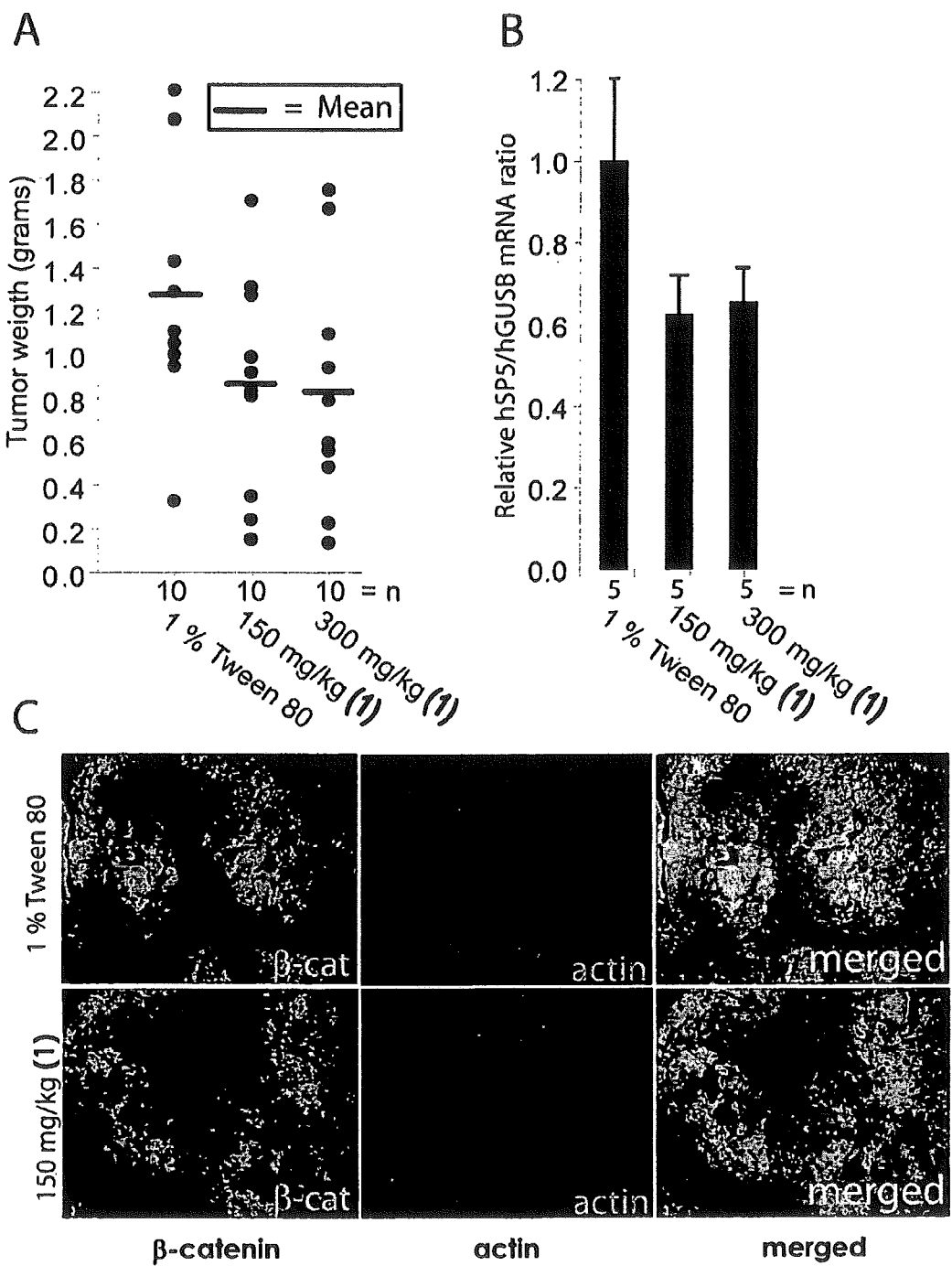

FIG. 10 shows the results of xenografts of colon cancer cells in immunodeficient mice: A) dot plot of total tumor weight after 29 days treatment with compound No. 1—the line (−) depicts the mean values of tumor weights; B) real-time RT-PCR with detection of Sp5 mRNA normalized to hGUSB mRNA in tumors from treated and control animal cohorts; and C) immunohistochemistry with antibodies against β-catenin labelling grafted SW480 cells and antibody against activated stroma (anti-smooth muscle actin)—no change in stroma versus SW480 cell distribution could be seen.

Figure 11:
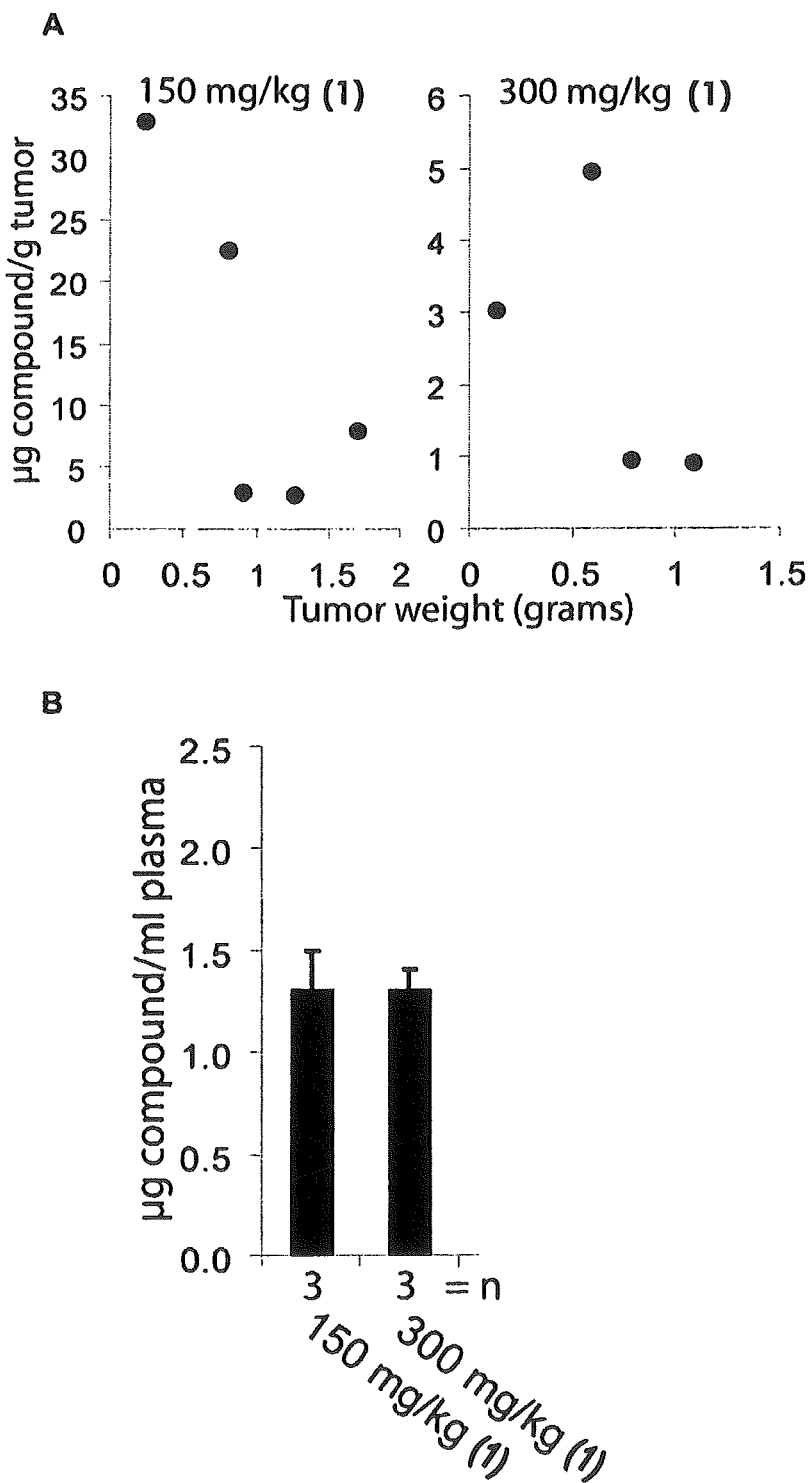

FIG. 11 shows the levels of compound No. 1 in treated animals. Accumulation of compound No. 1 in tumors (A) and in plasma (B) is shown 29 days after injection.

Figure 12:
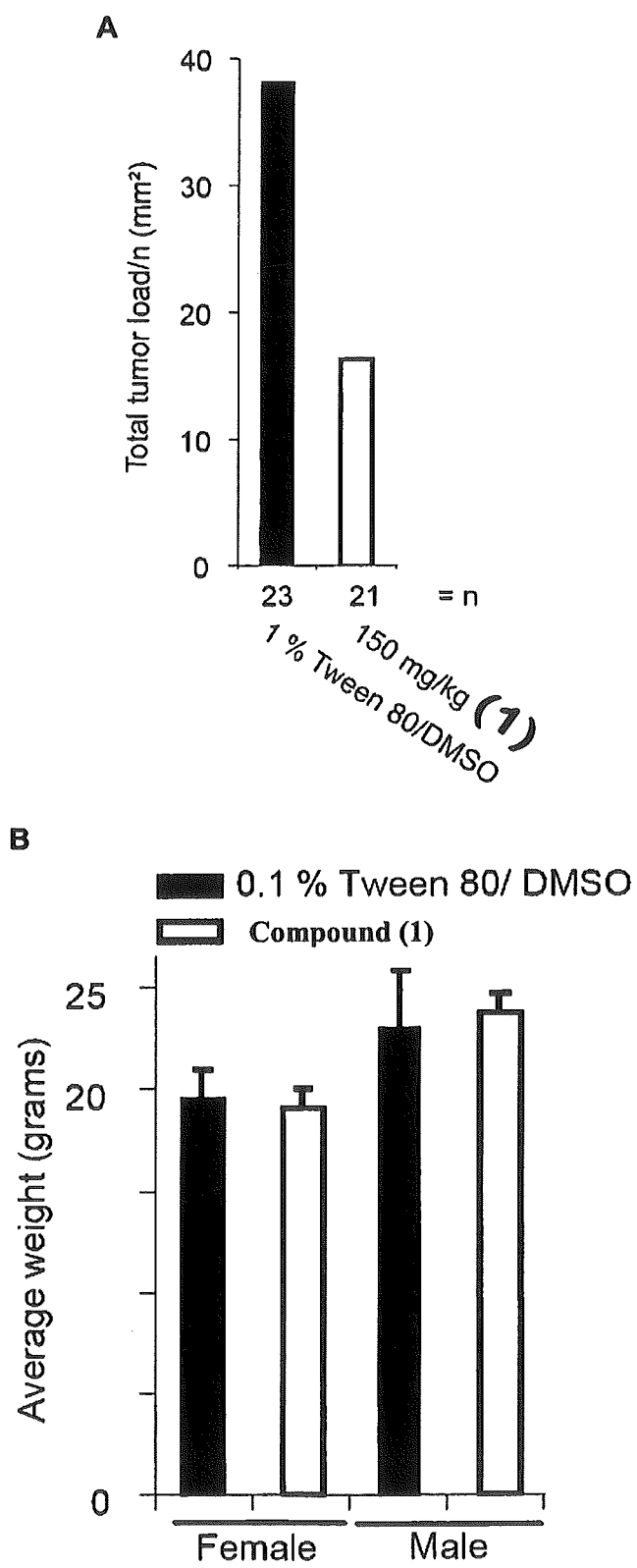

FIG. 12 shows A) the sum of all tumors in the small intestine (in $mm^2$) after treatment with compound No. 1; and B) the body weight of $APC^{Min}$ mice injected with compound No. 1 or DMSO.

Figure 13:
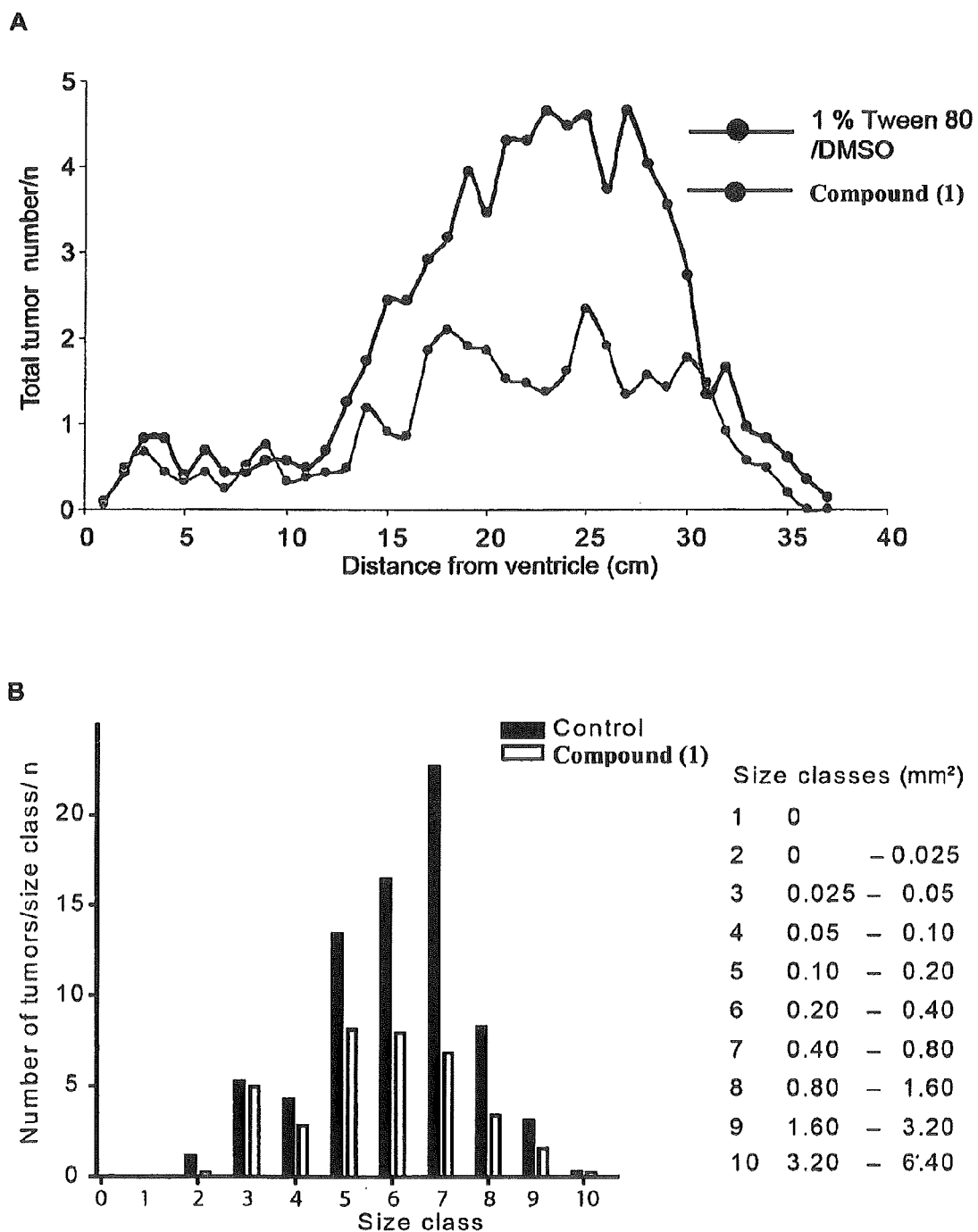

FIG. 13 shows the effect of compound No. 1 on incidence of adenoma polyposis in APC(+/−) mice. A) is a dot plot with lines showing the distribution and frequency of tumours along the small intestine starting from the ventricle (cm). B)

shows a histogram with the number of tumours in the small intestine in different size classes (mm²) as listed in the table to the right of the histogram.

The compounds prepared in Examples 1 to 8 are intermediates for use in preparing the end products in Examples 9 to 17. The compounds prepared in Examples 9 to 17 and 33 to 65 are final products of formula I.

EXAMPLE 1

Preparation of Intermediate 1.4

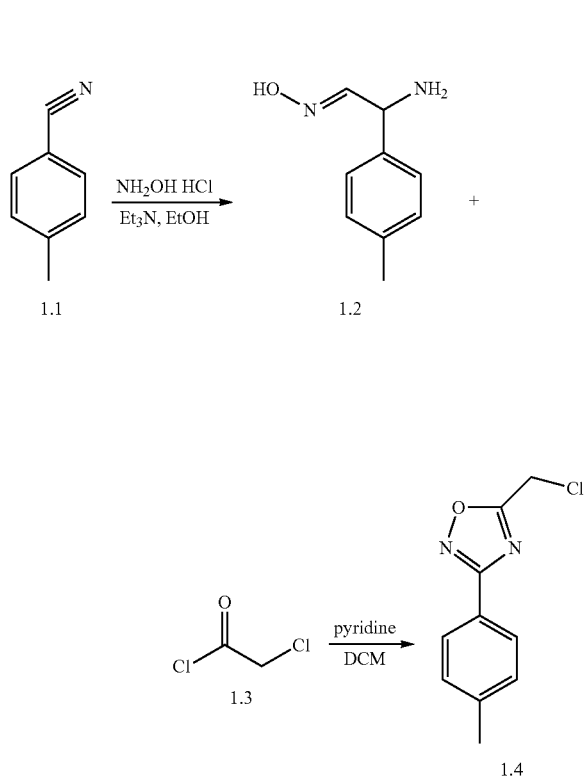

(a) Preparation of Compound 1.2:

To a stirred suspension of NH$_2$OH HCl (2.9 g, 43 mmol) in EtOH was added Et$_3$N (5.3 g, 52 mmol), then it was stirred for 30 mins at ambient temperature. Compound 1.1 (5 g, 43 mmol) was added and warmed to 50° C. overnight. The resulting solution was concentrated directly in vacuum to remove EtOH and residue was taken up by Et$_2$O and extracted by 2N HCl solution. The HCl layer was adjusted to pH 7-8 with 2N sodium hydroxide solution and a white solid formed. This was filtrated and dried under vacuum at 50° C. overnight to give a pale solid (4.5 g). Yield: 64%.

$^1$H NMR (400 MHz, DMSO-d6) δ (ppm): 9.53 (1H, s, O—H), 7.56-7.54 (2H, dd, Ph-H), 7.18-7.16 (2H, dd, Ph-H), 5.74 (2H, s, —NH$_2$).

(b) Preparation of Compound 1.4:

To a stirred suspension of Compound 1.2 (500 mg, 3.3 mmol) in DCM was added pyridine (443 mg, 3.9 mmol) and Compound 1.3 (443 mg, 3.9 mmol) with ice-bath. The mixture was then stirred for three hours at ambient temperature. After that, it was warmed to 40° C. and stirred overnight. The resulting solution was purified by silica gel column to give a white solid (350 mg). Yield: 51%.

$^1$H NMR (400 MHz, DMSO-d6) δ (ppm): 7.92-7.90 (2H, dd, Ph-H), 7.40-7.38 (2H, dd, Ph-H), 5.18 (2H, s, —CH$_2$—), 2.39 (3H, s, —CH$_3$—).

EXAMPLE 2

Preparation of Intermediate 2.4

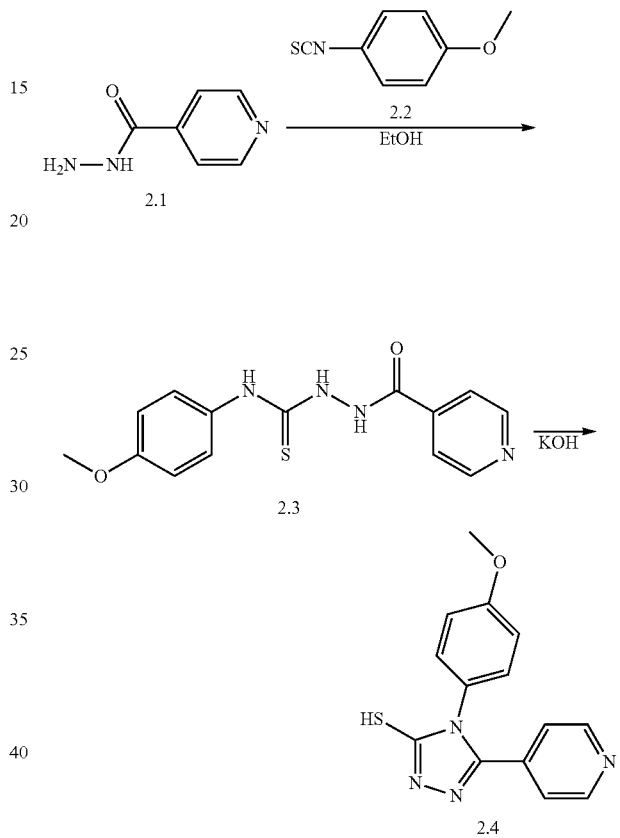

(a) Preparation of Compound 2.3:

To a stirred suspension of compound 2.1 (1.37 g, 10 mmol) in 30 ml EtOH was added Compound 2.2 (1.65 g, 10 mmol). Then it was refluxed for one hour and the white precipitate (Compound 2.3, 2.2 g) was collected by filtration. Yield: 73%.

$^1$H NMR (400 MHz, DMSO-d6) δ (ppm): 10.84 (1H, s, —NH), 9.77-9.74 (2H, d, —NH), 8.77-8.75 (2H, dd, Py-H), 7.85-7.83 (2H, dd, Py-H), 7.26-7.24 (2H, dd, Ph-H), 6.91-6.88 (2H, dd, Ph-H), 3.74 (3H, s, —CH$_3$O—). ESI MS: 303 ([M+H]$^+$)

(b) Preparation of Compound 2.4:

A stirred suspension of Compound 2.3 (2 g, 6.6 mmol) in 2N KOH solution was heated to 80° C. for 2 hours. After the reaction mixture was cooled down to ambient temperature, 3N HCl was added to acidify the solution. The white precipitate (Compound 2.4, 1.7 g) was collected by filtration. Yield: 90%.

$^1$H NMR (400 MHz, DMSO-d6) δ (ppm): 14.31 (1H, s, —SH), 8.59-8.58 (2H, dd, Py-H), 7.34-7.31 (2H, dd, Py-H), 7.26-7.24 (2H, dd, Ph-H), 7.07-7.05 (2H, dd, Ph-H), 3.80 (3H, s, —CH₃O—). ESI MS: 285 ([M+H]⁺)

EXAMPLE 3

Preparation of Intermediate 3.4

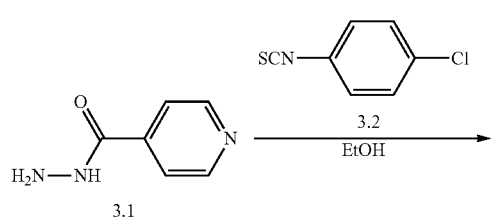

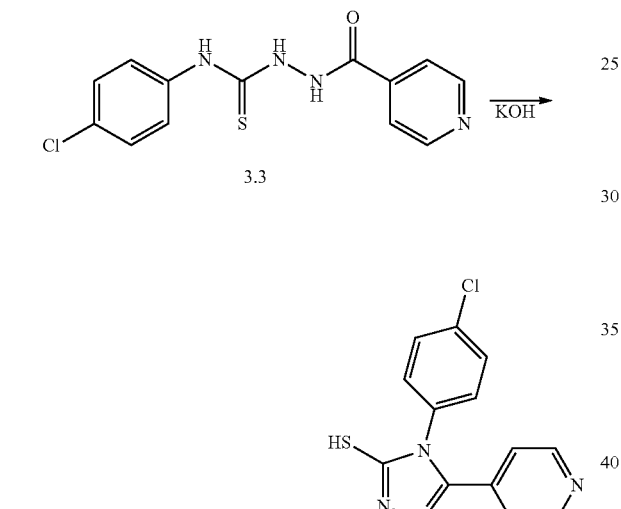

(a) Preparation of Compound 3.3:

To a stirred suspension of compound 3.1 (1.37 g, 10 mmol) in 30 ml EtOH was added Compound 3.2 (1.7 g, 10 mmol). Then it was refluxed for one hour and the white precipitate (Compound 3.3, 2 g) was collected by filtration. Yield: 65%.

¹H NMR (400 MHz, DMSO-d6) δ (ppm): 10.84 (1H, s, —NH), 9.87 (2H, s, —NH), 8.78-8.77 (2H, dd, Py-H), 7.85-7.84 (2H, dd, Py-H), 7.50-7.47 (2H, dd, Ph-H), 7.40-7.38 (2H, dd, Ph-H). ESI MS: 307 ([M+H]⁺)

(b) Preparation of Compound 3.4:

A stirred suspension of Compound 3.3 (1.6 g, 5.2 mmol) in 2N KOH solution was heated to 80° C. for 2 hours. After the reaction mixture was cooled down to ambient temperature, 3N HCl was added to acidify the solution. The white precipitate (Compound 3.4, 1.2 g) was collected by filtration. Yield: 80%.

¹H NMR (400 MHz, DMSO-d6) δ (ppm): 14.39 (1H, s, —SH), 8.61-8.60 (2H, dd, Py-H), 7.63-7.61 (2H, dd, Py-H), 7.49-7.47 (2H, dd, Ph-H), 7.27-7.26 (2H, dd, Ph-H).

ESI MS: 289 ([M+H]⁺)

EXAMPLE 4

Preparation of Intermediate 4.5

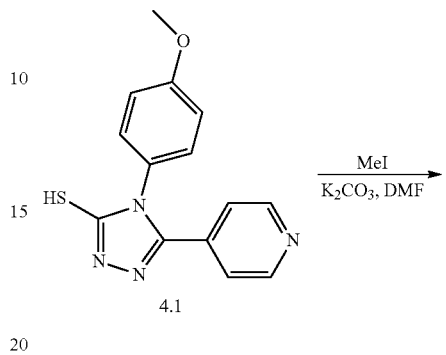

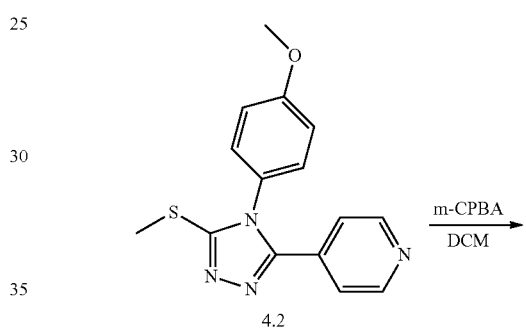

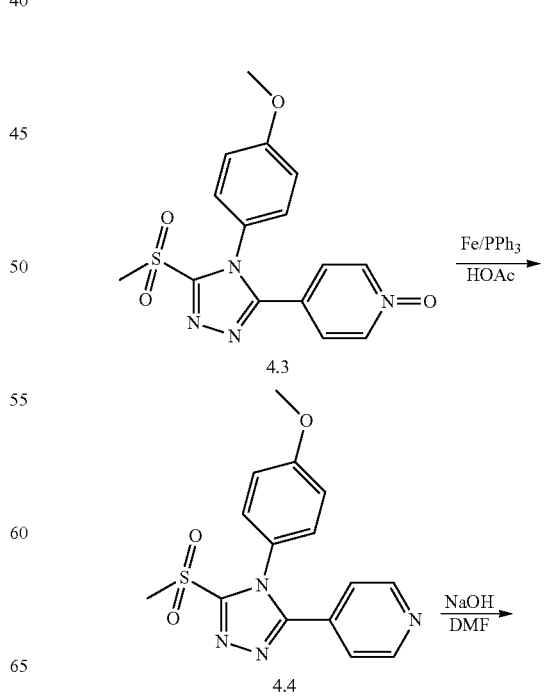

7.23 (2H, dd, Ph-H), 7.04-7.02 (2H, dd, Ph-H), 3.80 (3H, s, —CH₃O). LCMS: 269 ([M+H]⁺)

EXAMPLE 5

Preparation of Intermediate 5.3

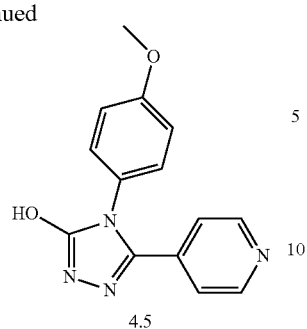

4.5

(a) Preparation of Compound 4.2:

To a stirred mixture of $K_2CO_3$ (0.95 g, 7 mmol) and Compound 4.1 (1 g, 3.5 mmol) in 20 ml DMF was added MeI (0.6 g, 4.2 mmol) dropwise over 5 mins. The mixture was stirred at ambient temperature for 2 hours and poured into the water. The white precipitate (Compound 4.2, 750 mg) was collected by filtration. Yield: 71%.

¹H NMR (400 MHz, DMSO-d6) δ (ppm): 8.58-8.57 (2H, dd, Py-H), 7.43-7.40 (2H, dd, Py-H), 7.32-7.31 (2H, dd, Ph-H), 7.12-7.10 (2H, dd, Ph-H), 3.83 (3H, s, —CH₃O—), 2.63 (3H, s, CH₃—). ESI MS: 299 ([M+H]⁺)

(b) Preparation of Compound 4.3:

To a stirred solution of Compound 4.2 (500 mg, 1.7 mmol) in DCM (50 ml) at 0° C. was added m-CPBA portion wise (1.15 g, 6.8 mmol). The reaction mixture was then warmed up to ambient temperature and stirred for 3 hours. The resulting solution was purified by silica gel column to give 320 mg of a white solid. Yield: 55%.

¹H NMR (400 MHz, DMSO-d6) δ (ppm): 8.25-8.23 (2H, dd, Py-H), 7.57-7.55 (2H, dd, Py-H), 7.35-7.34 (2H, dd, Ph-H), 7.11-7.09 (2H, d, Ph-H), 3.83 (3H, s, —CH₃O—), 3.42 (3H, s, CH₃—). LCMS: 347 ([M+H]⁺)

(c) Preparation of Compound 4.4:

Compound 4.3 (300 mg, 0.87 mmol), PPh₃ (227 mg, 0.87 mmol) and Fe (73 g, 1.3 mmol) were refluxed in 6 ml HOAc for 30 mins. The mixture was then cooled down to ambient temperature and the white precipitate (Compound 4.4, 180 mg) was collected by chromatography. Yield: 63%.

¹H NMR (400 MHz, DMSO-d6) δ (ppm): 8.25-8.23 (2H, dd, Py-H), 7.57-7.55 (2H, dd, Py-H), 7.35-7.34 (2H, dd, Ph-H), 7.11-7.09 (2H, dd, Ph-H), 3.83 (3H, s, —CH₃O—), 3.42 (3H, s, CH₃). LCMS: 331 ([M+H]⁺)

(d) Preparation of Compound 4.5:

To a stirred solution of Compound 4.4 (160 mg, 0.48 mmol) in DMF (6 ml) was added NaOH (77 mg, 1.9 mmol) and the mixture was heated to 80° C. for 2.5 hours. After the reaction mixture was cooled down to ambient temperature, 3N HCl was added to acidify the solution. Then the white precipitate (Compound 4.5, 85 mg) was collected by chromatography. Yield: 65%.

¹H NMR (400 MHz, DMSO-d6) δ (ppm): 12.39 (1H, s, —OH), 8.56 (2H, dd, Py-H), 7.28-7.25 (2H, dd, Py-H), 7.25-

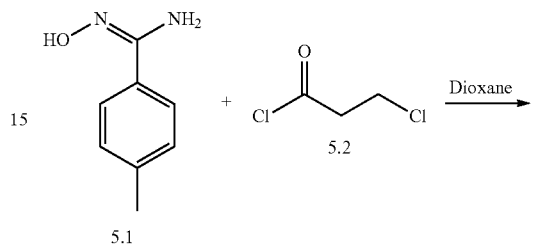

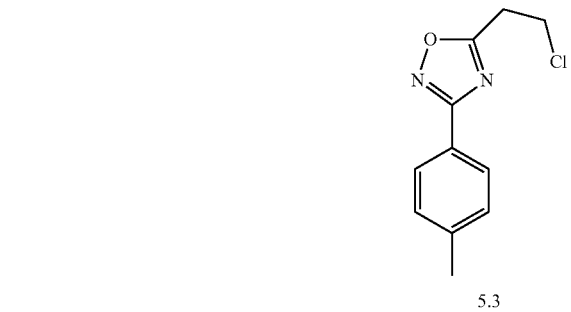

Compound 5.1 (550 mg, 3.66 mmol) was dissolved in dioxane (40 ml) and compound 5.2 (500 mg, 3.66 mmol) was added at 0° C. The mixture was heated to 80° C. and stirred for 1 hour, then the mixture was cooled to ambient temperature and BF₃.Et₂O (1 ml) was added. The mixture was warmed to 80° C. and stirred overnight. Following concentration, column chromatography (DCM: MeOH=80:1) yielded the desired product as a white solid, 93 mg. Yield: 11.5%.

¹H NMR (400 MHz, DMSO-d6) δ (ppm): 7.91-7.89 (2H, dd, Ph-H), 7.39-7.37 (2H, dd, Ph-H), 4.08 (2H, t, —CH₂—), 3.53 (2H, t, —CH₂—), 2.38 (3H, s, CH₃—).

EXAMPLE 6

Preparation of Intermediate 6.4

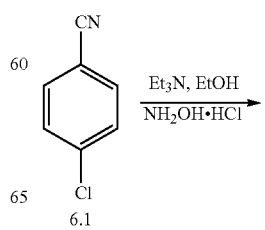

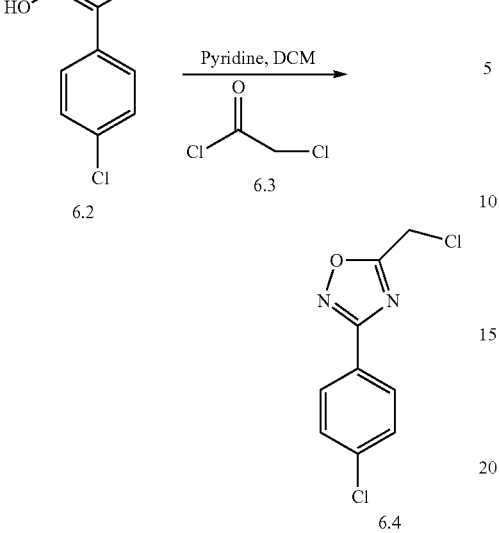

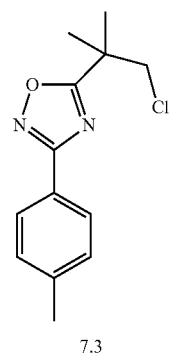

(a) Preparation of Compound 6.2:

To a solution of compound 6.1 (5 g, 37.9 mmol) in EtOH (30 mL) was added NH$_2$OH HCl (2.6 g, 37.9 mmol). The mixture was stirred at ambient temperature for 0.5 hours. Then the temperature was increased up to 50° C. for one night. The solvent was removed. The residue was poured into water, extracted with CH$_2$Cl$_2$, washed with brine, dried over Na$_2$SO$_4$ and concentrated to give a white solid, 4.5 g. Yield: 64.7%.

$^1$H NMR (400 MHz, DMSO-d6) δ (ppm): 9.74 (1H, s, O—H), 7.70-7.68 (2H, dd, Ph-H), 7.45-7.43 (2H, dd, Ph-H), 5.89 (2H, s, —NH$_2$).

(b) Preparation of Compound 6.4:

To a solution of compound 6.2 (1 g, 5.45 mmol) in DCM (20 mL) was added pyridine (861 mg, 10.9 mmol) at ambient temperature and compound 6.3 (738 mg, 6.54 mmol) in an ice bath. The mixture was stirred at ambient temperature for 1 hour. Then the temperature was raised up to 40° C. for one night. The mixture was poured into water, extracted with CH$_2$Cl$_2$, washed with brine, dried over Na$_2$SO$_4$, concentrated, and finally purified by column chromatography to yield 700 mg of a white solid. Yield: 57.4%.

$^1$H NMR (400 MHz, DMSO-d6) δ (ppm): 8.04-8.02 (2H, dd, Ph-H), 7.68-7.65 (2H, dd, Ph-H), 5.198 (2H, s, —CH$_2$—).

EXAMPLE 7

Preparation of Intermediate 7.3

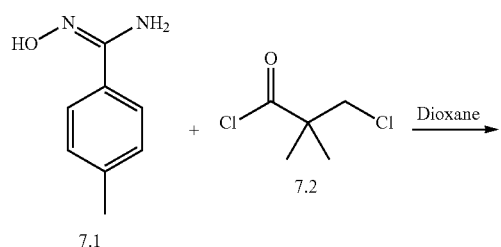

To a stirred suspension of compound 7.1 (500 mg, 3.3 mmol) in dioxane (20 ml) was added compound 7.2 (517 mg, 3.3 mmol). The mixture was then stirred for 3 hours under reflux. After that, it was poured into the water and extracted with ethyl acetate. Concentration and chromatography gave 300 mg of the desired product as a colourless oil. Yield: 36%.

$^1$H NMR (400 MHz, DMSO-d6) δ (ppm): 7.90-7.88 (2H, dd, Ph-H), 7.37-7.35 (2H, dd, Ph-H), 4.00 (2H, s, —CH2-), 2.38 (3H, s, CH$_3$—), 1.52 (6H, s, CH$_3$—). LC-MS m/z: 251 ([M+H]$^+$).

EXAMPLE 8

Preparation of Intermediate 8.2

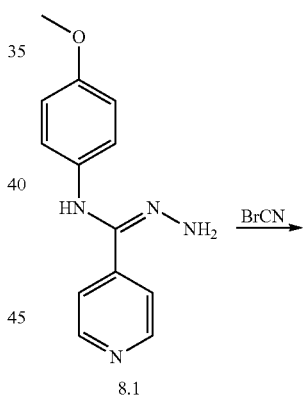

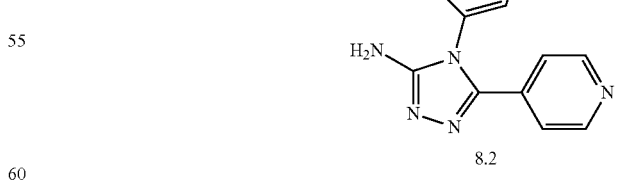

Compound 8.1 (220 mg, 0.91 mmol) was dissolved in dioxane (3 ml) and then BrCN (96 mg, 0.91 mmol), NaHCO3 (92 mg, 1.09 mmol) and H$_2$O (3 ml) were added. The mixture was stirred for 2 hours at ambient temperature and filtered. The residue was purified by column chromatography on silica and gave a yellow solid (70 mg). Yield: 28.81%.

¹HNMR (400 MHz, DMSO) δ (ppm): 8.46 (2H, d, Py-H), 7.32-7.30 (2H, d, Py-H), 7.18-7.17 (2H, d, Ph-H), 7.10-7.08 (2H, d, Ph-H), 5.90 (2H, s, —NH₂), 3.82 (3H, s, —OCH₃).

ESI MS: 268 ([M+H]⁺).

EXAMPLE 9

Preparation of Compound (3)

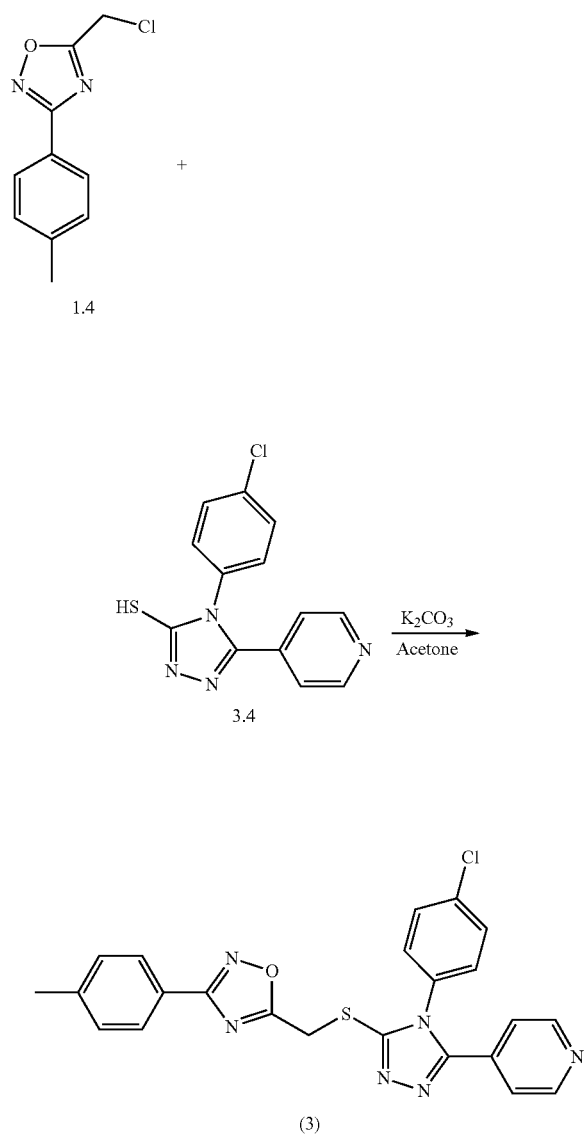

(3)

To a stirred suspension of Compound 1.4 (100 mg, 0.48 mmol) in acetone (12 ml) was added Compound 3.4 (138 mg, 0.48 mmol) and K₂CO₃ (83 mg, 0.6 mmol). Then it was stirred for 1 hour under reflux. The resulting solution was concentrated directly in vacuum to remove acetone and the residue was extracted with ethyl acetate. Purification by silica gel column gave 80 mg of a white solid. Yield: 36%.

¹H NMR (400 MHz, DMSO-d6) δ (ppm): 8.61-8.60 (2H, dd, Py-H), 7.88-7.86 (2H, dd, Ph-H), 7.69-7.67 (2H, dd, Py-H), 7.58-7.56 (2H, dd, Ph-H), 7.40-7.38 (2H, dd, Ph-H), 7.32-7.30 (2H, dd, Ph-H), 4.81 (2H, s, —CH₂—), 2.39 (3H, s, CH₃—). ESI MS: 461 ([M+H]⁺). HPLC: 98%.

EXAMPLE 10

Preparation of Compound (4)

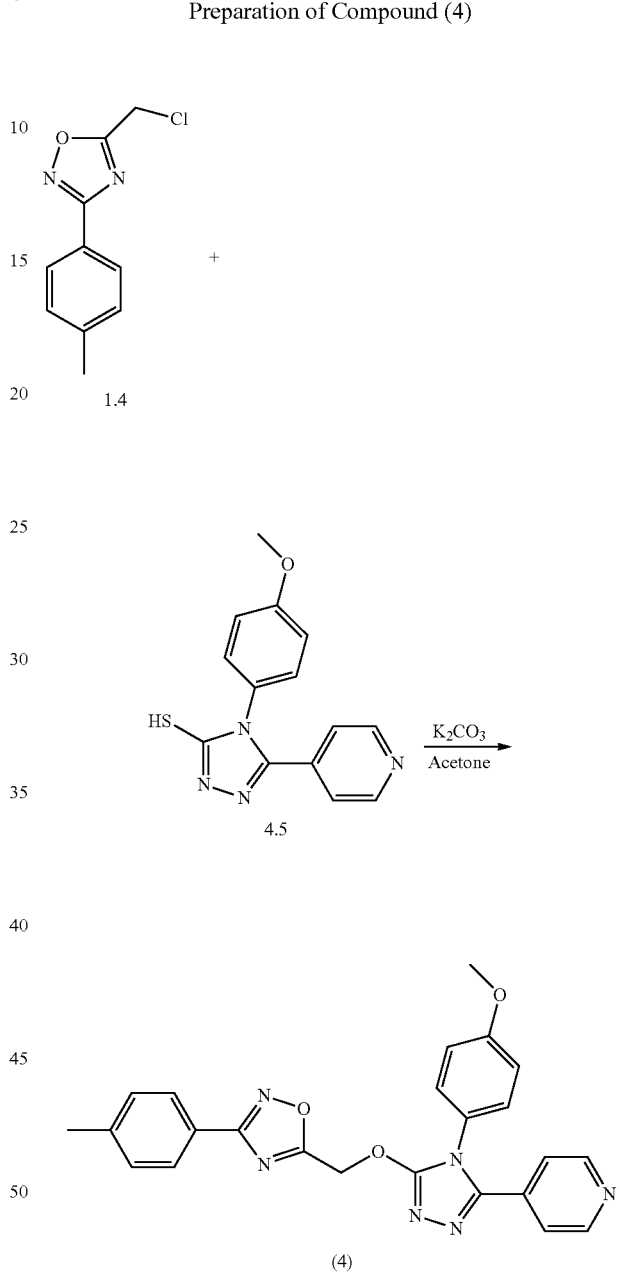

(4)

To a stirred suspension of Compound 1.4 (38 mg, 0.18 mmol) in acetone (5 ml) was added Compound 4.5 (50 mg, 0.18 mmol) and K₂CO₃ (31 mg, 0.23 mmol). Then it was stirred at reflux overnight. The resulting solution was concentrated directly in vacuum to remove acetone and the residue was extracted with ethyl acetate. Purification by silica gel column gave 30 mg of a white solid. Yield: 38%.

¹H NMR (400 MHz, DMSO-d6) δ (ppm): 8.59-8.57 (2H, dd, Py-H), 7.92-7.90 (2H, dd, Ph-H), 7.40-7.38 (2H, dd, Py-H), 7.36-7.34 (2H, dd, Ph-H), 7.26-7.24 (2H, dd, Ph-H), 7.08-7.05 (2H, dd, Ph-H), 5.59 (2H, s, —CH₂—), 3.81 (3H, s, —CH₃O—), 2.39 (3H, s, CH₃—).

ESI MS: 441 ([M+H]⁺). HPLC: 98%.

EXAMPLE 11

Preparation of Compound (2)

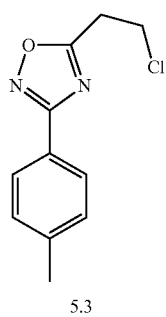
5.3

+

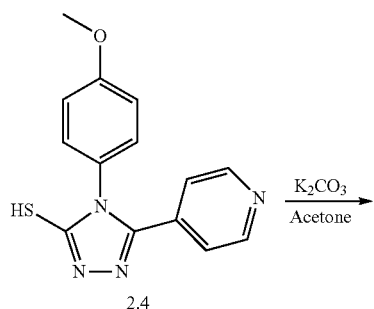
2.4

→

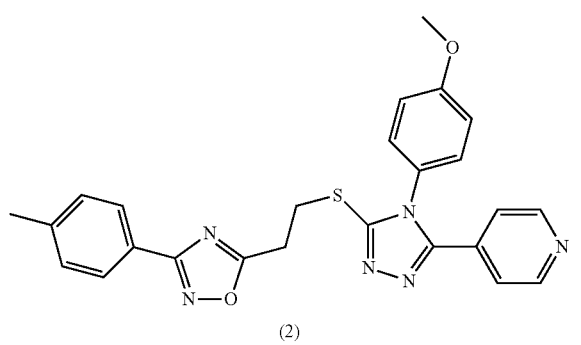
(2)

Compound 2.4 (77 mg, 0.270 mmol) was dissolved in acetone (7 ml) and K$_2$CO$_3$ (47 mg, 0.328 mmol) and Compound 5.3 (60 mg, 0.270 mmol) was added. The mixture was heated to 50° C. and stirred for 2 hours. Then the mixture was concentrated and extracted with ethyl acetate. Column chromatography (PE:EA=2:1) yielded the desired product as a white solid, 30 mg. Yield: 23.62%.

$^1$H NMR (400 MHz, DMSO-d6) δ (ppm): 8.58-8.56 (2H, dd, Py-H), 7.90-7.88 (2H, dd, Ph-H), 7.38-7.36 (2H, dd, Py-H), 7.31-7.29 (2H, dd, Ph-H), 7.21-7.20 (2H, dd, Ph-H), 7.07-7.05 (2H, dd, Ph-H), 4.77-4.74 (2H, t, —CH$_2$—), 3.81 (3H, s, CH$_3$O—), 3.66-3.62 (2H, t, —CH$_2$—), 2.38 (3H, s, CH$_3$—). ESI MS: 471 ([M+H]$^+$). HPLC: 99.8%.

EXAMPLE 12

Preparation of Compound (5)

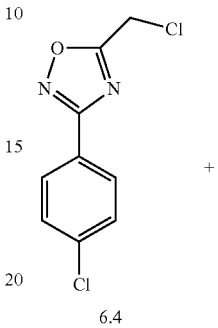
6.4

+

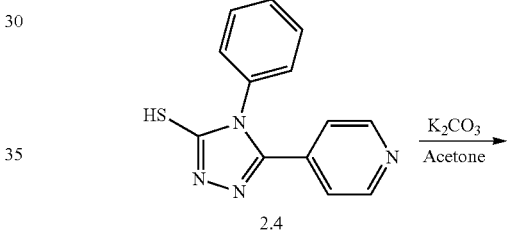
2.4

→

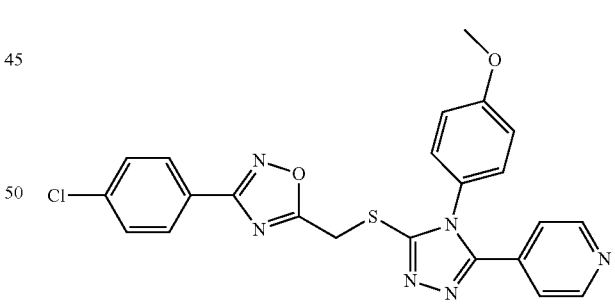
(5)

To a solution of compound 6.4 (100 mg, 0.445 mmol) in acetone (10 mL) was added compound 2.4 (127 mg, 0.445 mmol). The mixture was stirred under reflux for 1.5 hours. Then the solvent was removed, water was poured into the mixture, extracted with ethyl acetate, washed with brine, dried over Na$_2$SO$_4$. Following concentration and recrystallisation, 100 mg of a white solid were obtained. Yield: 47%.

$^1$H NMR (400 MHz, DMSO-d6) δ (ppm): 8.58-8.56 (2H, dd, Py-H), 7.99-7.98 (2H, dd, Ph-H), 7.66-7.63 (2H, dd, Py-H), 7.43-7.41 (2H, dd, Ph-H), 7.31-7.30 (2H, dd, Ph-H), 7.11-7.09 (2H, dd, Ph-H), 4.81 (2H, s, —CH$_2$—), 3.81 (3H, s, —CH$_3$O—). ESI MS: 476 ([M+H]$^+$). HPLC: 98.9%.

EXAMPLE 13

Preparation of Compound (6)

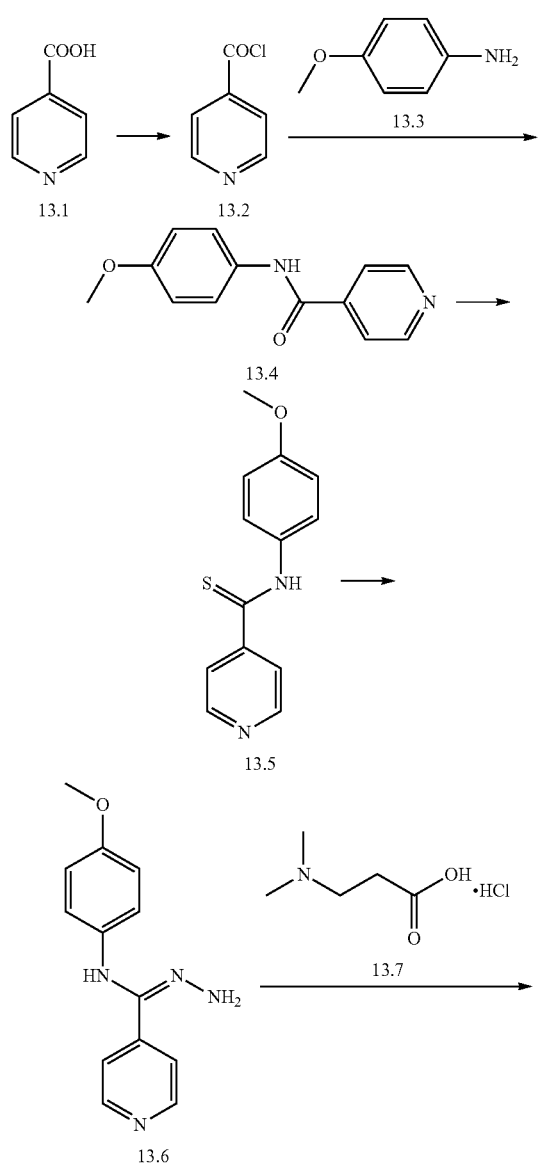

(a) Preparation of Compound 13.2:

A solution of compound 13.1 (1 g, 8.1 mmol) in SOCl$_2$ (10 mL) was refluxed for 2 hours. Then the SOCl$_2$ was removed under vacuum to yield 1.16 g of a white solid. Yield: 99%.

(b) Preparation of Compound 13.4:

A mixture of compound 13.2 (1.16 g, 8.2 mmol) and compound 13.3 (0.91 g, 7.4 mmol) in DCM (100 mL) was stirred at ambient temperature for 30 mins. The yellow solid formed during the reaction was isolated by suction filtration and recrystallised in methanol to obtain 1.27 g of the desired product (yellow solid). Yield: 68%.

$^1$H NMR (400 MHz, DMSO-d6) δ (ppm): 10.79 (1H, s), 8.99 (2H, d, J=6.0 Hz), 8.27 (2H, d, J=6.0 Hz), 7.71 (2H, d, J=8.0 Hz), 6.96 (2H, d, J=8.0 Hz), 3.77 (3H, s).

(c) Preparation of Compound 13.5:

A mixture of compound 13.4 (1 g, 4.4 mmol) and Lawesson's Reagent (1.77 g, 4.4 mmol) in toluene (100 mL) was refluxed for 3 hours. The yellow solid formed during the reaction was isolated by suction filtration, washed in toluene (20 mL) and EtOEt (20 mL) to obtain 1.05 g of the desired product. Yield: 98%. LC-MS m/z: 245.3 ([M+H]$^+$)

(d) Preparation of Compound 13.6:

A mixture of compound 13.5 (100 mg, 0.41 mmol) in dioxane (10 mL), N$_2$H$_4$.H$_2$O (102 mg, 2.05 mmol) was added, stirred at 50° C. for 20 mins. Then the solution was poured into water (20 mL), extracted twice with ethyl acetate (20 mL×2), washed with water (20 mL) and brine (20 mL). Following drying by anhydrous Na$_2$SO$_4$ and concentration, 85 mg of the desired product was obtained (yellow solid). Yield: 86%.

(e) Preparation of Compound (6):

To the mixture of compound 13.7 (108 mg, 0.7 mmol) in toluene (5 mL), DCC (724 mg, 3.5 mmol) was added and stirred for 10 mins. Compound 13.6 (170 mg, 0.7 mmol) dissolved in toluene (5 mL) was added dropwise, then refluxed over night. The solvent was removed under reduced pressure, the residue dissolved in DCM (20 mL), washed with 1N NaOH (20 mL), water (20 mL) and brine (20 mL). Following concentration, 20 mg of the desired product was obtained by column chromatography (DCM:MeOH=50:1-10:1) and P-HPLC as a yellow sticky solid. Yield: 9%.

$^1$H NMR (400 MHz, CDCl3) δ (ppm): 8.54 (2H, d, J=6.0 Hz), 7.32 (2H, d, J=6.0 Hz), 7.16 (2H, d, J=8.8 Hz), 7.04 (2H, d, J=8.8 Hz), 3.90 (3H, s), 2.87 (4H, t), 2.28 (6H, s).

EXAMPLE 14

Preparation of Compound (18)

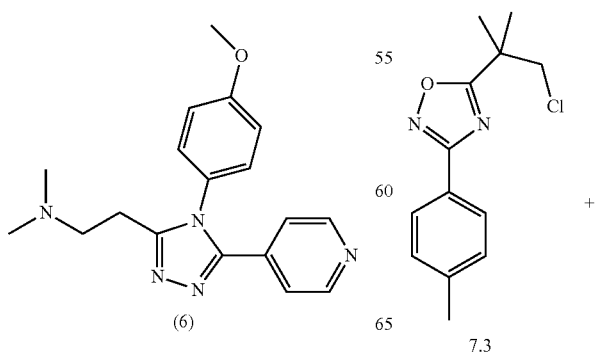

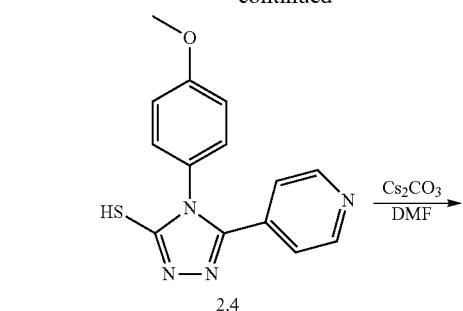

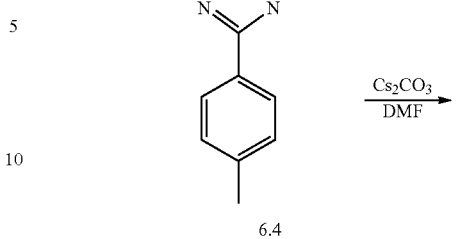

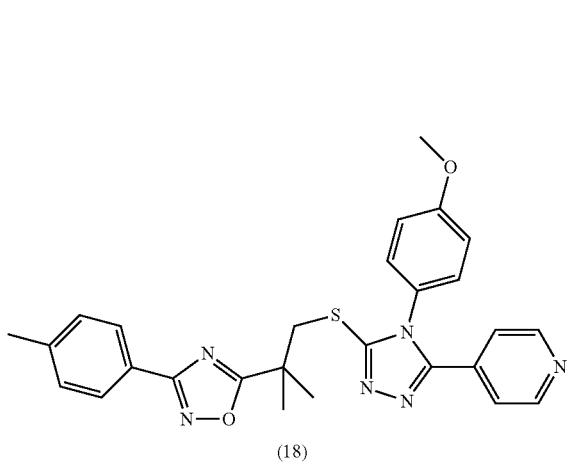

(18)

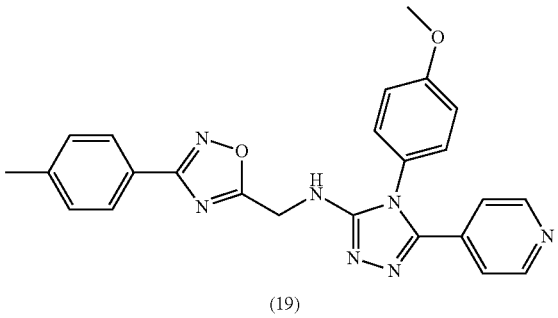

(19)

Compound 2.4 (125 mg, 0.44 mmol) was dissolved in DMF (10 ml) and Cs₂CO₃ (286 mg, 0.88 mmol), then compound 7.3 (110 mg, 0.44 mmol) was added. The mixture was raised to 100° C. and stirred overnight, then the mixture was poured into water and extracted with ethyl acetate. Column chromatography yielded the desired product as a white solid (28 mg). Yield: 13%.

¹H NMR (400 MHz, DMSO-d6) δ (ppm): 8.49-8.47 (2H, dd, Py-H), 7.80-7.78 (2H, dd, Ph-H), 7.37-7.35 (2H, dd, Py-H), 7.30-7.28 (2H, dd, Ph-H), 7.10-7.09 (2H, dd, Ph-H), 7.09-7.07 (2H, dd, Ph-H), 3.81 (3H, s, CH₃O—), 3.76 (2H, s, —CH₂—), 2.34 (3H, s, CH₃—), 1.52 (6H, s, CH₃—). ESI-MS: 499 ([M+H]⁺). HPLC: 99.2%

EXAMPLE 15

Preparation of Compound (19)

Compound 8.2 (60 mg, 0.22 mmol) was dissolved in DMF (6 ml) and Cs₂CO₃ (73 mg, 0.22 mmol). Compound 6.4 (23 mg, 0.11 mmol) was added, the mixture was heated to 70° C. and stirred for 2.5 hours. Then the mixture was poured into water and extracted with ethyl acetate. Column chromatography yielded the desired product as a yellow solid (5 mg).

Compound 8.2 (80 mg, 0.3 mmol) was dissolved in DMF (6 ml) and Cs₂CO₃ (97 mg, 0.3 mmol). Compound 6.4 (31 mg, 0.15 mmol) was added, the mixture was heated to 70° C. and stirred for 2 hours. Then the mixture was poured into water and extracted with ethyl acetate. The resultant product was purified by silica gel column to give a yellow solid (6 mg).

¹HNMR (400 MHz, CDCl3) δ (ppm): 8.53-8.52 (2H, dd, Py-H), 7.92-7.90 (2H, dd, Ph-H), 7.32-7.28 (6H, dd, Py-H, Ph-H), 7.12-7.10 (2H, dd, Ph-H), 5.00-4.98 (2H, d, —CH₂—), 4.59-4.56 (1H, t, —NH—), 3.92 (3H, s, CH₃O—), 2.42 (3H, s, CH₃—). ESI MS: 440 ([M+H]⁺). HPLC: 90%.

EXAMPLE 16

Preparation of Compound (1)

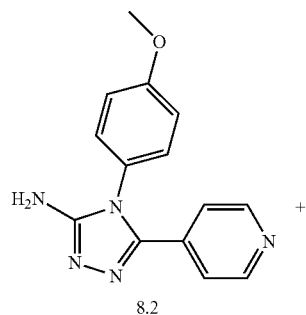

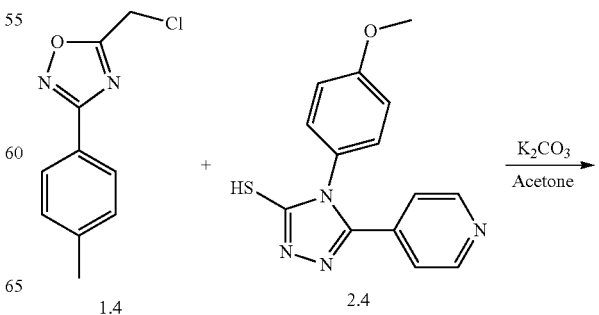

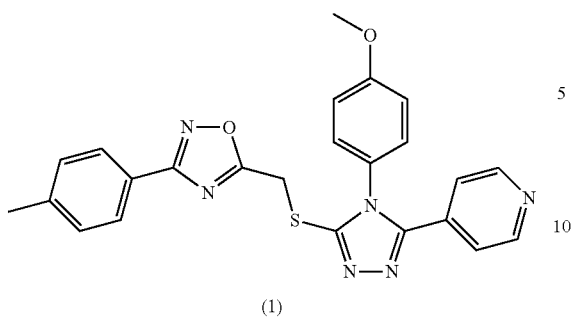

(1)

Starting from Compounds 1.4 and 2.4, Compound (1) is prepared analogously to Compound (3) in Example 9.

EXAMPLE 17

Preparation of Compound (58)

The following reaction scheme may be used to prepare Compound (58):

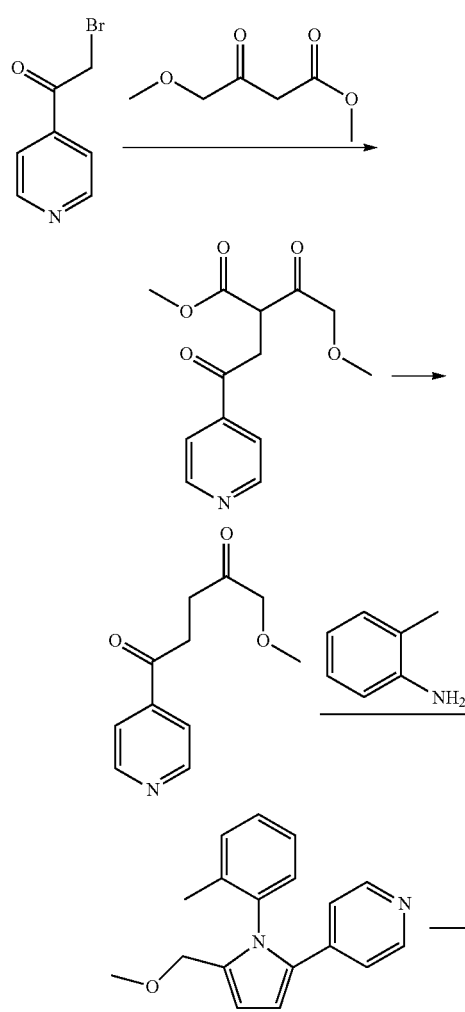

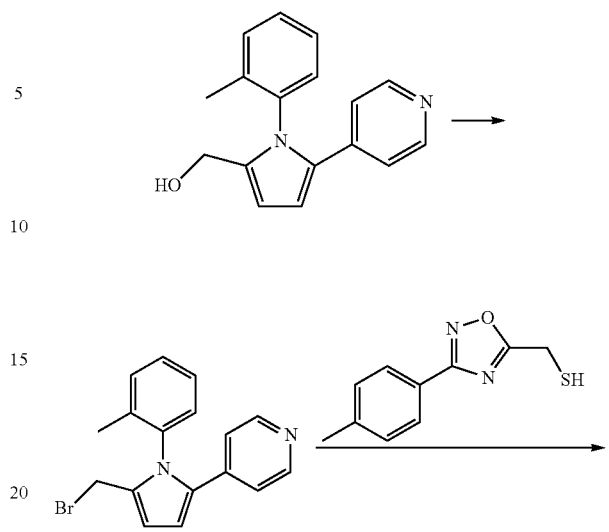

(58)

Examples 18 to 21 are examples of formulations in which reference to the "active substance" denotes one or more compounds according to the invention, including the salts thereof.

EXAMPLE 18

Tablets Containing 100 mg of Active Substance

Each tablet contains:

| | |
|---|---|
| active substance | 100 mg |
| lactose | 80.0 mg |
| corn starch | 34.0 mg |
| polyvinylpyrrolidone | 4.0 mg |
| magnesium stearate | 2.0 mg |

The active substance, lactose and corn starch are mixed together and uniformly moistened with an aqueous solution of the polyvinylpyrrolidone. The moist composition is screened (2.0 mm mesh size) and dried at 50° C. The lubricant is added and the final mixture is compressed to form tablets. Final weight of each tablet is 220 mg

EXAMPLE 19

Tablets Containing 150 mg of Active Substance

Each tablet contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |

The active substance is mixed with lactose, corn starch and silica and moistened with an aqueous polyvinylpyrrolidone solution. The moist composition is passed through a screen with a mesh size of 1.5 mm. The resulting granules are dried at 45° C., then mixed with the magnesium stearate. Tablets are pressed from the mixture. Each tablet weighs 300 mg.

EXAMPLE 20

Ampoules Containing 10 mg Active Substance

Each ampoule contains:

| | |
|---|---|
| active substance | 10.0 mg |
| 0.01N hydrochloric acid | q.s. |
| double-distilled water | ad 2.0 ml |

The active substance is dissolved in the necessary amount of 0.01 N HCl, made isotonic with common salt, sterile filtered and transferred into 2 ml ampoules.

EXAMPLE 21

Ampoules Containing 50 mg of Active Substance

Each ampoule contains:

| | |
|---|---|
| active substance | 50.0 mg |
| 0.01N hydrochloric acid | q.s. |
| double-distilled water | ad 10.0 ml |

The active substance is dissolved in the necessary amount of 0.01 N HCl, made isotonic with common salt, sterile filtered and transferred into 10 ml ampoules.

EXAMPLE 22

Inhibition of Canonical Wnt Signaling In Vitro

Inhibition of Wnt signaling by compound No. 1 was quantified in vitro using a Luciferase assay in HEK293 cells transiently transfected with SuperTOPFlash plasmid (ST-Luc) (Veeman M T et al., Curr. Biol. 13: 680-685, 2003) at concentrations from 0.1-10 μM. HEK293 cells were purchased from ATCC (American Type Culture Collection) and maintained according to suppliers recommendations.

Experimental

Transfection was performed using 80000 HEK293 cells seeded in 48-well plates coated with poly-L lysine. After 24 hours, 0.25 μg total plasmid DNA (0.23 μg SuperTOPFlash+ 0.02 μg pRL-TK (*Renilla*)—Promega) and 0.75 μl FuGENE6 (Roche) was combined in a total volume in 25 μl Opti-MEM® (Invitrogen) as described by the manufacturer (Roche). The transfection mixture was added to the plated cells and media were changed after 24 hours.

The Luciferase assay was performed by incubating transfected cells for 24 hours with various concentrations of compound No. 1 in 30% Wnt3a-CM (Wnt3a containing conditioned medium from L Wnt3a cells was harvested as described by ATCC). All treated reporter cells were finally lysed and the firefly luciferase and *Renilla* activities were measured on a 20/20n Luminometer (Turner BioSystems) as described in the Dual-Glo™ Luciferase Assay System Technical Manual (Promega).

Results

Figure 1:
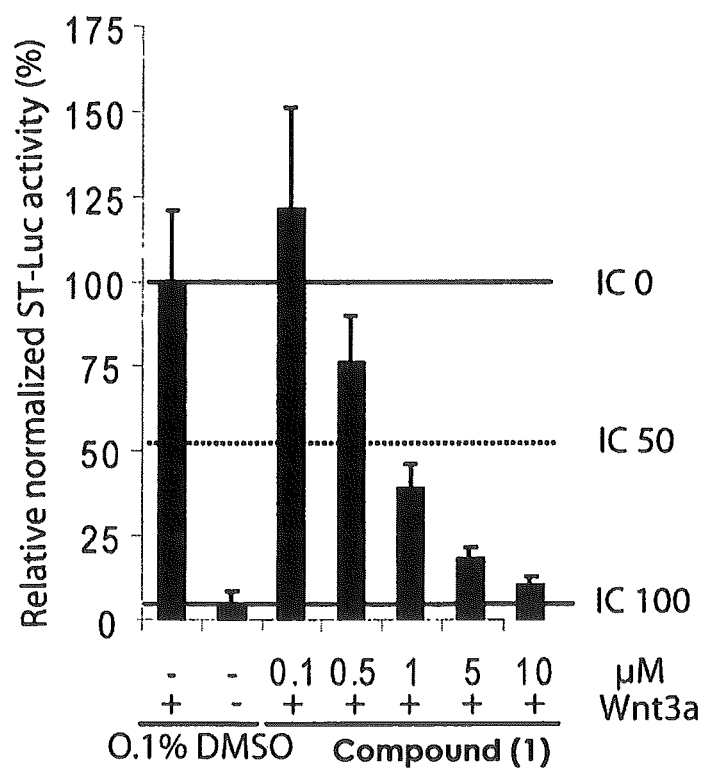

FIG. 1 shows the results of incubation of the cells with 0.1-10 μM of compound No. 1. Compound No. 1 shows a strong reduction of canonical Wnt signaling by the ST-Luc assay ($IC_{50}=1$ μM).

EXAMPLE 23

Specificity of the Wnt Pathway Inhibitors In Vitro

Figure 2:
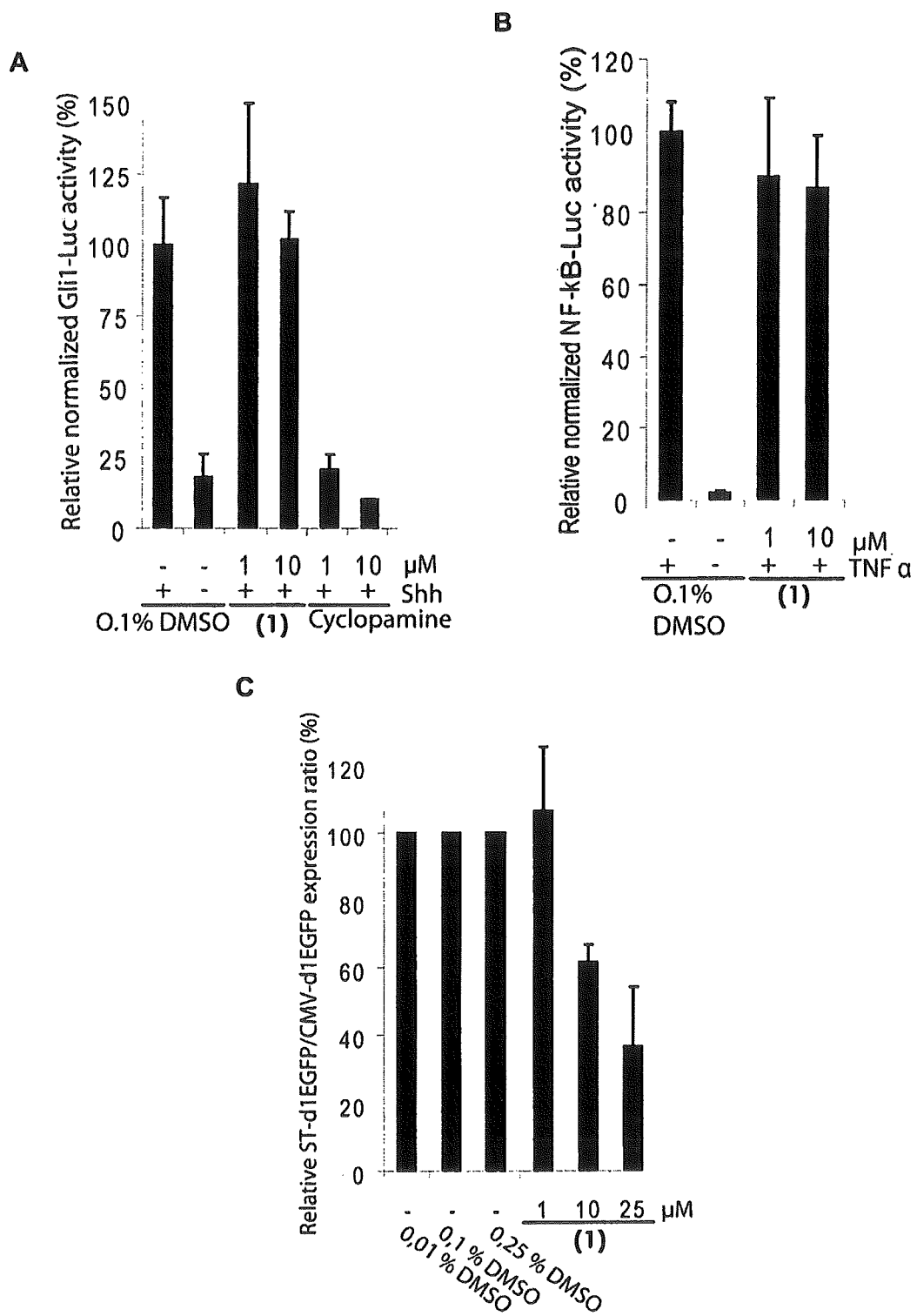

To test the specificity of compound No. 1, three cell lines were used:

1) a stable reporter line for sonic hedgehog pathway, Shh Light II cells (Glil-Luc-purchased from ATCC and maintained according to suppliers recommendations);

2) HEK293 cells transiently transfected with a NF-κB-Luciferase reporter (NF-κB-Luc—purchased from Promega). Results are shown in FIGS. 2A and 2B; and 3) the SW480 colorectal cell line, which has an aberrant Wnt activity caused by spontaneous mutations in the APC locus, transfected with the construct ST-d1EGFP. In this cell line, d1EGFP reporter is activated without using Wnt-3a CM, i.e. the cell line has permanently "switched on" Wnt signaling pathway.

Experimental

1) The Shh Light II assay was performed by seeding 100000 Light II cells in 48-well plates and incubating them for 48 hours with 10 or 1 μM of compound No. 1 in 50% Shh-CM (Shh conditioned medium was harvested from PANC-1 cells that carried lentivirus (produced using ViraPower Lentiviral Systems (Invitrogen)) with Shh cDNA (mouse Shh cDNA was cloned into a pLenti6.2-GW/EmGFP Expression Control Vector)).

2) Transfection was performed as described in Example 22, but using 0.23 μg NF-κB-Luciferase and 0.02 μg *Renilla*. Transfected cells were incubated for 24 hours with 1 or 10 μM of compound No. 1 in 10 ng/ml rTNF-α (R&D Systems).

3) ST-d1EGFP (created by cloning the promoter from the SuperTOPFlash construct into d1EGFP-N1 (Clontech) after excision of CMV promoter) was transfected in SW480 cells (purchased from ATCC and maintained according to suppliers recommendations). 100000 ST-d1EGFP SW480 and SW480 CMV-d1EGFP (Clontech) SW480 cells were plated on 12-well plates and 1, 10 or 25 μM of compound No. 1 (or 0.01%, 0.1% or 0.25% DMSO—controls) was added to the cells the following day. After a 72 hour incubation, samples were trypsinized and analysed for d1EGFP expression on a PAS-PPCS flowcytometer and cell sorter (Partec).

Results

Compound No. 1 shows no substantial activating or inhibitory effect against either the Hh (Shh) or TNF-α pathways (FIGS. 2A and 2B). However, FIG. 2C shows a dose dependent inhibition of the Wnt signaling pathway in SW480 cells (the ratio of activity of ST-d1EGFP to CMV-d1EGFP was reduced by 63.5% for 25 M compound No. 1).

It can thus be concluded that compound No. 1 is a specific inhibitor of the Wnt signaling pathway. The results from FIG. 2C suggest that the compound acts in the pathway despite of a mutated APC gene product, i.e. at or downstream of the Axin/APC/β-catenin/GSK-3β complex (the "destruction complex").

EXAMPLE 24

In Vivo Efficacy and Specificity of Wnt Pathway Inhibitors

To examine the in vivo efficacy and specificity of compound No. 1 in obstructing canonical Wnt signaling, a *Xenopus laevis* axis duplication assay was performed. Injection of ectopic XWnt8 mRNA into the prospective ventral side activates canonical Wnt pathway signaling and induces a secondary body axis. This assay provides a reliable method to test biological effects of compounds with potential effects on Wnt signaling.

Experimental

Capped XWnt8 mRNA was synthesized from linearized plasmid template using a mMESSAGE mMACHINE kit (Ambion). 4 nlxWnt8 (10 pg), with compound No. 1 or vehicle, was injected into the equatorial regions of the two prospective ventral blastomeres of four-cell stage *Xenopus* embryos. The embryos were incubated at 19° C. and axis duplication was scored after 36 hours.

Results

Figure 3:
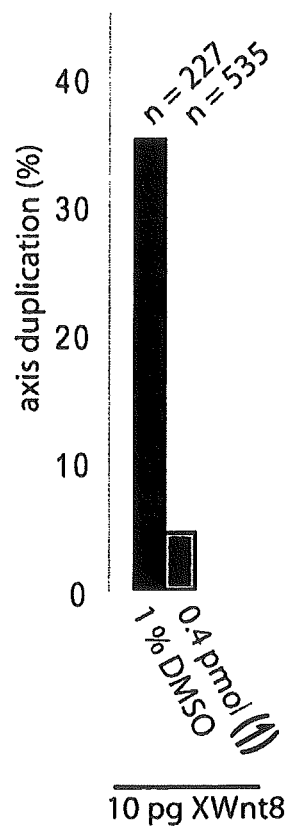
FIG. 3 shows: A) quantification of inhibition of double axis formation in *Xenopus* embryos by compound No. 1-n, number of embryos examined for each group; and B) an example of embryos with a duplicated axis induced by XWnt8 and its blockage by compound No. 1.
Figure 3:
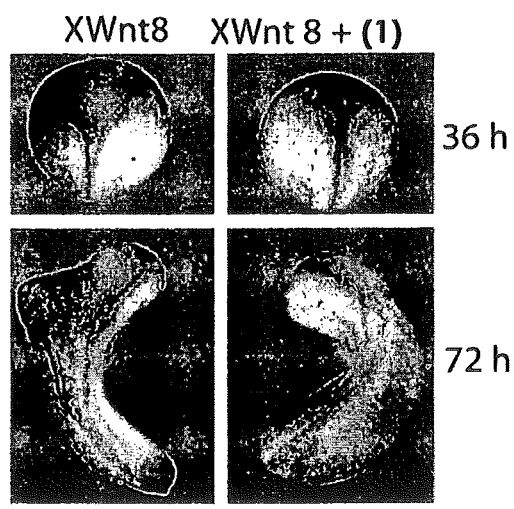

As seen in FIGS. 3A and 3B, injection of 0.4 pmol of compound No. 1 led to an 87% reduction (n=535) in double axis formation compared to DMSO controls (n=283).

EXAMPLE 25

Specific Inhibition of Wnt Target Gene Expression

A real-time RT-PCR analysis was employed to confirm specific inhibition of expressed Wnt target genes.

Experimental

100000 DLD-1 (purchased from ATCC and maintained according to suppliers recommendations) or SW480 cells were seeded in 12-well plates. After 24 hours, solutions containing compound No. 1 were added at 10 or 25 μm final concentrations. Media containing the test compound were changed daily for 3 days.

mRNA was harvested using a GenElute™ Mammalian Total RNA Miniprep Kit (Sigma). cDNA was synthesized from the purified mRNA with AffinityScript™ QPCR cDNA Synthesis Kit (Stratagene). Real Time RT-PCR (SYBR Green PCR Mastermix, Stratagene) was performed using the following primers on a Mx3000P® QPCR System real-time thermal cycler (Stratagene):

```
Axin2 forward:
5'-CCCAAGCCCCATAGTGCCCAAAG-3'    (SEQ ID NO. 1)

Axin2 reverse:
5'-CAGGGGAGGCATCGCAGGGTC-3'      (SEQ ID NO. 2)

Sp5 forward:
5'-GCGGCGAGGGGCAAGGGC-3'         (SEQ ID NO. 3)

Sp5 reverse:
5'-CGCCGAGGCATGGACACCCG-3'       (SEQ ID NO. 4)

Nkd1 forward:
5'-TCACTCCAAGCCGGCCGCC-3'        (SEQ ID NO. 5)
```

```
-continued
Nkd1 reverse:
5'-TCCCGGGTGCTTCGGCCTATG-3'      (SEQ ID NO. 6)

GAPDH forward:
5'-GCCCCCTCTGCTGATGCCCCCA-3'     (SEQ ID NO. 7)

GAPDH reverse:
5'-TGGGTGGCAGTGGCATGG-3'         (SEQ ID NO. 8)

hGUSB forward
5'-TGGTTGGAGAGCTCATTTGGA-3'      (SEQ ID NO. 9)

hGUSB reverse
5'-GCACTCTCGTCGGTGACTGTT-3'      (SEQ ID NO. 10)
```

Results were calculated as the ratio of expression of target gene to a control gene (GAPDH).

Results

Figure 4:
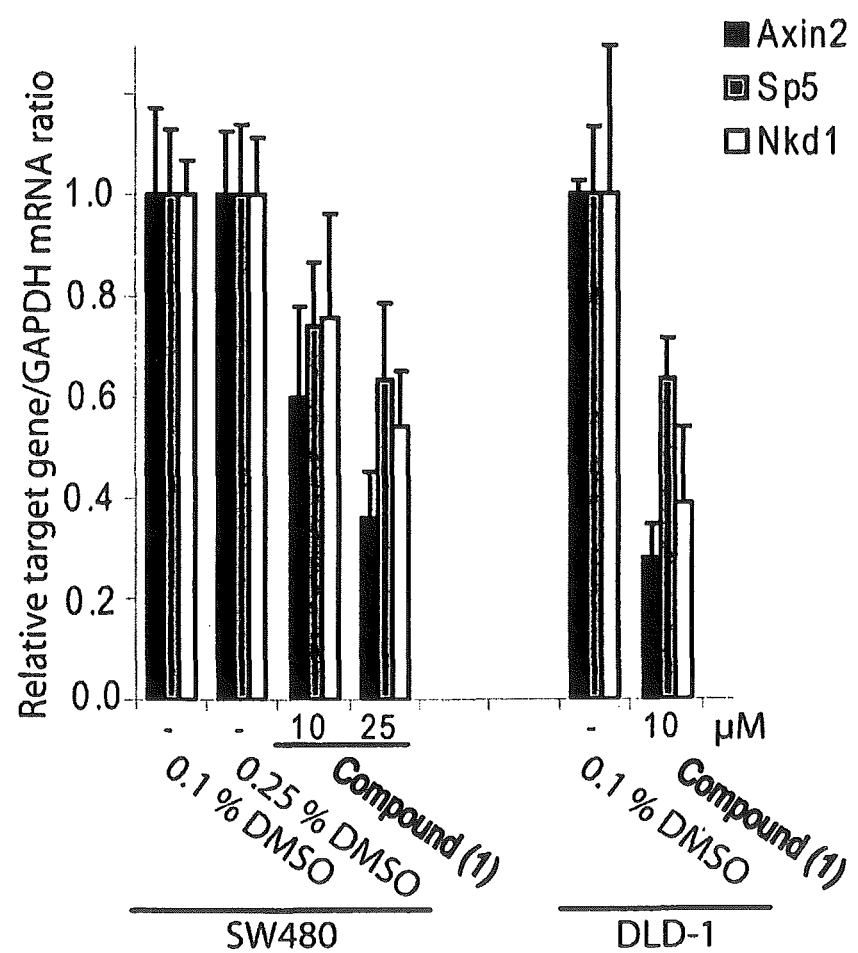
FIG. 4 shows the results of real-time RT-PCR which demonstrates relative decreased expression of Axin2, Sp5 and Nkd1 genes in colon cancer cells SW480 and DLD-1. Average values from three independent experiments are shown.

In both SW480 and in DLD-1 cells, a dose dependent reduction of Axin2, SP5 and NKD1 mRNA levels was observed after 72-hour incubation with 10 (or 25) M of compound No. 1 (FIG. 4). In general, reduction in target gene expression was more pronounced in DLD-1 cells at the 10 μM concentration.

EXAMPLE 26

Gene Expression Analysis Following Wnt Pathway Inhibition

A microarray analysis using an Illumina® array was performed in triplicate to investigate differential gene expression in cells treated with a Wnt pathway inhibitor.

Experimental mRNA from 10 μM and 25 μM compound No. 1-treated SW480 cells was obtained from three independent experiments (harvested as described in Example 25) and was amplified for hybridization on Illumina® BeadChips (using the Illumina® TotalPrep RNA amplification Kit (Ambion Inc.) #IL1791), using 400 ng of the total RNA. In vitro transcription reactions were incubated overnight (14 hr).

Labeled cRNA was hybridized to Illumina® Human-6 v3 BeadChips (Illumina, San Diego, Calif.) at 58° C. overnight, according to the Illumina® Whole-Genome Gene Expression Protocol for BeadStation (Doc. #11226030.rev.C, Illumina Inc.). The hybridized BeadChip was stained with streptavidin-Cy3 (Amersham™, PA43001) for visualization and scanned with an Illumina® BeadArray Reader. The scanned images were imported into BeadStudio 3.1.3.0 (Illumina Inc) for extraction and quality control. A criterion of 0.5-fold change in expression was applied to the analysis.

Results

The following p-value cut-offs gave these final hit numbers: 10 M compound No. 1 (p=0.02: 384 hits) and 25 μM compound No. 1 (p=0.02: 881 hits).

Transcription of known Wnt target genes were found to be affected in cells treated with compound No. 1 (for a list of target genes see e.g. http://www.stanford.edu/~rnusse/wntwindow.html). A list of differentially expressed genes of interest is given below in tables 1 and 2. Table 1 shows examples of genes that were down-regulated on addition of 10 μM or 25 μM compound No. 1; and table 2 shows examples of genes that were up-regulated. Many known Wnt target genes (column 3) were influenced in treated cells. Some genes were influenced that are also affected in Ls174T colorectal cancer cells expressing an inducible dominant negative form of TCF-4 (column 4) (van de Wetering et al., *Mol. Cell. Biol.* (2008) 28(8), p. 2732-44). Other influenced genes that are important for cell cycle control and other genes correlated to regulated canonical Wnt signaling are also shown. The degree of modulation (column 5) is an indication of the degree of change between the non-treated and compound No. 1 treated samples. Tables 1 and 2 are sorted to show the most down-(or up-) regulated genes first:

TABLE 1

| Description of gene target | Accession No. | Wnt target | Ls174T target | Degree of modulation | 10 μM Compound 1 | 25 μM Compound 1 |
|---|---|---|---|---|---|---|
| SPANXA1 | NM_013453 | | | --- | x | x |
| SPANXB2 | NM_145664 | | | --- | x | x |
| SPANXC | NM_145665 | | | --- | x | x |
| SPANXE | NM_022661 | | | --- | x | x |
| cysteine-rich, angiogenic inducer, 61 | NM_001554 | x | | --- | | x |
| LY6/PLAUR domain containing 5 | NM_001031749 | | | --- | x | x |
| ets variant gene 3 | NM_005240 | | | -- | | x |
| dickkopf homolog 1 (Xenopus laevis) | NM_012242 | x | | -- | x | x |
| inhibitor of DNA binding 2, dominant negative helix-loop-helix protein | NM_002166 | x | | -- | x | x |
| adenomatosis polyposis coli down-regulated 1 | NM_153000 | | | -- | | x |
| frizzled homolog 2 (Drosophila) | NM_001466 | x | | -- | | x |
| Sp5 transcription factor | NM_001003845 | x | | – | | x |
| matrix metallopeptidase 7 (matrilysin, uterine) | NM_002423 | x | | – | | x |
| CCAAT/enhancer binding protein (C/EBP), delta | NM_005195 | | | – | x | x |
| naked cuticle homolog 1 (Drosophila) | NM_033119 | x | | – | x | x |
| homeobox B2 | NM_002145 | | | – | x | x |
| cell division cycle associated 8 | NM_018101 | x | x | – | | x |
| paired related homeobox 2 | NM_016307 | | | – | | x |
| axin 2 | NM_004655 | x | | – | x | x |
| homeobox B5 | NM_002147 | | | – | x | x |
| tumor necrosis factor receptor superfamily, member 19 | NM_148957 | | | – | | x |
| p53 and DNA damage regulated 1 | NM_030815 | | | – | | x |
| cell division cycle 25 homolog C (S. pombe) | NM_001790 | | | – | | x |
| homeobox B7 | NM_004502 | | | – | x | x |
| alkaline phosphatase, liver/bone/kidney | NM_000478 | | | – | x | x |
| topoisomerase (DNA) II alpha 170 kDa | NM_001067 | | | – | | x |
| fibroblast growth factor 20 | NM_019851 | | | – | | X |
| SRY (sex determining region Y)-box 18 | NM_018419 | x | | – | x | X |
| cyclin-dependent kinase 8 | NM_001260 | | | – | | X |
| pituitary tumor-transforming 1 | NM_004219 | x | | – | | X |
| origin recognition complex, subunit 1-like (yeast) | NM_004153 | x | x | – | | X |
| PDZ and LIM domain 1 | NM_020992 | | | – | | X |
| forkhead box M1 | NM_202003 | | | – | | X |
| cyclin B2 | NM_004701 | | | – | | X |
| bone morphogenetic protein 7 | NM_001719 | | | – | | X |
| prickle homolog 2 (Drosophila) | NM_198859 | | | – | x | X |
| baculoviral IAP repeat-containing 5 | NM_001012271 | x | x | – | | X |
| sex comb on midleg-like 1 (Drosophila) | NM_001037535 | | | – | | X |
| cyclin-dependent kinase inhibitor 1B (p27, Kip1) | NM_004064 | | | – | | X |
| disabled homolog 2, mitogen-responsive phosphoprotein (Drosophila) | NM_001343 | | | – | | X |
| gastrin | NM_000805 | x | | – | x | |
| dynein, light chain, LC8-type 2 | NM_080677 | | | – | | X |
| catenin (cadherin-associated protein), alpha-like 1 | NM_003798 | | | – | x | |
| frizzled homolog 4 (Drosophila) | NM_012193 | x | | – | x | X |
| dynein, light chain, roadblock-type 1 | XR_042456 | | | – | | X |
| patched homolog 1 | NM_001083607 | | | – | | X |

TABLE 1-continued

| Description of gene target | Accession No. | Wnt target | Ls174T target | Degree of modulation | 10 μM Compound 1 | 25 μM Compound 1 |
|---|---|---|---|---|---|---|
| (Drosophila) | | | | | | |
| TEA domain family member 4 | NM_201443 | x | x | – | x | X |
| slowmo homolog 1 (Drosophila) | NM_006553 | | | – | | x |
| dynein, axonemal, heavy chain 3 | NM_017539 | | | – | | X |
| c-abl oncogene 1, receptor tyrosine kinase | NM_007313 | | | – | | X |
| ephrin-A4 | NM_005227 | | | – | | X |
| mitogen-activated protein kinase kinase kinase kinase 1 | NM_007181 | | | – | | X |
| paired box 6 | NM_001604 | | | – | | X |
| runt-related transcription factor 2 | NM_004348 | x | | – | | X |

"- - -" denotes very strong down-regulation ($\log^2$ ratio of between −1.5 and −2);
"- -" denotes strong down-regulation ($\log^2$ ratio of between −1.0 and −1.5); and
"-" denotes moderate down-regulation ($\log^2$ ratio of between −0.5 and −1.0).

TABLE 2

| Description of gene target | Accession No. | Wnt target | Ls174T target | Degree of modulation | 10 μM Compound 1 | 25 μM Compound 1 |
|---|---|---|---|---|---|---|
| nitric oxide synthase 3 (endothelial cell) | NM_000603 | | | +++ | | X |
| interleukin 8 | NM_000584 | x | | ++ | | X |
| LY6/PLAUR domain containing 6B | NM_177964 | | | ++ | x | X |
| peroxisome proliferator-activated receptor gamma | NM_138711 | | | ++ | x | X |
| transmembrane 4 L six family member 5 | NM_003963 | x | x | ++ | x | |
| snail homolog 2 (Drosophila) | NM_003068 | x | | ++ | | X |
| Kruppel-like factor 6 | NM_001300 | | | ++ | x | X |
| notum pectinacetylesterase homolog (Drosophila) | NM_178493 | x | | ++ | x | |
| ephrin-B2 | NM_004093 | x | | ++ | | X |
| plasminogen activator, urokinase | NM_002658 | | | + | | X |
| secreted frizzled-related protein 5 | NM_003015 | | | + | x | |
| plasminogen activator, urokinase receptor | NM_001005377 | x | | + | | X |
| Kruppel-like factor 4 (gut) | NM_004235 | | | + | x | X |
| met proto-oncogene (hepatocyte growth factor receptor) | NM_000245 | x | | + | | X |
| FYN oncogene related to SRC, FGR, YES | NM_002037 | x | x | + | x | |
| sal-like 4 (Drosophila) | NM_020436 | x | | + | | X |
| FOS-like antigen 1 | NM_005438 | x | | + | | X |
| bone morphogenetic protein 1 | NM_006129 | | | + | | X |
| mitogen-activated protein kinase kinase kinase 1 | NM_005921 | | | + | x | |
| low density lipoprotein receptor-related protein 5 | NM_002335 | | | + | x | |
| WNT1 inducible signaling pathway protein 3 | NM_003880 | x | | + | x | X |
| forkhead box F1 | NM_001451 | | | + | | X |
| epidermal growth factor receptor (erythroblastic leukemia viral (v-erb-b) oncogene homolog, avian) | NM_005228 | x | | + | | X |
| A kinase (PRKA) anchor protein 1 | NM_003488 | | | + | | X |
| dynein, axonemal, heavy chain 5 | NM_001369 | | | + | | X |
| low density lipoprotein receptor-related protein 5-like | NM_182492 | | | + | | X |
| T-cell lymphoma invasion and metastasis 1 | NM_003253 | x | | + | x | |
| mitogen-activated protein kinase kinase 3 | NM_002756 | | | + | x | X |

TABLE 2-continued

| Description of gene target | Accession No. | Wnt target | Ls174T target | Degree of modulation | 10 µM Compound 1 | 25 µM Compound 1 |
|---|---|---|---|---|---|---|
| CD44 molecule (Indian blood group) | NM_001001392 | x | x | + | | X |

"+++" denotes very strong up-regulation ($log^2$ ratio of between 1.5 and 2);
"++" denotes strong up-regulation ($log^2$ ratio of between 1.0 and 1.5); and
"+" denotes moderate up-regulation ($log^2$ ratio of between 0.5 and 1.0).

EXAMPLE 27

Induction of G1/S Arrest of a SW480 Colon Carcinoma Cell Line

Upon inhibition of canonical Wnt signaling, some cancer cell lines are partially arrested at the G1 phase of the cell cycle (van de W M et al. Cell 111: 241-250, 2002) demonstrating the importance of the Wnt pathway in tumor cell growth. Thus, the effect of compound No. 1 on cell growth was tested in SW480 cell lines using MTS analysis (MTS is the colorimetric substrate 3-(4,5-dimethylthiazol-2-yl)-5-(3-carboxymethoxyphenyl)-2-(4-sulfophenyl)-2H-tetrazolium).

Experimental 3000 cells were seeded on 96 well plates in quadruplicates for each sample. The following day, cell culture medium was mixed with compound No. 1 in various concentrations or with 0.5% DMSO vehicle (control) and added to the wells.

Eight wells of seeded control cells, defining incubation time 0 ($t_0$), were incubated with 20 µl substrate in 100 µl phenol-free D-MEM (Invitrogen) for 3 hours, as described in the CellTiter 96® AQ$_{ueous}$ Non-Radioactive Cell Proliferation Assay (MTS) protocol (Promega). The $A_{490}$ value was recorded.

Samples were measured after 72 hours. The following formula was used to determine the single well relative $A_{490}$ sample values: ((Sample $A_{490}$–Average $A_{490}$ $t_0$)×100)/(Average $A_{490}$ 0.5% DMSO control–Average $A_{490}$ $t_0$).

Results

Figure 5:
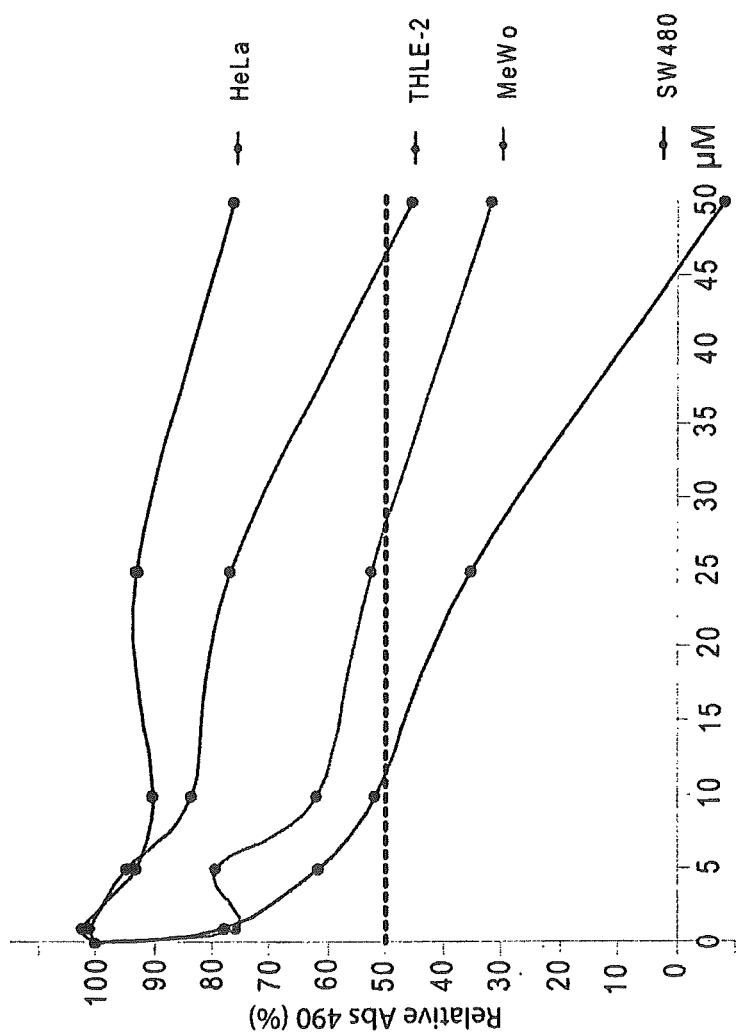
FIG. 5 shows the result of an MTS assay showing a concentration-dependent relative decrease in cell growth of SW480 colorectal cells compared to control cell lines HeLa, THLE-2 and MeWo. Shown are pooled data from two independent experiments.

Results (shown in FIG. 5) demonstrate a concentration-dependent reduction of proliferation of SW480 cells after treatment with compound No. 1 with an IC$_{50}$ value of approximately 11.5 µM. In contrast, only a minor growth reduction was observed in control cell lines lacking endogenous canonical Wnt activity, such as HeLa (cervical adenocarcinoma), THLE2 (hepatocytes) and MeWo (melanoma) cells.

EXAMPLE 28

Analysis of Cell Cycle Progression

Cell cycle progression was measured by BrdU labeling of cultured cells that were counterstained with propidium iodide (PI).

Experimental

SW480 cells were seeded and exposed to compounds for 3 days changing medium every day as described in Example 24. After a 30 minute incubation with 10 µM BrdU, the cells were trypsinized and stained with 1:100 diluted mouse anti-BrdU antibody (Roche) and Alexa Fluor® 488 goat anti-mouse antibody (A 11001, Invitrogen). Counterstaining was done with 10 µg/mL PI in 200 µg/mL RNase I (both Sigma). Samples were analyzed on the PAS-PPCS flow cytometer and cell sorter (Partec).

Results

FACS analysis of double-labelled cells showed that treated colorectal cells were partially arrested in G1 phase of the cell cycle.

Figure 6:
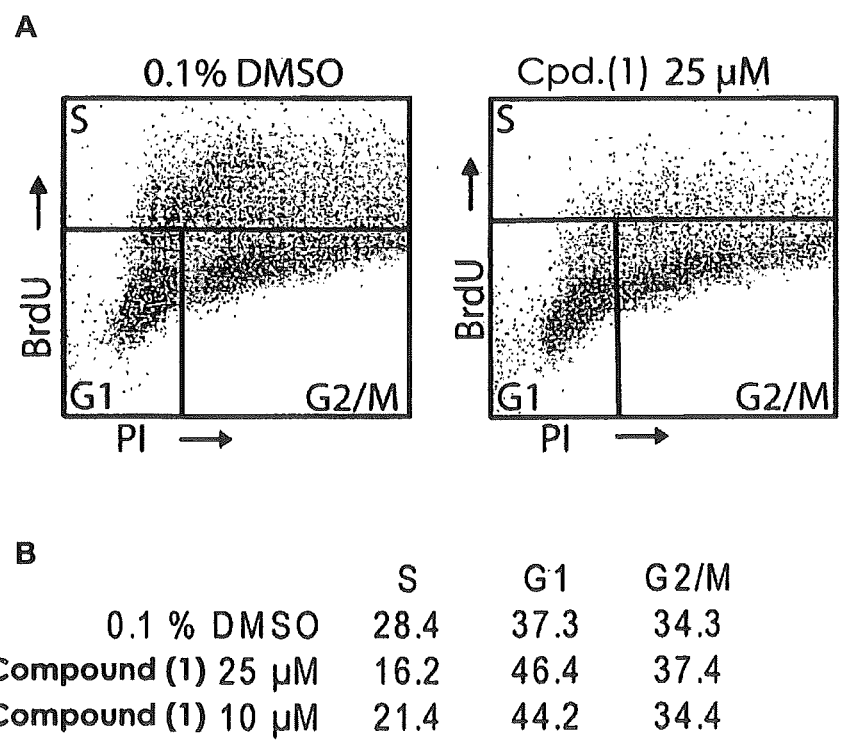
FIG. 6 shows BrdU/PI double labelling of SW480 cells treated with compound No. 1: A) scatter plot with depicted compartments representing cells in G1, S and G2/M phases of cell cycle; and B) representative data from several assays showing percentage of gated cells in each cell cycle phase in treated cells and DMSO controls.

After 72-hour treatment with either 25 or 10 µM of compound No. 1, the percentage of cells in S phase decreased and the G1 compartment increased compared to the DMSO control (FIG. 6). Incubation with 25 µM compound No. 1 nearly halved the number of cells in S-phase cells (the percentage falling from 28.4% to 16.2%) and increased G1-phase cells (from 37.3% to 46.4%).

EXAMPLE 29

Point of Action in the Wnt Pathway

The function of the GSK-3β protein (a serine/threonine protein kinase) can be blocked by LiCl leading to activation of canonical Wnt signaling by inefficient phosphorylation of β-catenin (Phiel C J et al., Annu. Rev. Pharmacol. Toxicol. 41: 789-813, 2001; and Klein P S et al., Proc. Natl. Acad. Sci. USA 93: 8455-8459, 1996). Therefore HEK293 cells were transiently transfected with a SuperTOPFlash reporter, and subsequently induced with 25 mM LiCl and exposed to various doses of compound No. 1.

Experimental

Transfection of HEK293 cells was performed as described in Example 22, but using 0.23 µg NF-κB-Luciferase and 0.02 µg Renilla. Following transfection, cells were incubated for 24 hours with 1 µM or 10 µM of compound No. 1 in 25 mM LiCl. All treated reporter cells were finally lysed and the firefly luciferase and Renilla activities were measured on a 20/20n Luminometer (Turner BioSystems) as described in the Dual-Glo™ Luciferase Assay System Technical Manual (Promega).

Results

As illustrated in FIG. 7, compound No. 1 antagonized LiCl-induced activation of canonical Wnt signaling with an IC$_{50}$ of 420 nM. These results indicate that the compound exerts its effect at the level of the GSK-3β/Axin/APC-destruction complex, or that it acts downstream of the destruction complex.

EXAMPLE 30

Action on β-catenin

The effect of compound No. 1 on the presence of β-catenin in the nucleus or in the cytoplasm of colorectal cancer SW480 cells was investigated. SW480 cells contain activating mutations in the APC gene, leading to elevated levels of nuclear β-catenin and aberrant canonical Wnt signaling. A Western blot analysis was carried out using cell lysates from compound-treated SW480 cells and an antibody against the active form of β-catenin (non-phosphorylated N-terminal—ABC).

In parallel, antibodies were used against total β-catenin (β-catenin), or β-catenin phosphorylated at the N-terminal (-β-catenin) which detects a degradable form of β-catenin.

Experimental

SW480 cells were seeded and treated with compound No. 1 as described in Example 25. Cell lysates were immunoblotted using monoclonal active-β-catenin (ABC—Millipore), monoclonal β-catenin (β-catenin—BD Transduction Laboratories™), phospho-β-catenin (pβ-catenin—Cell Signaling Technology) and actin (Sigma). Primary antibodies were visualized with secondary HRP conjugated antibodies (Santa Cruz Biotechnology) and enhanced chemiluminescent substrate (Pierce® ECL Western Blotting Substrate, Thermo Scientific).

For immunocytochemical experiments, SW480 cells were seeded and treated as described in Example 24. After 72 hours, cells were fixed in 4% PFA in PBS for 10 minutes. Immunostaining was performed as described in standard protocols. Primary antibody (monoclonal β-catenin, BD Transduction Laboratories™) and secondary antibody (Alexa Fluor® 594, Invitrogen) were diluted 1:1000. The samples were imaged by using a Zeiss Axiovert 200M Fluorescence/Live cell Imaging Microscope with X40 magnification and the same exposure times. Cells were stained with DAPI (4', 6-diamidino-2-phenylindole) according to standard protocols.

Results

Figure 8A:
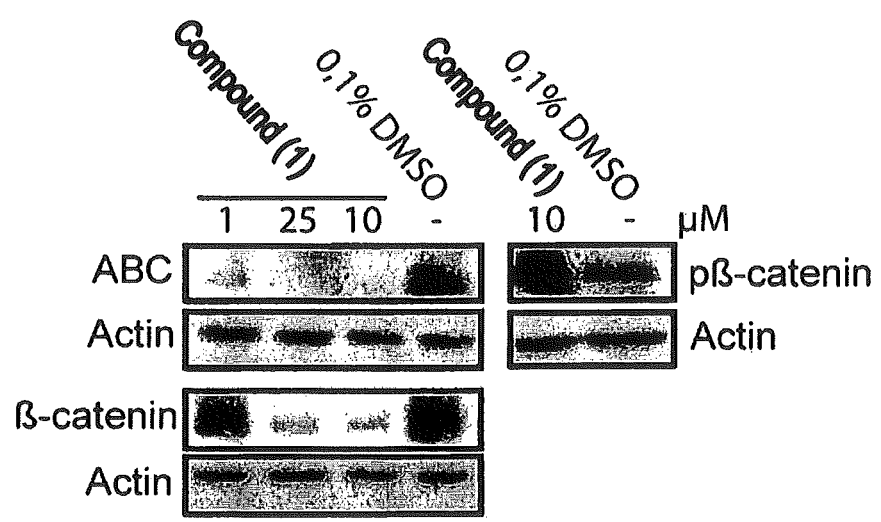

As seen in FIG. 8A (left), overall levels of total β-catenin were reduced after 72-hour exposure to compound No. 1. Strikingly, all concentrations of compound No. 1 led to an even stronger reduction of ABC.

Figure 8B:
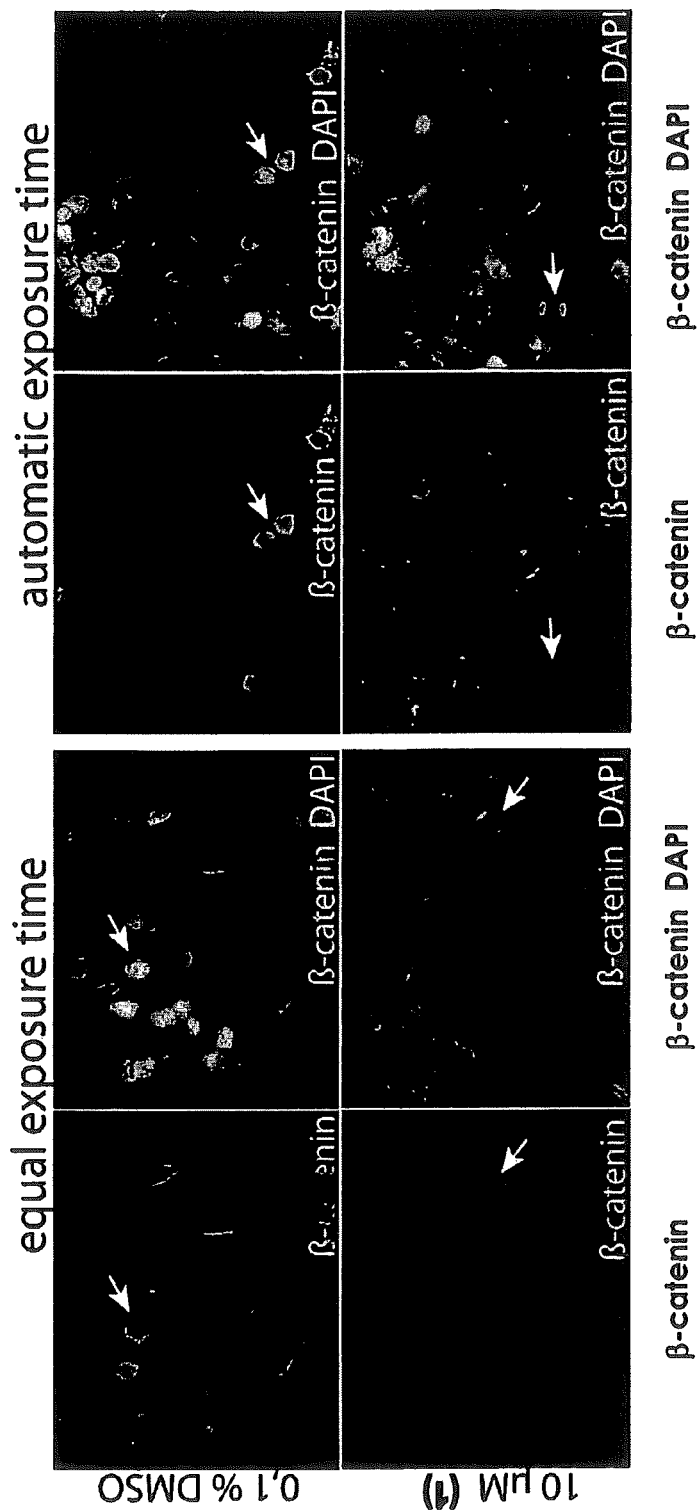

The level of degradable pβ-catenin temporarily increased 24 hours after adding compound No. 1 (FIG. 8A, right). Reduction of nuclear total β-catenin in SW480 cells was also seen using immunofluorescence with the β-catenin antibody after 72-hour incubation with the compound (FIG. 8B). In contrast to the alterations in nuclear β-catenin, cell membrane-associated β-catenin could still be observed.

EXAMPLE 31

Direct Action on β-catenin

To investigate a potential direct effect of compound No. 1 on β-catenin, HEK293 cells were transiently transfected with the ST-Luc reporter and with a series of constructs encoding various components of the Wnt pathway. These included full-length β-catenin, β-catenin with point mutations at N-terminal phosphorylation sites (dominant active, da-Cat), N-terminal deletion of β-catenin (ΔN-Cat) as another dominant active form, and β-catenin C-terminal transactivation domain fused to LEF-1 (CLEF) functioning as dominant active LEF-1. Plasmid amounts used for transfections were diminished to nanograms per 48-well plate to obtain a pathway induction in the range of 10-20 fold.

Experimental

Transfection was performed as described in Example 22, but using β-catenin variants co-transfected in the following plasmid combinations:

1) 0.215 µg SuperTOPFlash+0.02 µg Renilla+0.015 µg β-catenin;
2) 0.23 µg SuperTOPFlash+0.02 µg Renilla+0.2 ng da-Cat (dominant active β-catenin (S33, 37, 41 and 45A mutated);
3) 0.23 µg SuperTOPFlash+0.02 µg Renilla+0.2 ng ΔN-Cat (N-terminal deleted β-catenin; and
4) 0.23 µg SuperTOPFlash+0.02 µg Renilla+0.2 ng CLEF (β-catenin transactivation domain fused to LEF-1).

β-catenin plasmid version co-transfected HEK293 cells were exposed to compound No. 1 at 10 or 25 µM concentrations for 24 hours from time of transfection.

Results

FIG. 9 shows that activation of canonical Wnt signaling by overexpression of normal full-length β-catenin is reduced by compound No. 1. Interestingly, activation of the pathway by dominant active constructs da-Cat, CLEF and ΔN-Cat was not significantly antagonized by compound No. 1. These transfection experiments indicate that the function of compound No. 1 relates to the level of N-terminal phosphorylation of β-catenin. As long as phosphorylation cannot occur, e.g. due to targeted mutations in β-catenin, compound No. 1 is not able to inhibit ectopic canonical Wnt signaling.

EXAMPLE 32

Reduction of Tumor Growth in a CB17/SCID Xenograft Model

An in vivo examination of compound No. 1 was carried out to determine the efficacy of the compound in reducing tumor growth and to identify any potential side-effects.

SW480 colorectal cells were injected subcutaneously into CB17/SCID mice and palpable tumors were detected within 7 days in ~50% of the mice. Randomized groups of mice were injected (i.p.) daily with compound No. 1 at doses of 150 mg/kg or 30 mg/kg (delivered daily for five days followed by a 2-day pause) at termination, plasma was collected and tumors were isolated and weighed.

Experimental 40 female C.B-Igh-$1^b$/IcrTac-Prkdc$^{scid}$ mice (Taconic) were injected subcutaneously (s.c.) at the right posterior flank with $10^7$ SW480 cells diluted in 100 µl PBS. Injections were initiated when tumor formation was visible in 50% of the animals (7 days). Mice were randomized and divided into three treatment groups: 150 mg/kg compound No. 1, 300 mg/kg compound No. 1 and vehicle control 1% Tween® 80 (Sigma).

Daily injections (200 µl, i.p.) followed (two day injection intermissions after every fifth injection day) until experiment end (29 days). At the termination day, 24 hours after the last injection, blood was collected after cardiac puncture and the tumors were removed and weighed. The compound concentration in plasma and tumors was determined using an on-line and off-line Solid Phase Extraction-Capillary Liquid Chromatography (SPE-CapLC) instrumentation coupled to a Time of Flight (TOF) mass spectrometer, as previously described (Wilson, S. R. et al., J. Sep. Sci. 28: 1751-1758, 2005). A Zorbax SB $C_{18}$ 5 µm 150×0.3 mm column (Agilent, Sao Paulo, Calif., USA) was used for separation, and a Knauer K-2600 UV detector was used as a complimentary detector.

RNA was isolated from representative groups of tumors (n=5) and analysed by real-time RT-PCR as described in Example 25 for expression of Sp5. Results were calculated as the ratio of expression of Sp5 to a control gene (hGUSB).

As described in standard protocols, immunostaining was performed with rabbit polyclonal smooth muscle actin (Abcam) and monoclonal β-catenin (BD Transduction Laboratories™), both diluted 1:1000. Secondary antibodies used were 1:500 diluted Alexa Fluor® 594 goat anti-rabbit antibody and Alexa Fluor® 488 goat anti-mouse antibody. The sections were imaged by a Zeiss Axiovert 200M Fluorescence/Live cell Imaging Microscope with $X^{40}$ magnification and the same exposure times.

Results

A reduction in tumor size was observed of, on average, 33% for compound No. 1 at 150 mg/kg and 35% for compound No. 1 at 300 mg/kg (FIG. 10A). These values are statistically significant (Mann-Whitney rank sum test when the two groups, 150 mg/kg and 300 mg/kg, are pooled: P=0.045).

Real-time RT-PCR revealed that SP5 mRNA was down-regulated in tumors treated with compound No. 1 at both 150 mg/kg and 300 mg/kg doses (FIG. 10B).

Tumors were stained with antibodies against β-catenin and smooth muscle actin to identify any activated stroma within the tumor. Major changes in the distribution of tumor cells or stroma could not be observed and the proportion of human tumor cells and mouse stroma among treated vs. control groups was similar (FIG. 10C).

Compound No. 1 was readily detected in tumors and in plasma using LC-UV analysis (FIGS. 11A and B). Concentrations of compound No. 1 were measured to be: 1.9-32.9 µg/g (mean: 11.8 µg/g) in the cohort for 150 mg/kg and 0.9-4.9 µg/g (mean: 2.4 µg/g) in the cohort 300 mg/kg. Concentrations in plasma were measured to be: 1.3 µg/ml in the 150 mg/kg group and 1.3 µg/ml in the 300 mg/kg group. A higher concentration in tumors than in plasma indicates an accumulation of the compound in the tumors.

No obvious adverse side effects, such as weight loss were observed during treatment.

EXAMPLE 33

Preparation of Compound (113)

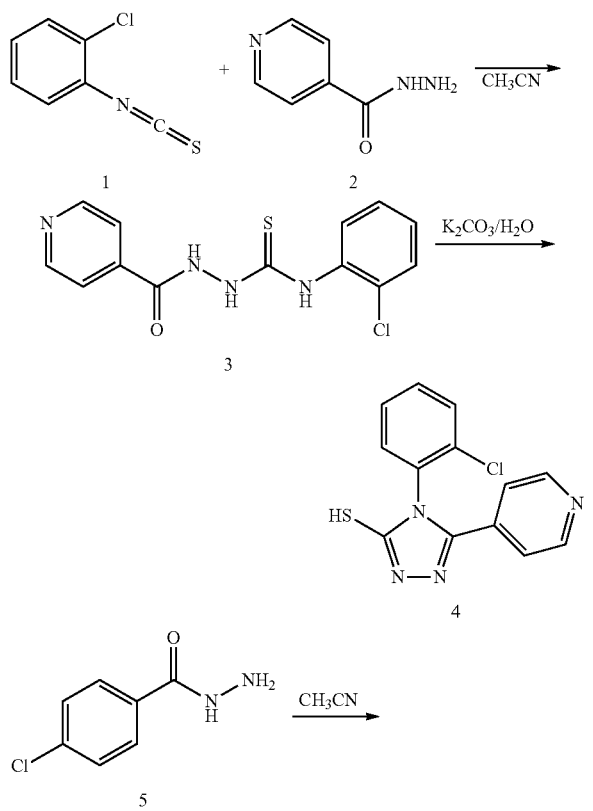

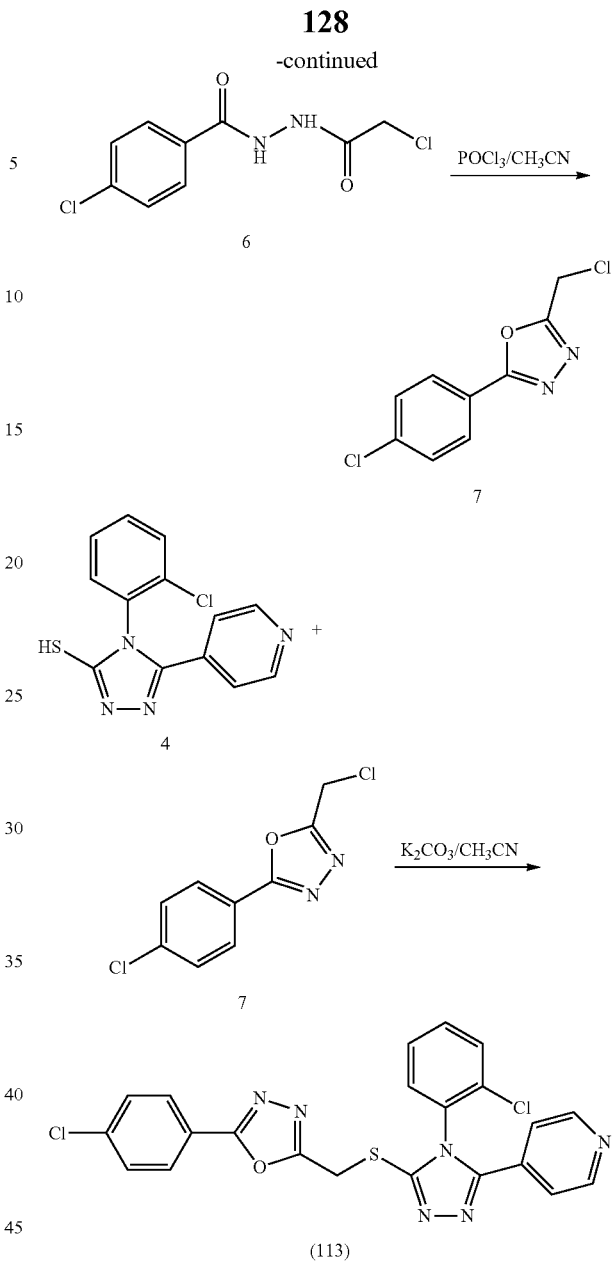

(a) Preparation of 4-(2-chlorophenyl)-5-(pyridin-4-yl)-4H-1,2,4-triazole-3-thiol 4

A mixture of 1-chloro-2-isothiocyanatobenzene 1 (3 g, 17.68 mmol) and isonicotinohydrazide 2 (2.43 g, 17.68 mmol) in acetonitrile was stirred at ambient temperature for 18 hours, concentrated to dryness, and 100 mL of 10% $K_2CO_3$ (aq.) was added. The resulting mixture was stirred under reflux for 6 hours. The clear solution was cooled to ambient temperature, washed with ether and acidified with 1N HCl. The solid was collected, washed with $H_2O$ and ether, and dried to afford compound 4 (4.3 g). Yield: 86%.

$^1$H-NMR (300 MHz, DMSO-$d_6$) δ (ppm): 8.68 (d, 2H), 7.80-7.58 (m, 4H), 7.28 (d, 2H).

(b) Preparation of 2-(chloromethyl)-5-(4-chlorophenyl)-1,3,4-oxadiazole 7

To a mixture of 4-chlorobenzohydrazide 5 (1 g, 5.86 mmol) and $K_2CO_3$ (0.97 g, 7.03 mmol) in acetonitrile (30 mL) was added 2-chloroacetyl chloride (0.68 g, 6.08 mmol) dropwise at ambient temperature. The resulting mixture was stirred at ambient temperature for 16 hours. The solid was collected, washed with H₂O and ether, and dried to afford 4-chloro-N'-(2-chloroacetyl)benzohydrazide 6 (1.2 g, 82%) which was used for the next step without further purification. A mixture of 4-chloro-N'-(2-chloroacetyl)benzohydrazide 6 (0.6 g, 2.43 mmol) and phosphorous oxychloride (0.37 g, 2.43 mmol) in acetonitrile (20 mL) was stirred under reflux for 16 hours and concentrated. The residue was subjected to flush column chromatography eluting with 10-25% acetone/hexanes to give compound 7 (0.45 g). Yield: 82%.

¹H-NMR (300 MHz, CDCl₃) δ (ppm): 8.02 (d, 2H), 7.53 (d, 2H), 4.78 (s, 2H).

(c) Preparation of 4-(5-((5-(4-chlorophenyl)-1,3,4-oxadiazol-2-yl)methylthio)-4-(2-chlorophenyl)-4H-1,2,4-triazol-3-yl)pyridine (Compound (113))

A mixture of compound 7 (0.13 g, 0.57 mmol), compound 4 (0.15 g, 0.52 mmol), and K₂CO₃ in acetonitrile was stirred at ambient temperature for 30 min and filtered. The filtrate was concentrated. The residue was subjected to flush column chromatography eluting with 25-50% acetone/hexanes to give compound (113) (0.23 g). Yield: 92%.

¹H-NMR (300 MHz, CHLOROFORM-d) δ (ppm): 8.56 (d, 2H), 7.93 (d, 2H), 7.60-7.26 (m, 8H), 4.72 (q, 2H). MS (ESI): 481.70. HPLC (Waters 625 LC system): 98%.

EXAMPLE 34

Preparation of Compound (114)

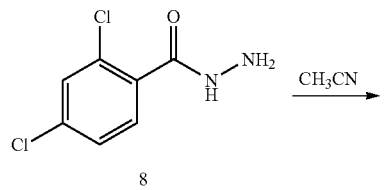

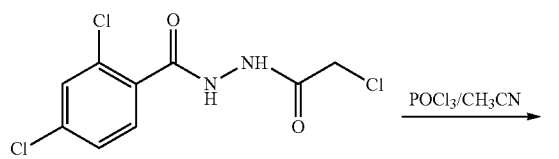

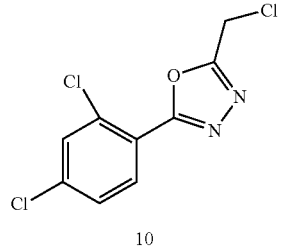

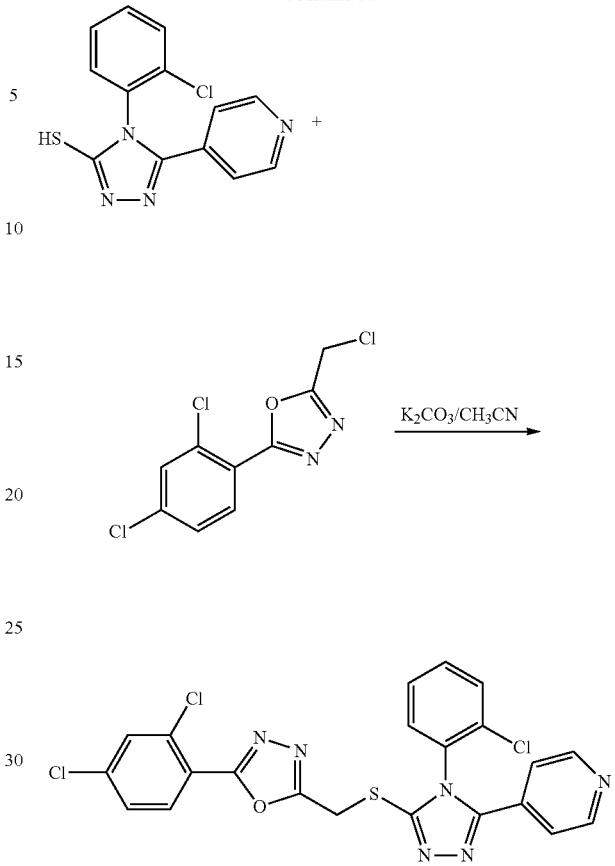

(a) Preparation of 2-(chloromethyl)-5-(2,4-dichlorophenyl)-1,3,4-oxadiazole 10

To a suspension of 2,4-dichlorobenzohydrazide 8 (451 mg, 2.2 mmol) in 20 mL of acetonitrile was added chloroacetyl chloride (260 mg, 2.3 mmol) followed by NaOH (100 mg, 2.3 mmol). The mixture was stirred at ambient temperature for 4 hours. The solid was collected by filtration, washed with water and dried to give 545 mg (88%) of compound 9 which was used for the next step without further purification. To a suspension of compound 9 (270 mg, 0.96 mmol) in 30 mL of acetonitrile was added 300 mg of POCl₃. The mixture was heated at reflux for 5 hours. After removal of the solvent, the residue was purified by column (1:1 of hexane/ethyl acetate) to give 200 mg of compound 10. Yield: 79%.

¹H-NMR (300 MHz, CHLOROFORM-d) δ (ppm): 7.97 (d, 1H), 7.60 (d, 1H), 7.42 (dd, 1H), 4.56 (s, 2H).

(b) Preparation of 4-(5-((5-(2,4-dichlorophenyl)-1,3,4-oxadiazol-2-yl)methylthio)-4-(2-chlorophenyl)-4H-1,2,4-triazol-3-yl)pyridine (Compound (114))

To a solution of compound 10 (180 mg, 0.68 mmol) and 4-(2-chlorophenyl)-5-(pyridin-4-yl)-4H-1,2,4-triazole-3-thiol 4 (197 mg, 0.68 mmol) in 20 mL of acetonitrile was added K₂CO₃ (188 mg, 1.38 mmol). The mixture was stirred at ambient temperature for 3 hours. After removal of solvent, the residue was purified by column (0-2% of MeOH in DCM) to give 300 mg of compound (114). Yield: 85%.

$^1$H-NMR (300 MHz, CHLOROFORM-d) δ (ppm): 8.58 (m, 2H), 7.93 (d, 1H), 7.30-7.70 (m, 8H), 4.80 (q, 2H). MS (ESI): 515.8. HPLC (Waters 625 LC system): 98%.

EXAMPLE 35

Preparation of Compound (138)

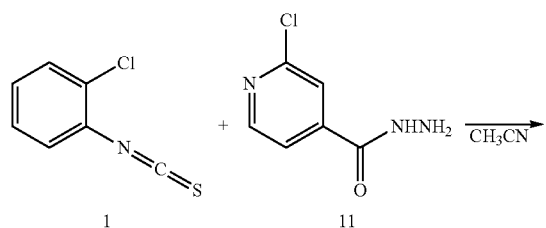

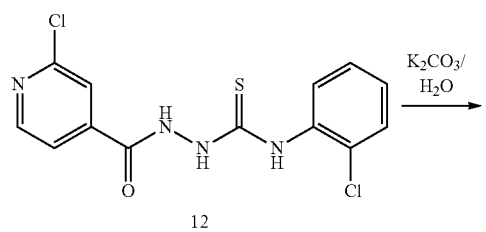

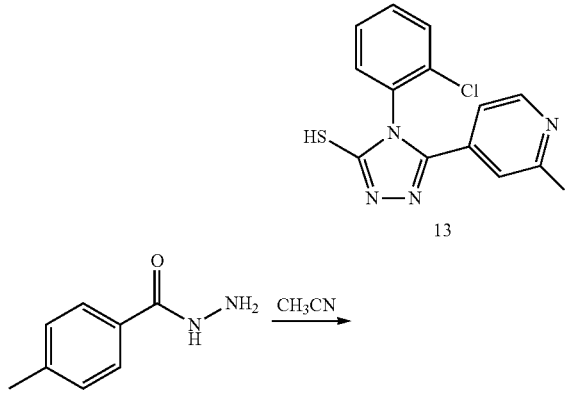

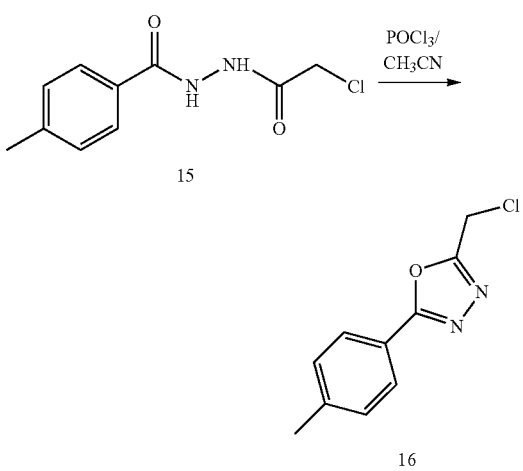

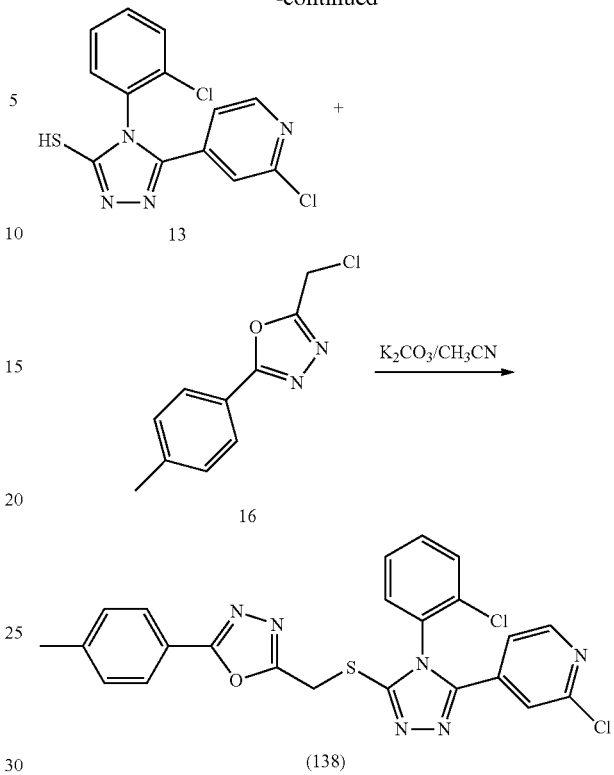

(a) Preparation of 4-(2-chlorophenyl)-5-(2-chloropyridin-4-yl)-4H-1,2,4-triazole-3-thiol 13

A mixture of 1-chloro-2-isothiocyanatobenzene 1 (0.4 g, 2.33 mmol) and 2-chloropyridine-4-carbohydrazide 11 (0.4 g, 2.33 mmol) in DMF was stirred at ambient temperature for 18 hours, concentrated to dryness, and 20 mL of 10% K$_2$CO$_3$ (aq.) was added. The resulting mixture was stirred under reflux for 6 hours. The clear solution was cooled to ambient temperature, washed with ether, and acidified with 1N HCl. The solid was collected, washed with H$_2$O and ether, and dried to afford compound 13 (4.3 g). Yield: 86%.

$^1$H-NMR (300 MHz, CHLOROFORM-d) δ (ppm): 8.30 (d, 1H), 7.63-7.18 (m, 5H), 7.16 (d, 1H).

(b) Preparation of 2-(chloromethyl)-5-p-tolyl-1,3,4-oxadiazole 16

To a mixture of 4-methylbenzohydrazide 14 (10 g, 66.59 mmol) and K$_2$CO$_3$ (16.57 g, 119.86 mmol) in acetonitrile (100 mL) was added 2-chloroacetyl chloride (9.02 g, 79.9 mmol) dropwise at ambient temperature. The resulting mixture was stirred at ambient temperature for 16 hours. The solid was collected, washed with H$_2$O and ether, and dried to afford N'-(2-chloroacetyl)-4-methylbenzohydrazide 15 (13 g, 82%) which was used for the next step without further purification.

A mixture of N'-(2-chloroacetyl)-4-methylbenzohydrazide 15 (6.0 g, 26.47 mmol) and phosphorous oxychloride (5.0 g, 32.84 mmol) in acetonitrile (20 mL) was stirred under reflux for 16 hours and concentrated. The residue was subjected to flush column chromatography eluting with 10-25% acetone/hexanes to give compound 16 (4 g). Yield: 72%.

$^1$H-NMR (300 MHz, CHLOROFORM-d) δ (ppm): 7.96 (d, 2H), 7.30 (d, 2H), 4.77 (s, 2H), 2.44 (s, 3H).

(c) Preparation of 4-(5-((5-p-tolyl-1,3,4-oxadiazol-2-yl)methylthio)-4-(2-chlorophenyl)-4H-1,2,4-triazol-3-yl)-2-chloropyridine (Compound (138))

A mixture of compound 16 (0.16 g, 0.74 mmol), compound 13 (0.2 g, 0.62 mmol), and K₂CO₃ in acetonitrile was stirred at ambient temperature for 30 min and filtered. The filtrate was concentrated. The residue was subjected to flush column chromatography eluting with 25-50% acetone/hexanes to give compound (138) (0.28 g). Yield: 93%.

¹H-NMR (300 MHz, CHLOROFORM-d) δ (ppm): 8.30 (d, 1H), 7.86 (d, 2H), 7.63-7.18 (m, 7H), 7.16 (d, 1H), 4.76 (q, 2H), 2.44 (s, 3H).

MS (ESI): 495.5. HPLC (Waters 625 LC system): 97%.

EXAMPLE 36

Preparation of Compound (109)

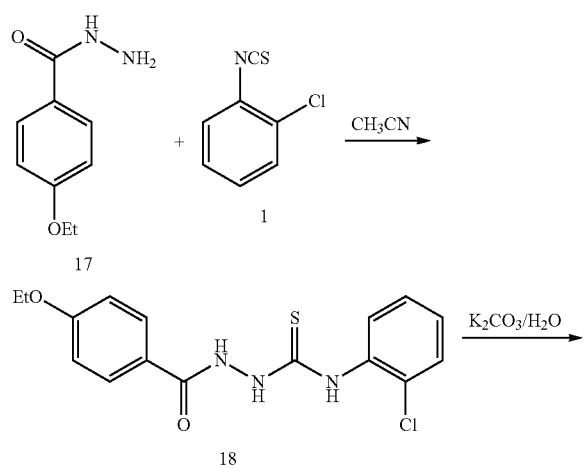

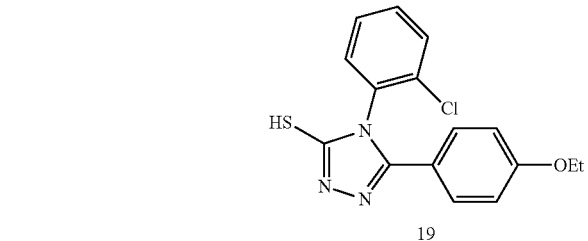

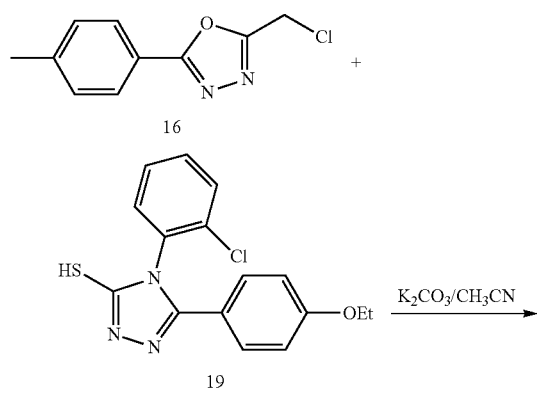

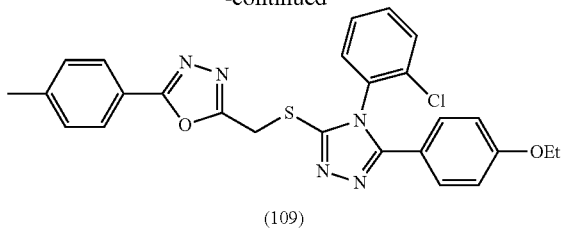

(109)

(a) Preparation of 4-(2-chlorophenyl)-5-(4-ethoxyphenyl)-4H-1,2,4-triazole-3-thiol 19

A mixture of 4-ethoxybenzohydrazide 17 (0.5 g, 2.77 mmol) and isonicotinohydrazide 1 (0.47 g, 2.77 mmol) in acetonitrile was stirred at ambient temperature for 18 hours, concentrated to dryness, and 20 mL of 10% K₂CO₃ (aq.) was added. The resulting mixture was stirred under reflux for 6 hours. The clear solution was cooled to ambient temperature, washed with ether, and acidified with 1N HCl. The solid was collected, washed with H₂O and ether, and dried to afford compound 19 (0.74 g). Yield: 80%.

¹H-NMR (300 MHz, DMSO-d₆) δ (ppm): 7.47-7.7.31 (m, 4H), 7.18 (d, 2H), 6.68 (d, 2H), 3.90 (q, 2H), 1.28 (t, 3H).

(b) Preparation of 3-((5-p-tolyl-1,3,4-oxadiazol-2-yl)methylthio)-4-(2-chlorophenyl)-5-(4-ethoxyphenyl)-4H-1,2,4-triazole (Compound (109))

A mixture of 2-(chloromethyl)-5-p-tolyl-1,3,4-oxadiazole 16 (0.13 g, 0.57 mmol), compound 19 (0.15 g, 0.52 mmol), and K₂CO₃ in acetonitrile was stirred at ambient temperature for 30 min and filtered. The filtrate was concentrated. The residue was subjected to flush column chromatography eluting with 25-50% acetone/hexanes to give compound (109).

¹H-NMR (300 MHz, CHLOROFORM-d) δ (ppm): 7.88 (d, 2H), 7.55 (d, 1H), 7.43 (t, 1H), 7.40-7.21 (m, 6H), 7.78 (d, 2H), 4.71 (q, 2H), 4.00 (q, 2H), 2.41 (s, 3H), 1.38 (t, 1H). MS (ESI): 504.8. HPLC (Waters 625 LC system): 94%.

EXAMPLE 37

Preparation of Compound (112)

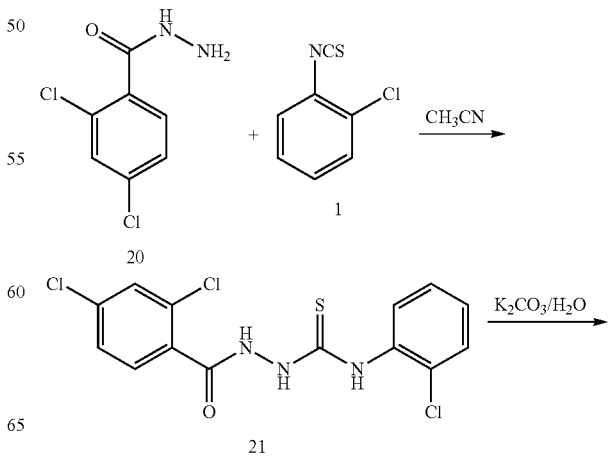

-continued

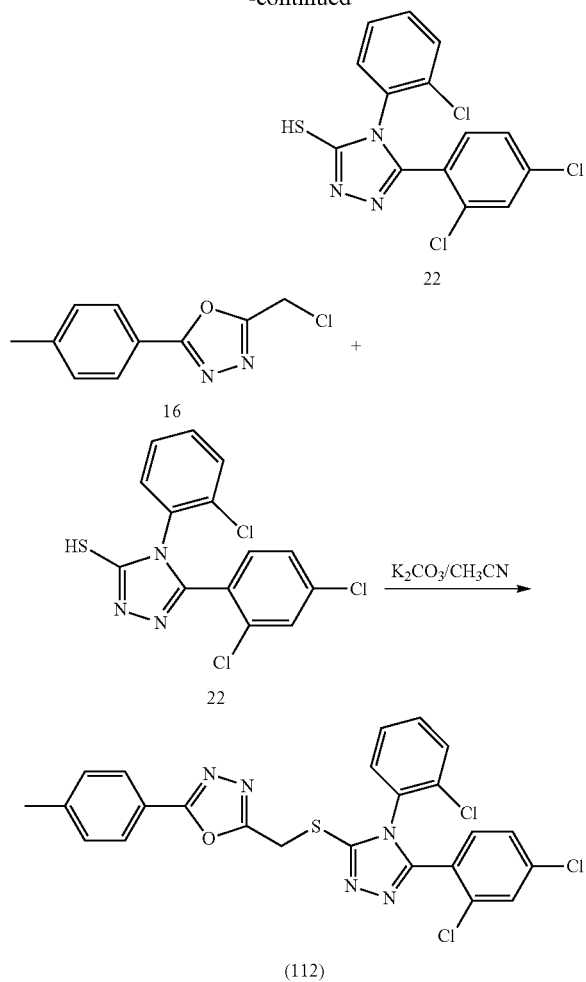

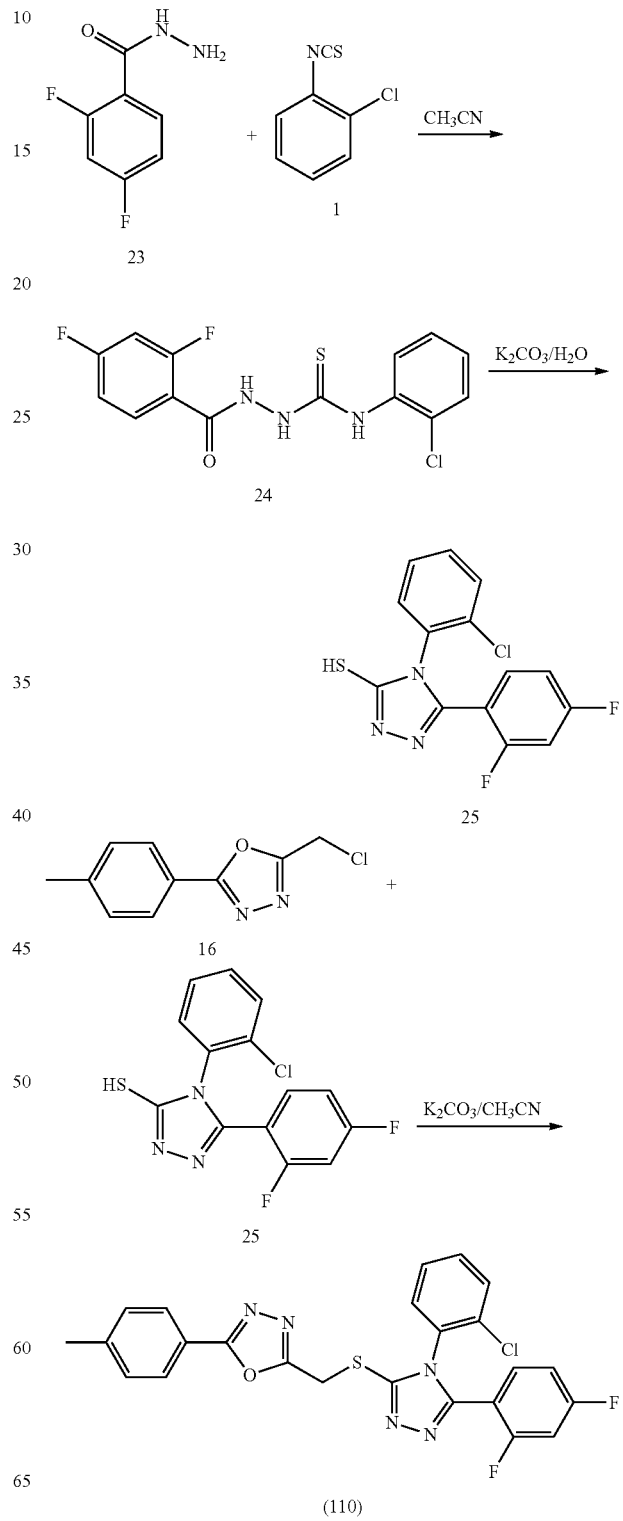

¹H-NMR (300 MHz, CHLOROFORM-d) δ (ppm): 7.90 (d, 2H), 7.20-7.50 (m, 9H), 4.73 (q, 2H), 2.43 (s, 3H). MS (ESI): 528.2. HPLC (Waters 625 LC system): 98%.

EXAMPLE 38

Preparation of Compound (110)

(a) Preparation of 5-(2,4-dichlorophenyl)-4-(2-chlorophenyl)-4H-1,2,4-triazole-3-thiol 22

1-chloro-2-isothiocyanatobenzene 1 (373 mg, 2.2 mmol) and 2,4-dichlorobenzohydrazide 20 (451 mg, 2.2 mmol) were mixed in 20 mL of acetonitrile and stirred at ambient temperature for 24 hours. After removal of solvent, the residue was mixed with 30 mL of 10% K₂CO₃ (aq.) solution. The mixture was heated at reflux for 18 hours. After acidifying to pH 7, the mixture was extracted with ethyl acetate (30 mL×2). The organic layer was separated, concentrated and purified by column (1:1 of hexane/ethyl acetate) to give 660 mg of compound 22. Yield: 84%.

¹H-NMR (300 MHz, CHLOROFORM-d) δ (ppm): 7.20-7.50 (m, 7H).

(c) Preparation of 3-((5-p-tolyl-1,3,4-oxadiazol-2-yl)methylthio)-5-(2,4-dichlorophenyl)-4-(2-chlorophenyl)-4H-1,2,4-triazole (Compound (112))

To a mixture of compound 22 (180 mg, 0.5 mmol) and 2-(chloromethyl)-5-p-tolyl-1,3,4-oxadiazole 16 (105 mg, 0.5 mmol) in acetonitrile was added K₂CO₃ (138 mg, 1.0 mmol). The mixture was stirred at ambient temperature for 2 hours. After removal of solvent, the residue was purified by column (1:1 of hexane/ethyl acetate) to give 200 mg of compound (112). Yield: 75%.

(a) Preparation of 4-(2-chlorophenyl)-5-(2,4-difluorophenyl)-4H-1,2,4-triazole-3-thiol 25

A mixture of 2,4-difluorobenzohydrazide 23 (0.5 g, 2.9 mmol) and isonicotinohydrazide 1 (0.49 g, 2.9 mmol) in acetonitrile was stirred at ambient temperature for 18 hours, concentrated to dryness, and 20 mL of 10% $K_2CO_3$ (aq.) was added. The resulting mixture was stirred under reflux for 6 hours. The clear solution was cooled to ambient temperature, washed with ether, and acidified with 1N HCl. The solid was collected, washed with $H_2O$ and ether, and dried to afford compound 25 (0.76 g). Yield: 80%.

$^1$H-NMR (300 MHz, DMSO-$d_6$) δ (ppm): 8.68 (d, J=4.8 Hz, 2H), 7.80-7.58 (m, 4H), 7.28 (d, J=15.7 Hz, 2H).

(b) Preparation of 3-((5-p-tolyl-1,3,4-oxadiazol-2-yl)methylthio)-4-(2-chlorophenyl)-5-(2,4-difluorophenyl)-4H-1,2,4-triazole (Compound (110))

A mixture of 2-(chloromethyl)-5-p-tolyl-1,3,4-oxadiazole 16 (0.13 g, 0.62 mmol), compound 25 (0.17 g, 0.52 mmol), and $K_2CO_3$ in acetonitrile was stirred at ambient temperature for 30 min and filtered. The filtrate was concentrated. The residue was subjected to flush column chromatography eluting with 25% acetone/hexanes to give compound (110) (0.25 g). Yield: 96%.

$^1$H-NMR (300 MHz, CHLOROFORM-d) δ (ppm): 7.88 (d, J=6.6 Hz, 2H), 7.56 (dd, J=6.6 Hz, 1H), 7.46-23 (m, 6H), 6.95 (t, J=3.0 Hz, 1H), 6.72 (t, J=8.7 Hz, 1H), 4.74 (q, J=15.0 Hz, 2H), 2.42 (s, 3H). MS (ESI): 496.5. HPLC (Waters 625 LC system): 96%.

EXAMPLE 39

Preparation of Compound (106)

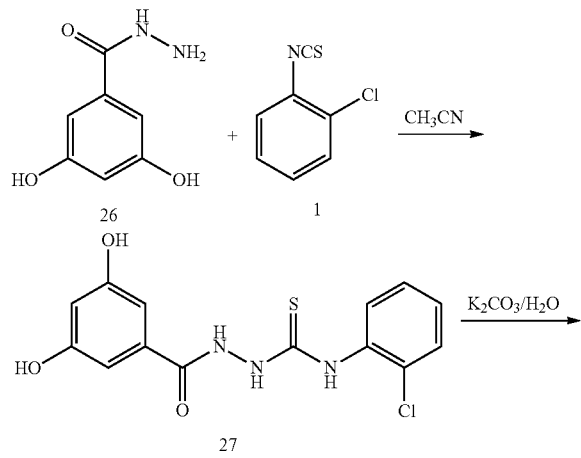

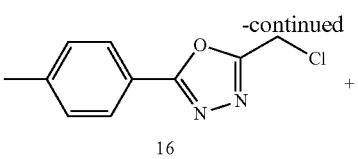

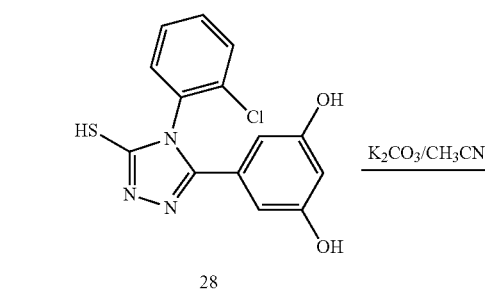

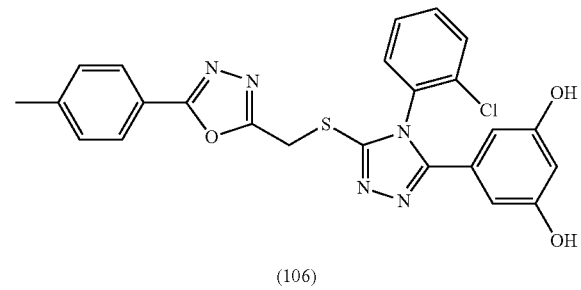

(a) Preparation of 5-(4-(2-chlorophenyl)-5-mercapto-4H-1,2,4-triazol-3-yl)benzene-1,3-diol 28

1-chloro-2-isothiocyanatobenzene 1 (1.0 g, 5.9 mmol) and 3,5-dihydroxybenzohydrazide 26 (1.0, 6.0 mmol) were mixed in 80 mL of acetonitrile and 20 mL of DMF. The mixture was stirred at ambient temperature for 5 hours. After removal of solvent, the residue was mixed with 60 mL of 10% $K_2CO_3$ (aq.) solution. The mixture was heated at reflux for 18 hours. After acidifying to pH 7, the mixture was extracted with ethyl acetate (80 mL×2). The organic layer was separated, concentrated and purified by column (5% of $CH_3OH$ in $CH_2Cl_2$) to give 1.7 g of compound 28. Yield: 90%.

$^1$H-NMR (300 MHz, DMSO-$d_6$) δ (ppm): 9.50 (s, 2H), 7.40-7.70 (m, 4H), 6.23 (t, 1H), 6.17 (d, 2H).

(b) Preparation of (5-((5-p-tolyl-1,3,4-oxadiazol-2-yl)methylthio)-4-(2-chlorophenyl)-4H-1,2,4-triazol-3-yl)benzene-1,3-diol (Compound (106))

Compound 28 (160 mg, 0.5 mmol), 2-(chloromethyl)-5-p-tolyl-1,3,4-oxadiazole 16 (105 mg, 0.5 mmol) and $K_2CO_3$ (138 mg, 1.0 mmol) were mixed in 20 mL of acetonitrile and stirred at ambient temperature for 2 hours. The solid was collected by filtration and purified by column (10% of $CH_3OH$ in $CH_2Cl_2$) to give 220 mg of compound (106). Yield: 90%.

¹H-NMR (300 MHz, DMSO-d₆) δ (ppm): 9.47 (s, 2H), 7.30-7.90 (m, 8H), 6.20 (m, 3H), 4.66 (q, 2H), 2.39 (s, 3H). MS (ESI): 492.4. HPLC (Waters 625 LC system): 95%.

EXAMPLE 40

Preparation of Compound (105)

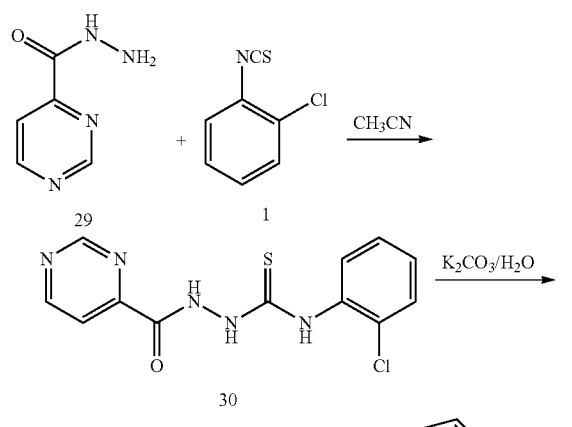

(a) Preparation of 4-(2-chlorophenyl)-5-(pyrimidin-4-yl)-4H-1,2,4-triazole-3-thiol 31

A mixture of pyrimidine-4-carbohydrazide 29 (0.5 g, 3.62 mmol) and isonicotinohydrazide 1 (0.6 g, 3.62 mmol) in acetonitrile was stirred at ambient temperature for 18 hours, concentrated to dryness, and 20 mL of 10% K₂CO₃ (aq.) was added. The resulting mixture was stirred under reflux for 6 hours. The clear solution was cooled to ambient temperature, washed with ether, and acidified with 1N HCl. The solid was collected, washed with H₂O and ether, and dried to afford compound 31 (0.76 g). Yield: 80%.

¹H-NMR (300 MHz, DMSO-d₆) δ (ppm): 8.68 (d, J=4.8 Hz, 2H), 7.80-7.58 (m, 4H), 7.28 (d, J=15.7 Hz, 2H).

(b) Preparation of 4-(5-((5-p-tolyl-1,3,4-oxadiazol-2-yl)methylthio)-4-(2-chlorophenyl)-4H-1,2,4-triazol-3-yl)pyrimidine (Compound (105))

A mixture of 2-(chloromethyl)-5-p-tolyl-1,3,4-oxadiazole 16 (0.17 g, 0.83 mmol), compound 31 (0.2 g, 0.69 mmol), and K₂CO₃ in acetonitrile was stirred at ambient temperature for 30 min and filtered. The filtrate was concentrated. The residue was subjected to flush column chromatography eluting with 25-50% acetone/hexanes to give compound (105) (0.26 g). Yield: 80%.

¹H-NMR (300 MHz, CHLOROFORM-d) δ (ppm): 8.82 (d, 2H), 8.23 (d, 1H), 7.89 (d, 2H), 7.55-7.26 (m, 6H), 4.82 (q, 2H), 2.41 (s, 3H). MS (ESI): 463.0. HPLC (Waters 625 LC system): 98%.

EXAMPLE 41

Preparation of Compound (111)

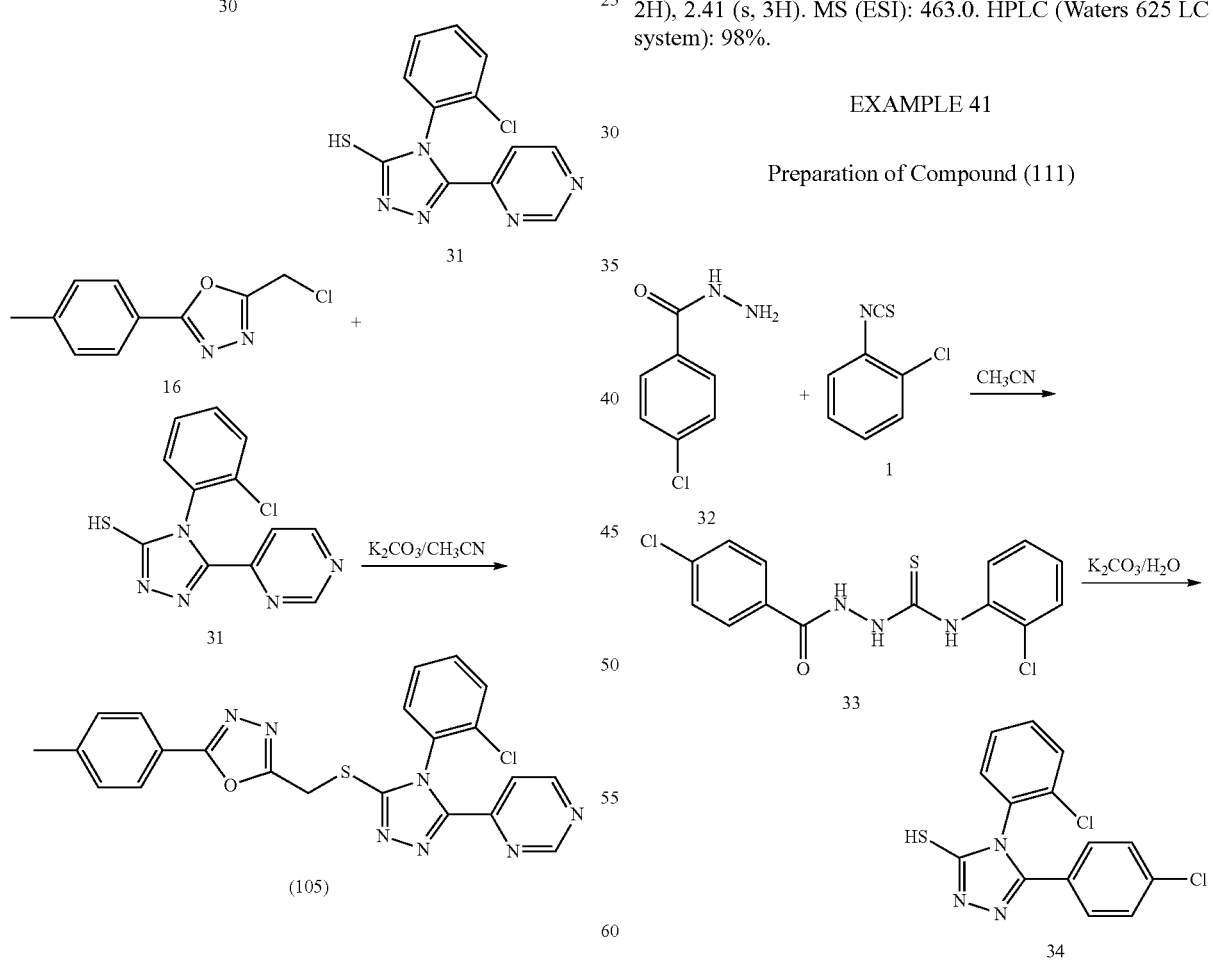

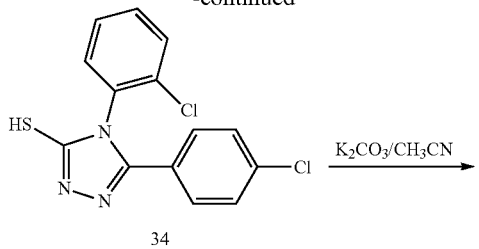
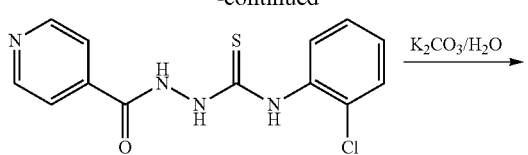
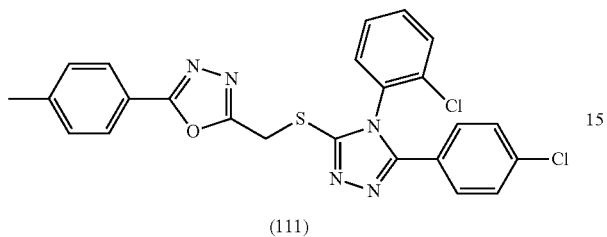
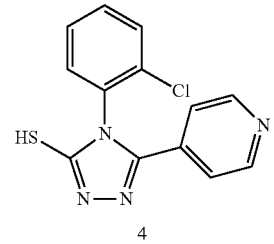

(a) Preparation of 4-(2-chlorophenyl)-5-(4-chlorophenyl)-4H-1,2,4-triazole-3-thiol 34

A mixture of 4-chlorobenzohydrazide 32 (0.5 g, 2.93 mmol) and isonicotinohydrazide 1 (0.5 g, 2.93 mmol) in acetonitrile was stirred at ambient temperature for 18 hours, concentrated to dryness, and 20 mL of 10% $K_2CO_3$ (aq.) was added. The resulting mixture was stirred under reflux for 6 hours. The clear solution was cooled to ambient temperature, washed with ether, and acidified with 1N HCl. The solid was collected, washed with $H_2O$ and ether, and dried to afford compound 34 (0.74 g). Yield: 80%.

$^1$H-NMR (300 MHz, DMSO-$d_6$) δ (ppm): 7.65-7.58 (m, 2H), 7.56-7.50 (m, 2H), 7.38-7.28 (m, 4H).

(b) Preparation of 3-((5-p-tolyl-1,3,4-oxadiazol-2-yl)methylthio)-4-(2-chlorophenyl)-5-(4-chlorophenyl)-4H-1,2,4-triazole (Compound (111))

A mixture of 2-(chloromethyl)-5-p-tolyl-1,3,4-oxadiazole 16 (0.15 g, 0.72 mmol), compound 34 (0.2 g, 0.62 mmol), and $K_2CO_3$ in actonitrile was stirred at ambient temperature for 30 min and filtered. The filtrate was concentrated. The residue was subjected to flush column chromatography eluting with 35% acetone/hexanes to give compound (111) (0.27 g). Yield: 88%.

$^1$H-NMR (300 MHz, CHLOROFORM-d) δ (ppm): 7.88 (d, 2H), 7.56 (d, 1H), 7.47 (t, 1H), 7.38-7.25 (m, 9H), 4.72 (q, 2H), 2.42 (s, 3H).

MS (ESI): 494.5. HPLC (Waters 625 LC system): 96%.

EXAMPLE 42

Preparation of Compound (117)

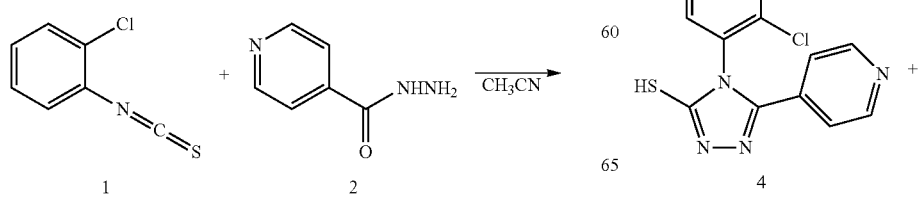
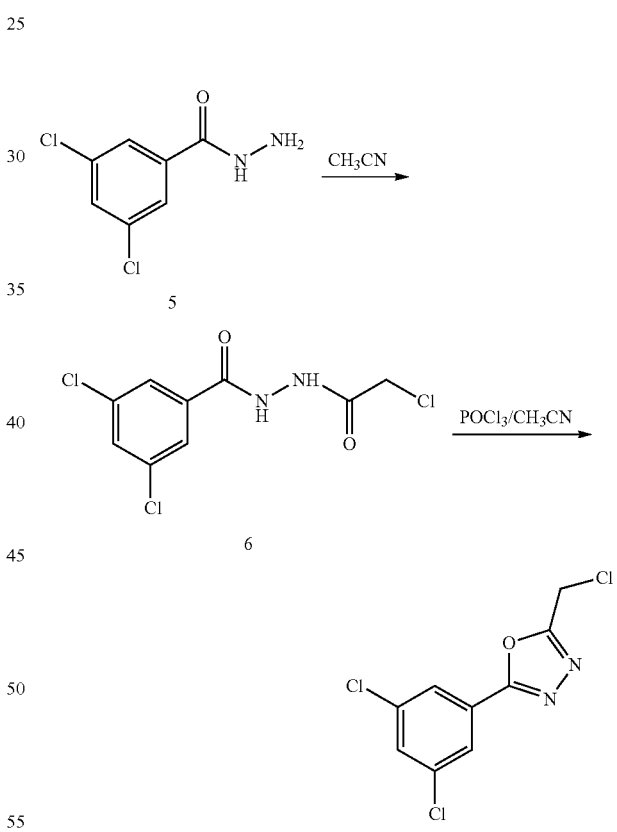

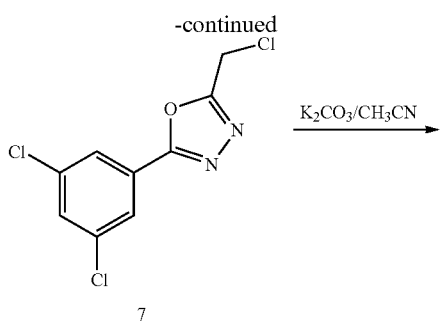

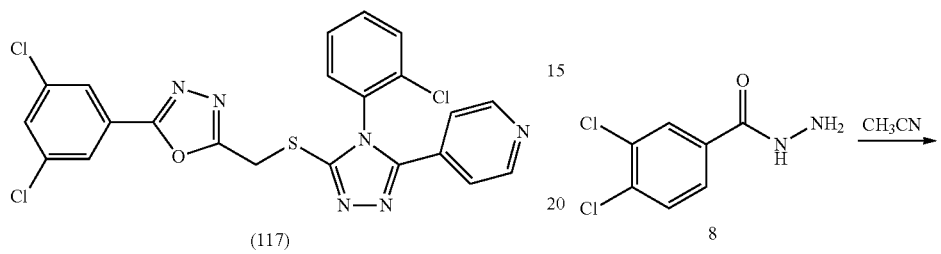

(a) Preparation of 4-(2-chlorophenyl)-5-(pyridin-4-yl)-4H-1,2,4-triazole-3-thiol 4

A mixture of 1-chloro-2-isothiocyanatobenzene 1 (3 g, 17.68 mmol) and isonicotinohydrazide 2 (2.43 g, 17.68 mmol) in acetonitrile was stirred at ambient temperature for 18 hours, concentrated to dryness, and 100 mL of 10% K$_2$CO$_3$ (aq.) was added. The resulting mixture was stirred under reflux for 6 hours. The clear solution was cooled to ambient temperature, washed with ether, and acidified with 1N HCl. The solid was collected, washed with H$_2$O and ether, and dried to afford compound 4 (4.3 g). Yield: 86%.

$^1$H-NMR (300 MHz, DMSO-d$_6$) δ (ppm): 8.68 (d, 2H), 7.80-7.58 (m, 4H), 7.28 (d, 2H).

(b) Preparation of 2-(chloromethyl)-5-(3,5-dichlorophenyl)-1,3,4-oxadiazole 7

To a mixture of 3,5-dichlorobenzohydrazide 5 (0.5 g, 2.4 mmol) and K$_2$CO$_3$ (0.61 g, 4.4 mmol) in acetonitrile (30 mL) was added 2-chloroacetyl chloride (0.41 g, 3.66 mmol) dropwise at ambient temperature. The resulting mixture was stirred at ambient temperature for 16 hours. The solid was collected, washed with H$_2$O and ether, and dried to afford 3,5-dichloro-N'-(2-chloroacetyl)benzohydrazide 6 (0.63 g, 92%) which was used for the next step without further purification. A mixture of 3,5-dichloro-N'-(2-chloroacetyl)benzohydrazide 6 (0.63 g, 2.24 mmol) and phosphorous oxychloride (0.51 g, 3.36 mmol) in acetonitrile (20 mL) was stirred under reflux for 16 hours and concentrated. The residue was subjected to flush column chromatography eluting with 10-25% acetone/hexanes to give compound 7 (0.52 g). Yield: 88%.

$^1$H-NMR (300 MHz, CDCl$_3$) δ (ppm): 7.91 (s, 2H), 7.53 (s, 1H), 4.78 (s, 2H).

(c) Preparation of 4-(5-((5-(3,5-dichlorophenyl)-1,3,4-oxadiazol-2-yl)methylthio)-4-(2-chlorophenyl)-4H-1,2,4-triazol-3-yl)pyridine (Compound (117))

A mixture of compound 7 (0.22 g, 0.83 mmol), compound 4 (0.2 g, 0.69 mmol), and K$_2$CO$_3$ in acetonitrile was stirred at ambient temperature for 30 min and filtered. The filtrate was concentrated. The residue was subjected to flush column chromatography eluting with 25-50% acetone/hexanes to give compound (117) (0.28 g). Yield: 80%.

$^1$H-NMR (300 MHz, CHLOROFORM-d) δ (ppm): 8.56 (d, 2H), 7.88 (d, 2H), 7.63-7.31 (m, 7H), 4.78 (q, 2H).

MS (Turbo Ion Spray TOF MS): 516.9998. HPLC (Waters 625 LC System): 96%.

EXAMPLE 43

Preparation of Compound (130)

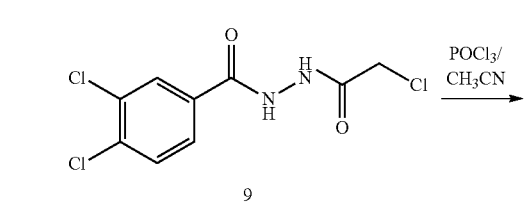

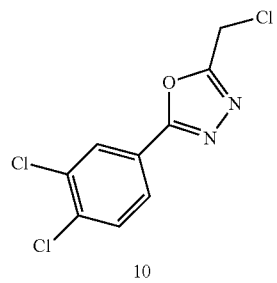

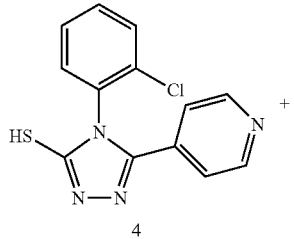

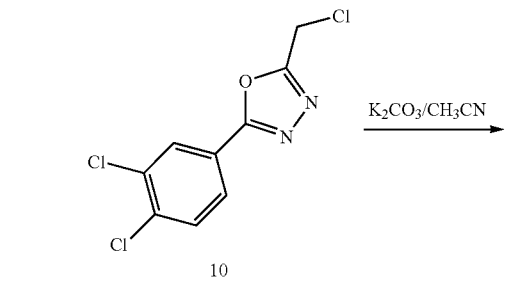

-continued

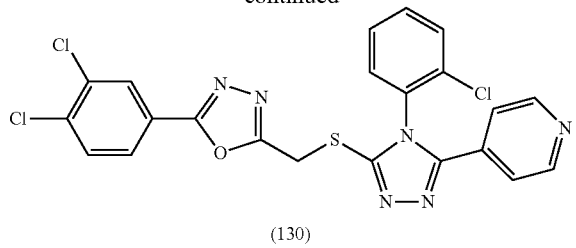
(130)

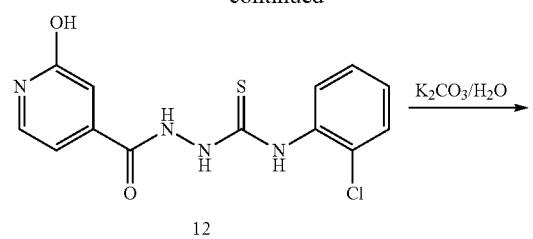
12

(a) Preparation of 2-(chloromethyl)-5-(3,4-dichlorophenyl)-1,3,4-oxadiazole 10

To a mixture of 3,4-dichlorobenzohydrazide 8 (0.5 mg, 2.43 mmol) and K₂CO₃ (0.61 g, 4.4 mmol) in acetonitrile (30 mL) was added 2-chloroacetyl chloride (0.41 g, 3.66 mmol) dropwise at ambient temperature. The resulting mixture was stirred at ambient temperature for 16 hours. The solid was collected, Washed with H₂O and ether, and dried to afford 3,4-dichloro-N'-(2-chloroacetyl)benzohydrazide 9 (0.59 g, 85%) which was used for the next step without further purification. A mixture of compound 9 (0.5.9 g, 2.24 mmol) and phosphorous oxychloride (0.51 g, 3.36 mmol) in acetonitrile (20 mL) was stirred under reflux for 16 hours and concentrated. The residue was subjected to flush column chromatography eluting with 10-25% acetone/hexanes to give compound 10 (0.43 g). Yield: 78%.
¹H-NMR (300 MHz, CDCl₃) δ (ppm): 7.88 (s, 1H), 7.12 (d, 2H), 4.78 (s, 2H).

(b) Preparation of 4-(5-((5-(3,4-dichlorophenyl)-1,3,4-oxadiazol-2-yl)methylthio)-4-(2-chlorophenyl)-4H-1,2,4-triazol-3-yl)pyridine (Compound (130))

To a solution of compound 10 (0.2 mg, 0.76 mmol) and 4-(2-chlorophenyl)-5-(pyridin-4-yl)-4H-1,2,4-triazole-3-thiol 4 (0.18 mg, 0.63 mmol) in 20 mL of acetonitrile was added K₂CO₃ (0.19 mg, 1.38 mmol). The mixture was stirred at ambient temperature for 3 hour. After removal of solvent, the residue was subjected to flush column chromatography eluting with 25-50% acetone/hexanes to give compound (130). Yield: 85%.
¹H-NMR (300 MHz, CHLOROFORM-d) δ (ppm): 8.58 (d, 2H), 8.08 (d, 1H), 7.86 (d, 1H), 7.63-7.26 (m, 7H), 4.76 (q, 2H).
MS (Turbo Ion Spray TOF MS): 517.0004. HPLC (Waters 625 LC System): 96%.

EXAMPLE 44

Preparation of Compound (116)

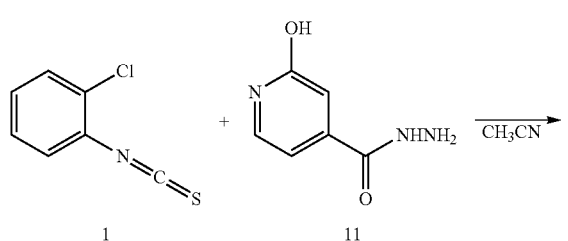

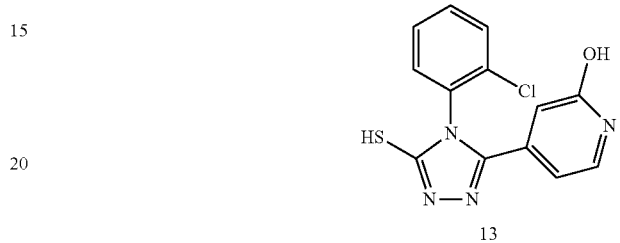
13

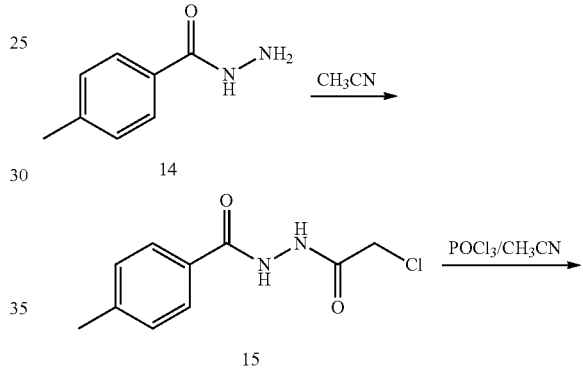
14

15

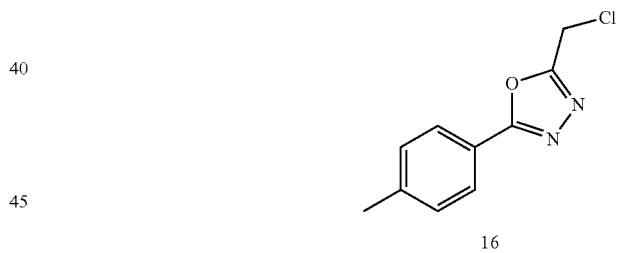
16

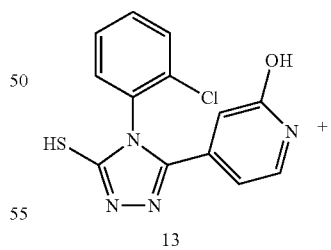
13

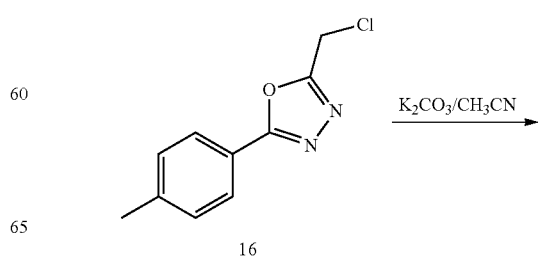
16

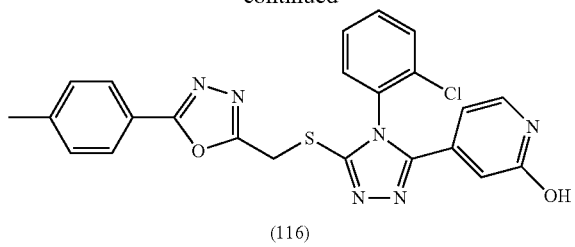

(a) Preparation of 4-(4-(2-chlorophenyl)-5-mercapto-4H-1,2,4-triazol-3-yl)pyridin-2-ol 13

A mixture of 1-chloro-2-isothiocyanatobenzene 1 (0.72 g, 4.25 mmol) and 2-hydroxypyridine-4-carbohydrazide 11 (0.65 g, 4.25 mmol) in DMF was stirred at ambient temperature for 18 hours, concentrated to dryness, and 20 mL of 10% $K_2CO_3$ (aq.) was added. The resulting mixture was stirred under reflux for 6 hours. The clear solution was cooled to ambient temperature, washed with ether, and acidified with 1N HCl. The solid was collected, washed with $H_2O$ and ether, and dried to afford compound 13 (0.98 g). Yield: 80%.

$^1$H-NMR (300 MHz, DMSO-$d_6$) δ (ppm): 7.72-7.53 (m, 4H), 7.38 (d, 1H), 6.28 (d, 1H), 5.88 (S, 1H).

(b) Preparation of 2-(chloromethyl)-5-p-tolyl-1,3,4-oxadiazole 16

To a mixture of 4-methylbenzohydrazide 14 (10 g, 66.59 mmol) and $K_2CO_3$ (16.57 g, 119.86 mmol) in acetonitrile (100 mL) was added 2-chloroacetyl chloride (9.02 g, 79.9 mmol) dropwise at ambient temperature. The resulting mixture was stirred at ambient temperature for 16 hours. The solid was collected, washed with $H_2O$ and ether, and dried to afford N'-(2-chloroacetyl)-4-methylbenzohydrazide 15 (13 g, 82%) which was used for the next step without further purification. A mixture of N'-(2-chloroacetyl)-4-methylbenzohydrazide 15 (6.0 g, 26.47 mmol) and phosphorous oxychloride (5.0 g, 32.84 mmol) in acetonitrile (20 mL) was stirred under reflux for 16 hours and concentrated. The residue was subjected to flush column chromatography eluting with 10-25% acetone/hexanes to give compound 16 (4 g). Yield: 72%.

$^1$H-NMR (300 MHz, CHLOROFORM-d) δ (ppm): 7.96 (d, 2H), 7.30 (d, 2H), 4.77 (s, 2H), 2.44 (s, 3H).

(c) Preparation of 4-(5-((5-p-tolyl-1,3,4-oxadiazol-2-yl)methylthio)-4-(2-chlorophenyl)-4H-1,2,4-triazol-3-yl)pyridin-2-ol (Compound (116))

A mixture of compound 16 (0.15 g, 0.74 mmol), 4-(4-(2-chlorophenyl)-5-mercapto-4H-1,2,4-triazol-3-yl)pyridin-2-ol 13 (0.2 g, 0.56 mmol), and $K_2CO_3$ in acetonitrile was stirred at ambient temperature for 30 min and filtered. The filtrate was concentrated. The residue was subjected to flush column chromatography eluting with 50-65% acetone/hexanes to give compound (116) (0.25 g). Yield: 80%.

$^1$H-NMR (300 MHz, CHLOROFORM-d) δ (ppm): 8.30 (d, 1H), 7.86 (d, 2H), 7.63-7.18 (m, 7H), 7.16 (d, 1H), 4.76 (q, 2H), 2.44 (s, 3H).

MS (Turbo Ion Spray TOF MS): 477.0926. HPLC (Waters 625 LC System): 95%.

EXAMPLE 45

Preparation of Compound (131)

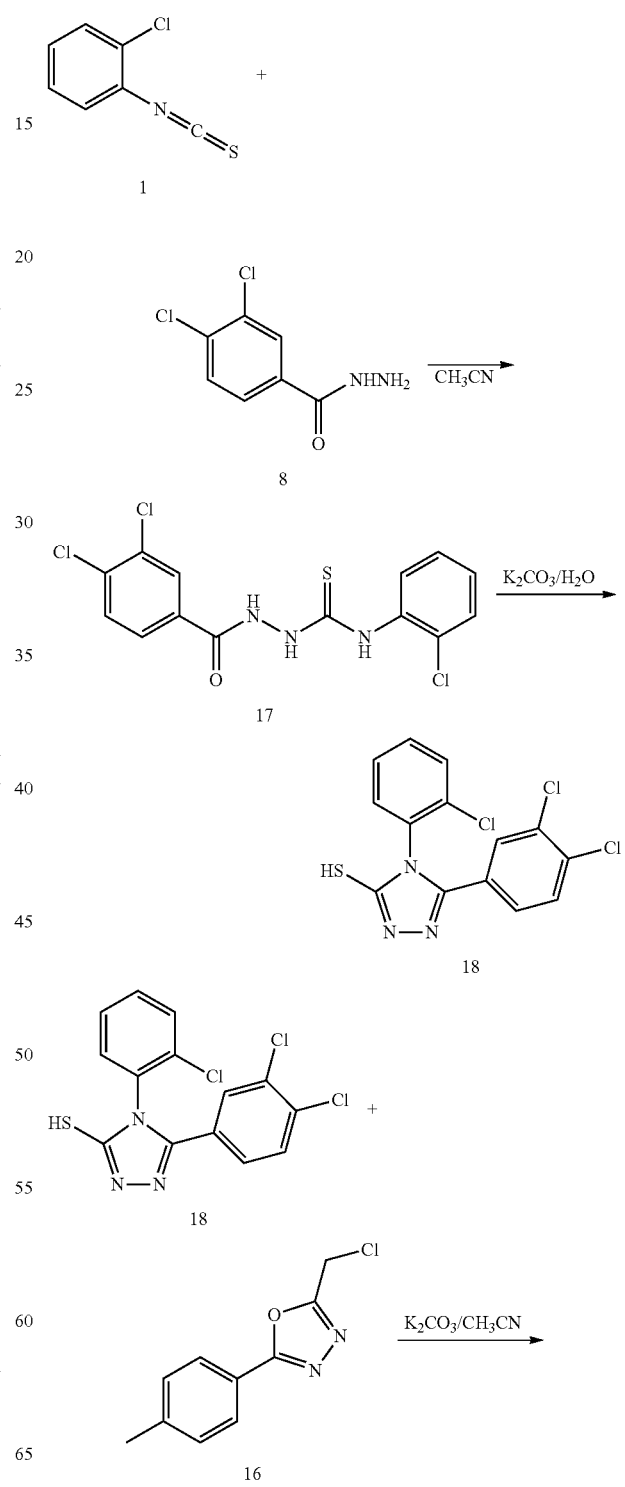

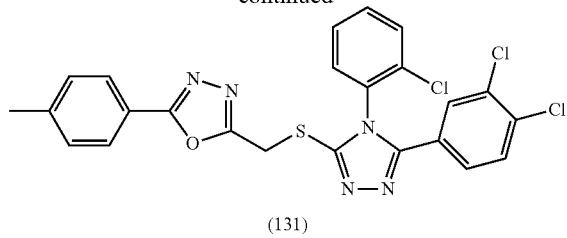

(131)

(a) Preparation of 4-(2-chlorophenyl)-5-(3,4-dichlorophenyl)-4H-1,2,4-triazole-3-thiol 18

A mixture of 3,4-dichlorobenzohydrazide 8 (0.5 g, 2.44 mmol) and isonicotinohydrazide 1 (0.41 g, 2.44 mmol) in acetonitrile was stirred at ambient temperature for 18 hours, concentrated to dryness, and 20 mL of 10% $K_2CO_3$ (aq.) was added. The resulting mixture was stirred under reflux for 6 hours. The clear solution was cooled to ambient temperature, washed with ether, and acidified with 1N HCl. The solid was collected, washed with $H_2O$ and ether, and dried to afford compound 18 (0.7 g). Yield: 82%.

$^1$H-NMR (300 MHz, DMSO-$d_6$) δ (ppm): 7.47-7.7.31 (m, 4H), 7.18 (d, 2H), 6.68 (d, 2H), 3.90 (q, 2H), 1.28 (t, 3H).

(b) Preparation of 3-((5-p-tolyl-1,3,4-oxadiazol-2-yl)methylthio)-4-(2-chlorophenyl)-5-(3,4-dichlorophenyl)-4H-1,2,4-triazole (Compound (131))

A mixture of 2-(chloromethyl)-5-p-tolyl-1,3,4-oxadiazole 16 (0.13 g, 0.57 mmol), compound 18 (0.15 g, 0.4 mmol), and $K_2CO_3$ in acetonitrile was stirred at ambient temperature for 30 min and filtered. The filtrate was concentrated. The residue was subjected to flush column chromatography eluting with 25-50% acetone/hexanes to give compound (131) (0.2 g). Yield: 88%.

$^1$H-NMR (300 MHz, CHLOROFORM-d) δ (ppm): 7.88 (d, 2H), 7.55 (d, 1H), 7.43 (t, 1H), 7.40-7.21 (m, 6H), 7.78 (d, 2H), 4.71 (q, 2H), 4.00 (q, 2H), 2.41 (s, 3H), 1.38 (t, 1H). MS (Turbo Ion Spray TOF MS): 530.0209. HPLC (Waters 625 LC System): 98%.

EXAMPLE 46

Preparation of Compound (132)

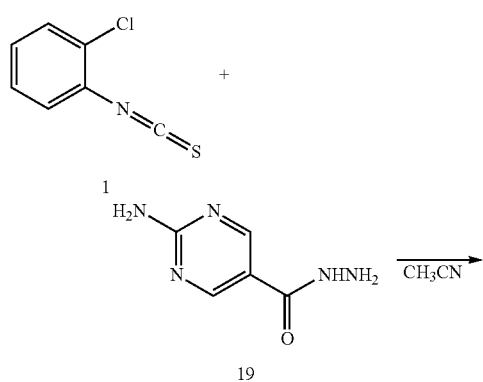

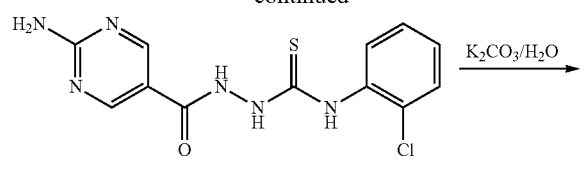

(132)

(a) Preparation of 5-(2-aminopyrimidin-5-yl)-4-(2-chlorophenyl)-4H-1,2,4-triazole-3-thiol 21

A mixture of 1-chloro-2-isothiocyanatobenzene 1 (0.42 mg, 2.2 mmol) and 2-aminopyrimidine-5-carbohydrazide 19 (451 mg, 2.2 mmol) in 20 mL of acetonitrile was stirred at ambient temperature for 18 hours, concentrated to dryness, and 20 mL of 10% $K_2CO_3$ (aq.) was added. The resulting mixture was stirred under reflux for 6 hours. The clear solution was cooled to ambient temperature, washed with ether, and acidified with 1N HCl. The solid was collected, washed with $H_2O$ and ether, and dried to afford compound 21 (0.59 g). Yield: 78%.

$^1$H-NMR (300 MHz, CHLOROFORM-d) δ (ppm): 7.20-7.50 (m, 7H).

(b) Preparation of 5-(5-((5-p-tolyl-1,3,4-oxadiazol-2-yl)methylthio)-4-(2-chlorophenyl)-4H-1,2,4-triazol-3-yl)pyrimidin-2-amine (Compound (132))

To a mixture of compound 21 (0.2 g, 0.6 mmol) and 2-(chloromethyl)-5-p-tolyl-1,3,4-oxadiazole 16 (0.2 g, 0.96 mmol) in acetonitrile was added $K_2CO_3$ (138 mg, 1.0 mmol). The mixture was stirred at ambient temperature for 2 hours. After removal of solvent, the residue was purified by column (5:95 of methanol/dichloromethane) to give compound (132) (0.2 g). Yield: 65%.

$^1$H-NMR (300 MHz, CHLOROFORM-d) δ (ppm): 7.90 (d, 2H), 7.20-7.50 (m, 9H), 4.73 (q, 2H), 2.43 (s, 3H).

MS (Turbo Ion Spray TOF MS): 477.1036. HPLC (Waters 625 LC System): 92%.

EXAMPLE 47

Preparation of Compound (115)

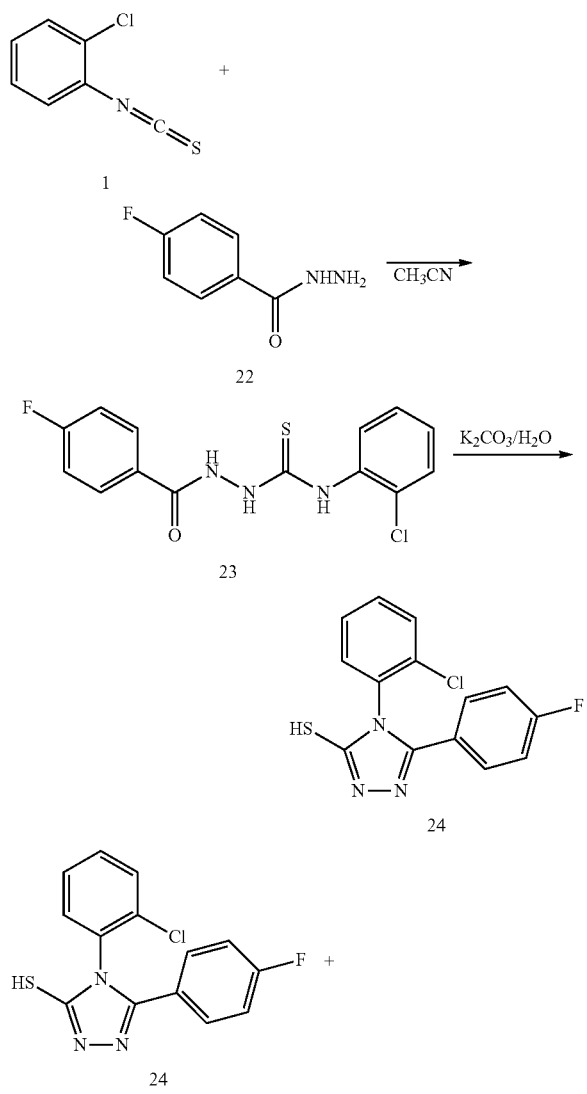

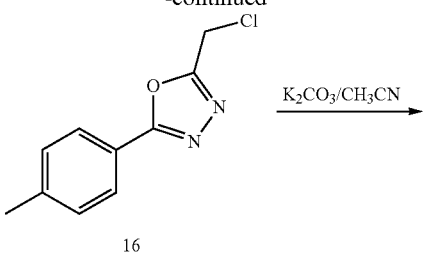

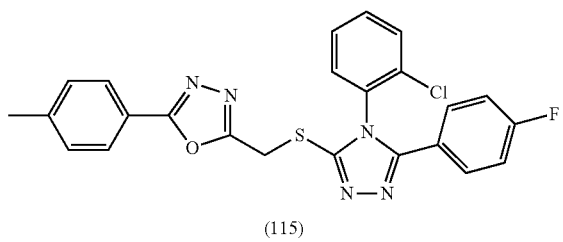

(a) Preparation of 4-(2-chlorophenyl)-5-(4-fluorophenyl)-4H-1,2,4-triazole-3-thiol 24

A mixture of 4-fluorobenzohydrazide 22 (0.5 g, 3.24 mmol) and isonicotinohydrazide 1 (0.55 g, 3.24 mmol) in acetonitrile was stirred at ambient temperature for 18 hours, concentrated concentrated to dryness, and 20 mL of 10% $K_2CO_3$ (aq.) was added. The resulting mixture was stirred under reflux for 6 hours. The clear solution was cooled to ambient temperature, washed with ether, and acidified with 1N HCl. The solid was collected, washed with $H_2O$ and ether, and dried to afford compound 24 (0.93 g). Yield: 94%.

$^1$H-NMR (300 MHz, DMSO-$d_6$) δ (ppm): 8.68 (d, J=4.8 Hz, 2H), 7.80-7.58 (m, 4H), 7.28 (d, J=15.7 Hz, 2H).

(b) Preparation of 3-((5-p-tolyl-1,3,4-oxadiazol-2-yl)methylthio)-4-(2-chlorophenyl)-5-(4-fluorophenyl)-4H-1,2,4-triazole (Compound (115))

A mixture of 2-(chloromethyl)-5-p-tolyl-1,3,4-oxadiazole 16 (0.13 g, 0.62 mmol), compound 24 (0.15 g, 0.49 mmol), and $K_2CO_3$ in acetonitrile was stirred at ambient temperature for 30 min and filtered. The filtrate was concentrated. The residue was subjected to flush column chromatography eluting with 25% acetone/hexanes to give compound (115) (0.23 g).

Yield: 98%.

$^1$H-NMR (300 MHz, CHLOROFORM-d) δ (ppm): 7.88 (d, J=6.6 Hz, 2H), 7.56 (dd, J=6.6 Hz, 1H), 7.46-23 (m, 6H), 6.95 (t, J=3.0 Hz, 1H), 6.72 (t, J=8.7 Hz, 1H), 4.74 (q, J=15.0 Hz, 2H), 2.42 (s, 3H).

MS (Turbo Ion Spray TOF MS): 478.0932. HPLC (Waters 625 LC System): 98%.

EXAMPLE 48

Preparation of Compound (66)

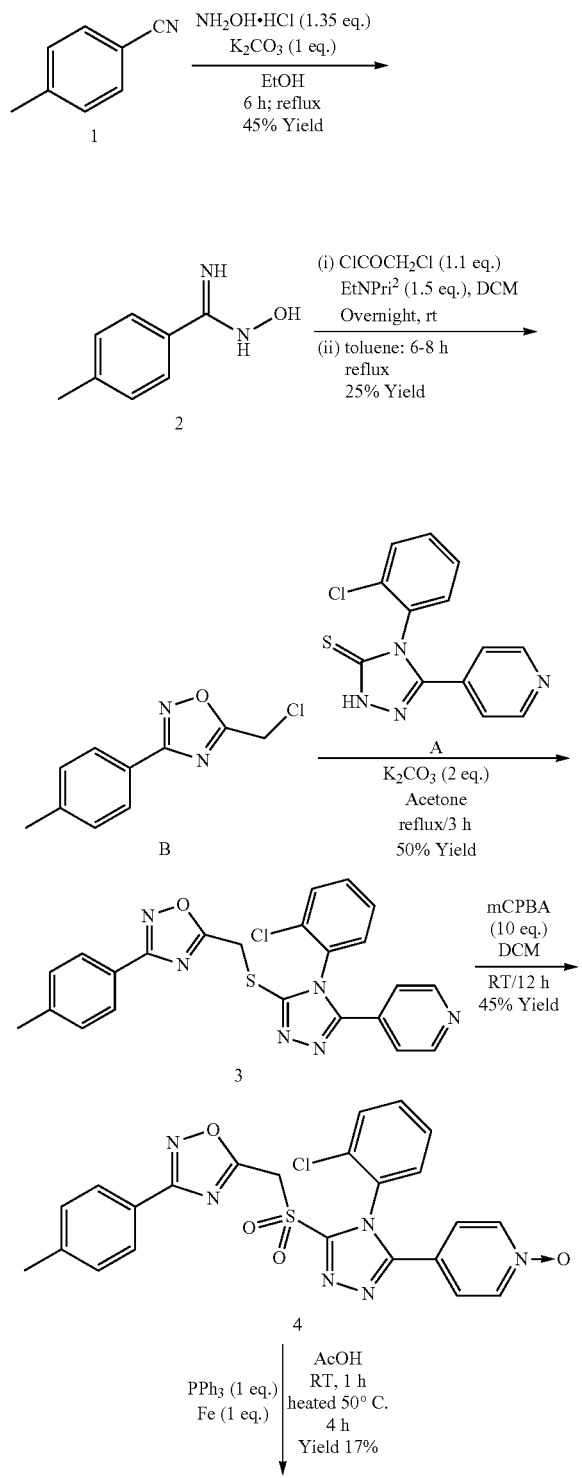

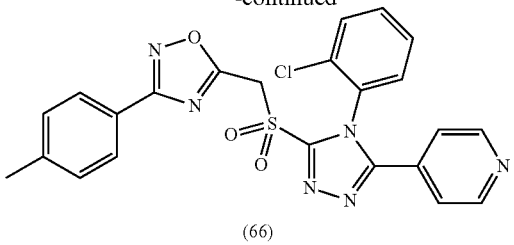

(a) Preparation of Compound 2:

To a solution of compound 1 (25 g, 213 mmol) in 120 ml of ethanol were added simultaneously hydroxylamine. HCl (19.90 g, 288 mmol) and $K_2CO_3$ (29.39 g, 213 mmol). The reaction mixture was stirred for 1 hour at ambient temperature and heated to reflux for 6 hours. Then the mixture was allowed to cool to ambient temperature, filtered and on evaporation of the filtrate gave crude residue which was triturated with a mixture of EtOAc/DCM to give compound 2 (tautomeric mixture) as a solid (14.4 g). Yield: 45%.

$^1$HNMR (400 MHz, DMSO-$d_6$): δ (ppm): 9.50 (1H, s), 7.55-7.45 (2H, d), 7.20-7.10 (2H, d), 5.75 (2H, s), 2.30 (3H, s).

(b) Preparation of Compound B:

To a solution of compound 2 (6 g, 40 mmol) in 75 ml of $CH_2Cl_2$ was added DIPEA (10.38 ml, 60 mmol) and stirred for 10 min at 0° C. This mixture was added slowly to chloroacetyl chloride (3.5 ml, 44 mmol) at 0° C. and the reaction mixture was stirred at ambient temperature overnight. The solvent was removed and the crude material was added to toluene (50 ml) and heated to reflux using Dean-Stark apparatus. After the completion of the reaction (monitored by TLC) the solvent was removed and the crude material purified by column chromatography using EtOAc:Hexane (20:80) as an eluent to afford compound B as a solid (2 g). Yield: 25%.

$^1$HNMR (400 MHz, $CDCl_3$): δ (ppm): 8.05-7.90 (2H, d), 7.35-7.25 (2H, d), 4.75 (2H, s), 2.45 (3H, s). Mass: 211.1 [M$^+$+2H], 209.2 [M$^+$+H].

(c) Preparation of Compound 3:

A mixture of compound B (0.5 g, 2.398 mmol), compound A (0.69 g, 2.398 mmol) and $K_2CO_3$ (0.66 g, 4.79 mmol) in acetone (30 mL) was heated to reflux for 3 hours. The reaction mixture was cooled to ambient temperature and filtered. The filtrate was evaporated and crude product was dissolved in EtOAc and washed with water, the organic phase was separated and dried ($Na_2SO_4$). The solvent was evaporated to obtain crude residue, which was purified by column chromatography (TEA eluted) using 2% MeOH:DCM as an eluent to give compound 3 (552 mg). Yield: 50%.

$^1$HNMR (400 MHz, DMSO-d6): δ (ppm): 8.63-8.57 (2H, d), 7.9-7.82 (3H, m), 7.75-7.60 (3H, m), 7.42-7:35 (2H, m), 7.32-7.25 (2H, m), 5.0-4.70 (2H, dd), 2.40 (3H, s). Mass: 461.9 [M$^+$+H] and 483.5 [M+Na].

(d) Preparation of Compound 4:

To a solution of compound 3 (300 mg, 0.651 mmol) in $CH_2Cl_2$ (15 mL) was added slowly drop-wise mCPBA in $CH_2Cl_2$ (20 mL) (1.123 g, 6.514 mmol) at 0° C. The reaction mixture was stirred at ambient temperature overnight. The solvent was removed and the crude residue was purified by column chromatography using 2% MeOH/DCM as an eluent to afford compound 4 as a solid (0.148 g). Yield: 45%.

$^1$HNMR (400 MHz, DMSO-d6): δ (ppm): 8.20-8.15 (2H, d), 7.85-7.80 (3H, m), 7.25-7.20 (3H, m), 7.40-7.30 (2H, m), 7.3-7.2 (2H, m), 4.9-4.7 (2H, dd), 2.40 (3H, s). LC-Mass: 509.6 [M$^+$+H].

(e) Preparation of Compound (66):

A mixture of compound 4 (148 mg, 0.292 mmol), PPh$_3$ (76 mg, 0.292 mmol) & Fe (16 mg, 0.292 mmol) in 20 ml of AcOH was stirred at ambient temperature for 0.5 hours, slowly heated to 50° C. and continuously stirred for 4 hours. After completion of the reaction (by TLC analysis), the product was concentrated to obtain a crude residue, which was purified by column chromatography using 20% EtOAc/hexane as an eluent to give partially pure material. This was further purified by Preparative TLC (EtOAc as an eluent) to afford pure compound (66) as an off-white solid (25 mg). Yield: 17%.

$^1$HNMR (400 MHz, CDCl$_3$): δ (ppm): 8.8-8.6 (2H, d), 7.9-7.8 (2H, d), 7.6-7.5 (2H, m), 7.40-7.30 (4H, m), 7.3 (1H, m), 7.2 (1H, m), 5.4-5.2 (2H, dd), 2.40 (3H, s).

Mass (−Ve mode): 491.1 [M$^+$−H] & 492.9. HPLC: 99.26%.

EXAMPLE 49

Preparation of Compound (67)

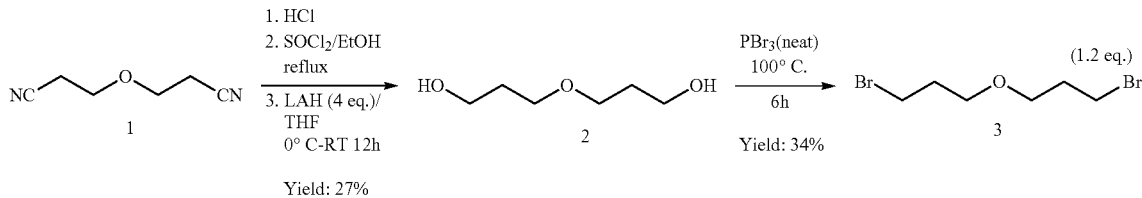

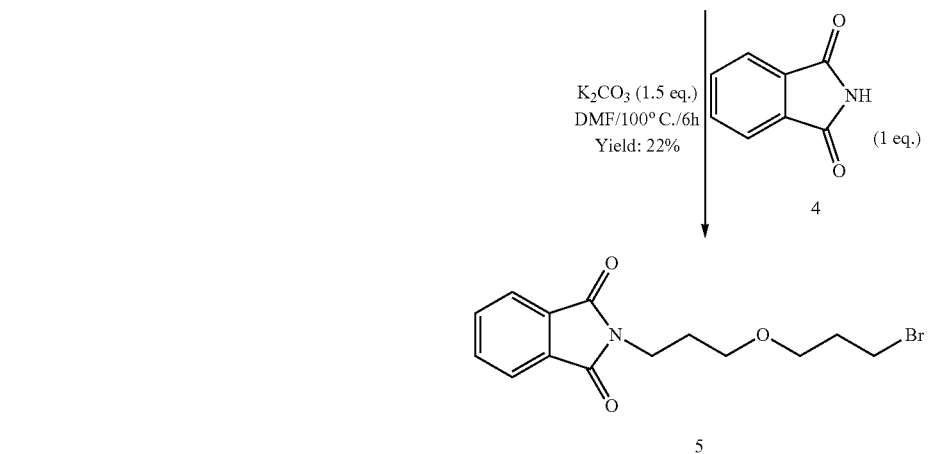

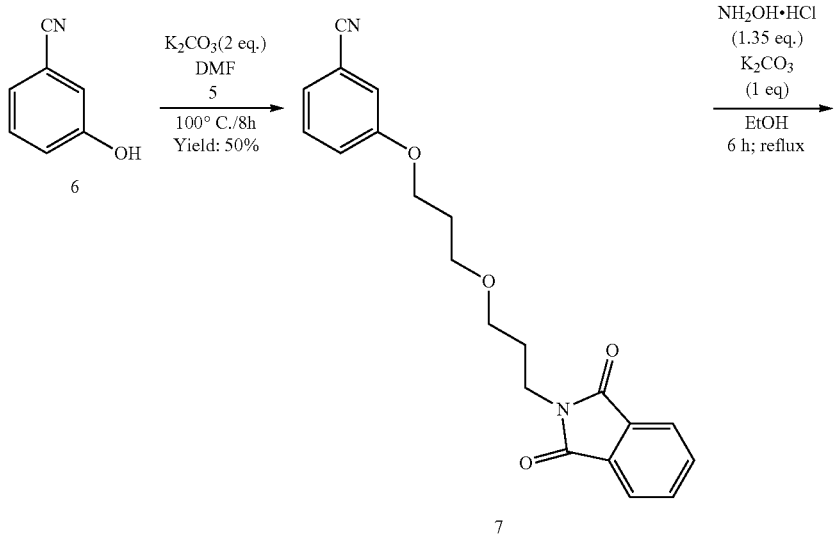

-continued
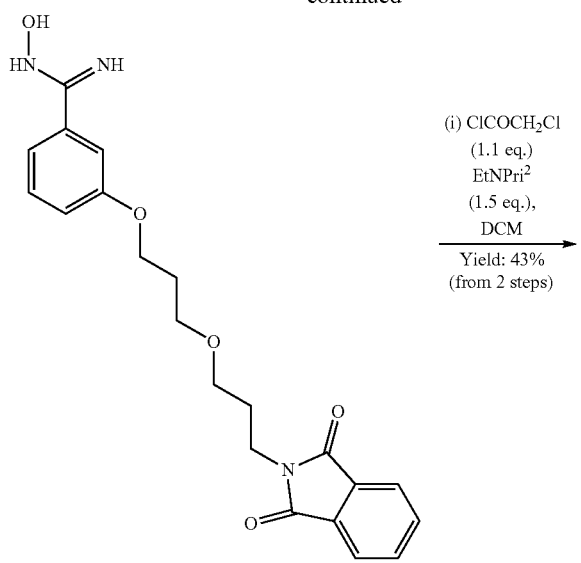
8
(i) ClCOCH₂Cl (1.1 eq.)
EtNPri² (1.5 eq.),
DCM
Yield: 43%
(from 2 steps)
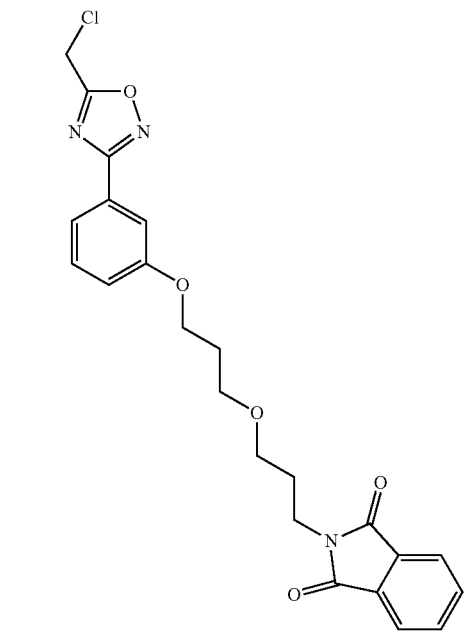
9
K₂CO₃ (2 eq.)
Acetone Reflux
Yield: 40%
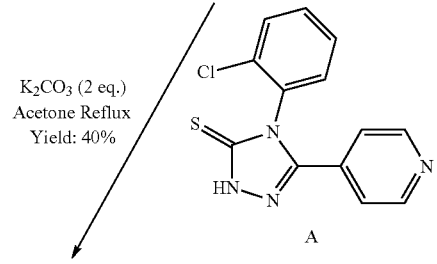
A

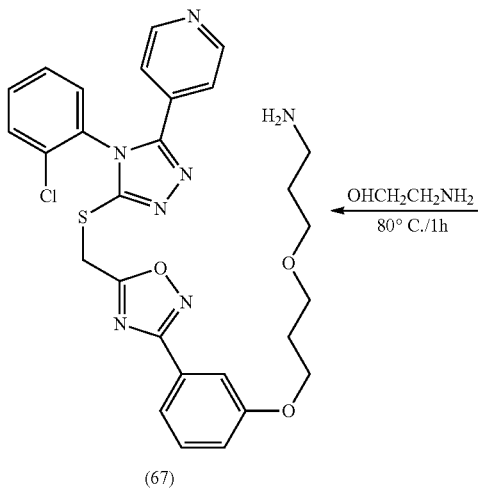

(67)

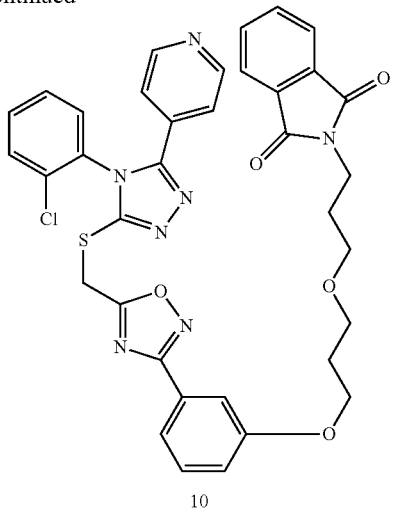

10

(a) Preparation of Compound 2:

To a flask containing compound 1 (29.14 g, 235 mmol) was added dropwise 10N HCl (307 mL) and the reaction mixture was stirred at ambient temperature for 3 hours. The solvent was removed and the product was dried in a vacuum desicator for 2 days to get an acid intermediate as a pale yellow gummy material (58 g crude) which was used in the next step without further purification. To a solution of the crude acid derivative (58 g) in 580 ml of ethanol was added $SOCl_2$ (36 mL) slowly drop wise at 0° C. and heated to reflux for 4 hours. Volatiles were removed under reduced pressure and the reaction mixture diluted with EtOAc and extracted with $CH_2Cl_2$. The organic layer was dried over anhydrous $Na_2SO_4$, filtered, concentrated under reduced pressure to give the ester derivative as a yellow liquid (50 g). To a stirred suspension of LAH (21.7 g, 573 mmol) in 200 ml of THF was added a solution of the ester derivative (50 g dissolved in 300 ml of THF) slowly drop wise at 0° C. and the reaction mixture stirred at ambient temperature overnight. This was then diluted with isopropyl ether (200 mL), quenched with 15% NaOH and filtered over Celite. Upon evaporation of the filtrate, this gave di-alcohol compound 2 as a pale yellow liquid (8.3 g). Yield: 27%.

$^1$HNMR (400 MHz, $CDCl_3$): δ (ppm): 3.80-3.70 (t, 4H), 3.70-3.60 (t, 4H), 2.90-2.80 (m, 4H). MS: 135.1 [$M^+$+H] peak, 152.7 [$M^+$+$H_2O$] peak (b) Preparation of Compound 3:

To a flask containing compound 2 (11 g, 82.0 mmol), $PBr_3$ (55 mL) was added slowly drop wise and the mixture stirred for 0.5 hours at ambient temperature followed by heating to 90° C. After being stirred for 3 hours at this temperature the reaction mixture was quenched with ice (500 g) slowly, stirred continuously for 10 minutes and extracted with $CH_2Cl_2$ (2×700 mL). The organic layer was dried over anhydrous $Na_2SO_4$, filtered and concentrated under reduced pressure to give compound 3 as a pale yellow liquid (7.24 g). Yield: 34%.

$^1$HNMR (400 MHz, $CDCl_3$): δ (ppm): 3.70-3.55 (t, 4H), 3.60-3.35 (t, 4H), 2.15-1.95 (m, 4H).

(c) Preparation of Compound 5:

To a stirred mixture of compound 4 (1 g, 6.8 mmol) and $K_2CO_3$ (2.8 g, 20 mmol) in 8 ml of DMF was added a solution of compound 3 (2.47 g, 9.5 mmol) in DMF (4 mL) and the mixture was heated to 80° C. for 4 hours. The reaction mixture was filtered and the filtrate was evaporated to obtain crude residue, which was dissolved again with EtOAc (50 mL) and the organic layer was washed with water (30 mL). The organic layer was dried over anhydrous $Na_2SO_4$, filtered and concentrated under reduced pressure to give a crude residue which was purified by column chromatography using 10% EtOAc/hexane as an eluent to give compound 5 as a colourless liquid (660 mg). Yield: 21%.

$^1$HNMR (400 MHz, $CDCl_3$): δ (ppm): 7.9-7.8 (m, 2H), 7.75-7.65 (m, 2H), 3.80-3.70 (m, 3H), 3.65-3.45 (m, 3H), 2.15-2.05 (m, 2H), 1.90-1.80 (m, 2H), 1.30-1.20 (m, 2H).

(d) Preparation of Compound 7:

A mixture of compound 5 (700 mg, 2.14 mmol), compound 6 (222 mg, 1.86 mmol) and $K_2CO_3$ (772 mg, 5.59 mmol, 2 eq.) in 10 ml of DMF was heated to 100° C. for 3 hours. The reaction mixture was brought to ambient temperature, filtered and the filtrate was evaporated to obtain a crude residue which was purified by column chromatography using EtOAc/hexane (50:50) as an eluent to obtain compound 7 as a colorless liquid (340 mg). Yield: 50%.

$^1$HNMR (400 MHz, $CDCl_3$): δ (ppm): 7.9-7.8 (m, 2H), 7.75-7.65 (m, 2H), 7.4-7.3 (m, 1H), 7.25-6.90 (m, 3H), 4.10-4.0 (m, 2H), 3.95-3.85 (m, 2H), 3.83-3.75 (m, 1H), 3.60-3.40 (m, 2H), 2.30-2.15 (m, 2H), 2.05-1.90 (m, 2H), 1.3-1.2 (m, 1H).

(e) Preparation of Compound 8:

To a solution of compound 7 (400 mg, 1.1 mmol) in 10 ml of ethanol were added simultaneously hydroxylamine. HCl (98 mg, 1.4 mmol) and $K_2CO_3$ (152 mg, 1.1 mmol) and the reaction mixture stirred for 1 hour at ambient temperature and heated to reflux for 4 hours. The mixture was allowed to cool to ambient temperature, filtered and on evaporation of the filtrate gave crude residue as a pale yellow gummy material which was used in the next step without any further purification (337 mg). Yield: 84%.

(e) Preparation of Compound 9:

To a solution of compound 8 (370 mg, 0.934 mmol) in 5 ml of $CH_2Cl_2$ was added DIPEA (180 mg, 1.4 mmol) at 0° C. and stirred for 10 minutes. Then chloroacetyl chloride (116 mg, 1.02 mmol) was added slowly at the same temperature and the mixture was warmed to ambient temperature and stirred overnight. Solvent was removed to give the crude compound which was used in the next step without any further purification. The crude compound was heated to reflux in toluene (25 ml) using Dean-Stark for 12 hours. Then the toluene was distilled and the crude material purified by column chromatography using EtOAc:Hexane (45:55) as an eluent to afford compound 9 as a pale yellow gummy material (212 mg). Yield: 50%.

$^1$HNMR (400 MHz, CDCl$_3$): δ (ppm): 7.9-7.32 (m, 8H), 4.75 (s, 2H), 4.15-3.75 (m, 6H), 3.6-3.4 (m, 2H), 2.3-1.9 (m, 4H). MS: 477.9 [M$^+$+Na] peak (f) Preparation of Compound 10:

A mixture of compound 9 (120 mg, 0.263 mmol), compound A (76 mg, 0.263 mmol) and K$_2$CO$_3$ (72.58 mg, 0.526 mmol) was heated under reflux in 25 ml of acetone for 3 hours. The reaction mixture was cooled to ambient temperature, filtered and the filtrate was evaporated to obtain crude residue which was purified by column chromatography using MeOH/DCM (15:85) as an eluent to obtain compound 10 as a yellow colored gummy material (75 mg). Yield: 40%.

$^1$HNMR (400 MHz, CDCl$_3$): δ (ppm): 8.6-8.5 (d, 2H), 7.9-7.8 (m, 2H), 7.75-7.60 (m, 2H), 7.65-7.50 (m, 4H), 7.5-7.4 (t, 1H), 7.45-7.25 (m, 4H), 4.90-4.60 (dd, 2H), 4.10-4.0 (m, 2H), 4.0-3.90 (m, 1H), 3.85-3.75 (m, 2H), 3.60-3.40 (m, 3H), 2.05-1.9 (m, 3H).

MS: 708.5 [M$^+$] peak (g) Preparation of Compound (67):

A mixture of compound 10 (100 mg, 0.141 mmol) and ethanolamine (1 mL) was heated to 80° C. for 10-15 minutes, cooled to ambient temperature, diluted with water and extracted with DCM. Concentration of the organic layer gave crude residue which was purified by preparative TLC using 10% MeOH:CH$_2$Cl$_2$ as an eluent to afford compound (67) as a semi-solid (30 mg). Yield: 37%.

$^1$HNMR (400 MHz, CDCl$_3$): δ (ppm): 8.6-8.5 (d, 2H), 7.65-7.50 (m, 4H), 7.5-7.4 (t, 1H), 7.45-7.20 (m, 4H), 7.08-6.95 (m, 1H), 4.90-4.60 (dd, 2H), 4.20-4.05 (m, 2H), 3.65-3.45 (m, 4H), 2.90-2.75 (m, 1H), 2.10-2.0 (m, 2H), 1.35-1.20 (m, 2H), 1.0-0.8 (m, 1H).

Mass: 578.2 [M$^+$] peak; 74.42% pure by HPLC.

EXAMPLE 50

Preparation of Compounds (99a) and (99b)

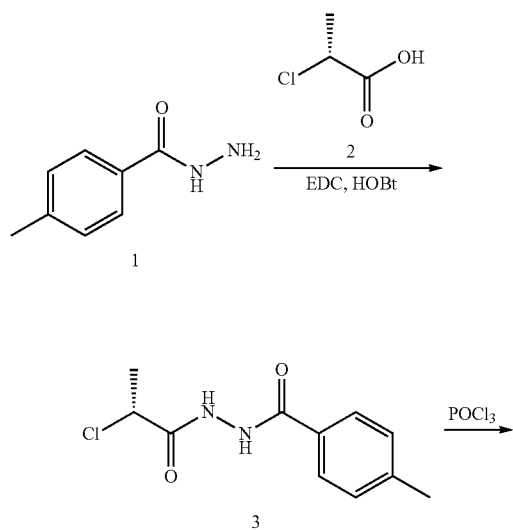

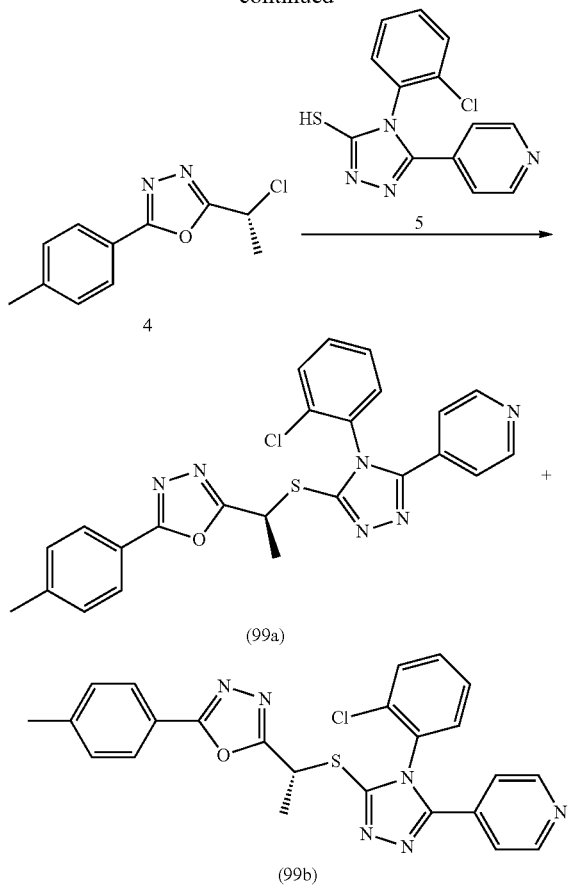

(a) Preparation of Compound 3:

Compound 1 (1.384 g, 9.2 mmol), EDC (2.638 g, 13.8 mmol) and HOBt (1.863 g, 13.8 mmol) were dissolved in DCM (15 ml) and Compound 2 (998 mg, 9.2 mmol) was added. The mixture was stirred at ambient temperature for 2 hours. The mixture was concentrated and purified by chromatography to give desired product 3 as a white solid (760 mg). Yield: 34%.

(b) Preparation of Compound 4:

Compound 3 (760 mg, 3.35 mmol) was suspended in POCl$_3$ (6 ml) and the reaction mixture was heated to 110° C. for 2.5 hours. The mixture was allowed to cool to ambient temperature and quenched by adding water, then it was extracted with EA and purified by chromatography eluting with (DCM: MeOH=20:1) to give Compound 4 as a white solid (415 mg). Yield: 55%.

(c) Preparation of Compounds (99a) and (99b):

To a solution of compound 4 (250 mg, 1.12 mmol) in acetone (10 mL) was added compound 5 (324 mg, 1.12 mmol) and K$_2$CO$_3$ (310 g, 2.24 mmol). The mixture was stirred at reflux for 2 hours. Then water was poured into the mixture and extracted with EA. The EA layer was concentrated and purified by chromatography (EA) to give compound (99a) as a yellow semi-solid (with low polarity, 60 mg, yield: 11%) and compound (99b) as a yellow semi-solid (45 mg, yield: 8%).

$^1$HNMR of Compound (99a) (400 MHz, CDCl3): δ (ppm): 8.57-8.55 (2H, dd, Py-H), 7.87-7.14 (10H, m, Py-H, Ph-H), 5.34-5.31 (1H, q, —CH—), 2.42 (3H, s, —CH$_3$), 1.93-1.91 (3H, d, CH3-). ESI MS: 475 ([M+H]$^+$.

HPLC (Waters SunFire C18 4.6*100 mm column, 25° C.; 30-95% of Acetonitrile (0.03% TFA) over 8 minutes, in water (0.03% TFA), 1 ml/min): 96%. Compound elutes at 4.55 min. $[a]_{20}^{589}$=−13.25 (C=0.40, CH$_2$Cl$_2$).

$^1$HNMR of Compound (99b) (400 MHz, CDCl3): δ (ppm): 8.58-8.56 (2H, dd, Py-H), 7.87-7.27 (10H, m, Py-H, Ph-H), 5.25-5.23 (1H, q, —CH—), 2.42 (3H, s, —CH$_3$), 1.99-1.98 (3H, d, CH3-). ESI MS: 475 ([M+H]$^+$.

HPLC (Boston Symmetrix ODS-R 5 μm 4.6*100 mm column, 25° C.; 30-95% of Acetonitrile (0.03% TFA) over 8 minutes, in water (0.03% TFA), 1 ml/min): 95%. Compound elutes at 5.137 min. $[a]_{20}^{589}$=−2.5-4 (C=0.40, CH$_2$Cl$_2$).

EXAMPLE 51

Preparation of Compound (100)

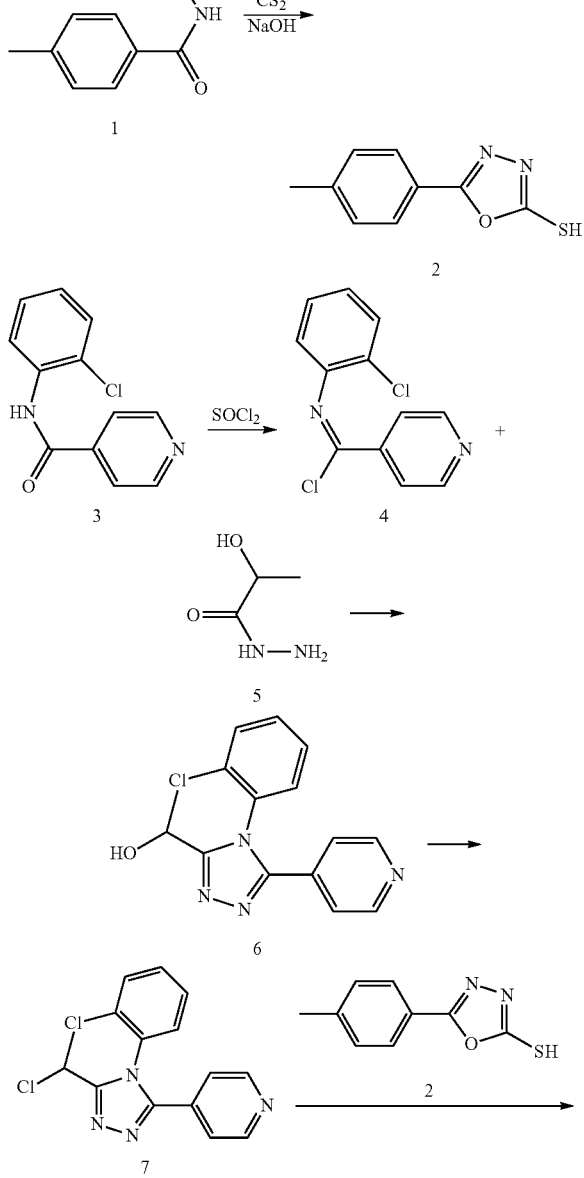

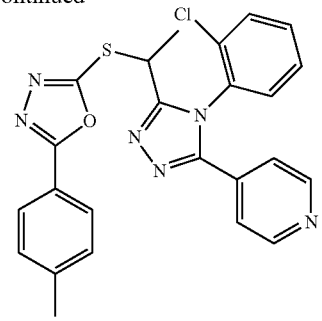

(100)

(a) Preparation of Compound 2:

Compound 1 (1.0 g, 6.66 mmol), CS$_2$ (3.0 g, 39.47 mmol) and NaOH (2.66 g, 66.50 mmol) were refluxed in EtOH overnight. Then TLC showed compound 1 disappeared. The mixture was concentrated and dissolved in H$_2$O. HCl (aq.) was added to pH=2 and extracted with EA. The EA phase was washed with brine, dried with Na$_2$ SO$_4$, concentrated and crystallized with Et$_2$O to give desired product 2 as a light yellow solid (800 mg). Yield: 62.5%.

$^1$HNMR (400 MHz, DMSO-d6): δ (ppm): 14.685 (1H, s, —SH), 7.771-7.752 (2H, d, Ph-H), 7.398-7.379 (2H, d, Ph-H), 2.378 (3H, s, —CH$_3$).

(b) Preparation of Compound 6:

To a stirred solution of compound 4 (970 mg, 3.86 mmol) and Et$_3$ N (1.95 g, 19.31 mmol) in toluene, was added compound 5 (804 mg, 7.73 mmol). The mixture was then refluxed under Ar atmosphere for about 40 hours. Then TLC showed compound 4 had essentially disappeared. The mixture was concentrated and dissolved in DCM. The DCM phase was washed with brine, dried with Na$_2$ SO$_4$ and purified by gel column to give desired product compound 6 as a white solid (550 mg). Yield: 47.4%.

$^1$HNMR (400 MHz, DMSO-d6): δ (ppm): 8.581-8.571 (2H, d, Py-H), 7.934-7.586 (4H, m, Py-H, Ph-H), 7.301-7.280 (2H, m, Ph-H), 5.585-5.456 (1H, m, —OH), 4.756-4.484 (1H, m, —CH), 1.526-1.422 (3H, m, —CH$_3$).

(c) Preparation of Compound 7:

Compound 6 (40 mg, 0.133 mmol) was stirred in SOCl$_2$ at 55-60° C. under Ar atmosphere for 4.5 hours. TLC showed compound 6 had disappeared. The mixture was concentrated in vacuum to give crude product compound 7 as a yellow solid (43 mg). Yield: 100%.

(d) Preparation of Compound (100):

Compound 7 (150 mg, 0.470 mmol), compound 2 (117 mg, 0.609 mmol) and Cs$_2$ CO$_3$ (306 mg, 0.939 mmol) were refluxed in acetone under Ar atmosphere overnight. TLC showed compound 7 had disappeared. The mixture was concentrated and dissolved in DCM. The DCM phase was washed with water and brine, dried with Na$_2$ SO$_4$ and purified by gel column. The crude product was purified again by pre-TLC (DCM:MeOH=1:20) to give two isomers: compound (100a): 85 mg, light yellow solid (with low polarity); and compound (100b): 32 mg, light grey solid (with high polarity).

$^1$HNMR of compound (100a): (400 MHz, DMSO-d6): δ (ppm): 8.607-8.592 (2H, d, Py-H), 7.919-7.900 (1H, d, Py-H), 7.808-7.787 (3H, m, Py-H, Ph-H), 7.674-7.639 (1H, t, Ph-H), 7.606-7.587 (1H, t, Ph-H), 7.409-7.388 (2H, d, Ph-H), 7.291-7.279 (2H, d, Ph-H), 4.718-4.667 (1H, m, —CH), 2.395 (3H, s, —CH3), 1.878-1.861 (3H, d, —CH3). ESI MS: 475.1 (M+H), HPLC (Waters SunFire C18 4.6*100 mm column, 25° C.; 20-95% of Acetonitrile (0.03% TFA) over 8 minutes, in water (0.03% TFA), 1 ml/min): 95.5%. Compound elutes at 5.436 min. $[a]_{20}^{589}$=0 (C=0.25, CH$_2$Cl$_2$). HPLC of compound (100b): (Waters SunFire C18 4.6*100 mm column, 25° C.; 20-95% of Acetonitrile (0.03% TFA) over 8 minutes, in water (0.03% TFA), 1 ml/min): Compound elutes at 5.317 min. $[a]_{20}^{589}$=+10.8 (C=0.25, CH$_2$Cl$_2$).

EXAMPLE 52

Preparation of Compound (68)

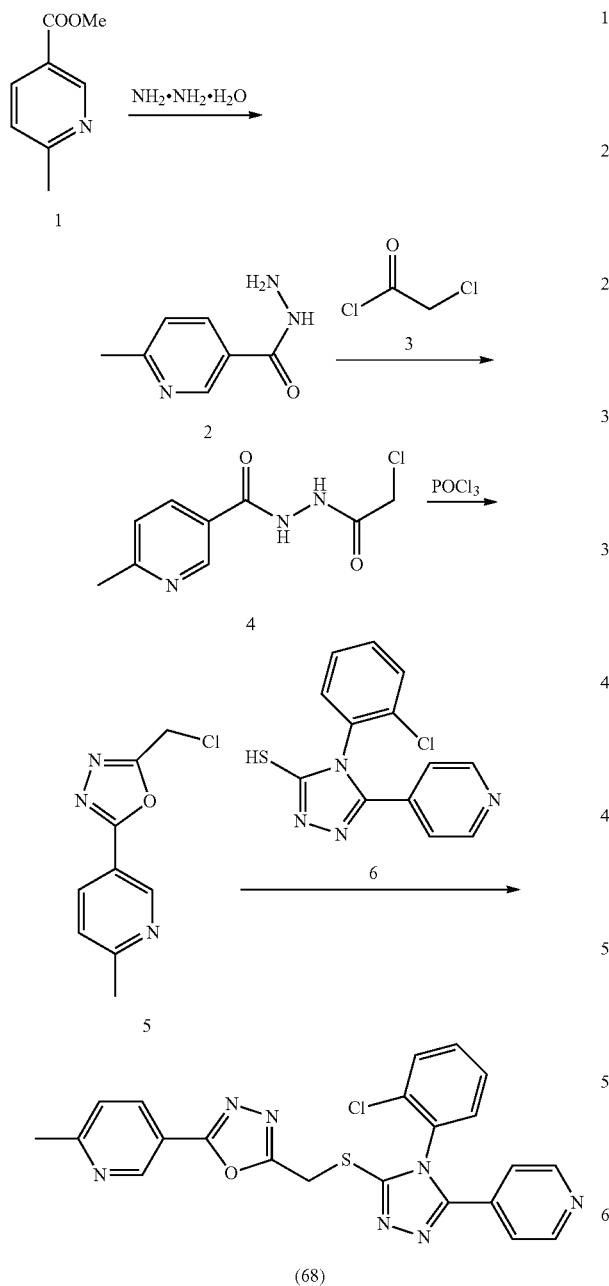

(a) Preparation of Compound 2:
Compound 1 (3 g, 19.85 mmol) was dissolved in MeOH (15 ml) and NH$_2$NH$_2$.H$_2$O (5.46 g, 109.2 mmol) was added. The mixture was stirred and raised to 90° C. for 2 hours. The mixture was concentrated and purified by chromatography to give desired product 2 as a white solid (2.1 g). Yield: 67%.

(b) Preparation of Compound 4:
To a solution of compound 2 (2.1 g, 13.9 mmol) in acetonitrile was added simultaneously compound 3 (1.57 g, 13.9 mmol) and 50% sodium hydroxide (0.56 g, 13.9 mmol) while maintaining the internal temperature below 10° C. After 30 mins, the mixture was extracted with EA and then the EA layer was concentrated to give compound 4 as a white solid (2.2 g). Yield: 68%.

(c) Preparation of Compound 5:
Compound 4 (900 mg, 3.95 mmol) was suspended in POC$_3$ (6 ml) and the reaction mixture was heated to 110° C. for 2.5 hours. The mixture was allowed to cool to ambient temperature and quenched by adding water, then it was extracted with EA and purified by chromatography eluting with (DCM: MeOH=20:1) to give compound 5 as a white solid (300 mg). Yield: 37%.
$^1$HNMR (400 MHz, DMSO-d6): δ (ppm): 9.05-7.51 (3H, m, Py-H), 5.16 (2H, s, —CH$_2$—), 2.59 (3H, s, CH$_3$—).

(d) Preparation of Compound (68):
To a solution of compound 5 (200 mg, 0.96 mmol) in acetone (10 ml) was added compound 6 (278 mg, 0.96 mmol) and K$_2$CO$_3$ (265 g, 1.92 mmol). The mixture was stirred at reflux for 2 hours. Then the mixture was poured into water and extracted with EA. The EA layer was concentrated and purified by chromatography to give compound (68) as a white solid (122 mg). Yield: 85%.
$^1$HNMR (400 MHz, DMSO-d6): δ (ppm): 8.96-7.29 (11H, m, Py-H, Ph-H), 4.85-4.74 (2H, m, —CH$_2$—). ESI MS: 462 [M+H]$^+$, HPLC: 99%.

EXAMPLE 53

Preparation of Compound (104)

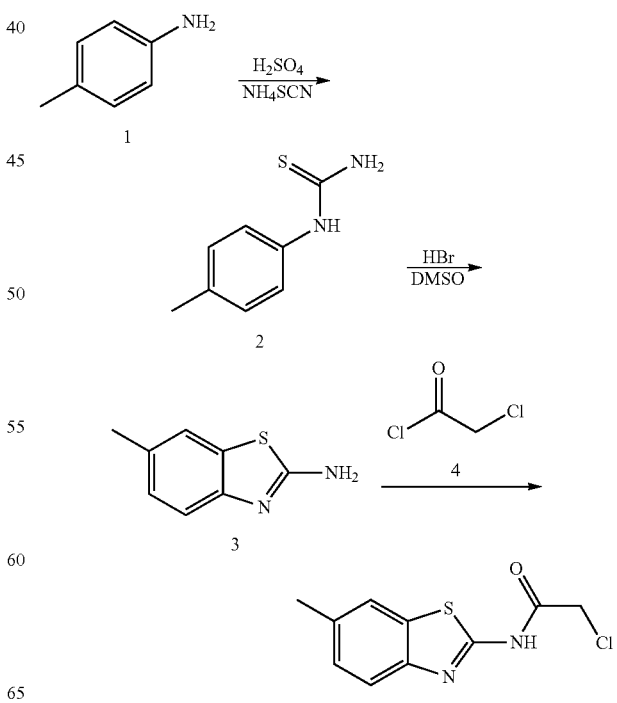

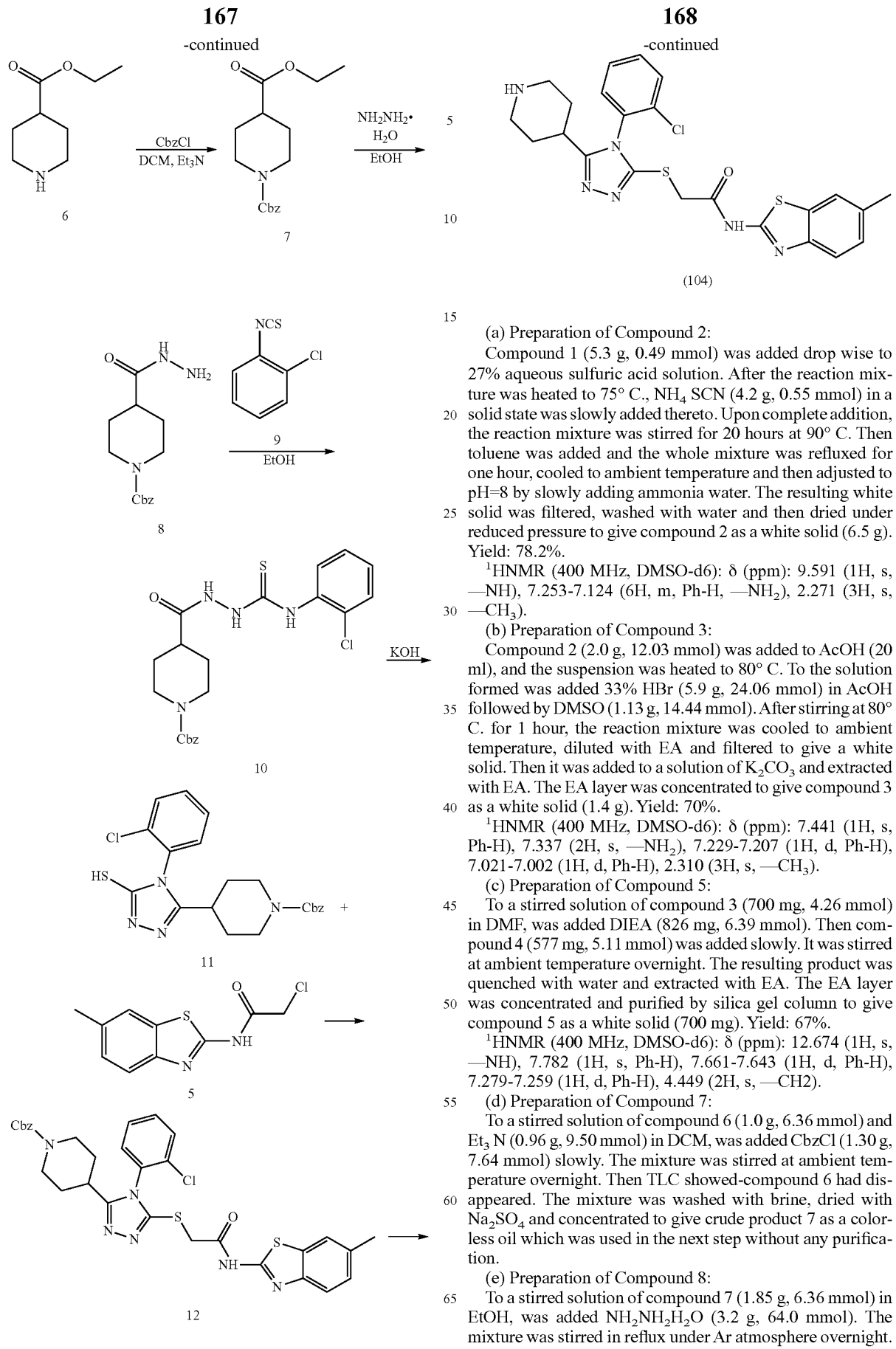

(a) Preparation of Compound 2:

Compound 1 (5.3 g, 0.49 mmol) was added drop wise to 27% aqueous sulfuric acid solution. After the reaction mixture was heated to 75° C., $NH_4$ SCN (4.2 g, 0.55 mmol) in a solid state was slowly added thereto. Upon complete addition, the reaction mixture was stirred for 20 hours at 90° C. Then toluene was added and the whole mixture was refluxed for one hour, cooled to ambient temperature and then adjusted to pH=8 by slowly adding ammonia water. The resulting white solid was filtered, washed with water and then dried under reduced pressure to give compound 2 as a white solid (6.5 g). Yield: 78.2%.

$^1$HNMR (400 MHz, DMSO-d6): δ (ppm): 9.591 (1H, s, —NH), 7.253-7.124 (6H, m, Ph-H, —$NH_2$), 2.271 (3H, s, —$CH_3$).

(b) Preparation of Compound 3:

Compound 2 (2.0 g, 12.03 mmol) was added to AcOH (20 ml), and the suspension was heated to 80° C. To the solution formed was added 33% HBr (5.9 g, 24.06 mmol) in AcOH followed by DMSO (1.13 g, 14.44 mmol). After stirring at 80° C. for 1 hour, the reaction mixture was cooled to ambient temperature, diluted with EA and filtered to give a white solid. Then it was added to a solution of $K_2CO_3$ and extracted with EA. The EA layer was concentrated to give compound 3 as a white solid (1.4 g). Yield: 70%.

$^1$HNMR (400 MHz, DMSO-d6): δ (ppm): 7.441 (1H, s, Ph-H), 7.337 (2H, s, —$NH_2$), 7.229-7.207 (1H, d, Ph-H), 7.021-7.002 (1H, d, Ph-H), 2.310 (3H, s, —$CH_3$).

(c) Preparation of Compound 5:

To a stirred solution of compound 3 (700 mg, 4.26 mmol) in DMF, was added DIEA (826 mg, 6.39 mmol). Then compound 4 (577 mg, 5.11 mmol) was added slowly. It was stirred at ambient temperature overnight. The resulting product was quenched with water and extracted with EA. The EA layer was concentrated and purified by silica gel column to give compound 5 as a white solid (700 mg). Yield: 67%.

$^1$HNMR (400 MHz, DMSO-d6): δ (ppm): 12.674 (1H, s, —NH), 7.782 (1H, s, Ph-H), 7.661-7.643 (1H, d, Ph-H), 7.279-7.259 (1H, d, Ph-H), 4.449 (2H, s, —CH2).

(d) Preparation of Compound 7:

To a stirred solution of compound 6 (1.0 g, 6.36 mmol) and $Et_3$ N (0.96 g, 9.50 mmol) in DCM, was added CbzCl (1.30 g, 7.64 mmol) slowly. The mixture was stirred at ambient temperature overnight. Then TLC showed-compound 6 had disappeared. The mixture was washed with brine, dried with $Na_2SO_4$ and concentrated to give crude product 7 as a colorless oil which was used in the next step without any purification.

(e) Preparation of Compound 8:

To a stirred solution of compound 7 (1.85 g, 6.36 mmol) in EtOH, was added $NH_2NH_2H_2O$ (3.2 g, 64.0 mmol). The mixture was stirred in reflux under Ar atmosphere overnight.

TLC showed compound 7 had disappeared. The mixture was concentrated and washed with Et₂O to give desired product 8 as a white solid (1.2 g). Yield: 68%.

(f) Preparation of Compound 10:

To a stirred suspension of compound 8 (500 mg, 2.2 mmol) in EtOH (10 ml) was added compound 9 (373 mg, 2.2 mmol). Then the mixture was refluxed for one hour and the white precipitate compound 10 (644 mg) was collected by filtration. Yield: 80%.

(g) Preparation of Compound 11:

To a suspension of compound 10 (600 mg, 1.34 mmol) in H₂O (15 ml) was added KOH (1.5 g, 26.9 mmol). The reaction mixture was heated to reflux for 2 hours. After that, the reaction mixture was cooled down to ambient temperature and 3N HCl was added to acidify the solution to pH=3. The white precipitated compound 11 (333 mg) was collected by filtration. Yield: 58%.

(h) Preparation of Compound 12:

To a stirred suspension of compound 11 (180 mg, 0.42 mmol) in acetone (10 ml) was added compound 5 (100 mg, 0.42 mmol) and K₂CO₃ (69 mg, 0.50 mmol). The mixture was stirred at 60° C. for 2 hours. Then acetone was removed and water was added into the mixture. The mixture was filtered and the solid was dried and crystallized by Et₂O to afford compound 12 (170 mg). Yield: 65%.

¹HNMR (400 MHz, DMSO-d6): δ (ppm): 12.588 (1H, s, —NH), 7.834-7.358 (12H, m, Ph-H), 5.061 (2H, s, —CH₂), 4.224 (2H, s, —CH₂), 3.951-3.919 (2H, d, —CH₂), 2.855-2.833 (2H, m, —CH₂), 2.611-2.574 (1H, m, —CH), 2.418 (3H, s, —CH₃), 1.796-1.601 (4H, m, —CH₂).

(i) Preparation of Compound (104):

Compound 7 (100 mg, 0.16 mmol) was added to HBr/AcOH solution under ice bath. The solution was stirred at 0° C. for 2 hours. The mixture was poured into NaHCO₃ a.q. solution and extracted by DCM. The DCM layer was concentrated and purified by pre-TLC to give compound (104) as a white solid (35 mg). Yield: 38%.

¹HNMR (400 MHz, DMSO-d6): δ (ppm): 7.799-7.573 (7H, m, Ph-H, —NH), 7.210 (1H, m, Ph-H), 4.144 (2H, s, —SCH₂), 2.980-2.958 (2H, m, —CH2), 2.434-2.393 (5H, m, —CH2, —CH3), 1.693-1.615 (4H, m, —CH2). ESI MS: 499 (M), HPLC: 94%.

¹HNMR (400 MHz, CD₃OD): δ (ppm): 7.627-7.607 (1H, d, Ph-H), 7.531-7.489 (4H, m, Ph-H), 7.416-7.376 (1H, t, Ph-H), 7.150-7.129 (1H, d, Ph-H), 2.978-2.948 (2H, d, —CH2), 2.508-2.390 (3H, m, —CH2, —CH), 2.336 (3H, s, —CH3), 1.756-1.673 (4H, m, —CH2).

EXAMPLE 54

Preparation of Compound (70)

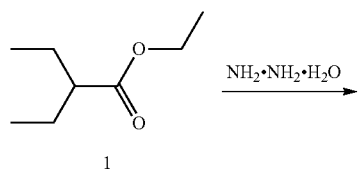

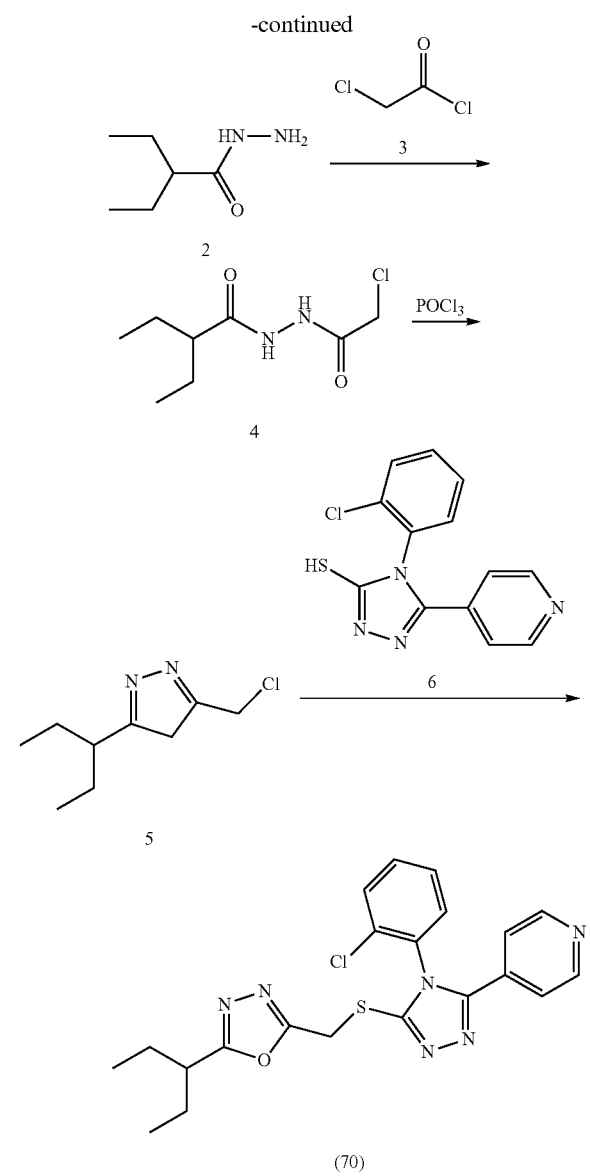

(a) Preparation of Compound 2:

Compound 1 (3 g, 20 mmol) was dissolved in MeOH (20 ml) and NH₂NH₂.H₂O (5.2 ml) was added. The mixture was stirred and raised to 90° C. overnight. Then the mixture was concentrated and crystallized from Et₂O to give desired product compound 2 as a white solid (500 mg). Yield: 19%.

(b) Preparation of Compound 4:

To a solution of compound 2 (500 mg, 3.84 mmol) in acetonitrile was added simultaneously compound 3 (434 mg, 3.84 mmol) and 50% sodium hydroxide (154 mg, 3.84 mmol) while maintaining the internal temperature below 10° C. After 30 mins, the mixture was extracted with EA and then the EA layer was concentrated to give a white solid compound 4 (400 mg). Yield: 50%.

¹HNMR (400 MHz, DMSO-d6): δ (ppm): 10.21 (H, s, —NH), 9.93 (H, s, —NH), 4.10-4.07 (2H, s, —CH₂—), 2.06-1.97 (1H, m, CH), 1.49-1.32 (4H, m, —CH₂—), 0.89-0.81 (6H, m, —CH₃).

(c) Preparation of Compound (70):

To a solution of compound 5 (0.87 mmol) in acetone (8 ml) was added compound 6 (251 mg, 0.87 mmol) and K₂CO₃

(240 g, 1.74 mmol). The mixture was stirred at reflux for 2 hours. Then acetone was removed, water was poured into the mixture and extracted with EA. The EA phase was concentrated and purified by chromatography to give compound (70) as a yellow semi-solid (120 mg). Yield: 31%.

¹HNMR (400 MHz, DMSO-d6): δ (ppm): 8.61-8.60 (2H, dd, Py-H), 7.83-7.29 (6H, m, Py-H, Ph-H), 4.74-4.62 (2H, m, —CH₂—), 2.84-2.81 (1H, m, —CH—), 1.69-1.60 (4H, m, —CH₂—), 0.86-0.78 (6H, m, —CH₃). ESI MS: 441[M+H]⁺, HPLC: 98%.

EXAMPLE 55

Preparation of Compound (101)

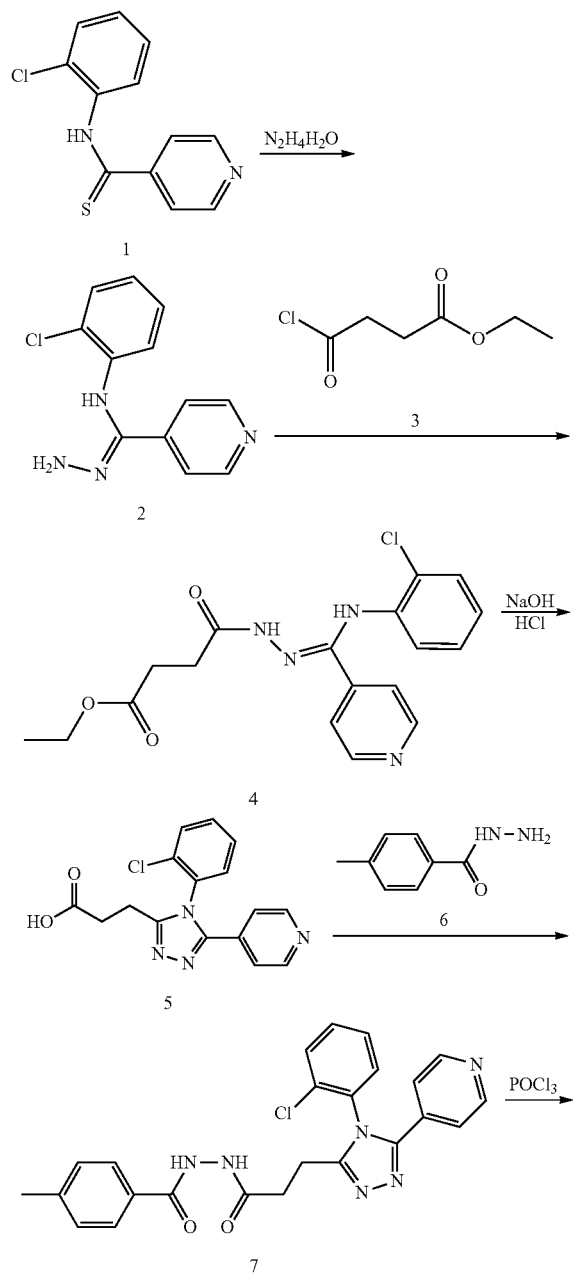

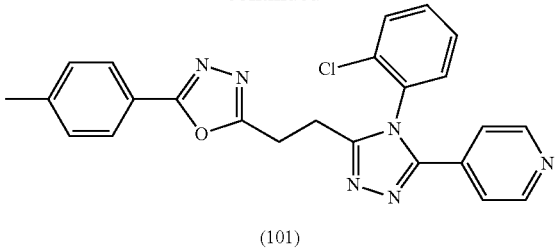

(a) Preparation of Compound 2:

To a suspension of compound 1 (500 mg, 2.0 mmol) in dioxane (15 ml) was added NH₂NH₂.H₂O (3 g, 60.0 mmol). The reaction mixture was heated to reflux for 2 hours. Then the reaction mixture was poured into water and extracted with EA. The EA layer was dried and concentrated to afford compound 2 as a colorless oil (400 mg). Yield: 81%.

(b) Preparation of Compound 4:

To a suspension of compound 2 (400 mg, 1.62 mmol) in acetonitrile (10 ml) was added compound 3 (266 mg, 1.62 mmol) and 50% sodium hydroxide (64.8 mg, 1.62 mmol) under ice water-bath. After 30 mins, the mixture was extracted with EA and then the EA layer was concentrated to give compound 4 as a white solid (485 mg). Yield: 80%.

(c) Preparation of Compound 5:

Compound 4 (300 mg, 0.8 mmol) was added to a 22% NaOH solution (320 mg, 8 mmol) and the suspension was refluxed overnight. The resulting suspension was adjusted to pH=5 using 1N HCl solution. The mixture was concentrated directly to give compound 5 as a white solid (800 mg).

(d) Preparation of Compound 7:

To a suspension of compound 5 (328 mg, 1.0 mmol) in DCM (10 ml) was added compound 6 (150 mg, 1.0 mmol), EDC (288 mg, 1.5 mmol) and HOBt (202 mg, 1.5 mmol). The mixture was stirred at ambient temperature for 2 hours. The mixture was concentrated and purified by chromatography to give compound 7 as a white solid (230 mg). Yield: 50%.

(e) Preparation of Compound (101):

The mixture of compound 7 (100 mg, 0.22 mmol) in POCl₃ (10 ml) was refluxed for 5 hours. POCl₃ was evaporated and the residue was extracted by DCM from NaHCO₃ a.q. solution. The DCM layer was concentrated and purified by chromatography to give Compound (101) as a white solid (50 mg). Yield: 50%.

¹HNMR (400 MHz, DMSO-d6): δ (ppm): 8.585-8.574 (2H, d, Py-H), 7.894-7.773 (4H, m, Py-H, Ph-H), 7.707-7.631 (2H, m, Ph-H), 7.401-7.381 (2H, d, Ph-H), 7.285-7.273 (2H, d, Ph-H), 3.429-3.393 (2H, t, —CH2), 3.126-2.959 (2H, m, —CH2), 2.384 (3H, s, —CH3).

ESI MS: 443 (M+H), HPLC: 97%.

EXAMPLE 56

Preparation of Compound (102)

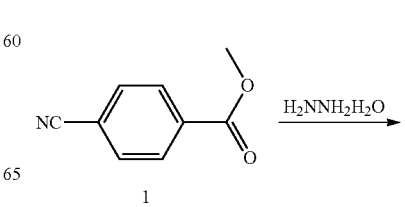

-continued

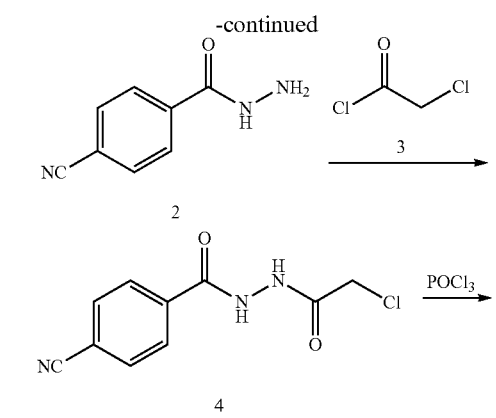

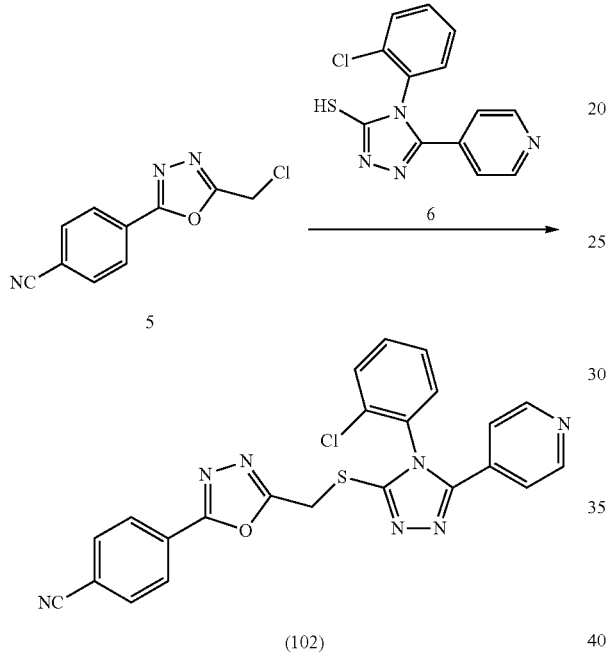

(a) Preparation of Compound 2:

Compound 1 (3 g, 18.6 mmol) was dissolved in MeOH (15 ml) and NH$_2$NH$_2$.H$_2$O (5.13 g, 102.4 mmol) was added. The mixture was stirred and raised to 90° C. for 2 hours. The mixture was concentrated and purified by chromatography to give desired product compound 2 as a white solid (2.3 g). Yield: 76.7%.

(b) Preparation of Compound 4:

To a solution of compound 2 (1 g, 6.2 mmol) in acetonitrile was added simultaneously compound 3 (0.7 g, 6.2 mmol) and 50% sodium hydroxide (0.248 g, 6.2 mmol) while maintaining the internal temperature below 10° C. After 30 mins, the mixture was extracted with EA and then the EA layer was concentrated to give compound 4 as a white solid (1 g). Yield: 67%.

(c) Preparation of Compound 5:

Compound 4 (1 g, 4.2 mmol) was suspended in POCl$_3$ (6 ml) and the reaction mixture was heated to 110° C. for 2.5 hours. The mixture was allowed to cool to ambient temperature and quenched by adding water, then it was extracted with EA and the EA layer was concentrated and purified by chromatography eluting with (DCM: MeOH=20:1) to give compound 5 as a white solid (719 mg). Yield: 78%.

$^1$HNMR (400 MHz, DMSO-d6): δ (ppm): 8.19-8.18 (2H, dd, Ph-H), 8.10-8.08 (2H, dd, Ph-H), 5.17 (2H, s, —CH$_2$—).

(d) Preparation of Compound (102):

To a solution of compound 5 (350 mg, 1.58 mmol) in acetone (10 ml) was added compound 6 (458 mg, 1.58 mmol) and K$_2$CO$_3$ (438 mg, 3.17 mmol). The mixture was stirred at refluxing for 2 hours. Then the mixture was poured into water and extracted with EA. The EA layer was concentrated and purified by chromatography to give compound (102) as a yellow solid (329 mg). Yield: 44%.

$^1$HNMR (400 MHz, DMSO-d6): δ (ppm): 8.60-8.59 (2H, d, Py-H), 8.09-7.29 (10H, m, Py-H, Ph-H), 4.87-4.76 (2H, m, —CH$_2$—). ESI MS: 472 [M+H]$^+$, HPLC: 99%.

EXAMPLE 57

Preparation of Compound (71)

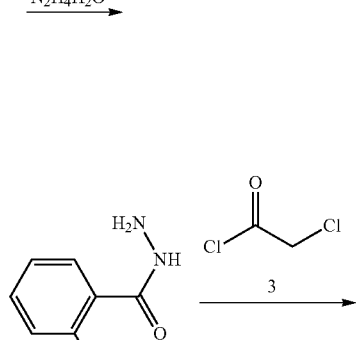

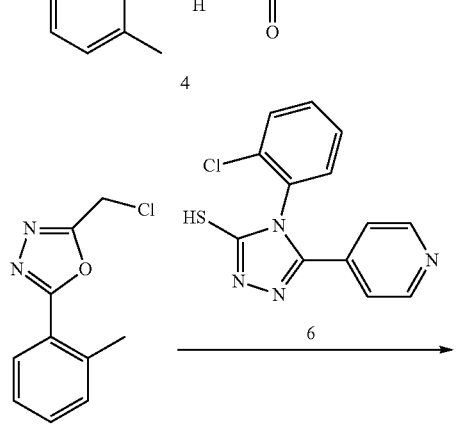

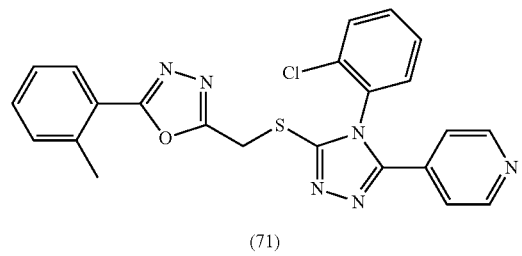

(a) Preparation of Compound 4:

To a solution of compound 2 (2.3 g, 15.3 mmol) in acetonitrile was added simultaneously compound 3 (1.73 g, 15.3 mmol) and 50% sodium hydroxide (0.61 g, 15.3 mmol) while maintaining the internal temperature below 10° C. After 30 mins, the mixture was extracted with EA and then the EA layer was concentrated to give Compound 4 as a white solid (2.3 g). Yield: 66%.

(b) Preparation of Compound 5:

Compound 4 (2.3 g, 10.5 mmol) was suspended in POCl$_3$ (10 ml) and the reaction mixture was heated to 110° C. for 2.5 hours. The mixture was allowed to cool to ambient temperature and quenched by adding water, then it was extracted with EA and purified by chromatography eluting with (DCM: MeOH=20:1) to give Compound 5 as a white solid (1 g). Yield: 45%.

(c) Preparation of Compound (71):

To a solution of compound 5 (200 mg, 0.97 mmol) in acetone (10 ml) was added compound 6 (278 mg, 0.97 mmol) and K$_2$CO$_3$ (270 g, 1.94 mmol). The mixture was stirred at reflux for 2 hours. Then acetone was removed and water was poured into the mixture, followed by extraction with EA. The EA layer was concentrated and chromatography gave compound (71) as a white solid (220 mg). Yield: 49%.

$^1$HNMR (400 MHz, DMSO-d6): δ (ppm): 8.60-8.59 (2H, dd, Py-H), 7.84-7.29 (10H, m, Py-H, Ph-H), 4.86-4.75 (2H, m, —CH$_2$—), 2.57 (3H, s, CH$_3$—). ESI MS: 461[M+H]$^+$, HPLC: 98%.

EXAMPLE 58

Preparation of Compound (72)

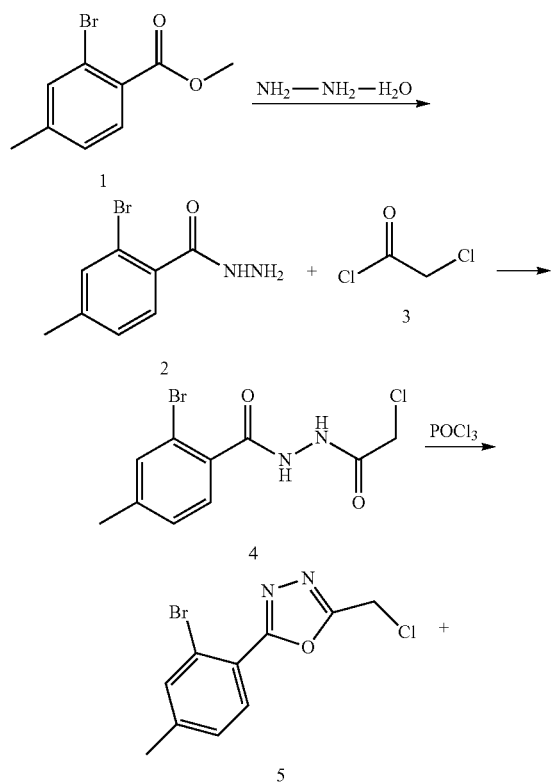

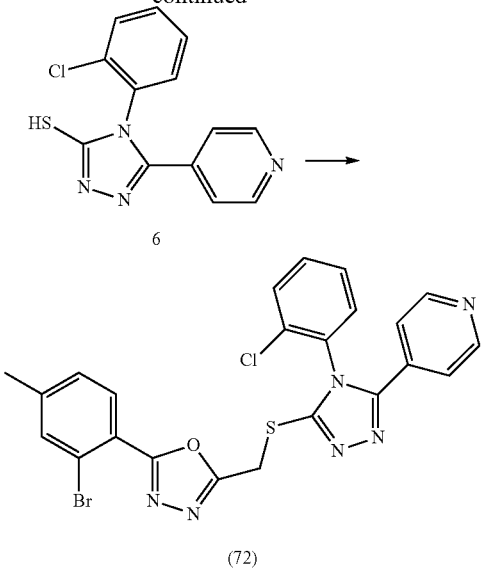

(a) Preparation of Compound 2:

The solution of compound 1 (2 g, 8.7 mmol) and NH$_2$NH$_2$.H$_2$O (4.4 g, 87 mmol) in EtOH (50 ml) was heated to reflux for 24 hours. Then the mixture was concentrated and the residue was washed with EA/PE to give compound 2 as a white solid (1.8 g). Yield: 90%.

$^1$HNMR (400 MHz, DMSO-d6): δ (ppm): 9.0 (1H, b, —NH), 7.49 (1H, d, Ar—H), 7.20-7.26 (2H, m, Ar—H), 2.34 (3H, s, CH$_3$—).

(b) Preparation of Compound 4:

To a solution of compound 2 (1.5 g, 6.6 mmol) in acetonitrile (30 mL) were added simultaneously compound 3 (0.57 mL, 7.2 mmol) and a solution of NaOH (288 mg in water 0.4 ml, 7.2 mmol) and the internal temperature maintained below 10° C. After 1 hour, the mixture was added to water (50 ml) and extracted by EA. The EA layer was concentrated to give compound 4 as a white solid (1.8 g). Yield: 90%.

$^1$HNMR (400 MHz, DMSO-d6): δ (ppm): 10.50 (1H, b, —NH), 10.42 (1H, b, —NH), 7.55 (1H, s, Ar—H), 7.29-7.38 (2H, m, Ar—H), 4.19 (2H, s, —CH$_2$—), 2.35 (3H, s, CH$_3$—).

(c) Preparation of Compound 5:

Compound 4 (1.2 g, 3.9 mmol) was suspended in POCl$_3$ (5 ml), and then the reaction mixture was heated to 110° C. for 5 hours. The mixture was allowed to cool to ambient temperature and quenched by adding water, then the mixture was extracted with EA. The EA layer was concentrated to give a residue which was purified by recrystallization (DCM: PE) to give compound 5 as a light grey solid (800 mg). Yield: 71%.

$^1$HNMR (400 MHz, CDCl$_3$): δ (ppm): 7.83 (1H, d, Ar—H), 7.59 (1H, s, Ar—H), 7.27 (1H, m, Ar—H), 4.80 (2H, s, —CH$_2$—), 2.41 (3H, s, CH$_3$—).

(d) Preparation of Compound (72):

To a solution of compound 5 (100 mg, 0.35 mmol) in acetone (10 mL) was added compound 6 (101 mg, 0.35 mmol) and K$_2$CO$_3$ (60 mg, 0.43 mmol). The mixture was stirred at reflux for 1.5 hours. Then the solvent was removed, water (15 mL) was added into the mixture, extracted with EA, washed with brine and dried over Na$_2$SO$_4$. The EA layer was concentrated and chromatography (DCM/MeOH=50/1) gave compound (72) as a white solid (158 mg). Yield: 84%.

¹HNMR (400 MHz, CDCl₃): δ (ppm): 8.56-8.58 (2H, m, Py-H), 7.22-7.79 (9H, m, Ph-H, Py-H), 4.71-4.88 (2H, m, —CH₂—), 2.40 (3H, s, CH₃—). ESI MS: ([M+H]⁺=539, HPLC: 97.6%.

EXAMPLE 59

Preparation of Compound (73)

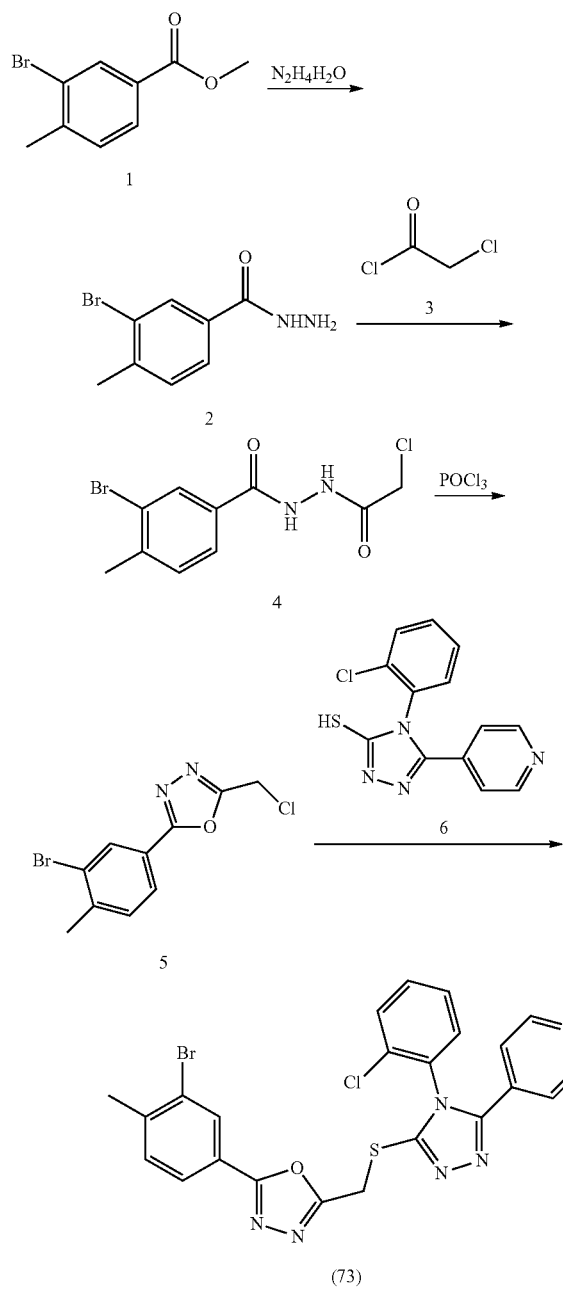

(a) Preparation of Compound 2:

The solution of compound 1 (2 g, 8.7 mmol) and NH₂NH₂.H₂O (4.4 g, 87 mmol) in EtOH (50 ml) was heated to reflux for 24 hours. Then the mixture was cooled to around 0° C. Then the precipitated solid was filtered. The solid was dried to give compound 2 as a white solid (1.7 g). Yield: 85%.

¹HNMR (400 MHz, DMSO-d6): δ (ppm): 9.83 (1H, b, —NH), 7.80 (1H, d, Ar—H), 7.71-7.73 (1H, dd, Ar—H), 7.42 (1H, d, Ar—H), 2.36 (3H, s, CH₃—).

(b) Preparation of Compound 4:

To a solution of compound 2 (1.6 g, 7.0 mmol) in acetonitrile (30 mL) were added simultaneously compound 3 (0.62 mL, 7.7 mmol) and a solution of NaOH (308 mg in water 1 ml, 7.7 mmol) and the internal temperature maintained below 10° C. After 1 hour the mixture was added to water (50 ml) and extracted by EA. The EA layer was concentrated to give compound 4 as a light yellow solid (2.2 g). Quantitative yield.

(c) Preparation of Compound 5:

Compound 4 (2.1 g, 6.8 mmol, crude) was suspended in POCl₃ (6 ml), and then the reaction mixture was heated to 110° C. for 5 hours. The mixture was allowed to cool to ambient temperature and quenched by adding water, then the mixture was extracted with EA. The EA layer was concentrated to give a residue which was purified by column chromatography eluting with (DCM: MeOH=50:1) to give light grey solid compound 5 (1.7 g). Yield: 87%.

¹HNMR (400 MHz, CDCl₃): δ (ppm): 8.23 (1H, S, Ar—H), 7.91 (1H, d, Ar—H), 7.38 (1H, d, Ar—H), 4.78 (2H, s, —CH₂—), 2.48 (3H, s, CH₃—).

(d) Preparation of Compound (73):

To a solution of compound 5 (100 mg, 0.35 mmol) in acetone (8 mL) was added compound 6 (101 mg, 0.35 mmol) and K₂CO₃ (60 mg, 0.43 mmol). The mixture was stirred at reflux for 1.5 hours. Then the solvent was removed, water (15 mL) was added into the mixture, extracted with EA, washed with brine and dried over Na₂ SO₄. The EA layer was concentrated and chromatography (DCM/MeOH=40/1) gave compound (73) as a white solid (100 mg). Yield: 53%.

¹HNMR (400 MHz, CDCl₃): δ (ppm): 8.58 (2H, d, Py-H), 8.15 (1H, d, Ar—H), 7.83-7.86 (1H, m, Ar—H), 7.33-7.62 (7H, m, Ph-H, Py-H), 4.72-4.82 (2H, m, —CH₂—), 2.47 (3H, s, CH₃—).

ESI MS: ([M+H]⁺=539, HPLC: 99.3%.

EXAMPLE 60

Preparation of Compound (102)

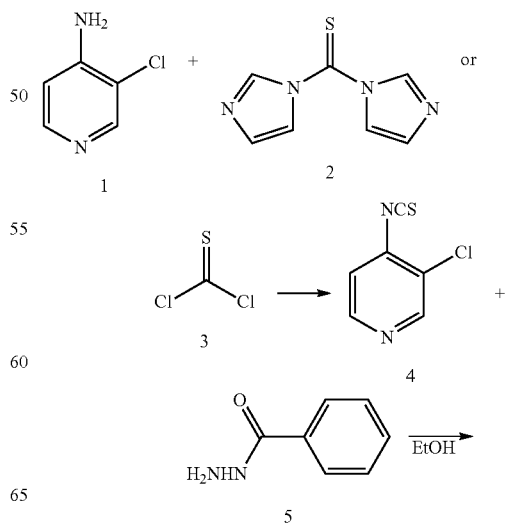

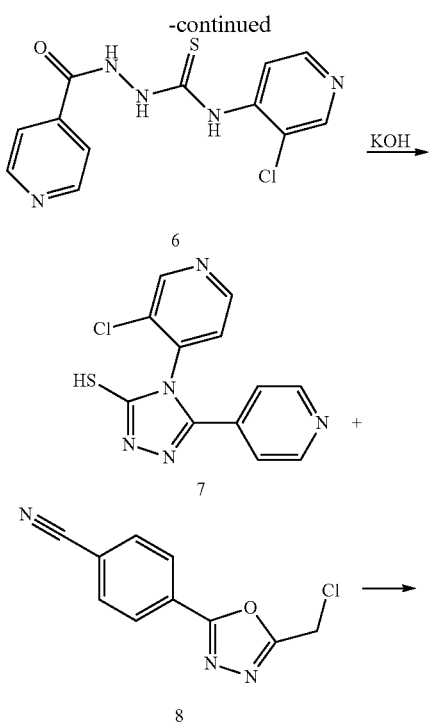

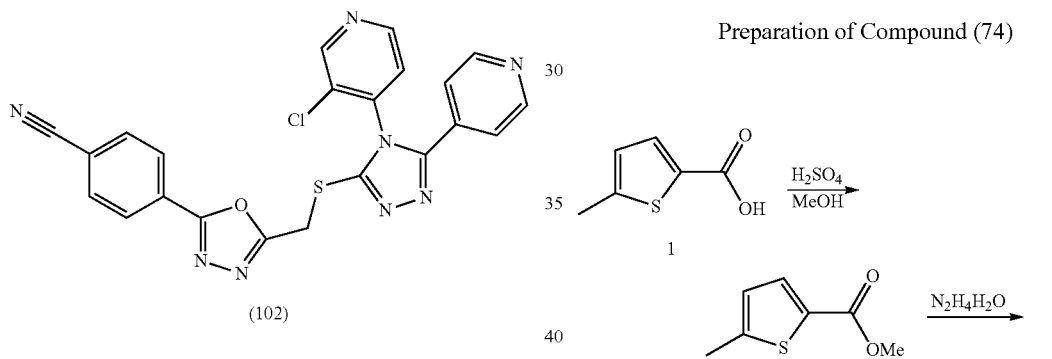

(a) Preparation of Compound 4:

Compound 1 (200 mg, 1.56 mmol) was dissolved in toluene (70 mL) at 0° C. and compound 3 (0.16 mL, 2.03 mmol) was added. The reaction mixture was stirred at reflux for 6 hours and the reaction was cooled to 0° C. The residue was washed with aqueous KHCO₃ (15 mL) and H₂O (20 mL). The mixture was extracted with DCM (50 mL×4), the organic layer was washed with brine (15 mL) and dried (MgSO₄), and concentrated to give crude product which was purified by column chromatography on silica gel eluting with EA:PE=10:1 to give compound 4 (90 mg) (also confirmed by LC-MS). Yield: 34%.

¹HNMR (400 MHz, CDCl₃): δ (ppm): 8.62 (1H, s, Py-H), 8.45-8.47 (1H, d, Py-H), 7.11-7.12 (1H, d, Py-H)

(b) Preparation of Compound 6:

Compound 4 (83 mg, 0.49 mmol) and Compound 5 (67 mg, 0.49 mmol) were dissolved in EtOH (7 mL). The reaction was stirred at reflux for 4 hours and the yellow precipitated compound 6 was collected by filtration (110 mg) (also confirmed by LC-MS). Yield: 73%.

¹HNMR (400 MHz, DMSO-d6): δ (ppm): 11.07 (1H, b, —NH), 10.31 (1H, s, —NH), 9.80 (1H, s, —NH), 8.457-8.80 (4H, m, Py-H), 7.68-7.85 (3H, m, Py-H).

(c) Preparation of Compound 7:

Compound 6 (1.25 g, 4.07 mmol) and 10M KOH (4 mL, 40.7 mmol) was dissolved in ethylene glycol (40 mL) and the reaction was stirred at 130° C. for 14 hours (LC-Ms showed that there was 4.12% of Compound 7 in the mixture). The solvent was removed by reduced pressure, the residue was quenched in aqueous H₂O (50 mL) and AcOH (4 mL, 10M). The mixture was extracted with EA (8×30 mL), the organic layer was washed with brine (10 mL) and dried (MgSO₄), and concentrated to give crude product. It was purified over pre-HPLC to give a yellow solid (19 mg). Yield: 1.5%.

¹HNMR (400 MHz, CDCl₃+CD₃OD): δ (ppm): 8.54-8.76 (4H, m, Py-H), 7.49 (1H, d, Py-H), 7.27 (2H, d, Py-H).

(d) Preparation of Compound (102):

Compound 7 (19 mg, 0.066 mmol), compound 8 (44 mg, 0.2 mmol) and K₂CO₃ (11.4 mg, 0.083 mmol) were dissolved in acetone (5 mL) and the reaction mixture was stirred at 65° C. for 5 hours and then evaporated in vaccuo. The mixture was triturated with water (10 mL) and extracted with EA (3×30 mL). The organic layer was washed with brine (10 mL) and dried (MgSO₄), and concentrated to give crude product which was purified over pre-HPLC to give a yellow solid (3 mg) (also confirmed by LC-MS). Yield: 9.6%.

¹HNMR (400 MHz, CD₃OD): δ (ppm): 8.91 (2H, s), 8.75 (1H, s), 8.59 (1H, s), 8.48-8.49 (2H, d), 8.22-8.25 (2H, d), 7.97-7.99 (2H, d), 7.92-9.93 (1H, d).

EXAMPLE 61

Preparation of Compound (74)

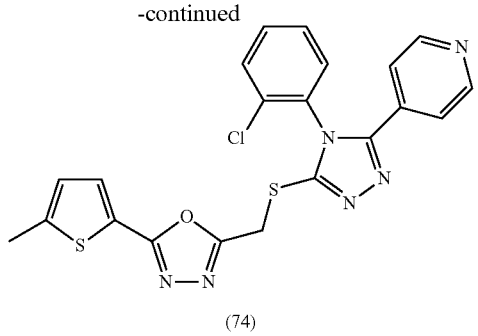

(74)

(a) Preparation of Compound 2:

Compound 1 (5 g, 35 mmol) was dissolved in MeOH (50 ml). The mixture was cooled to 0° C. and $H_2SO_4$ (3 ml) was added drop wise. Then the mixture was stirred at 30° C. for 4 days. The mixture was treated with aqueous $Na_2CO_3$ and adjusted to pH=8, followed by extraction with EA. The organic layer was concentrated and purified with column chromatography (PE: EA=10:1) to give compound 2 as a yellow oil (5.4 g). Yield: 98%.

(b) Preparation of Compound 3:

$NH_2NH_2.H_2O$ (6.2 ml, 128 mmol) was added to a solution of compound 2 (2 g, 12.8 mmol) in EtOH (10 ml). The mixture was stirred at reflux overnight. The mixture was concentrated and washed with EA and PE to give compound 3 as a yellow solid (1.8 g). Yield: 90%.

$^1$HNMR (400 MHz, $CDCl_3$): δ (ppm): 7.43 (1H, d, NH—), 7.35 (1H, d, Ar—H), 6.74 (1H, d, Ar—H), 3.50 (2H, b, $NH_2$—), 2.51 (3H, s, $CH_3$—).

(c) Preparation of Compound 5:

To a solution of compound 3 (1.77 g, 11.3 mmol) in acetonitrile (30 mL) were added simultaneously compound 4 (1.28 g, 11.3 mmol) and 50% sodium hydroxide (452 mg, 11.3 mmol) while maintaining the internal temperature below 10° C. After 1 hour the mixture was extracted with EA and then concentrated to obtain a yellow solid (2.22 g). Yield: 82%.

$^1$HNMR (400 MHz, $CDCl_3$): δ (ppm): 10.42 (1H, s, NH—), 10.32 (1H, s, NH—), 7.65 (1H, d, Ar—H), 6.89 (1H, s, Ar—H), 4.18 (2H, d, —$CH_2$—), 2.51 (3H, m, $CH_3$—).

(d) Preparation of Compound 6:

Compound 4 (2 g, 8.5 mmol) was suspended in $POCl_3$ (13 mL) and the reaction mixture was heated to 110° C. overnight. The mixture was allowed to cool to ambient temperature and quenched by adding cold water, then it was extracted with EA and purified by chromatography eluting with (DCM: MeOH=20:1) to give a yellow solid (700 mg). Yield: 38%.

$^1$HNMR (400 MHz, $CDCl_3$): δ (ppm): 7.60 (1H, d, Ar—H), 6.85 (1H, d, Ar—H), 4.74 (2H, s, —$CH_2$—), 2.57 (3H, s, $CH_3$—).

(e) Preparation of Compound (74):

To a solution of compound 7 (150 mg, 0.51 mmol) in acetone (12 mL) was added compound 6 (111 mg, 0.51 mmol) and $K_2CO_3$ (89 mg, 0.65 mmol). The mixture was stirred at 60° C. for 2 hours. Then the solvent was removed, water was poured into the mixture, extracted with EA, washed with brine and dried over $Na_2SO_4$. Concentration and chromatography gave a light yellow solid (130 mg). Yield: 54%.

$^1$HNMR (400 MHz, $CDCl_3$): δ (ppm): 8.57 (2H, d, Py-H), 7.32-7.60 (7H, m, Ph-H, Py-H), 6.81 (1H, dd, Ar—H), 4.65-4.80 (2H, m, —$CH_2$—), 2.55 (3H, s, $CH_3$—).

ESI MS: ([M+H]$^+$=467, HPLC: 99.8%.

EXAMPLE 62

Preparation of Compound (103)

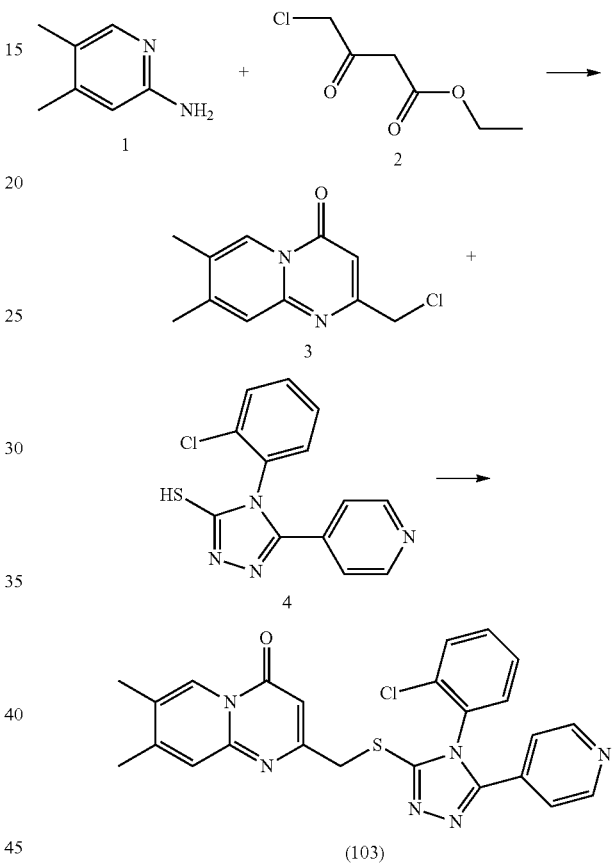

(103)

(a) Preparation of Compound 3:

PPA (10 mL) was added to the mixture of compound 1 (400 mg, 3.27 mmol) and compound 2 (539 mg, 3.27 mmol). The mixture was heated to 100° C. for 0.5 hours. Then it was poured into water and extracted with EA, washed with brine and dried over $Na_2SO_4$. Concentration and chromatography gave a brown solid (350 mg). Yield: 48%.

$^1$HNMR (400 MHz, $CDCl_3$): δ (ppm): 8.82 (1H, s), 7.52 (1H, s), 6.55 (1H, s), 4.52 (2H, s), 2.44 (3H, s), 2.37 (3H, s).

(b) Preparation of Compound (103):

To a solution of compound 4 (196 mg, 0.68 mmol) in acetone (20 mL) was added compound 3 (150 mg, 0.68 mmol) and $K_2CO_3$ (118 mg, 0.85 mmol). The mixture was stirred at 60° C. for 2 hours. Then the solvent was removed, water was poured into the mixture, extracted with DCM, washed with brine and dried over $Na_2SO_4$. Concentration and chromatography gave a white solid (148 mg). Yield: 45.8%.

¹HNMR (400 MHz, CDCl₃): δ (ppm): 8.79 (1H, s), 8.58 (2H, b), 7.37-7.61 (7H, m), 6.53 (1H, s), 4.50-4.59 (2H, J₁=21.6 Hz, J₂=13.6 Hz, q), 2.41 (3H, s), 2.35 (3H, s).

EXAMPLE 63

Preparation of Compound (98)

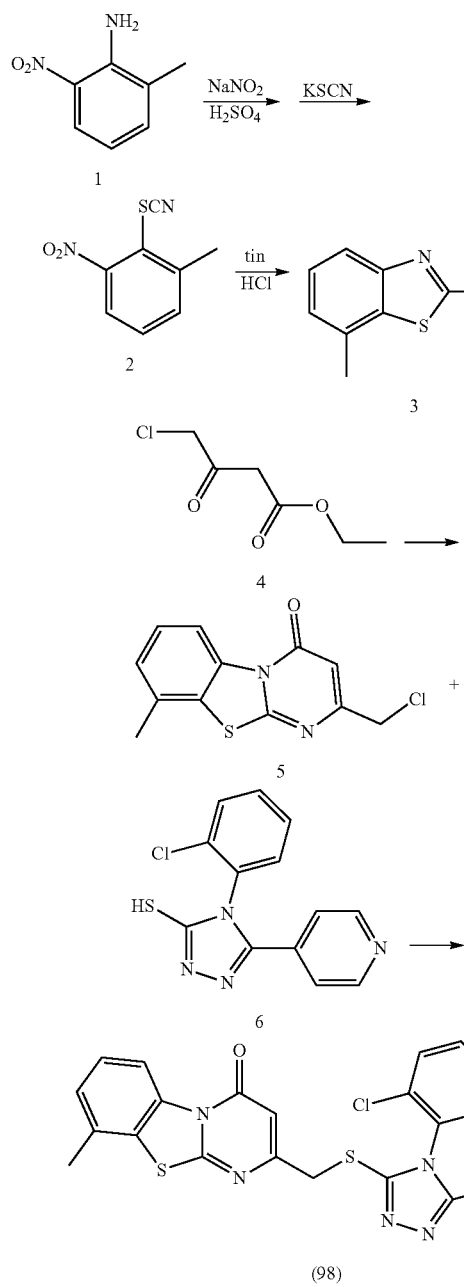

(a) Preparation of Compound 2:

In a solution of H₂SO₄/H₂O (4.2 mL/14.5 mL, 78.8 mmol), compound 1 (3 g, 19.7 mmol) was suspended. After cooling, diazotization was accomplished by adding NaNO₂/H₂O (1.4 g/5 mL, 20.4 mmol). Then to a cold solution (−5° C.) was added KSCN/H₂O (2.48 g/5 mL, 25.61 mmol) and CuSCN (2.3 g, 19.1 mmol). After standing overnight, the mixture was heated to 60° C. for 5 minutes, cooled and extracted with EA. The mixture was dried over MgSO₄, concentrated and purified by chromatography to give an orange solid (2.5 g). Yield: 65%.

¹HNMR (400 MHz, CDCl₃): δ (ppm): 7.83 (1H, d, Ar—H), 7.53-7.65 (2H, m, Ar—H), 2.78 (3H, s, CH₃—).

(b) Preparation of Compound 3:

Tin (10 g) and compound 2 (2.22 g, 11.4 mmol) was added in conc. HCl (40 mL) with shaking. It was heated to 65° C. until almost all of the tin was dissolved. The solution was decanted to remove the remaining tin, cooled and filtered to give a white salt. This product was decomposed with Na₂CO₃ and aminobebzothiazole was extracted with EA. Evaporation of EA gave a grey solid (1.0 g). Yield: 53%.

¹HNMR (400 MHz, CDCl₃): δ7.39 (1H, d, Ar—H), 7.21-7.25 (1H, m, Ar—H), 6.93-6.95 (1H, m, Ar—H), 5.46 (2H, s, NH₂—), 2.44 (3H, s, CH₃—).

(c) Preparation of Compound 5:

PPA (10 mL) was added to the mixture of compound 3 (1 g, 6 mmol) and compound 4 (1 g, 6 mmol). The mixture was heated to 100° C. for 0.5 hours. Then it was poured into water and extracted with EA, washed with brine and dried over Na₂SO₄. Concentration and chromatography gave a yellow solid (135 mg). Yield: 8.5%.

¹HNMR (400 MHz, CDCl₃): δ (ppm): 8.91 (1H, d, Ar—H), 7.32-7.47 (2H, m, Ar—H), 6.59 (1H, s, Ar—H), 4.47 (2H, s, —CH₂—), 2.52 (3H, s, CH₃—).

(d) Preparation of Compound (98):

To a solution of compound 6 (130 mg, 0.45 mmol) in acetone (10 mL) was added compound 5 (120 mg, 0.45 mmol) and K₂CO₃ (78 mg, 0.56 mmol). The mixture was stirred at 60° C. for 2 hours. Then after removal of the solvent, water was poured into the mixture, extracted with DCM, washed with brine and dried over Na₂SO₄. Concentration and chromatography gave a yellow solid (120 mg). Yield: 52%.

¹HNMR (400 MHz, CDCl₃): δ (ppm): 8.88-8.90 (1H, J=8.0 Hz, d), 8.55-8.57 (2H, J₁=8.4 Hz, J₂=1.6 Hz, q), 7.30-7.62 (8H, m), 6.59 (1H, s), 4.46-4.47 (2H, J=6.0 Hz, d), 2.51 (3H, s).

EXAMPLE 64

Preparation of Compound (43)

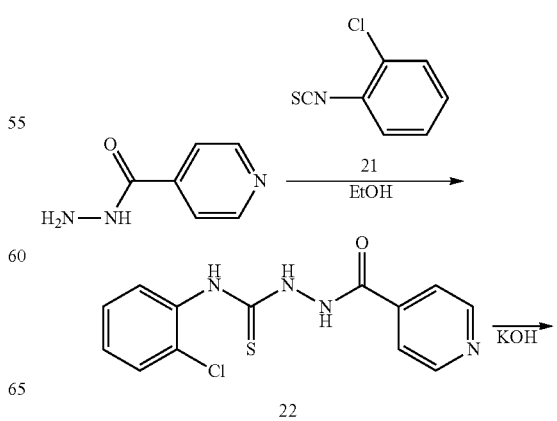

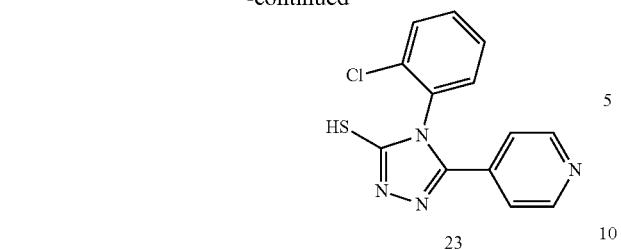

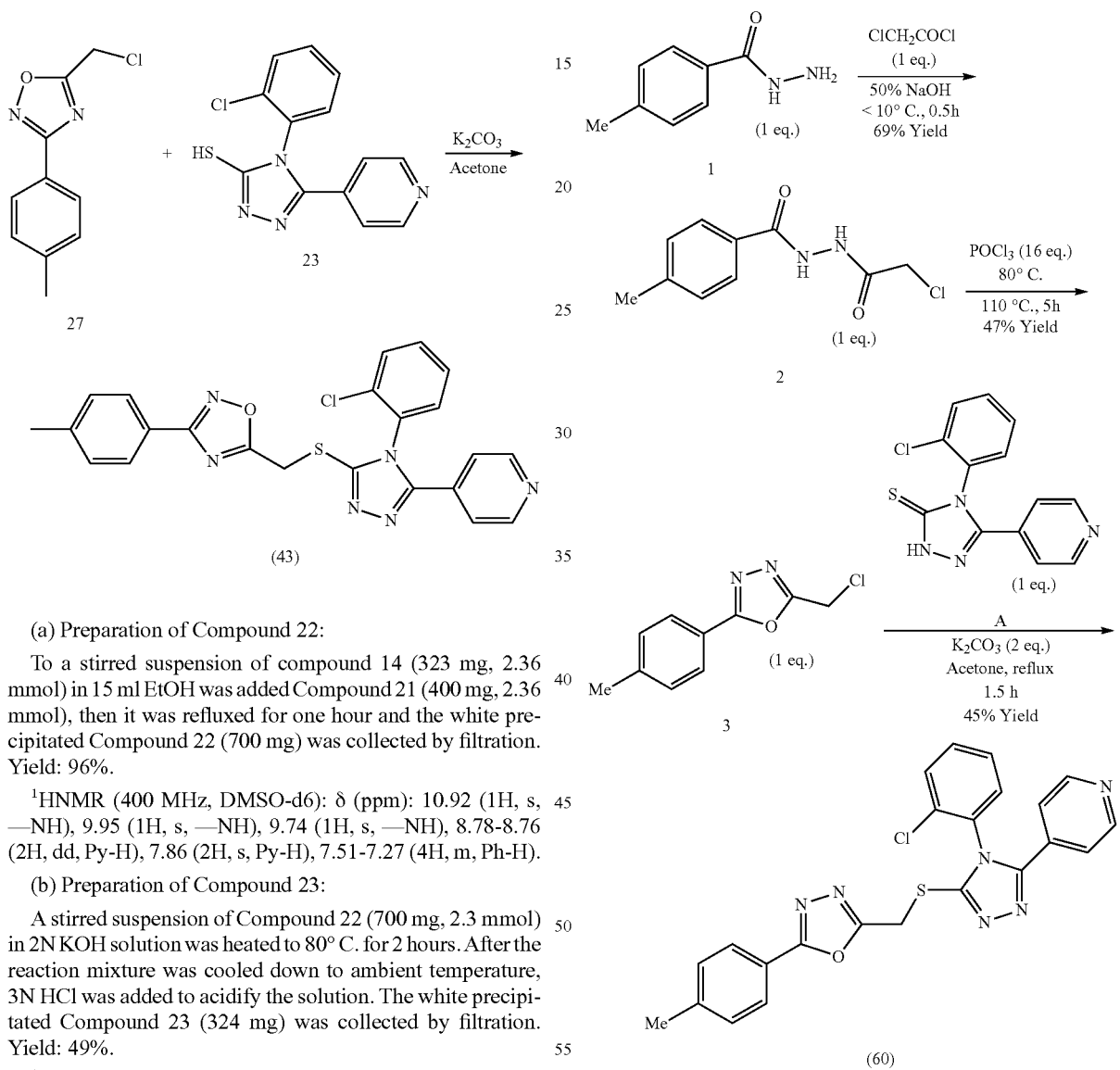

(a) Preparation of Compound 22:

To a stirred suspension of compound 14 (323 mg, 2.36 mmol) in 15 ml EtOH was added Compound 21 (400 mg, 2.36 mmol), then it was refluxed for one hour and the white precipitated Compound 22 (700 mg) was collected by filtration. Yield: 96%.

$^1$HNMR (400 MHz, DMSO-d6): δ (ppm): 10.92 (1H, s, —NH), 9.95 (1H, s, —NH), 9.74 (1H, s, —NH), 8.78-8.76 (2H, dd, Py-H), 7.86 (2H, s, Py-H), 7.51-7.27 (4H, m, Ph-H).

(b) Preparation of Compound 23:

A stirred suspension of Compound 22 (700 mg, 2.3 mmol) in 2N KOH solution was heated to 80° C. for 2 hours. After the reaction mixture was cooled down to ambient temperature, 3N HCl was added to acidify the solution. The white precipitated Compound 23 (324 mg) was collected by filtration. Yield: 49%.

$^1$HNMR (400 MHz, DMSO-d6): δ (ppm): 14.50 (1H, s, —SH), 8.61-8.59 (2H, dd, Py-H), 7.78-7.25 (6H, m, Py-H, Ph-H).

(c) Preparation of Compound (43):

To a stirred suspension of Compound 27 (85 mg, 0.37 mmol) in acetone (8 ml) was added Compound 23 (100 mg, 0.37 mmol) and K$_2$CO$_3$ (97 mg, 0.7 mmol), then it was stirred for 2 hours at reflux. The resultant product was concentrated directly in vacuum to remove acetone and the residue was extracted with EA. This was purified by silica gel column to give a white solid, 80 mg.

Yield: 47%.

$^1$HNMR (400 MHz, DMSO-d6): δ (ppm): 8.60-8.59 (2H, dd, Py-H), 7.88-7.29 (10H, m, Py-H, Ph-H), 7.81-7.32 (8H, m, Ph-H), 4.86-4.85 (2H, d, —CH$_2$—), 2.38 (3H, s, CH$_3$—).

ESI MS: 461.3 ([M+H]$^+$), HPLC: 98.9%

EXAMPLE 65

Preparation of Compound (60)

(a) Preparation of Compound 2:

To a solution of compound 1 (0.9 g, 5.99 mmol) in acetonitrile (8 ml) were added simultaneously chloroacetyl chloride (0.67 g, 5.99 mmol) and 50% sodium hydroxide (240 mg in 0.48 ml of water) while maintaining the internal temperature below 10° C. The reaction mixture was stirred at this temperature for 30 min. The reaction was quenched with water and the compound was extracted with ethyl acetate. The solvent was removed to obtain compound 2 (0.9 g) as a white solid. Yield: 69%.

¹HNMR (400 MHz, DMSO-d₆): δ (ppm): 10.4 (1H, s, —NH), 10.3 (1H, s, —NH), 7.80-7.70 (2H, d, Ar—H), 7.35-7.20 (2H, d, Ar—H), 4.2 (2H, s, —CH₂—), 2.35 (3H, s, —CH₃—).

MS: 229.4 [M⁺+2H] peak.

(b) Preparation of Compound 3:

The compound 2 (0.9 g, 4 mmol) was suspended in POCl₃ (6 ml, 64.3 mmol) and the reaction mixture was heated to 110° C. for 5 hours. The reaction mixture was cooled to ambient temperature and quenched with water. The compound was extracted with ethyl acetate and the solvent was removed. The crude material was purified by chromatography eluting with (EtOAc:Hexane=40:60) to give compound 3 as a solid (400 mg). eld: 47%.

¹HNMR (400 MHz, DMSO-d₆): δ 7.93-7.88 (2H, d, Ar—H), 7.48-7.40 (2H, d, Ar—H), 5.15 (2H, s, —CH₂—), 2.4 (3H, s, —CH₃). MS: 210.8 [M⁺+2H] peak.

(c) Preparation of Compound (60):

A mixture of compound 3 (80 mg, 0.383 mmol), compound A (110 mg, 0.383 mmol) and K₂CO₃ (106 mg, 0.768 mmol) was refluxed in 10 ml of acetone for 1.5 hours. The reaction mixture was cooled to ambient temperature, filtered and the filtrate was evaporated to obtain crude residue which was purified by column chromatography eluting with (MeOH:CH₂Cl₂=2:98) to obtain compound (60) as a solid (80 mg). Yield: 45%.

¹HNMR (400 MHz, DMSO-d₆): δ (ppm): 8.65-8.50 (2H, d, Py-2H), 7.84-7.78 (3H, m, Ar—H), 7.76-7.755 (3H, m, Ar—H), 7.44-7.38 (2H, m, Ar—H), 7.32-7.26 (2H, m, Ar—H) 4.54-4.52 (2H, dd, —CH₂—), 2.4 (3H, s, —CH₃—). LC-MS: 461.9 [M+H]⁺. HPLC: 99.19%.

EXAMPLE 66

Activity of Compounds in Wnt Assay

HEK293 cells were transfected, grown and assayed as described in Example 22. 24 hours after seeding, the cells were incubated for an additional 24 hours with 10 μM concentrations of compounds in 30% Wnt3a-CM.

The percent activities shown in Table 3 are calculated relative to DMSO as a control. Some values shown are averages of multiple measurements. Compound XAV939 (Novartis; Huang et al., *Nature* (2009), 461, pp. 614-20) which is used as a positive control, has an activity of 7%.

TABLE 3

| Compound | % activity |
|---|---|
| 1 | 15.4 |
| 2 | 31.8 |
| 3 | 32.5 |
| 4 | 98.4 |
| 5 | 10 |
| 6 | 55.7 |
| 7 | 5.6 |
| 8 | 28.5 |
| 10 | 10.1 |
| 11 | 9.3 |
| 12 | 38.8 |
| 13 | 34.5 |
| 14 | 63.5 |
| 15 | 69.1 |
| 16 | 71.8 |
| 17 | 76.8 |
| 18 | 32.3 |
| 19 | 44.1 |
| 21 | 90.1 |
| 25 | 59 |

TABLE 3-continued

| Compound | % activity |
|---|---|
| 27 | 80.3 |
| 30 | 78 |
| 33 | 79.6 |
| 41 | 9.4 |
| 42 | 14.6 |
| 43 | 7.8 |
| 44 | 10.4 |
| 45 | 78.1 |
| 46 | 13.3 |
| 47 | 8.7 |
| 48 | 9.9 |
| 56 | 55.1 |
| 57 | 51.8 |
| 60 | 17.3 |
| 62 | 58 |
| 63 | 99 |
| 66 | 25.6 |
| 67 | 12.7 |
| 68 | 17 |
| 69 | 26 |
| 71 | 31 |
| 72 | 20 |
| 73 | 29 |
| 74 | 13 |
| 77 | 51 |
| 79 | 16 |
| 80 | 32 |
| 81 | 89 |
| 82 | 83 |
| 85 | 43 |
| 87 | 52 |
| 88 | 99 |
| 89 | 94 |
| 92 | 84 |
| 93 | 91 |
| 97 | 80 |
| 99a | 11 |
| 99b | 12 |
| 100a | 22 |
| 100b | 5 |
| 101 | 23 |
| 103 | 20 |
| 105 | 4.4 |
| 106 | 14.5 |
| 107 | 4.5 |
| 108 | 0.8 |
| 109 | 0.6 |
| 110 | 2 |
| 111 | 0.7 |
| 112 | 0.3 |
| 113 | 4.9 |
| 114 | 4.2 |
| 115 | 5 |
| 116 | 7 |
| 117 | 9 |
| 130 | 9 |
| 131 | 4 |
| 132 | 32 |

EXAMPLE 67

IC₅₀ and GI₅₀ Values of Compounds

IC₅₀ values were calculated using STF/REN HEK293 cells prepared essentially according to Example 22. Briefly, HEK293 cells (80,000 cells per well) were seeded in 48-well plates coated with poly-L lysine. 24 hours after seeding, the cells were incubated for an additional 24 hours with various compound concentrations in 50% Wnt3a-CM. After compound exposure, the cells were lysed and the firefly luciferase and *Renilla* activities were measured on a 20/20n Luminometer (Turner BioSystems) as described in the Dual-Glo™ Luciferase Assay System Technical Manual (Promega).

Growth inhibition curves were prepared using SW480 cells, prepared essentially according to Example 23. SW480 cells (3000 cells per well) were seeded on 96 well plates (eight replicates per treatment). 24 hours later and daily thereafter, cell culture media (including 10% FBS) was mixed with various compound concentrations or with 0.1% DMSO vehicle and then added to the wells. Sixteen wells of seeded control cells, defining incubation time zero (to =24 hour after cell seeding), were incubated with 20l substrate in 100 μl of phenol-free D-MEM (Invitrogen) for 2 hours, as described in the CellTiter 96® AQueous Non-Radioactive Cell Proliferation Assay protocol (MTS, Promega). The $A_{490}$ was recorded. The treatment samples were likewise measured after 72 hours. The following formula was used to determine the single well relative $A_{490}$ sample values:

((Sample $A_{490}$–Average $A_{490}t_0$)*100)/(Average $A_{490}t_{72}$ 0.1% DMSO control–Average $A_{490}t_0$)

XLfit (idbs) was used to determine the $IC_{50}$ and $GI_{50}$ values in inhibition experiments. The data were fit to the following formulae:

$IC_{50}$: Langmuir Binding Isotherm:

fit=((A+(B*x))+(((C−B)*(1−exp((−1*D)*x)))/D))

res=(y−fit)

$GI_{50}$: Eadie-Hofstee Model:

fit=(A+((B*x)/((C*(D+1))+x)))

inv=(((y−A)*(C*(D+1)))/((A+B)−y))

res=(y−fit)

Table 4 shows the $IC_{50}$ and $GI_{50}$ values of certain compounds. Some values shown are average values from multiple experiments (nt=not tested). XAV939, used as a positive control, has an $IC_{50}$ value of less than 100 nM.

TABLE 4

| Compound | $IC_{50}$ nM | $GI_{50}$ μM |
|---|---|---|
| 1 | 1006 | 11.5 |
| 5 | 950 | 10 |
| 7 | 880 | 7.5 |
| 8 | 2100 | 10.5 |
| 10 | 3300 | 13.5 |
| 11 | 1500 | >25 |
| 12 | 10,000 | nt |
| 13 | 7100 | nt |
| 18 | 5900 | >25 |
| 19 | 8800 | >25 |
| 21 | 10,000 | nt |
| 25 | 10,000 | nt |
| 41 | 470 | <5 |
| 42 | 400 | 8 |
| 43 | 160 | 8 |
| 44 | 570 | 22 |
| 45 | nt | nt |
| 46 | 700 | 9 |
| 47 | 950 | nt |
| 48 | 220 | 9 |
| 60 | <100 | nt |
| 66 | 1750 | nt |
| 67 | <100 | nt |
| 68 | 381 | nt |
| 72 | 551 | nt |
| 74 | 371 | nt |
| 99a | 241 | nt |
| 99b | 163 | nt |
| 105 | 29 | nt |
| 108 | 218 | nt |
| 110 | 872 | nt |
| 112 | 688 | nt |

TABLE 4-continued

| Compound | $IC_{50}$ nM | $GI_{50}$ μM |
|---|---|---|
| 113 | 59 | nt |
| 114 | 795 | nt |
| 116 | 262 | nt |
| 117 | 834 | nt |
| 130 | 151 | nt |

EXAMPLE 68

In Vitro Cell Proliferation Assay

Control and colon carcinoma cell lines were assessed for reduction in cell proliferation following treatment with known Wnt-pathway modulators and with various compounds.

Experimental

Compound IWR-1 (Chen et al., *Nat. Chem. Biol.* (2009), 5, pp. 100-7), a known Wnt pathway inhibitor, was obtained from Sigma. Test compounds were synthesised as described in the preceding examples.

Control cell lines used were HeLa cells (cell growth not controlled by canonical Wnt signalling) and colorectal cancer cell lines LS174T and HCT116 (with mutant β-catenin N-terminal phosphorylation sites). Target cell lines used were colorectal cancer cell lines WiDr, LoVo, HCT-8, HCT-15, COL0205, DLD-1, HT-29, SW620, SW1463, SW480 which all carry a mutant APC gene. Target cells, along with L Wnt3a-expressing cells and HEK293 cells, were purchased from ATCC (American Type Culture Collection) and maintained according to the supplier's recommendations. Wnt3a containing conditioned media (Wnt3a-CM) from L Wnt3a expressing cells was harvested as described by ATCC.

For the experiment giving the results shown in Table 5, cells (3000 per well) were seeded on 96 well plates (eight replicates per treatment). After 24 hours, and daily thereafter, cell culture medium (including 10% FBS) was mixed with 10 μM compounds or with 0.1% DMSO vehicle and then added to the wells. Sixteen wells of seeded control cells, defining incubation time zero ($t_0$=24 hour after cell seeding), were incubated with 20 μl substrate in 100 μl phenol free D-MEM (Invitrogen) for 2 hours, as described in the CellTiter 96® AQueous Non-Radioactive Cell Proliferation Assay protocol (Promega). The $A_{490}$ was recorded. The treatment samples were likewise measured after 72 hours.

For the experiment giving the results shown in Table 6, cells were exposed to cell culture medium (including 10% FBS) containing 10 μM of the compound to be tested 24 hours after seeding (3000 cells on 96-well plates). Medium was changed daily. After 72 hours, an MTS assay (CellTiter 96® AQ$_{ueous}$ Non-Radioactive Cell Proliferation Assay—Promega) was carried out according to the standard procedure. 0.1% DMSO was used as a control.

The quantity of reduced MTS product (as measured by the absorbance at 490 nm) is directly proportional to the number of living cells in the culture and thus allows a direct comparison of cell proliferation in each case. DMSO was used as a control. The following formula was used to determine single well relative $A_{490}$ sample values:

((Sample $A_{490}$–Average $A_{490}t_0$)*100)/(Average $A_{490}t_{72}$ 0.1% DMSO control–Average $A_{490}t_0$)

Results

Table 5 shows the results of the MTS assay on SW480 colon carcinoma cells after 72 hours using 10 μM of various compounds. The proliferation of SW480 cells (in percent) is the $A_{492}$ value relative to that of the DMSO control.

TABLE 5

| Compound | Cell proliferation (%) for test compounds |
|---|---|
| 1 | 52 |
| 60 | 49 |
| 68 | 60 |
| 72 | 55 |
| 79 | 70 |
| 99a | 58 |
| 99b | 72 |
| 100a | 46 |
| 100b | 66 |
| 101 | 47 |
| 103 | 67 |
| 105 | 54 |
| 106 | 63 |
| 107 | 47 |
| 108 | 42 |
| 109 | 33 |
| 110 | 50 |
| 111 | 44 |
| 112 | 39 |
| 113 | 56 |
| 114 | 69 |
| 115 | 60 |
| 116 | 70 |
| 117 | 85 |
| 130 | 72 |
| 131 | 53 |

Table 6 shows the results of the MTS assay carried out as described above and shows cell growth of the various mutant APC colorectal cells compared to control cell lines. Data shown are $A_{490}$-percentage values relative to the DMSO control, calculated as described above, and represent averages from 2 to 4 independent experiments (except SW1463 cells treated with IWR-1 which reports only a single experiment). Compounds IWR-1 and XAV939 are known Wnt pathway inhibitors.

TABLE 6

| Cell line | Cell proliferation (%) for test compounds | | | |
|---|---|---|---|---|
| | IWR-1 | XAV939 | compound (43) | compound (60) |
| HeLa (control) | 77 | 92 | 92 | 92 |
| HCT116 (control) | 83 | 109 | 86 | 87 |
| LS174T (control) | 63 | 97 | 99 | 105 |
| WiDr | 61 | 94 | 76 | 70 |
| LoVo | 73 | 129 | 64 | 67 |
| HCT-8 | 70 | 105 | 69 | 51 |
| COLO205 | 55 | 116 | 33 | 53 |
| HCT-15 | 64 | 90 | 54 | 54 |
| DLD-1 | 97 | 102 | 76 | 78 |
| HT-29 | 33 | 100 | 63 | 58 |
| SW620 | 48 | 102 | 33 | 50 |
| SW1463 | 57 | 64 | 1 | 12 |
| SW480 | 62 | 103 | 51 | 59 |
| Mean proliferation (control cell lines) | 74 | 99 | 92 | 95 |
| Mean proliferation (APC mutant cell lines) | 62 | 101 | 52 | 55 |
| Ratio of means | 0.83 | 1.01 | 0.56 | 0.58 |

Conclusions

Investigating cell proliferation of SW480 cells treated with several compounds indicated that these compounds all act to reduce proliferation of the cancer cells, in some cases by up to 77%.

The effects of compounds (43) and (60) were tested on various cell lines. The control cells (those without mutations in the APC gene) were not significantly affected by compound (43) or (60). However, compounds (43) and (60) both display similar patterns in reduced cell growth in target colorectal cancer cell lines carrying mutations in the APC gene (mean cell proliferation of 52% and 55%, respectively). Compounds (43) and (60) show a high specificity of action against colorectal cancer cells which carry APC mutations (ratios of 0.56 and 0.58, respectively).

In contrast, the control compounds (both of which have recently been shown to be inhibitors of the Wnt pathway) were not selective in inhibiting growth of the APC mutant cancer cell lines. Compound XAV939 showed no substantial effect on cell growth of any of the tested cell lines (except SW1463: 64% proliferation). Control compound IWR-1 reduced proliferation of both control cell lines (mean 74% proliferation) and APC mutant cell lines (mean 62% proliferation). However, the specificity of action of IWR-1 is low (ratio of 0.83).

Thus, compounds (43) and (60) are highly selective inhibitors of the Wnt pathway in vitro, acting to reduce proliferation only in cancer cells which carry a mutant APC gene.

EXAMPLE 69

Effect of Compound (1) on Tumour Growth In Vivo

The effect of compound (1) on tumour growth on $Apc^{Min}$ mice was investigated.

Experimental

Cages containing three C57BL/6 females were crossed with one C57BL/6J-$Apc^{Min}$ male. The mice were fed with 2018SX Teklad Global 18% Protein Extruded Rodent Diet (Harlan™). 5-7 day old pups were randomized and divided into two treatment groups; the test group was treated with compound (1) and the control group treated with control vehicle (1% Tween®80—Sigma). Test solutions were administered daily by subcutaneous injection into the back of the neck (10 μl solution per gram of animal weight, solution 15 mg/ml compound). Two day injection intermissions followed after every fifth injection day. At the age of 21 days, mice were genotyped and $Apc^{Min}$ animals were sorted into a males and females. At the same time, subcutaneous injection of the solutions was substituted by oral administration. For oral application, compound (1) was dissolved in DMSO to 150 mg/kg. DMSO alone was used as a vehicle control (5 μl solution per gram of animal weight, solution 30 mg/ml). Administration was terminated at the age of 9 weeks and animals euthanased. The small intestine and colon of each animal was dissected, fixed in 10% PFA and stained with 1% methylene blue. Intestines were divided into anonymous and coded samples before manual analysis by microscopy. The frequency, distribution and size of the tumors were quantified. The mice were weighted twice a week throughout the experiment. All animal experiments were approved by local ethics authorities at Forsøksdyrutvalget, Oslo, Norway, and were carried out following accepted ethical standards.

Results

The effects of compound (1) on total tumour load is shown in FIG. 12A. FIG. 12B shows the effect of administration of compound (1) on the average weight of the mice in the two groups. No substantial difference in the bodyweight of male or female mice was detected after the treatments.

Statistical analysis and descriptive statistics from the experiment assessing small intestine tumors are shown in Tables 7 and 8 below. Table 7 shows the statistics on numbers of tumours. For each statistical comparison, a Shapiro-Wilk normality test was performed along with a Students t-test if passed (P>0.05). When normality could not be achieved in the Shapiro-Wilk test, a Mann-Whitney rank sum test was used instead of Students t-test. The α-level was set to 0.05 and a difference with P<0.05 was considered to be statistically significant. Sample size (n), median, range, maximum, minimum, mean, standard deviation, standard error, and confidence intervals (C.I. of mean) are listed.

TABLE 7

| Group | n | Median | Max | Min | Range | Mean | Std. Dev. | Std. Error | C.I. of mean |
|---|---|---|---|---|---|---|---|---|---|
| Control Female | 12 | 45.5 | 295 | 26 | 269 | 76 | 81.4 | 23.5 | 51.7 |
| Control Male | 11 | 45 | 181 | 25 | 156 | 73.5 | 58.6 | 17.7 | 39.4 |
| Test female | 11 | 33 | 51 | 19 | 32 | 33.5 | 10 | 3 | 6.7 |
| Test male | 10 | 37 | 53 | 22 | 31 | 39.1 | 9.7 | 3.1 | 6.9 |
| Control (male + female) | 23 | 45 | 295 | 25 | 270 | 74.8 | 69.8 | 14.6 | 30.2 |
| Test (male + female) | 21 | 35 | 53 | 19 | 34 | 36.1 | 10.1 | 2.2 | 4.6 |

TABLE 8

| Comparison | Shapiro-Wilk test | Test used | α-level | p-value |
|---|---|---|---|---|
| Control female vs. Control male | Failed (P ≤ 0.050) | Mann-Whitney | 0.05 | 0.926 |
| Test female vs. Test male | Passed (P = 0.850) | Students t-test | 0.05 | 0.207 |
| Test female vs. Test male | Passed (P = 0.850) | Mann-Whitney | 0.05 | 0.169 |
| Control (male + female) vs. Test (male + female) | Failed (P ≤ 0.050) | Mann-Whitney | 0.05 | 0.036 |

Statistical analysis and descriptive statistics from the experiment assessing colon tumors are shown in Tables 9 and 10 below. The data were analysed in the same way as the data in Tables 7 and 8.

TABLE 9

| Group | n | Median | Max | Min | Range | Mean | Std. Dev. | Std. Error | C.I. of mean |
|---|---|---|---|---|---|---|---|---|---|
| Control (male + female) | 23 | 1 | 6 | 0 | 6 | 1.783 | 1.906 | 0.397 | 0.824 |
| Test (male + female) | 21 | 0 | 2 | 0 | 2 | 0.429 | 0.746 | 0.163 | 0.34 |

TABLE 10

| Comparison | Shapiro-Wilk test | Test used | α-level | p-value |
|---|---|---|---|---|
| Control (male + female) vs. Test (male + female) | Failed (P ≤ 0.050) | Mann-Whitney | 0.05 | 0.003 |

FIG. 13A shows the distribution and frequency of tumours along the small intestine starting from the ventricle (cm). The last two-thirds of the small intestines treated with compound (1) contains fewer tumors than the control group. The histogram shown in FIG. 13B indicates the number of tumours in the small intestine in different size classes ($mm^2$). Treatment with compound (1) especially decreases the frequency of tumors between 0.10 $mm^2$ and 3.20 $mm^2$. The number of animals in each group and was used to normalize the values in FIGS. 13A and 13B.

Conclusions

Experiments were performed to determine the effect of compound (1) on the inhibition of tumour formation and growth in the small intestine and colon of $Apc^{Min}$ (multiple intestinal neoplasia, Min) mice. $Apc^{Min}$ mice harbour mutations in one allele of the APC tumor suppressor gene and these mice develop polyposis and colon adenocarcinoma due to frequent spontaneous mutations in the second allele. Thus, the $Apc^{Min}$ mouse line provides an excellent animal model for human colon cancer.

The effect of compound (1) on tumor formation in these mice after subcutaneous and oral application was determined. Effects on body weight (FIG. 12B) or other considerable discomfort could not be detected among any of the animals. As no significant difference in tumour frequency in the small intestine could be detected between males and females, the data from two sexes were combined and considered as one group during analysis.

A significant reduction of tumor number in the small intestine was detected after injections with compound (1) (see Tables 7 and 8). The mean number of intestinal tumours in the control group was 74.8, whereas in the group treated with compound (1) the mean value was 36.1 (P=0.036). A statistically significant reduction of the number of tumors in the colon was also detected after treatment with compound (1). The mean number of colon tumours in the control group was 1.78, whereas in the group treated with compound (1) the mean value was 0.42 (P=0.003).

The small intestine was divided into several sections according to the distance from the ventricle (in cm). In mice treated with compound (1), the last two-thirds of the small intestine had substantially fewer tumours when compared to the control (FIG. 13A). Furthermore, the tumours could be sorted by size into size classes in $mm^2$. The tumour frequencies, especially among those between 0.10 $mm^2$ and 3.20 $mm^2$, were drastically reduced after treatment with compound (1) (FIG. 13B). Additionally, when tumour frequency and size were combined as a total tumor load (sum of all tumors in $mm^2/n$), the inhibition of formation and growth of tumors in the small intestine by was clearly visible (control: 38.1 $mm^2$/subject and compound (1): 16.4 $mm^2$/subject).

The results from in vivo experiments on $Apc^{Min}$ mice show that compounds of the present invention have the capacity to obstruct aberrant Wnt signaling in vivo and can reduce development of intestinal cancer.

EXAMPLE 70

Kinase and Phosphatase Profile of Compound (1)

Experimental

A diverse panel of phosphatases and kinases was exposed in vitro to 10 μM compound (1) or to 0.1% DMSO. Experiments were performed according to the KinaseProfiler™ Service Assay Protocol (Millipore).

Results

Tables 11 and 12 (below) show the mean percentage activity of two independent measurements in the phosphatase and kinase screen, respectively. The 0.1% DMSO control value was set to 100%. Both human (h) and yeast (y) proteins were used in the assay.

TABLE 11

| Phosphatase | Activity (%) |
| --- | --- |
| CD45(h) | 108 |
| DUSP22(h) | 101 |
| HePTP(h) | 106 |
| LMPTP-B(h) | 100 |
| MKP5(h) | 99 |
| PP2A(h) | 87 |
| PTP-1B(h) | 105 |
| PTPb(h) | 106 |
| PTP MEG1(h) | 92 |
| PTPN22(h) | 99 |
| RPTPm(h) | 103 |
| SHP-1(h) | 102 |
| TCPTP(h) | 100 |
| TMDP(h) | 97 |
| VHR(h) | 103 |
| YopH(y) | 94 |

TABLE 12

| Kinase | Activity (%) |
| --- | --- |
| Abl(h) | 93 |
| ALK(h) | 91 |
| AMPKα1(h) | 95 |
| ASK1(h) | 106 |
| Aurora-A(h) | 95 |
| CaMKI(h) | 97 |
| CDK1/cyclinB(h) | 101 |
| CDK2/cyclinA(h) | 106 |
| CDK6/cyclinD3(h) | 94 |
| CDK7/cyclinH/MAT1(h) | 108 |
| CDK9/cyclin T1(h) | 115 |
| CHK1(h) | 106 |
| CK1γ1(h) | 100 |
| CK2(h) | 105 |
| CK2α2(h) | 104 |
| cKit(h) | 116 |
| c-RAF(h) | 98 |
| cSRC(h) | 100 |
| DRAK1(h) | 116 |
| eEF-2K(h) | 117 |
| EGFR(h) | 108 |
| EphA5(h) | 99 |
| EphB4(h) | 105 |
| Fyn(h) | 83 |
| GRK5(h) | 104 |
| GSK3β(h) | 90 |
| IGF-1R(h) | 149 |
| IKKα(h) | 109 |
| IRAK4(h) | 98 |
| JAK2(h) | 118 |
| JNK3(h) | 93 |
| KDR(h) | 104 |
| LOK(h) | 109 |
| Lyn(h) | 109 |
| MAPK2(h) | 105 |
| MAPKAP-K2(h) | 85 |
| MEK1(h) | 108 |
| MKK7β(h) | 90 |
| MLK1(h) | 99 |
| Mnk2(h) | 108 |
| MSK2(h) | 108 |
| MST1(h) | 106 |
| NEK2(h) | 94 |
| p70S6K(h) | 113 |
| PAK2(h) | 99 |
| PDGFRβ(h) | 129 |
| PI3 Kinase (p110b/p85a)(h) | 94 |
| Pim-1(h) | 91 |
| PKA(h) | 86 |
| PKBα(h) | 79 |
| PKCα(h) | 105 |
| PKCθ(h) | 109 |
| PKG1α(h) | 106 |
| Plk3(h) | 104 |
| PRAK(h) | 55 |
| ROCK-I(h) | 100 |
| Rse(h) | 108 |
| Rsk1(h) | 108 |
| SAPK2a(h) | 106 |
| SRPK1(h) | 96 |
| TAK1(h) | 104 |

Conclusions

No extensive inhibition of kinase or phosphatase activity was detected in the presence of 10 μM compound (1).

The invention claimed is:

1. A method of treatment of a human or non-human animal body to combat a condition or disease which is affected by over-activation of signaling in the Wnt pathway, comprising administering to the human or non-human a compound of the formula

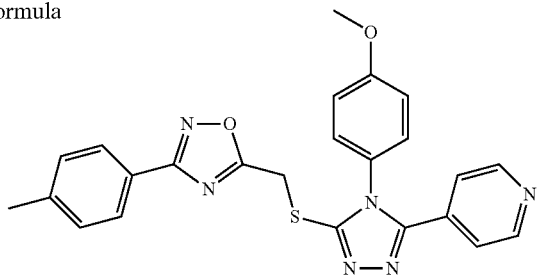

or a pharmaceutically acceptable salt thereof, wherein the condition or disease which is affected by over-activation of signaling in the Wnt pathway is colon cancer.

* * * * *